US012697388B2

(12) United States Patent
Adusumilli et al.

(10) Patent No.: US 12,697,388 B2
(45) Date of Patent: Aug. 4, 2026

(54) CHIMERIC ANTIGEN RECEPTORS TARGETING CD127 AND USE THEREOF

(71) Applicants: MEMORIAL SLOAN-KETTERING CANCER CENTER, New York, NY (US); OSE IMMUNOTHERAPEUTICS, Nantes (FR)

(72) Inventors: Prasad S. Adusumilli, New York, NY (US); Nicolas Poirier, Treillieres (FR)

(73) Assignees: MEMORIAL SLOAN-KETTERING CANCER CENTER, New York, NY (US); OSE IMMUNOTHERAPEUTICS, Nantes (FR)

( * ) Notice: Subject to any disclaimer, the term of this patent is extended or adjusted under 35 U.S.C. 154(b) by 778 days.

(21) Appl. No.: 18/049,876

(22) Filed: Oct. 26, 2022

(65) Prior Publication Data

US 2023/0087125 A1 Mar. 23, 2023

Related U.S. Application Data

(63) Continuation of application No. PCT/US2021/029372, filed on Apr. 27, 2021.

(60) Provisional application No. 63/015,923, filed on Apr. 27, 2020.

(51) Int. Cl.
| | |
|---|---|
| *A61K 40/15* | (2025.01) |
| *A61K 40/11* | (2025.01) |
| *A61K 40/31* | (2025.01) |
| *A61K 40/42* | (2025.01) |
| *A61P 35/00* | (2006.01) |
| *C12N 5/0783* | (2010.01) |

(52) U.S. Cl.
CPC .......... *A61K 40/4255* (2025.01); *A61K 40/11* (2025.01); *A61K 40/15* (2025.01); *A61K 40/31* (2025.01); *A61K 40/4211* (2025.01); *A61K 40/4212* (2025.01); *A61K 40/4217* (2025.01); *A61K 40/4276* (2025.01); *A61P 35/00* (2018.01); *C12N 5/0636* (2013.01); *A61K 2239/31* (2023.05); *A61K 2239/38* (2023.05); *A61K 2239/48* (2023.05); *A61K 2239/55* (2023.05)

(58) Field of Classification Search
None
See application file for complete search history.

(56) References Cited

U.S. PATENT DOCUMENTS

| | | | |
|---|---|---|---|
| 4,956,778 | A | 9/1990 | Naito |
| 5,091,513 | A | 2/1992 | Huston et al. |
| 5,132,405 | A | 7/1992 | Huston et al. |
| 5,399,346 | A | 3/1995 | Anderson et al. |
| 11,230,602 | B2 * | 1/2022 | Poirier .................... A61P 43/00 |
| 2005/0196754 | A1 | 9/2005 | Drmanac et al. |
| 2017/0037369 | A1 | 2/2017 | Ramsborg et al. |
| 2019/0315875 | A1 | 10/2019 | Durum et al. |
| 2022/0064309 | A1 * | 3/2022 | Durum ............... C07K 16/2866 |
| 2023/0056345 | A1 * | 2/2023 | Kong ..................... A61K 40/11 |

FOREIGN PATENT DOCUMENTS

| | | | |
|---|---|---|---|
| WO | WO 2014/087010 A1 | 6/2014 |
| WO | WO 2015/189302 A1 | 12/2015 |
| WO | WO 2017/149394 A1 | 9/2017 |
| WO | WO 2019/043065 A1 | 3/2019 |
| WO | WO 2021/076887 A1 | 4/2021 |

OTHER PUBLICATIONS

Edwards et al., JMB 2003, v.334,pp. 103-118.*
Ferrara et al, 2015.*
Lloyd et al., 2009, Protein Engineering, v.22, pp. 159-168.*
Adachi et al., "IL-7 and CCL19 expression in CAR-T cells improves immune cell infiltration and CAR-T cell survival in the tumor," Nat Biotechnol 36:346-351 (2018).
Akkapeddi et al., "A fully human anti-IL-7Rα antibody promotes antitumor activity against T-cell acute lymphoblastic leukemia," Leukemia 33:2155-2168 (2019).
Al-Rawi et al., "Aberrant expression of interleukin-7 (IL-7) and its signalling complex in human breast cancer," Eur J Cancer 40:494-502 (2004).
Altschul et al., "Basic Local Alignment Search Tool," J. Mol. Biol. 215:403-410 (1990).
Altschul et al., "Gapped BLAST and PSI-BLAST: a new generation of protein database search programs," Nucleic Acids Res. 25(17):3389-3402 (1997).
Anderson, "Prospects for Human Gene Therapy," Science 226:401-409 (1984).
Barata et al., "Activation of PI3K Is Indispensable for Interleukin 7-mediated Viability, Proliferation, Glucose Use, and Growth of T Cell Acute Lymphoblastic Leukemia Cells," J Exp Med. 200(5):659-669 (2004).
Barata et al., "Flip the coin: IL-7 and IL-7R in health and disease," Nature Immunology 20(12):1584-1593 (2019) Nat Immunol 20, 1584-1593 (2019).
Barata et al., "Interleukin-7 promotes survival and cell cycle progression of T-cell acute lymphoblastic leukemia cells by down-regulating the cyclin-dependent kinase inhibitor p27kip1," Blood 98(5):1524-1531 (2001).
Belarif et al., "IL-7 receptor blockade blunts antigen-specific memory T cell responses and chronic inflammation in primates," Nat Comm 9:4483 (2018).
Belarif et al., "IL-7 receptor influences anti-TNF responsiveness and T cell gut homing in inflammatory bowel disease," J Clin Invest 129:1910-1925 (2019).

(Continued)

*Primary Examiner* — Michail A Belyavskyi
(74) *Attorney, Agent, or Firm* — Baker Botts L.L.P.

(57) ABSTRACT

The presently disclosed subject matter provides methods for treating neoplasia using cells comprising an antigen-recognizing receptor (e.g., a chimeric antigen receptor (CAR)) that specifically targets CD127.

26 Claims, 89 Drawing Sheets

Specification includes a Sequence Listing.

(56)            References Cited

OTHER PUBLICATIONS

Blomer et al., "Highly Efficient and Sustained Gene Transfer in Adult Neurons with a Lentivirus Vector," Journal of Virology 71:6641-6649 (1997).

Bregni et al., "Human Peripheral Blood Hematopoietic Progenitors Are Optimal Targets of Retroviral-Mediated Gene Transfer," Blood 80:1418-1422 (1992).

Brentjens et al., "CD19-targeted T cells rapidly induce molecular remissions in adults with chemotherapy-refractory acute lymphoblastic leukemia," Sci Transl Med 5:177ra138 (2013).

Brigham et al., "Rapid Communication: In vivo Transfection of Murine Lungs with a Functioning Prokaryotic Gene Using a Liposome Vehicle," Am. J. Med. Sci. 298:278-281 (1989).

Brocks et al., "A TNF receptor antagonistic scFv, which is not secreted in mammalian cells, is expressed as a soluble mono- and bivalent scFv derivative in insect cells," Immunotechnology 3(3):173-184 (1997).

Carrette et al., "IL-7 signaling and CD127 receptor regulation in the control of T cell homeostasis," Semin Immunol 24:209-217 (2012).

Cayouette et al., "Adenovirus-Mediated Gene Transfer of Ciliary Neurotrophic Factor Can Prevent Photoreceptor Degeneration in the Retinal Degeneration (rd) Mouse," Human Gene Therapy 8:423-430 (1997).

Cherkassky et al., "Human CAR T cells with cell-intrinsic PD-1 checkpoint blockade resist tumor-mediated inhibition," J Clin Invest 126:3130-3144 (2016).

Cornetta et al., "Gene Transfer into Primates and Prospects for Gene Therapy in Humans," Nucleic Acid Research and Molecular Biology 36:311-322 (1987).

Danos et al., "Safe and efficient generation of recombinant retroviruses with amphotropic and ecotropic host ranges," Proc Natl Acad Sci USA 85:6460-6464 (1988).

Dupont et al., "Artificial Antigen-Presenting Cells Transduced with Telomerase Efficiently Expand Epitope-Specific, Human Leukocyte Antigen-Restricted Cytotoxic T Cells," Cancer Res 65:5417-5427 (2005).

Eglitis et al., "Retroviral Vectors for Introduction of Genes into Mammalian Cells," BioTechniques 6:608-614 (1988).

Eguchi et al., "The New IASLC/ATS/ERS Lung Adenocarcinoma Classification: what the surgeon should know," Semin Thorac Cardiovasc Surg 26:210-222 (2014).

Extended European Search Report dated May 10, 2024 in Application No. EP 21795922.

Eyquem et al., "Targeting a CAR to the TRAC locus with CRISPRiCas9 enhances tumour rejection," Nature 543:113-117 (2017).

Felgner et al., "Lipofection: A highly efficient, lipid-mediated DNA-transfection procedure," Proc. Natl. Acad. Sci. USA. 84:7413-7417 (1987).

Fife et al., Inhibition of T cell activation and autoimmune diabetes using a B cell surface-linked CTLA-4 agonist, JCI 116(8):2252-2261 (2006).

Freyer et al., "Postrelapse survival in childhood acute lymphoblastic leukemia is independent of initial treatment intensity: a report from the Children's Oncology Group," Blood 117(11):3010-3015 (2011).

Friedmann, "Progress toward Human Gene Therapy," Science 244:1275-1281 (1989).

Fry et al., "Interleukin-7: master regulator of peripheral T-cell homeostasis?" Trends Immunol 22:564-571 (2001).

Ghorashian et al., "Enhanced CAR T cell expansion and prolonged persistence in pediatric patients with ALL treated with a low-affinity CD19 CAR," Nat Med 25:1408-1414 (2019).

Gianfelici et al., "IL7R overexpression in adult acute lymphoblastic leukemia is associated to JAK/STAT pathway mutations and identifies patients who could benefit from targeted therapies," Leukemia & Lymphoma 60(3):829-832 (2019).

Giomarelli et al., "Inhibition of thrombin-induced platelet aggregation using human single-chain Fv antibodies specific for TREM-like transcript-I," Thromb Haemost 97(6):955-963 (2007).

Gueugnon et al., "Identification of Novel Markers for the Diagnosis of Malignant Pleural Mesothelioma," Am J Pathol 178:1033-1042 (2011).

Helguera et al., "Visualization and quantification of cytotoxicity mediated by antibodies using imaging flow cytometry," J Immunol Methods 368(1-2):54-63 (2011).

Henriques et al., "IL-7 induces rapid clathrin-mediated internalization and JAK3-dependent degradation of IL-7Rα in T cells," Blood 115(16):3269-3277 (2010).

Hixon et al., "New anti-IL-7Rα monoclonal antibodies show efficacy against T cell acute lymphoblastic leukemia in pre-clinical models," Leukemia 34:35-49 (2020).

Ho et al., "Inhibition of Cocaine Binding to the Human Dopamine Transporter by a Single Chain Anti-Idiotypic Antibody: Its Cloning, Expression and Functional Properties," BioChem Biophys Acta 1638(3):257-266 (2003).

Hughes et al., "Retroviral Gene Transfer to Primitive Normal and Leukemic Hematopoietic Cells Using Clinically Applicable Procedures," J Clin Invest 89:1817-1824 (1992).

Husain et al., "Guidelines for Pathologic Diagnosis of Malignant Mesothelioma. 2017 Update of the Consensus Statement From the International Mesothelioma Interest Group," Arch Pathol Lab Med. 142(1):89-108 (2018).

Huston et al., "Protein engineering of antibody binding sites: Recovery of specific activity in an anti-digoxin single-chain Fv analogue produced in *Escherichia coli*," Proc. Natl. Acad. Sci USA 85:5879-5883 (1988).

International Search Report mailed Jul. 27, 2021 in International Application No. PCT/US2021/029372.

Jacobs et al., "IL-7 Is Essential for Homeostatic Control of T Cell Metabolism In Vivo," J Immunol. 184(7):3461-3469 (2010).

Johnson, "Gene Therapy for Cystic Fibrosis," Chest 107:77S-83S (1995).

Kabat et al., Sequences of Proteins of Immunological Interest, 4th U. S. Department of Health and Human Services, National Institutes of Health (1987) 7 pgs.

Kido et al., "Use of a retroviral vector with an internal opsin promoter to direct gene expression to retinal photoreceptor cells," Current Eye Research 15:833-844 (1996).

Lamers et al., "Treatment of Metastatic Renal Cell Carcinoma With CAIX CAR engineered T cells: Clinical Evaluation and Management of On target Toxicity," Mol Ther 21:904-912 (2013).

Laouar et al., "Overexpression of IL-7Rα provides a competitive advantage during early T-cell development," Blood 103(6):1985-1994 (2004).

Le Gal La Salle et al., "An Adenovirus Vector for Gene Transfer into Neurons and Glia in the Brain," Science 259:988-990 (1993).

Ledbetter et al., "Agonistic Activity of a CD40-Specific Single-Chain Fv Constructed from the Variable Regions of mAb G28-5," Crit Rev Immunol 17(5-6):427-435 (1997).

Lefranc et al., "IMGT unique numbering for immunoglobulin and T cell receptor variable domains and Ig superfamily V-like domains," Dev. Comp. Immunol. 27:55-77 (2003).

Lefranc, "The IMGT Unique Numbering for Immunoglobulins, T-Cell Receptors, and Ig-Like Domains," The Immunologist 7:132-136 (1999).

Li et al., "IL-7 Receptor Blockade Inhibits IL-17-Producing γδ Cells and Suppresses Melanoma Development," Inflammation 37(5):1444-1452 (2014).

Liu et al., "Affinity-Tuned ErbB2 or EGFR Chimeric Antigen Receptor T Cells Exhibit an Increased Therapeutic Index against Tumors in Mice," Cancer Res 75:3596-3607 (2015).

Liu et al., "CRISPR-Cas9-mediated multiplex gene editing in CAR-T cells," Cell Res 27:154-157 (2017).

Maude et al., "Chimeric Antigen Receptor T Cells for Sustained Remissions in Leukemia," N Engl J Med 371: 1507-1517 (2014).

Maus et al., "Making Better Chimeric Antigen Receptors for Adoptive T-cell Therapy," Clin Cancer Res 22:1875-1884 (2016).

McCoy et al., Natl Cancer Inst Monogr 37, 59-67 (1973).

Meybohm et al., "A Multicenter Trial of Remote Ischemic Preconditioning for Heart Surgery," N. Eng. J Med 373:1397-1407 (2015).

Meyerhoff et al., "Impact of mesothelioma histologic subtype on outcomes in the Surveillance, Epidemiology, and End Results database," J Surg Res 196:23-32 (2015).

(56)     References Cited

OTHER PUBLICATIONS

Miller et al., "Generation of Helper-Free Amphotropic Retroviruses That Transduce a Dominant-Acting, Methotrexate-Resistant Dihydrofolate Reductase Gene," Mol Cell Biol 5:431-437 (1985).

Miller et al., "Improved Retroviral Vectors for Gene Transfer and Expression," Biotechniques 7:980-990 (1989).

Miller et al., "Redesign of retrovirus packaging cell lines to avoid recombination leading to helper virus production," Mol Cell Biol 6:2895-2902 (1986).

Miller, "Retrovirus Packaging Cells," Human Gene Therapy 1:5-14 (1990).

Ming et al., "Interleukin-7 up-regulates cyclin D1 via activator protein-1 to promote proliferation of cell in lung cancer," Cancer Immunol Immunother 61:79-88 (2012).

Miyoshi et al., "Stable and efficient gene transfer into the retina using an HIV-based lentiviral vector," Proc. Natl. Acad. Sci. USA 94:10319-10323 (1997).

Moen, "Directions in Gene Therapy," Blood Cells 17:407-416 (1991).

Moosmayer et al., "A single-chain TNF receptor antagonist is an effective inhibitor of TNF mediated cytotoxicity," Ther Immunol 2(10):31-40 (1995).

Morgan et al., "Cancer Regression in Patients After Transfer of Genetically Engineered Lymphocytes," Science 314:126-129 (2006).

Morgan et al., "Case Report of a Serious Adverse Event Following the Administration of T Cells Transduced With a Chimeric Antigen Receptor Recognizing ERBB2," Mol Ther 18:843-851 (2010).

Myers et al., "Optimal alignments in linear space," Comput. Appl. Biosci., 4:11-17 (1988).

Naldini et al., "In Vivo Gene Delivery and Stable Transduction of Nondividing Cells by a Lentiviral Vector," Science 272:263-267 (1996).

Needleman et al., "A General Method Applicable to the Search for Similarities in the Amino Acid Sequence of Two Proteins," J. Mol. Biol. 48:443-453 (1970).

Newick et al., "CAR T Cell Therapy for Solid Tumors," Annu Rev Med 68:139-152 (2017).

Ono et al., "Plasmid DNAs directly injected into mouse brain with lipofectin can be incorporated and expressed by brain cells," Neuroscience Letters 117:259-263 (1990).

Overdijk et al., "Crosstalk between Human IgG Isotypes and Murine Effector Cells," J Immunol. 189(7):3430-3438 (2012).

Palmer et al., "Interleukin-7 Receptor Signaling Network: An Integrated Systems Perspective," Cell Mol Immunol 5:79-89 (2008).

Panelli et al., "A Tumor-Infiltrating Lymphocyte from a Melanoma Metastasis with Decreased Expression of Melanoma Differentiation Antigens Recognizes MAGE-12," J Immunol 164:4382-4392 (2000).

Panelli et al., "Expansion of Tumor-T Cell Pairs from Fine Needle Aspirates of Melanoma Metastases," J Immunol 164:495-504 (2000).

Papanicolaou et al., "Rapid expansion of cytomegalovirus—specific cytotoxic T lymphocytes by artificial antigen-presenting cells expressing a single HLA allele," Blood 102:2498-2505 (2003).

Park et al., "Long-Term Follow-up of CD19 CAR Therapy in Acute Lymphoblastic Leukemia," N Engl J Med 378:449-459 (2018).

Peter et al., "Protective effects of an anti-melanocortin-4 receptor scFv derivative in lipopolysaccharide-induced cachexia in rats," J Cachexia Sarcopenia Muscle 4(1):79-88 (2013).

Peter et al., "scFv Single Chain Antibody Variable Fragment as Inverse Agonist of the β2-Adrenergic Receptor," J Biol Chem 278(38):36740-36747 (2003).

Ribeiro et al., "IL-7R-mediated signaling in T-cell acute lymphoblastic leukemia," Adv Biol Regul. 53(2):211-222 (2013).

Rosenberg et al., "Gene Transfer Into Humans—Immunotherapy Of Patients With Advanced Melanoma, Using Tumor-Infiltrating Lymphocytes Modified By Retroviral Gene Transduction," N. Engl. J. Med 323:570-578 (1990).

Russell et al., "Does Lung Adenocarcinoma Subtype Predict Patient Survival? A Clinicopathologic Study Based on the New International Association for the Study of Lung Cancer/American Thoracic Society/European Respiratory Society International Multidisciplinary Lung Adenocarcinoma Classification," J Thorac Oncol 6:1496-1504 (2011).

Sadelain et al., "Targeting Tumours with Genetically Enhanced T Lymphocytes," Nat Rev Cancer 3:35-45 (2003).

Schmidts et al., "Making CAR T Cells a Solid Option for Solid Tumors," Front Immunol 9:2593 (2018) 10 pgs.

Schuster et al., "Chimeric Antigen Receptor T Cells in Refractory B-Cell Lymphomas," N Engl J Med 377:2545-2554 (2017).

Scupoli et al., "Interleukin 7 requirement for survival of T-cell acute lymphoblastic leukemia and human thymocytes on bone marrow stroma," Haematologica 92(2):264-266 (2007).

Scupoli et al., "Thymic epithelial cells promote survival of human T-cell acute lymphoblastic leukemia blasts: the role of interleukin-7," Haematologica. 88(11):1229-1237 (2003).

Sharp, "Gene Therapy," The Lancet 337:1277-1278 (1991).

Shen et al., "Engineering Peptide Linkers for scFv Immunosensors," Anal. Chem. 80(6):1910-1917 (2008).

Shieh et al., "Transgenic Expression of Single-Chain Anti-CTLA-4 Fv on β Cells Protects Nonobese Diabetic Mice from Autoimmune Diabetes," J Immunol 183(4):2277-2285 (2009).

Shochat et al., "Gain-of-function mutations in interleukin-7 receptor-α (IL7R) in childhood acute lymphoblastic leukemias," J Exp Med. 208(5):901-908 (2011).

Shum et al., "Constitutive signaling from an engineered IL-7 receptor promotes durable tumor elimination by tumor redirected T-cells," Cancer Discov 7:1238-1247 (2017).

Silva et al., "IL-7 Contributes to the Progression of Human T-cell Acute Lymphoblastic Leukemias," Cancer Res. 71(14):4780-4789 (2011).

Staubinger et al., "Liposomes as Carriers for Intracellular Delivery of Nucleic Acids," Methods in Enzymology 101:512-527 (1983).

Suzuki et al., "Clinical Impact of Immune Microenvironment in Stage I Lung Adenocarcinoma: Tumor Interleukin-12 Receptor β2 (IL-12Rβ2), IL-7R, and Stromal FoxP3/CD3 Ratio Are Independent Predictors of Recurrence," Journal of Clinical Oncology 31:490-498 (2013).

Tamarit et al., "Membrane Microdomains and Cytoskeleton Organization Shape and Regulate the IL-7 Receptor Signalosome in Human CD4 T-cells," J Biol Chem. 288(12):8691-8701 (2013).

Thomas et al., "Outcome of Treatment in Adults With Acute Lymphoblastic Leukemia: Analysis of the LALA-94 Trial," J Clin Oncol. 22(20):4075-4086 (2004).

Tolstoshev et al., "Gene expression using retroviral vectors," Current Opinion in Biotechnology 1:55-61 (1990).

Ujiie et al., "The tumoral and stromal immune microenvironment in malignant pleural mesothelioma: A comprehensive analysis reveals prognostic immune markers," OncoImmunology 4(6):e1009285 (2015).

Vanderven et al., "What Lies Beneath: Antibody Dependent Natural Killer Cell Activation by Antibodies to Internal Influenza Virus Proteins," EBioMedicine 8:277-290 (2016).

Wolff et al., "Direct Gene Transfer into Mouse Muscle in Vivo," Science 247:1465-1468 (1990).

Wu et al., "Receptor-mediated Gene Delivery and Expression in Vivo," Journal of Biological Chemistry 263:14621-14624 (1988).

Wu et al., "Targeting Genes: Delivery and Persistent Expression of a Foreign Gene Driven by Mammalian Regulatory Elements in Vivo," Journal of Biological Chemistry 264:16985-16987 (1989).

Xie et al., "Direct demonstration of MuSK involvement in acetylcholine receptor clustering through identification of agonist ScFv," Nat Biotech 15(8):768-771 (1997).

Xu et al., "Correction of the enzyme deficiency in hematopoietic cells of Gaucher patients using a clinically acceptable retroviral supernatant transduction protocol," Exp Hemat 22:223-230 (1994).

Yasunaga et al., "Immunoregulation by IL-7R-targeting antibody-drug conjugates: overcoming steroid-resistance in cancer and autoimmune disease," Sci Rep.7:10735 (2017).

Zenatti et al., "Oncogenic IL7R gain-of-function mutations in childhood T-cell acute lymphoblastic leukemia," Nat Genet 43(10):932-939 (2011).

Zhao et al., "Characteristics of an scFv Antibody Fragment that Binds to Immunoglobulin G of Graves' Disease Patients and

(56)          References Cited

OTHER PUBLICATIONS

Inhibits Autoantibody-Mediated Thyroid-Stimulating Activity,"
Hyrbidoma (Larchint) 27(6):445-451 (2008).

* cited by examiner

| Test Binding | ED50 (ng/ml) |
|---|---|
| scFv703–Fc VH-VL | 33,22 |
| scFv703–Fc VH-VL | 5,39 |

CAR-T CD127 expression levels

CTL of CAR-T (XD1) with A549G-IL7R-OE cells (18h)

CellTrace labeled PBMC were co-cultured with different CAR-T for 4 hours, PBMC numbers and IL-7R levels were investigated (n=3).

CellTrace labeled PBMC were co-cultured with different CAR-T for 18 hours, PBMC numbers and IL-7R levels were investigated (n=3).

PBMC were co-cultured with different CAR-T (1:1) for 3 days, and CD127 levels were investigated. Two donors were used: XD1 and XD3

IL7R-OE: overexpression IL-7R
with pLV-IL-7R lentivirus

IL7R-KO: Knock out IL-7R with
CRISPR-Cas9 system

H358 cells

RL1-A :: CD127-APC-A

IL-7R expression level

|         | A549G | H1299G | EKVXG | H358  |
|---------|-------|--------|-------|-------|
| Basal   | ND    | ND     | ND    | 48%   |
| IL7R-OE | 92%   | 99.9%  | 94%   | 99.8% |
| IL7R-KO | N/A   | N/A    | N/A   | 0.2%  |

MFI:

| Case # | Case # | Treg | CD25- FoxP3- |
|---|---|---|---|
| 35578106 | squamous cell | 232.9 | 622.43 |
| 35578840 | squamous cell | 146.1 | 710.5 |
| 35591861 | squamous cell | 139.55 | 282.99 |
| 35580646 | lung adeno | 85.16 | 412.89 |
| 35593228 | lung adeno | 225.1 | 1104.5 |
| 35524205 | lung adeno | 197.6 | 752.9 |
| 00512447 | lung adeno | 219.2 | 762.56 |

Expression of IL7R only on T cells (no expression on B cells/Nk cells/monocytes)

IL7Ra CAR : Donor H3
differentiation after spinoculation

IL7Ra CAR : Donor H4 differentiation after spinoculation

CHIMERIC ANTIGEN RECEPTORS TARGETING CD127 AND USE THEREOF

CROSS-REFERENCE TO RELATED APPLICATIONS

The present application is a continuation application of International Patent Application PCT/US2021/029372, filed Apr. 27, 2021, which claims priority to United States Provisional Patent Application No. 63/015,923 filed Apr. 27, 2020, the content of each of which is incorporated by reference in its entirety herein, and to each of which priority is claimed.

SEQUENCE LISTING

The present application contains a Sequence Listing which has been submitted in XML format and is hereby incorporated by reference in its entirety. Said XML copy, created on Oct. 26, 2022, is named 072734.1408.xml and is 56,712 bytes in size.

1. TECHNICAL FIELD

The presently disclosed subject matter provides methods for treating neoplasia (e.g., cancer) using cells comprising an antigen-recognizing receptor (e.g., a chimeric antigen receptor (CAR)) that specifically targets CD127.

2. BACKGROUND

Cell-based immunotherapy has curative potential for the treatment of cancer. T-cells and other immune cells can be modified to target tumor antigens through the introduction of genetic material coding for artificial or synthetic receptors for antigen, termed Chimeric Antigen Receptors (CARs), specific to selected antigens. Targeted T-cell therapy using CARs has shown recent clinical success in treating hematologic malignancies.

T-cell acute lymphoblastic leukemia (T-ALL) is an aggressive blood cancer, accounting for 10-15% of pediatric and 20-25% of adult ALL cases. More than 50% of adult and up to 30% of pediatric patients with T-ALL relapse. Current treatment options for T-ALL often result in suboptimal therapeutic efficacy, and the outcomes for patients who relapsed remain extremely poor. Significant progress has been made for the treatment of B-cell ALL with the recent approval of CD19- and CD22-targeted immunotherapy, including CD19 CAR; however, no drug has been approved by FDA since 2005 for treating T-ALL. Thus, there is unmet need for the development of an effective treatment for patients with relapsed and/or aggressive T-ALL.

3. SUMMARY OF THE INVENTION

The presently disclosed subject matter provides uses of cells comprising CD127-targeted antigen-recolonizing receptors (e.g., chimeric antigen receptors (CARs)) for treatments, e.g., for treating neoplasia.

The inventors developed IL-7R targeted CAR T cells and established their antitumor efficacy against cancer cells with IL-7R expression. The present disclosure is at least based on the surprising and unexpected discovery that cells (e.g., T cells) comprising a low-binding CD127-specific CAR (e.g., binds to human CD127 with an $ED_{50}$ of about 3300 ng/ml) showed higher cytotoxicity and proliferative capacity than cells (e.g., T cells) comprising a high-binding CD127-specific CAR (e.g., binds to human CD127 with an $ED_{50}$ of about 500 ng/ml).

It was discovered that transduction of IL-7R CAR T cells did not result in complete fratricide, and IL-7R CAR T-cell manufacturing and expansion was highly feasible. In fact, the bystander cytotoxicity on a proportion of normal T cells with high IL-7R expression imparted a beneficial effect for IL-7R CAR T cells due to repeated antigen stimulation and partial endogenous lymphodepletion that in turn promoted CAR T-cell expansion and persistence. Thus, the presently disclosed subject matter can be rapidly translated and fulfill an unmet clinical need to therapy-resistant CD127-positive tumors (e.g., T-ALL).

The presently disclosed subject matter provides methods for reducing tumor burden in a subject having a hematological tumor, treating and/or preventing a hematological tumor in a subject, and/or increasing or lengthening survival of a subject having a hematological tumor. In certain embodiments, the method comprises administering to the subject: a) an effective amount of cells comprising an antigen-recognizing receptor, b) a pharmaceutical composition comprising an effective amount of cells comprising an antigen-recognizing receptor; or c) a nucleic acid composition comprising a polynucleotide encoding an antigen-recognizing receptor.

In certain embodiments, the antigen-recognizing receptor comprises an extracellular antigen-binding domain, a transmembrane domain, and an intracellular signaling domain. In certain embodiments, the extracellular antigen-binding domain specifically binds CD127 with a binding affinity ($ED_{50}$) of about 30,000 ng/ml or more. In certain embodiments, the extracellular antigen-binding domain specifically binds to CD127 with a binding affinity ($ED_{50}$) of between about 30,000 ng/ml and 35,000 ng/ml. In certain embodiments, the extracellular antigen-binding domain is a single-chain variable fragment (scFv), a Fab, or a $F(ab)_2$. In certain embodiments, the extracellular antigen-binding domain is an scFv. In certain embodiments, the extracellular antigen-binding domain is a humanized scFv.

In certain embodiments, the extracellular antigen-binding domain comprises: a heavy chain variable region CDR1 comprising the amino acid sequence set forth in SEQ ID NO: 6; a heavy chain variable region CDR2 comprising the amino acid sequence set forth in SEQ ID NO: 7; and a heavy chain variable region CDR3 comprising the amino acid sequence set forth in SEQ ID NO: 8. In certain embodiments, the extracellular antigen-binding domain comprises: a light chain variable region CDR1 comprising the amino acid sequence set forth in SEQ ID NO: 9; a light chain variable region CDR2 comprising the amino acid sequence set forth in SEQ ID NO: 10; and a light chain variable region CDR3 comprising the amino acid sequence set forth in SEQ ID NO: 11.

In certain embodiments, the extracellular antigen-binding domain comprises a heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous or identical to the amino acid sequence set forth in SEQ ID NO: 12. In certain embodiments, the extracellular antigen-binding domain comprises a heavy chain variable region comprising the amino acid sequence set forth in SEQ ID NO: 12.

In certain embodiments, the extracellular antigen-binding domain comprises a light chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous or identical to the amino acid sequence set forth in SEQ ID NO: 13. In certain embodiments, the extracellular antigen-binding domain comprises a light chain variable region comprising the amino acid sequence set forth in SEQ ID NO: 13.

In certain embodiments, the extracellular antigen-binding domain comprises: (a) a heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous or identical to the amino acid sequence set forth in SEQ ID NO: 12; and (b) a light chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% homologous or identical to the amino acid sequence set forth in SEQ ID NO: 13.

In certain embodiments, the extracellular antigen-binding domain comprises: a heavy chain variable region comprising the amino acid sequence set forth in SEQ ID NO: 12; and a light chain variable region comprising the amino acid sequence set forth in SEQ ID NO: 13.

In certain embodiments, the extracellular antigen-binding domain comprises a linker between a heavy chain variable region and a light chain variable region. In certain embodiments, the linker consists of the amino acid sequence set forth in SEQ ID NO: 1, SEQ ID NO: 2, SEQ ID NO: 3, or SEQ ID NO: 4. In certain embodiments, the linker consists of the amino acid sequence set forth in SEQ ID NO: 1.

In certain embodiments, a signal peptide is covalently joined to the 5' terminus of the extracellular antigen-binding domain. In certain embodiments, extracellular antigen-binding domain comprises a heavy chain variable region and a light chain variable region, which are positioned from the N- to the C-terminus: $V_H$-$V_L$. In certain embodiments, the extracellular antigen-binding domain comprises the amino acid sequence set forth in SEQ ID NO: 14.

In certain embodiments, the transmembrane domain comprises a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, a synthetic peptide (not based on a protein associated with the immune response), or a combination thereof. In certain embodiments, the transmembrane domain comprises a CD28 polypeptide.

In certain embodiments, the intracellular signaling domain comprises a CD3ζ polypeptide. In certain embodiments, the intracellular signaling domain further comprises at least one co-stimulatory signaling region. In certain embodiments, the at least one co-stimulatory signaling region comprises a CD28 polypeptide, a 4-1BB polypeptide, an OX40 polypeptide, an ICOS polypeptide, a DAP-10 polypeptide, or a combination thereof. In certain embodiments, the at least one co-stimulatory signaling region comprises a CD28 polypeptide.

In certain embodiments, the antigen-recognizing receptor comprises the amino acid sequence set forth in SEQ ID NO: 27. In certain embodiments, the antigen-recognizing receptor is a chimeric antigen receptor (CAR) or a T-cell Receptor (TCR). In certain embodiments, the antigen-recognizing receptor is a CAR. In certain embodiments, the antigen-recognizing receptor is recombinantly expressed. In certain embodiments, the antigen-recognizing receptor is expressed from a vector. In certain embodiments, the polynucleotide comprises or consists of the nucleotide acid sequence set forth in SEQ ID NO: 28. In certain embodiments, the nucleic acid composition is a vector. In certain embodiments, the vector is a γ-retroviral vector.

In certain embodiments, the cell is transduced with the antigen-recognizing receptor. In certain embodiments, the antigen-recognizing receptor is constitutively expressed on the surface of the cell. In certain embodiments, the cell is an immunoresponsive cells. In certain embodiments, the cell is a cell of the lymphoid lineage or a cell of the myeloid lineage. In certain embodiments, the cell is selected from the group consisting of a T-cell, a Natural Killer (NK) cell, and a stem cell from which lymphoid cells may be differentiated. In certain embodiments, the cell is a T-cell. In certain embodiments, the T-cell is a cytotoxic T lymphocyte (CTL) or a regulatory T-cell. In certain embodiments, the stem cell is a pluripotent stem cell. In certain embodiments, the pluripotent stem cell is an embryoid stem cell or an induced pluripotent stem cell.

In certain embodiments, the pharmaceutical composition that further comprises a pharmaceutically acceptable carrier.

In certain embodiments, the methods described herein reduce the number of tumor cells, reduces tumor size, and/or eradicates the tumor in the subject.

In certain embodiments, the hematological tumor is selected from the group consisting of acute lymphoblastic leukemia (ALL), Hodgkin's lymphoma, non-Hodgkin's lymphoma, and T-cell cutaneous lymphoma. In certain embodiments, the acute lymphoblastic leukemia (ALL) is associated with gain-mutation of the IL7-R/TSLP pathway. In certain embodiments, the acute lymphoblastic leukemia (ALL) is T-cell acute lymphoblastic leukemia (T-ALL) or B-cell acute lymphoblastic leukemia (B-ALL). In certain embodiments, the tumor is T-cell acute lymphoblastic leukemia (T-ALL).

4. BRIEF DESCRIPTION OF THE DRAWINGS

FIGS. 1A-1B depict the constructs of presently disclosed exemplary single-chain variable fragments (scFvs) and CARs comprising extracellular antigen-binding domains that comprise such scFvs. FIG. 1A shows the constructs of presently disclosed exemplary scFvs, scFv703-Fc (VH-VL) and scFv703-Fc (VL-VH), and their binding affinity to CD127. FIG. 1B shows the constructs of presently disclosed exemplary CD127-targeted CARs, OSE703HL-28z and OSE703LH-28z. OSE703HL-28z comprises an extracellular antigen-binding domain that comprises scFv703-Fc (VH-VL), and OSE703LH-28z comprises an extracellular antigen-binding domain that comprises scFv703-Fc (VL-VH).

Figure 11A:
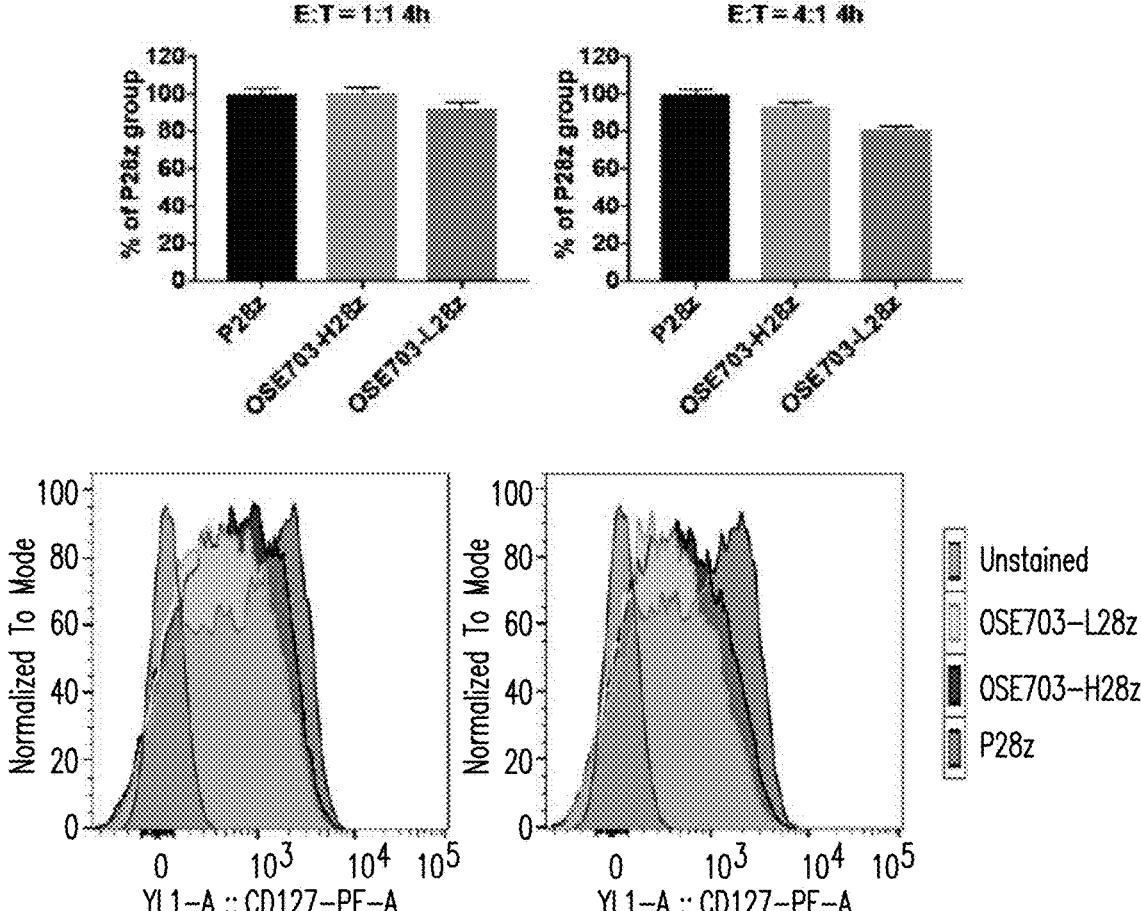
Figure 11B:
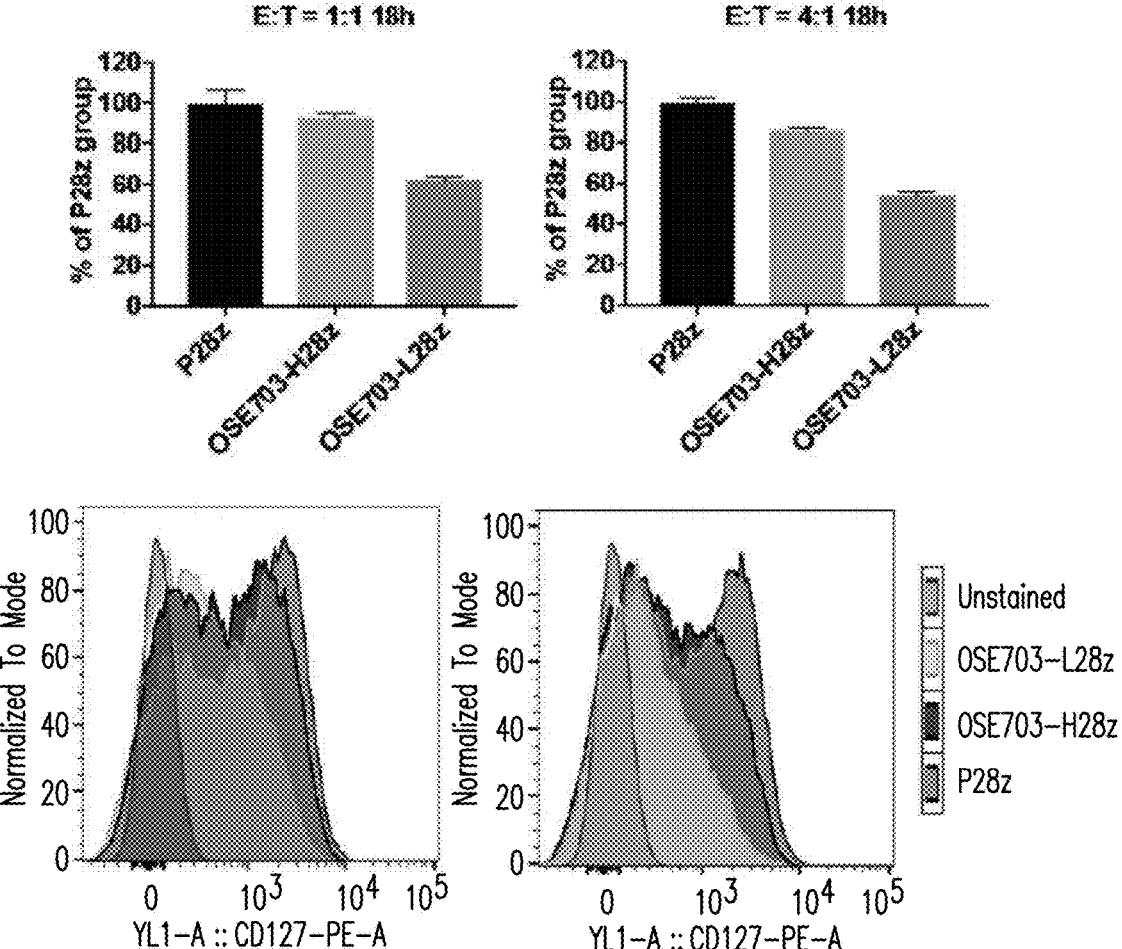
Figure 11C:
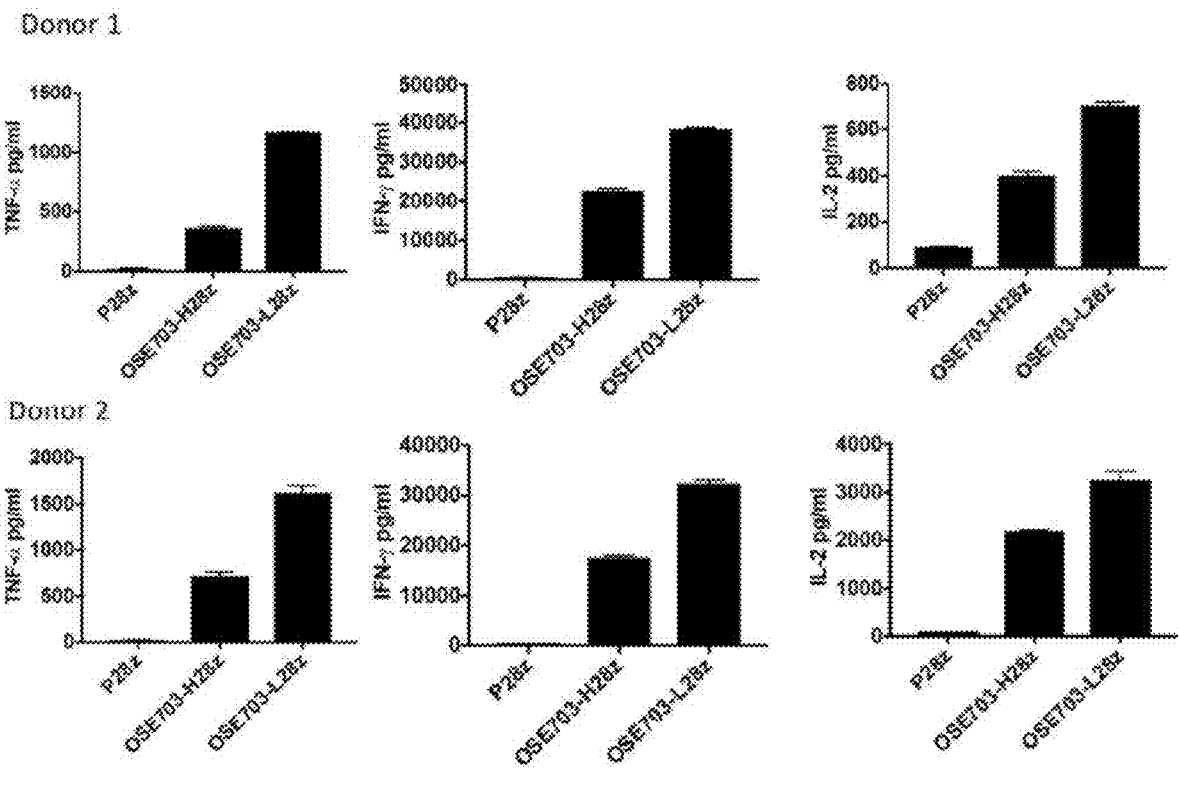

FIGS. 11A-11C show that OSE703LH-28z CAR (OSE703-H28z) and OSE703HL-28z (OSE703-L28z) killed CD127$^{high}$ PBMCs in different efficacy and had different ILR expression profile. OSE703LH-28z CAR (OSE703-H28z) or OSE703HL-28z (OSE703-L28z) T-cells were co-cultured with cell-tracer labeled PBMCs 4 hours (FIG. 11A), or 18 hours (FIG. 11B). In each of FIG. 11A, Top panel shows the quantification of PBMC numbers, lower panel shows the CD127 expression levels in cells. FIG. 11C shows cytokine accumulation following antigen stimulation as assessed by Luminex assay at 18 hours (E:T=3:1).

Figure 12:
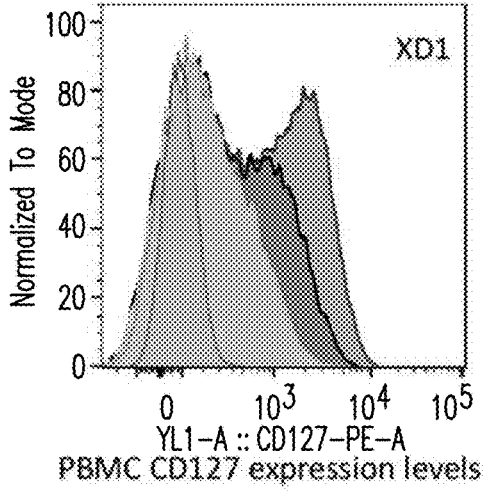
Figure 12:
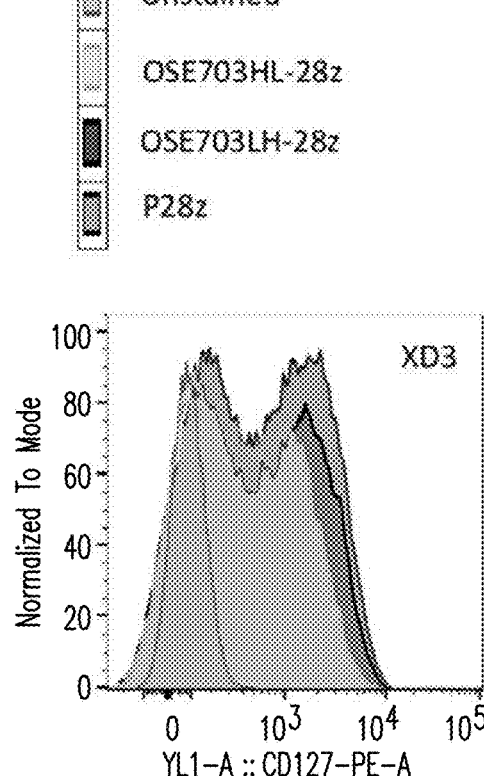

FIG. 12 depicts the FACS analysis of PBMC expressing high levels of CD127 co-cultured with the OSE703LH-28z and OSE703HL-28z CAR T-cells.

Figure 13:
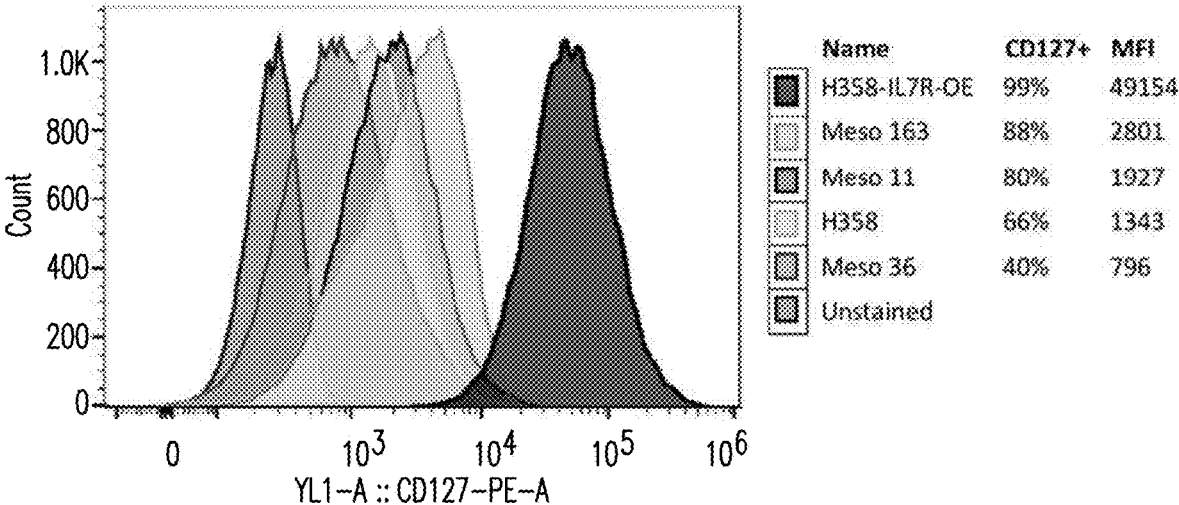

FIG. 13 depicts the expression of CD127 on different solid tumor cell lines, using an anti-CD127 antibody (eBioRDR5) for the staining assay.

Figure 14A:
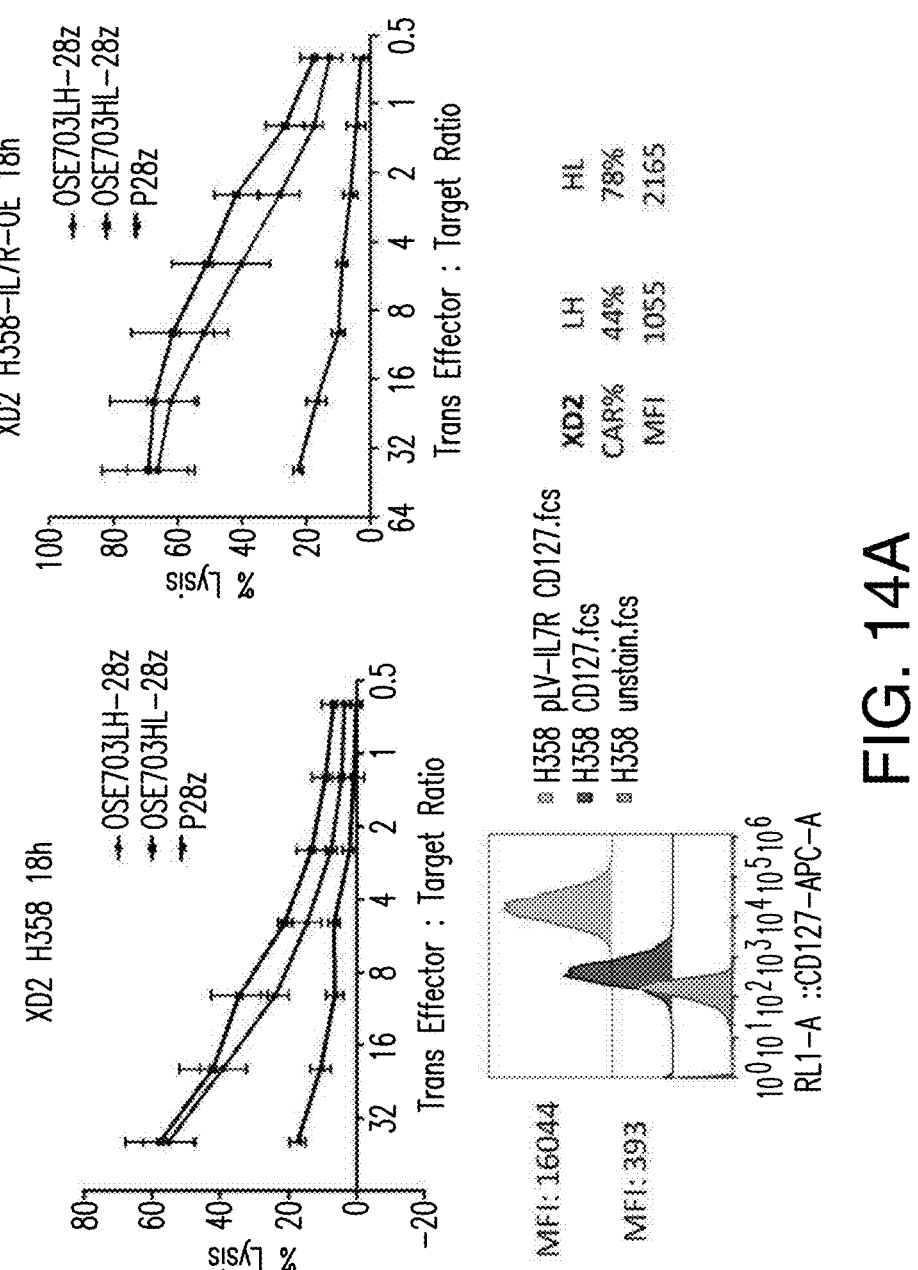
Figure 14B:
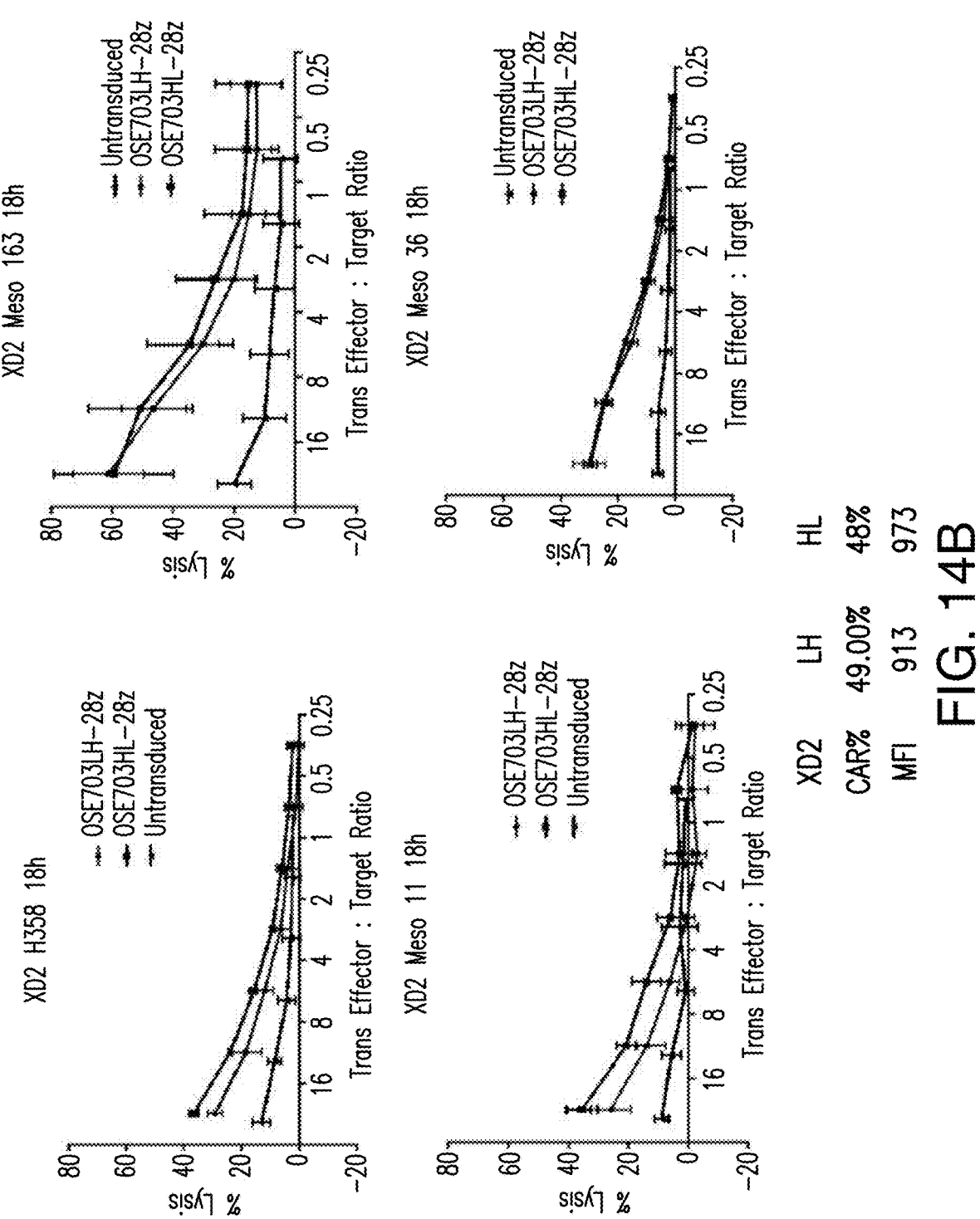
Figure 14C:
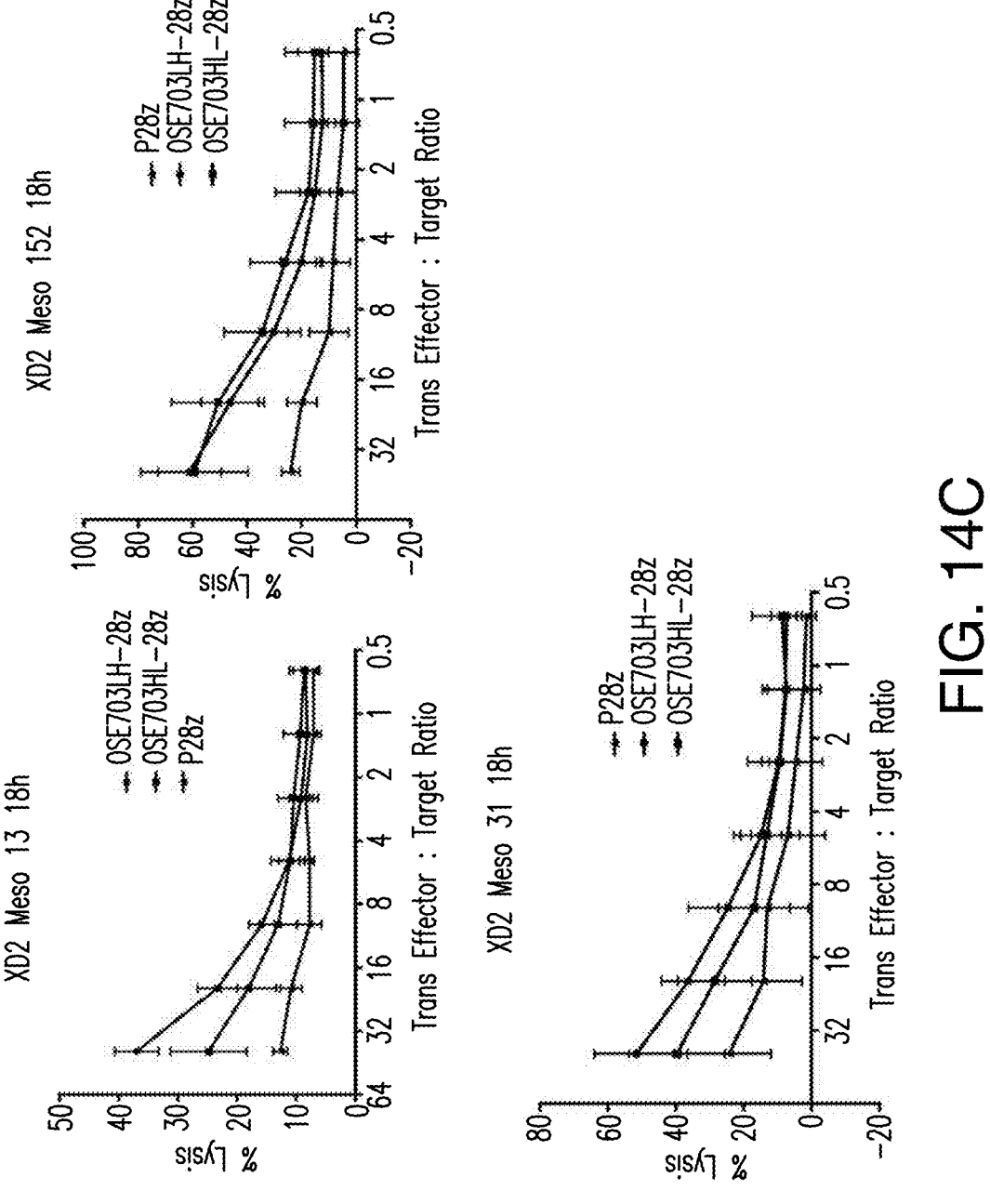
Figure 14D:
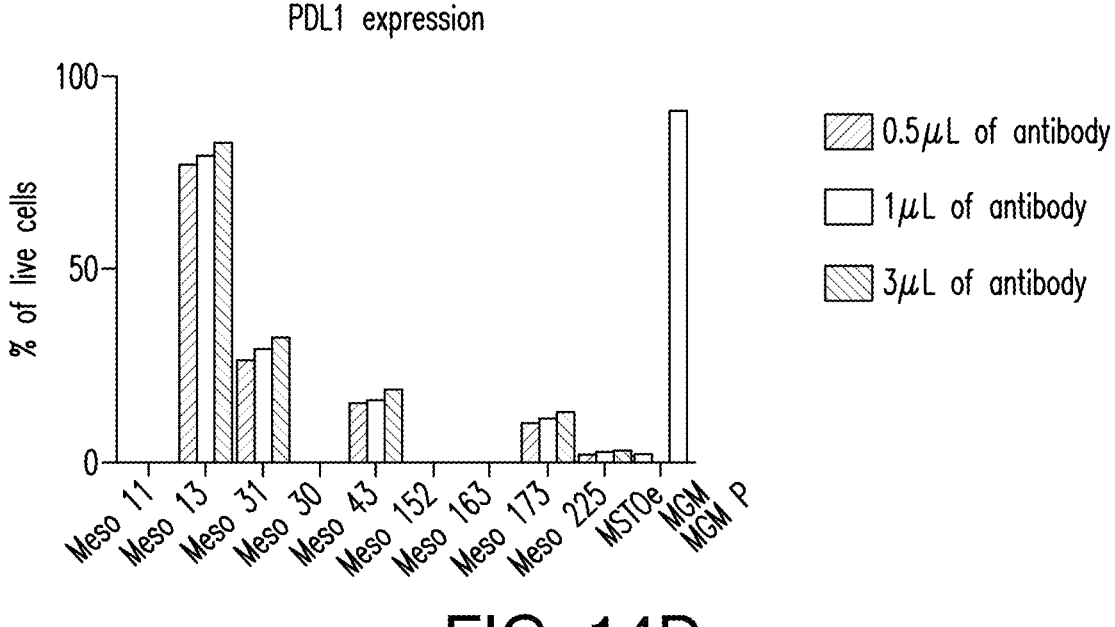

FIGS. 14A-14D show the killing capacity of OSE703HL-28z and OSE703LH-28z CAR T-cells. FIG. 14A shows the capacity of OSE703HL-28z and OSE703LH-28z CAR T-cells from donor XD2 in killing H358 cells, and IL-7R overexpressing H358 cells after 18 hours of incubation. FIG. 14B shows the capacity of OSE703HL-28z and OSE703LH-28z CAR T-cells from donor XD2 in killing H358, Meso 11, Meso 163, and Meso 36 cell lines after 18 hours of incubation. FIG. 14C shows the capacity of OSE703HL-28z and OSE703LH-28z CAR T-cells from donor XD2 in killing Meso 13, Meso 152 and Meso 31 cell lines after 18 hours of incubation. FIG. 14D shows the PDL1 expression on different cell lines.

Figure 15:
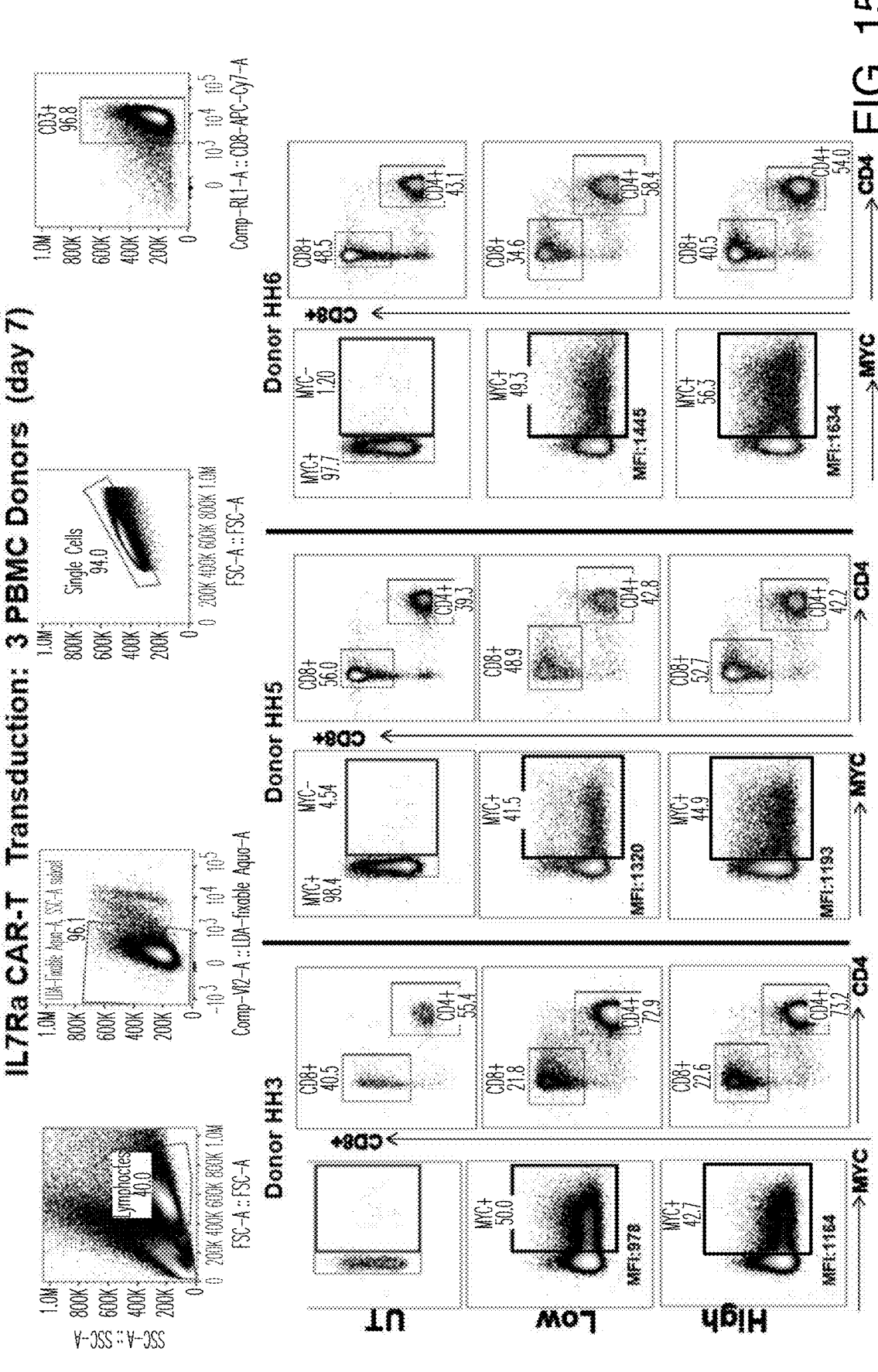

FIG. 15 depicts the representative FACS analysis of another donor T cells transduced with CAR; CAR transduction identified by Myc expression.

Figure 16A:
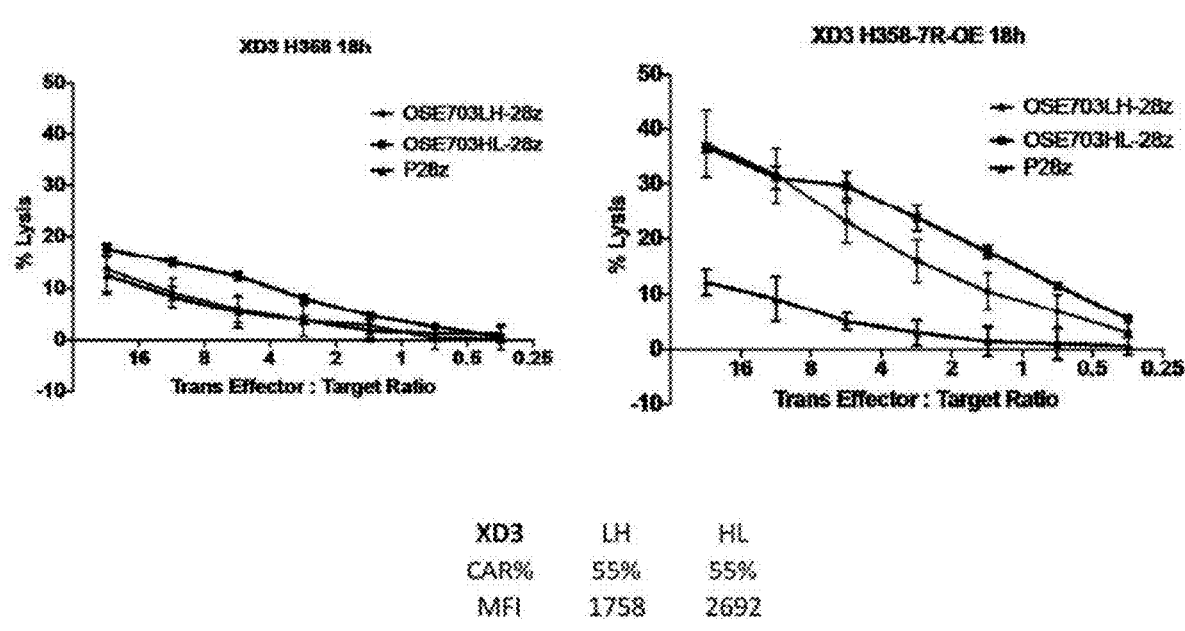
Figure 16B:
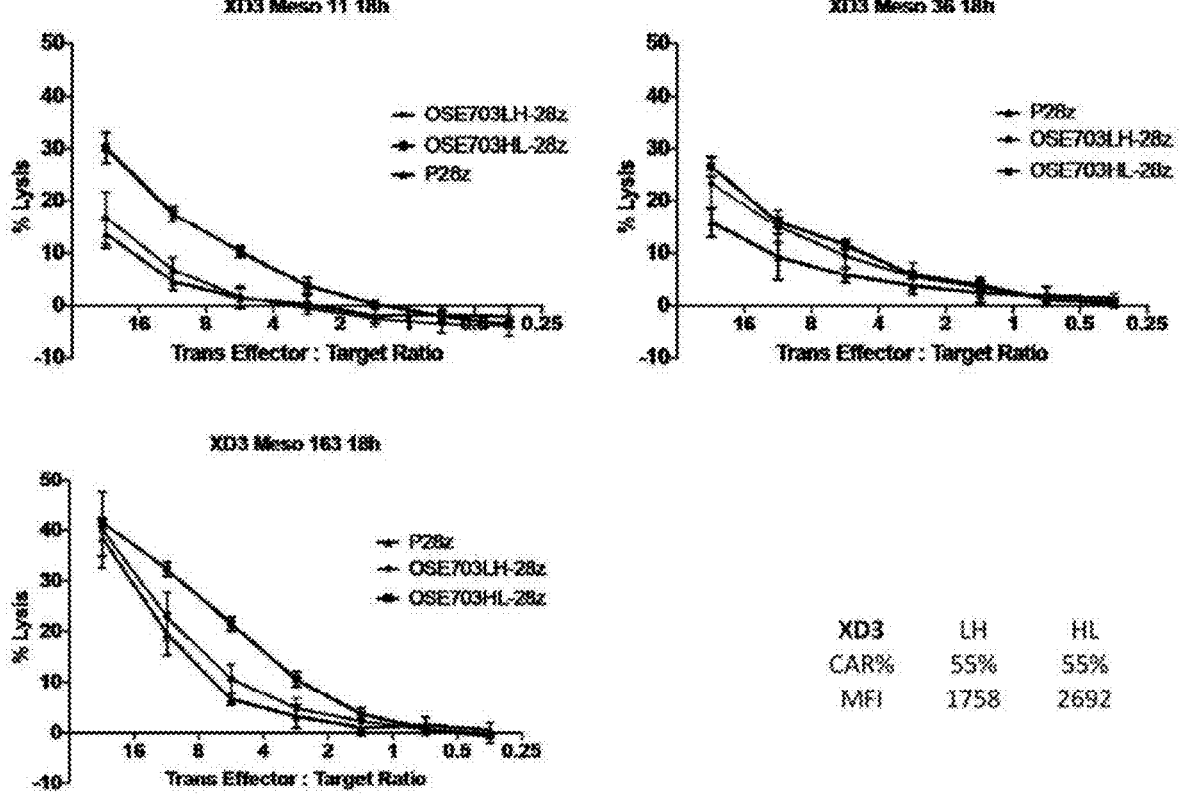

FIGS. 16A and 16B show the killing capacity of OSE703HL-28z and OSE703LH-28z CAR T-cells from donor XD3. FIG. 16A shows the capacity of OSE703HL-28z and OSE703LH-28z CAR T-cells from donor XD3 in killing H358 cells and IL-7R overexpressing H358 cells after 18 hours of incubation. FIG. 16B shows the capacity of OSE703HL-28z and OSE703LH-28z CAR T-cells from donor XD3 in killing Meso 11, Meso 163, and Meso 36 cell lines after 18 hours of incubation.

Figure 17:
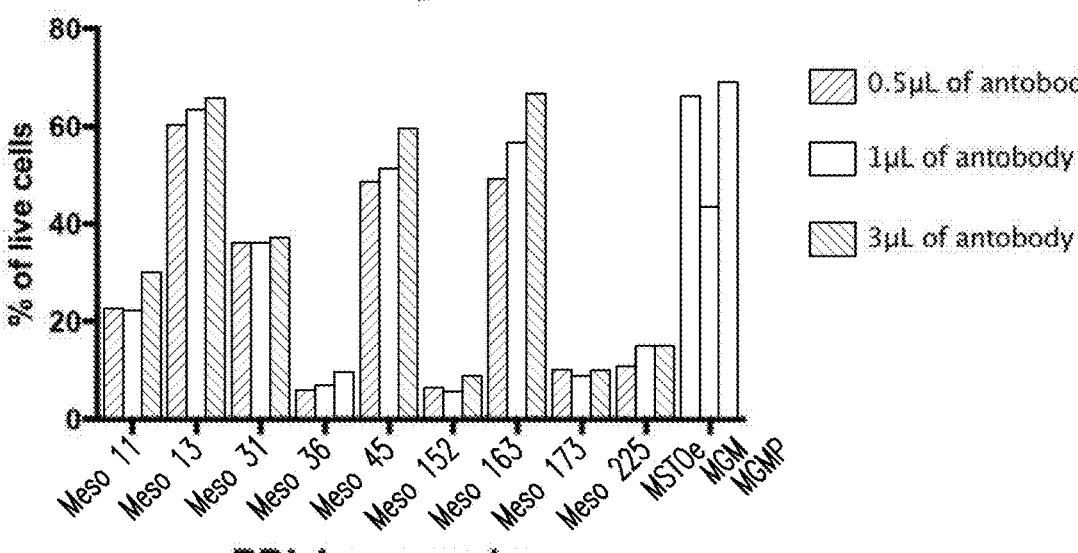
Figure 17:
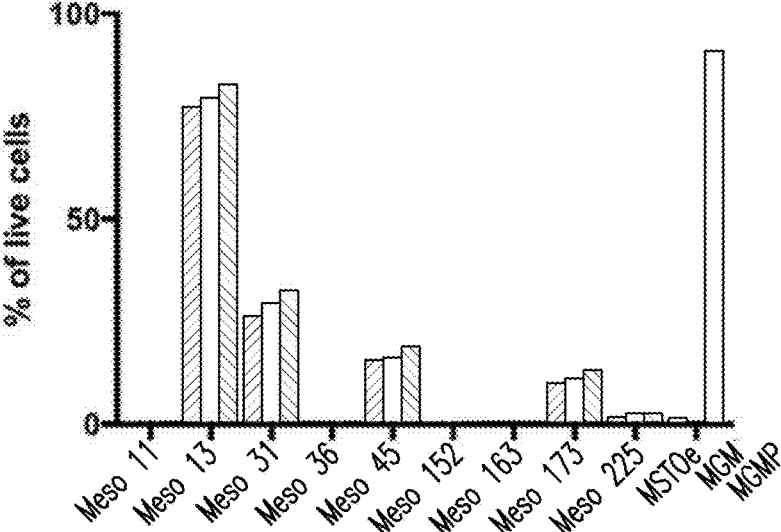

FIG. 17 shows the expression of IL-7R and PDL1 in cell lines derived from mesothelioma patient tumors. MSTOe, MGM and MGMP represent mesothelioma cell line, MSTO cell line with GFP-luciferase and mesothelin overexpression, and MGM cell line with PD-L1 overexpression respectively.

Figure 18:
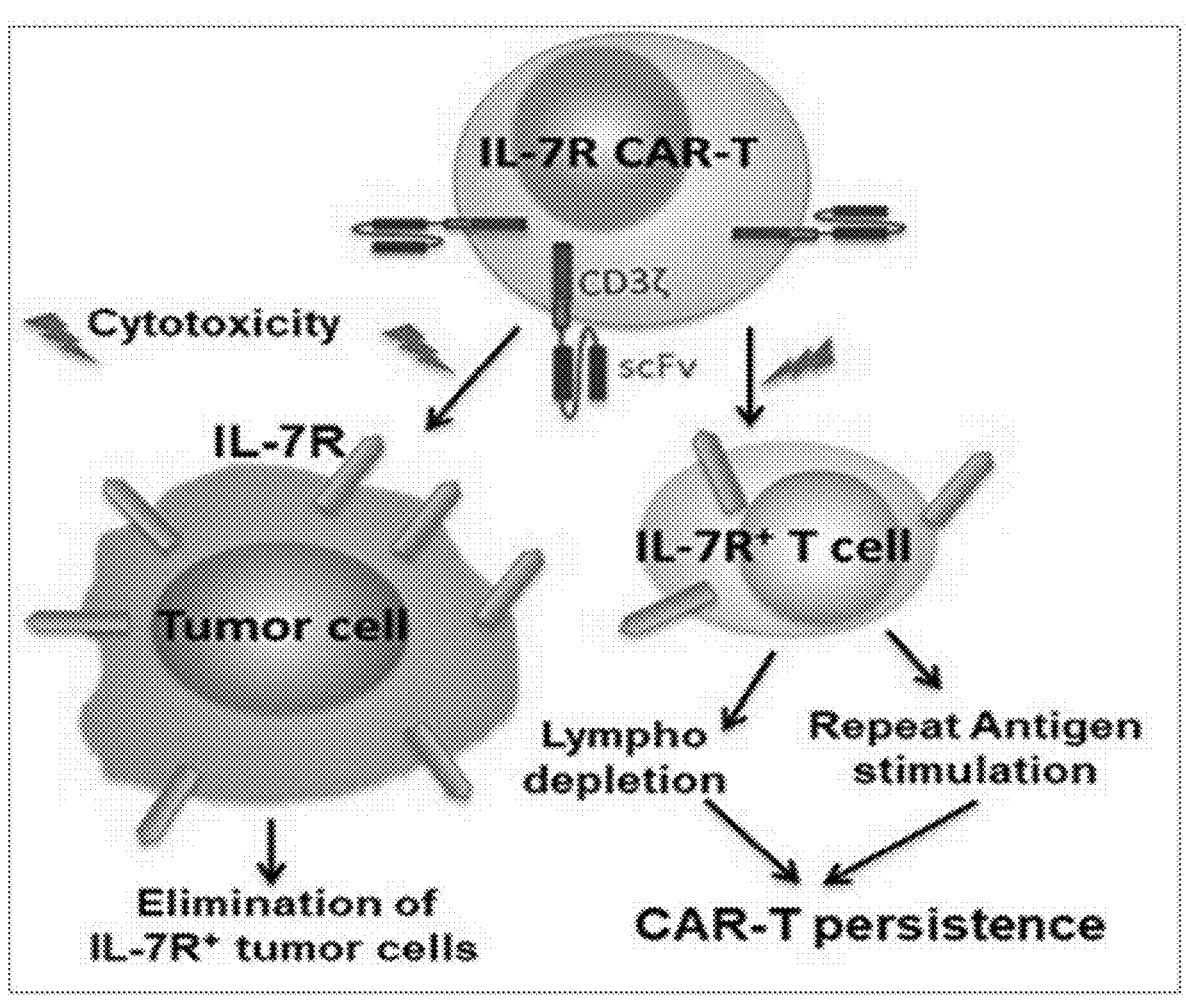

FIG. 18 is a graphic representation of the possible mechanisms of the presently disclosed CD127-targeted CAR T-cells in killing tumor cells, and further augmentation of their efficacy from bystander killing of IL7R overexpressing T cells thereby causing endogenous lymphodepletion that in turn potentiates CAR T cell proliferation and persistence.

Figure 19:
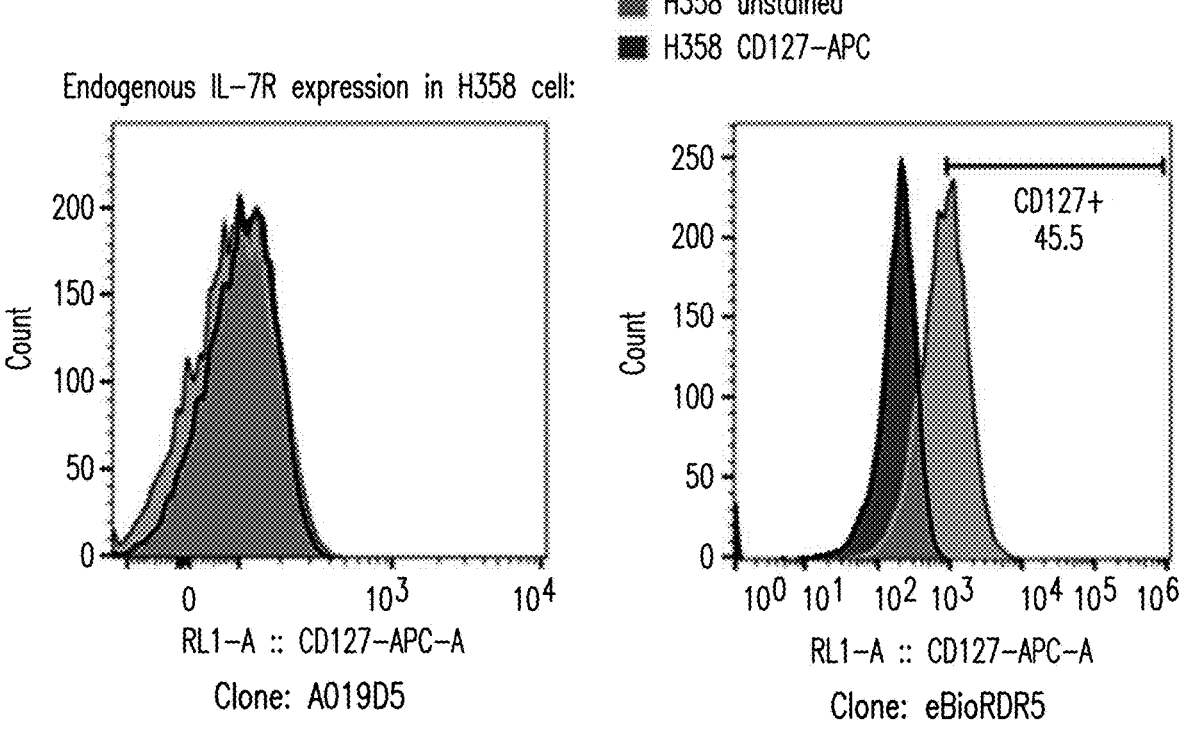

FIG. 19 shows the endogenous expression of IL-7R using clone A019D5 and eBioRDR5 of anti-CD127 antibodies.

Figure 20:
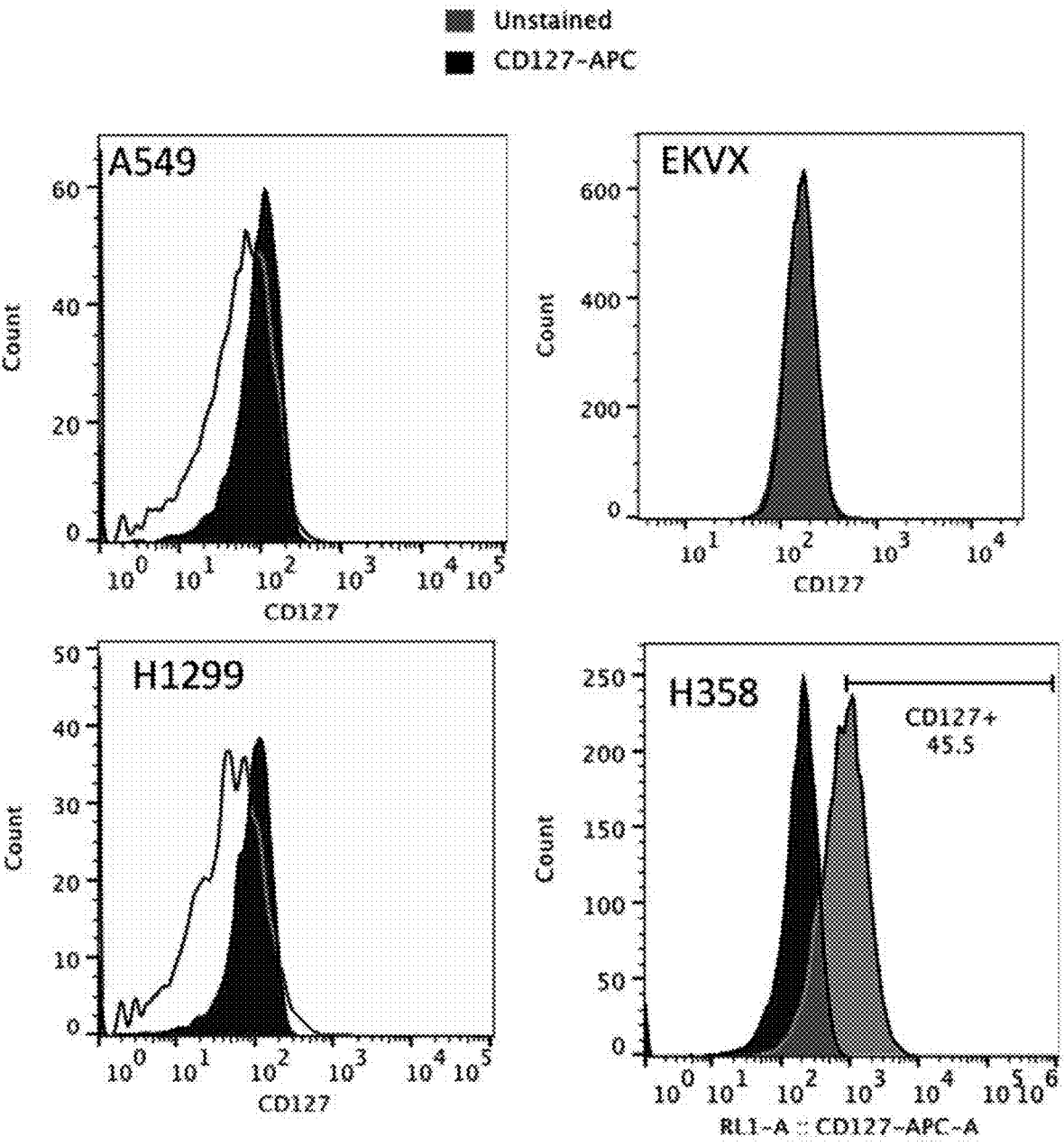

FIG. 20 depicts the expression of IL-7R in tumor cells including A549, EKVX, H1299 and H358.

Figure 21:
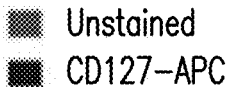
Figure 21:
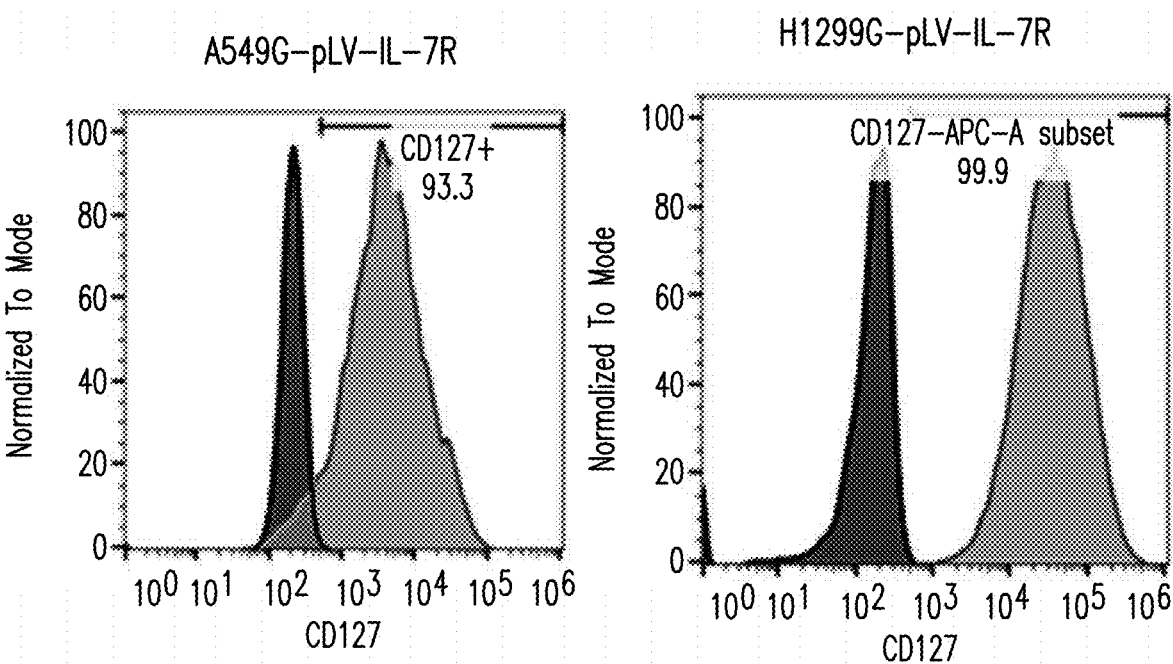
Figure 21:
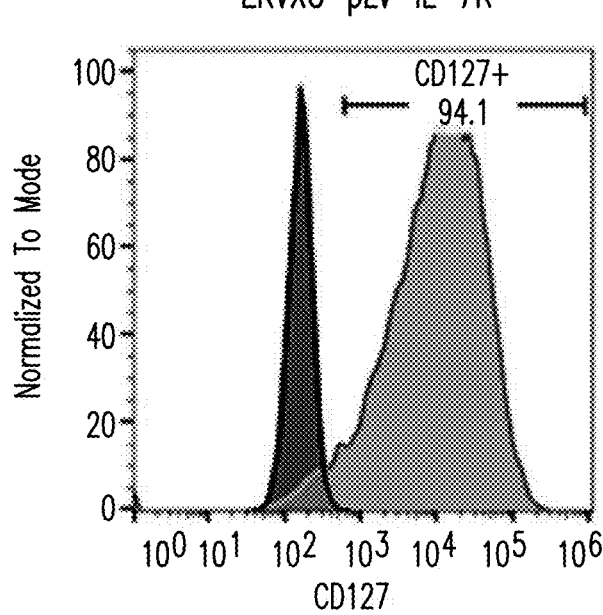

FIG. 21 shows the staining of tumor cell lines A549, H1299, and EKVX overexpressing IL-7R with pLV-IL-IL-7R lentivirus.

Figure 22:
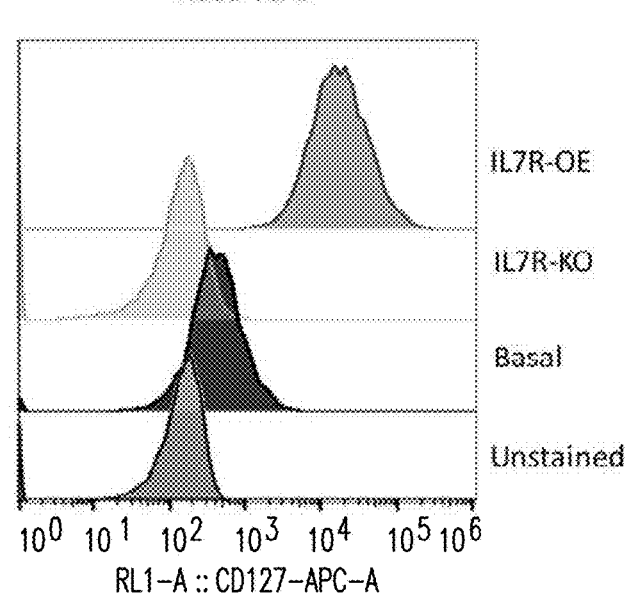

FIG. 22 shows the staining of H358 tumor cell line overexpressing or knockout of IL-7R.

Figure 23:
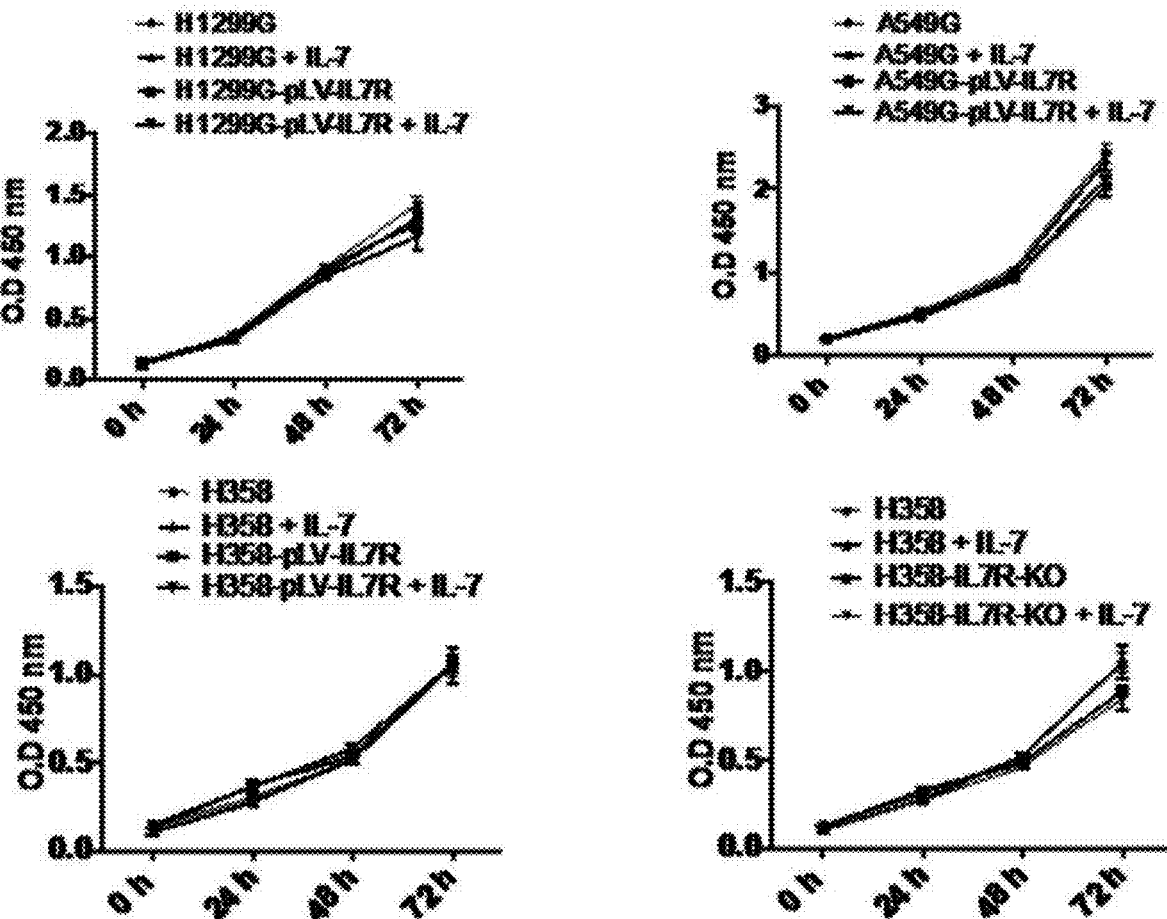

FIG. 23 depicts the effects of IL-7 on the proliferation of cells overexpressing the IL-7R. Cells were seeded $5 \times 10^3$/ well in 96 well plate, with or without 20 ng/ml IL-7 for 3 days.

Figure 24:
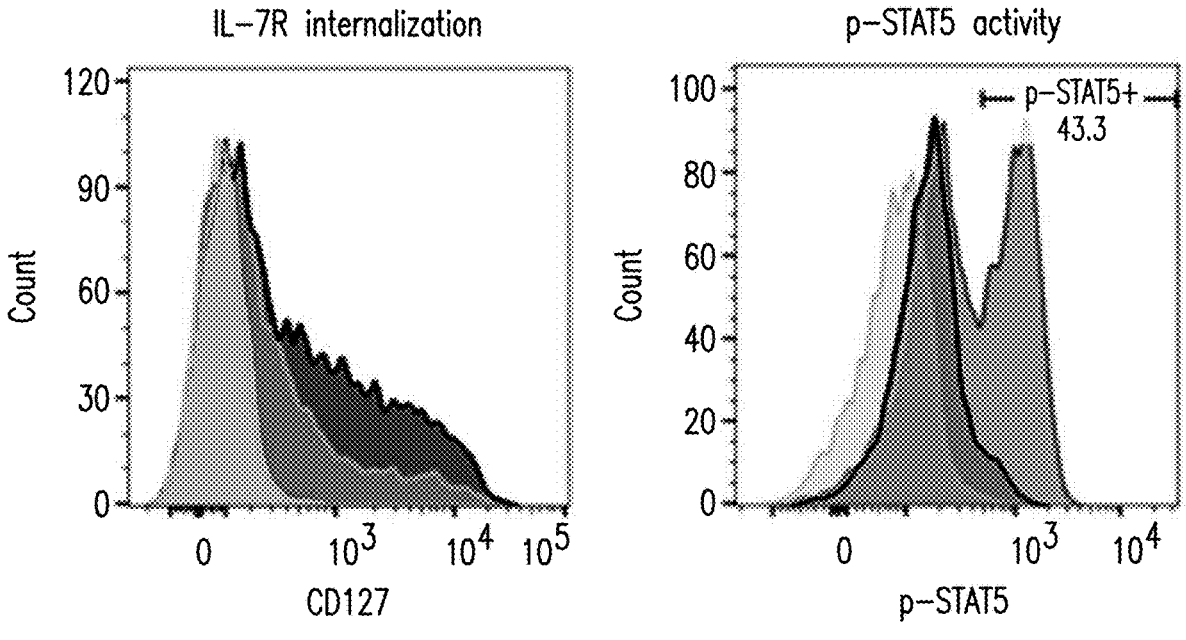

FIG. 24 shows the effects of IL-7 on IL-7R internalization and p-STAT5 activity in CD4$^+$ T-cells.

Figure 25:
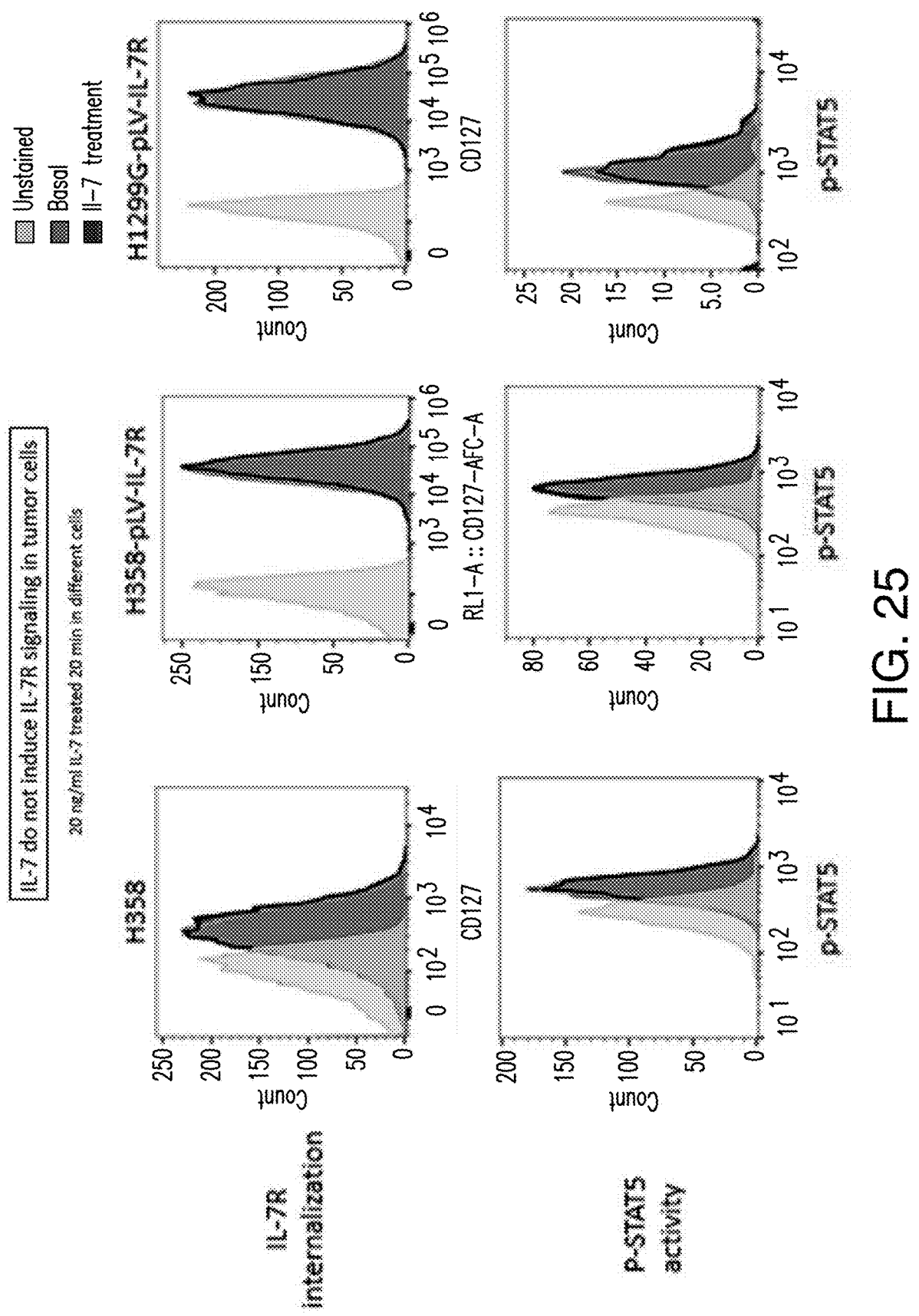

FIG. 25 shows IL-7R internalization and p-STAT5 activity in H358 cells, and cells overexpressing IL-7R (H358-pLV-IL-7R and H1299G-pLV-IL-7R) after treated with 20 ng/ml IL-7 for 20 minutes.

Figure 26A:
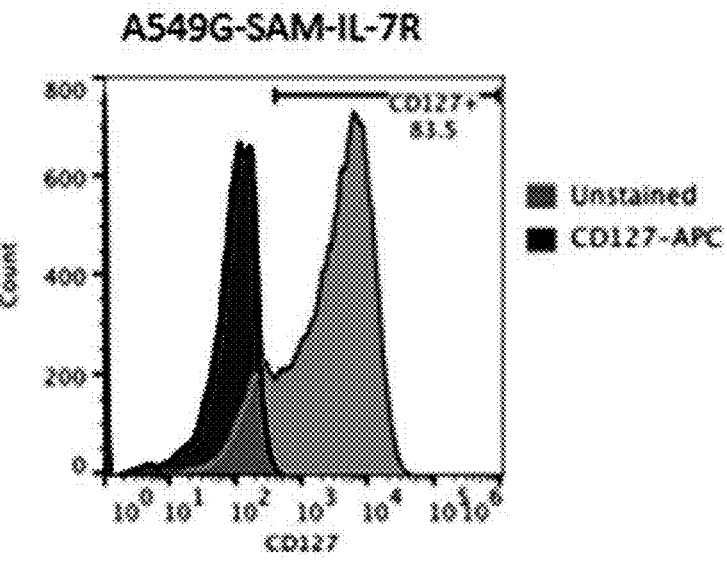
Figures 26B, 26C:
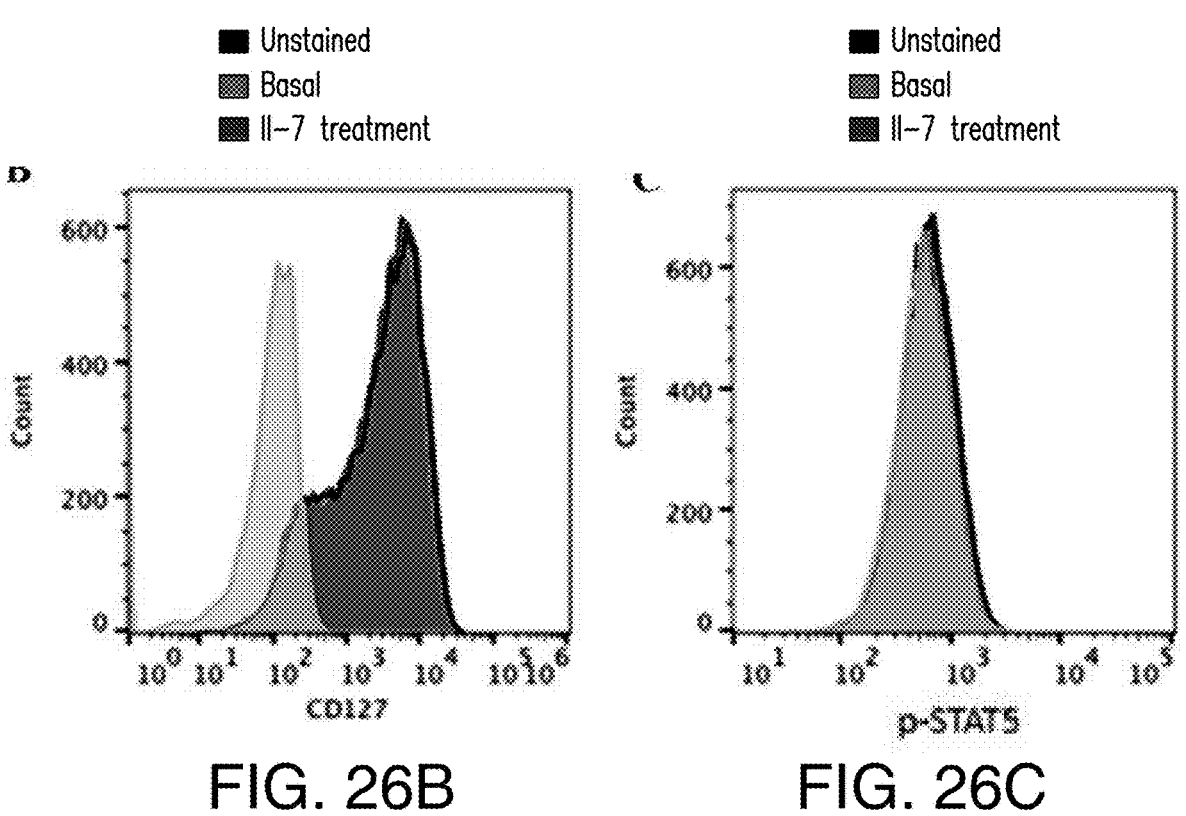

FIGS. 26A-26C show that IL-7 does not induce IL-7R signaling in A549G-SAM-IL-7R cells. FIG. 26A shows that A549G-SAM-IL-7R cells expressed CD127. FIG. 26B-26C shows IL-7R internalization (FIG. 26B) and p-STAT5 activity (FIG. 26C) in A549G-SAM-IL-7R cells treated with 20 ng/ml IL-7 for 20 minutes.

Figure 27:
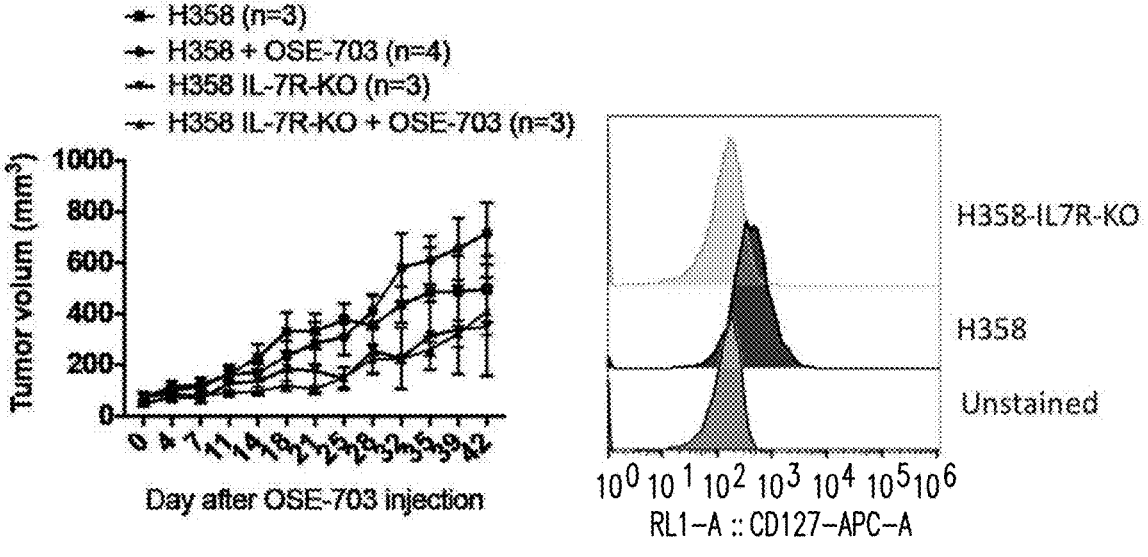

FIG. 27 depicts the tumor volume growth curves in SCID mice that received H358 and H358 IL-7R-KO xenografts, and were treated with OSE-703 anti-CD127 antibody.

Figure 28:
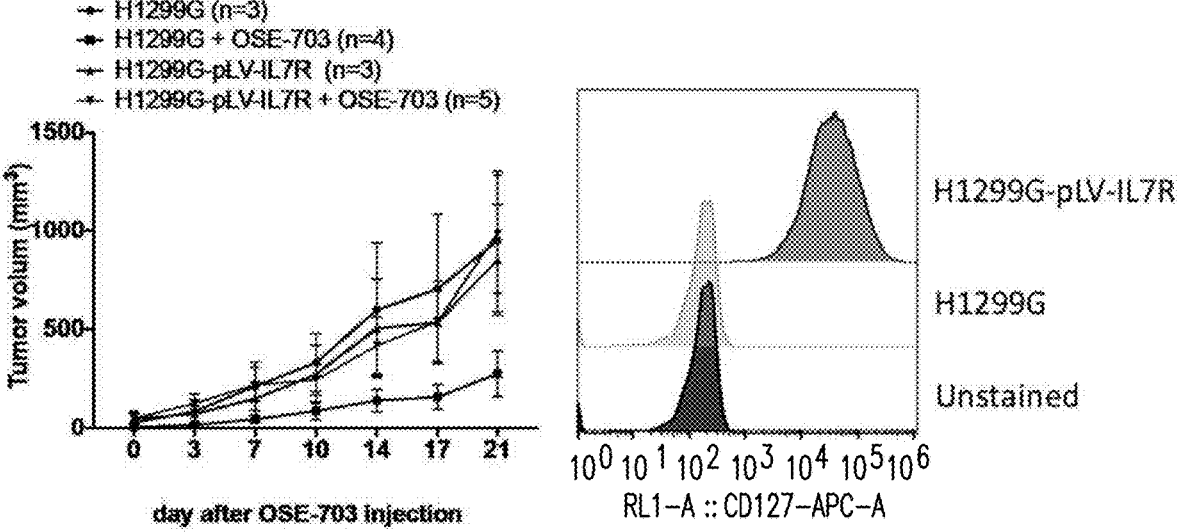

FIG. 28 depicts the tumor volume growth in SCID mice that received H1299G and H1299G-pLV-IL7R xenografts, and were treated with OSE-703 anti-CD127 antibody.

Figures 29A, 29B:
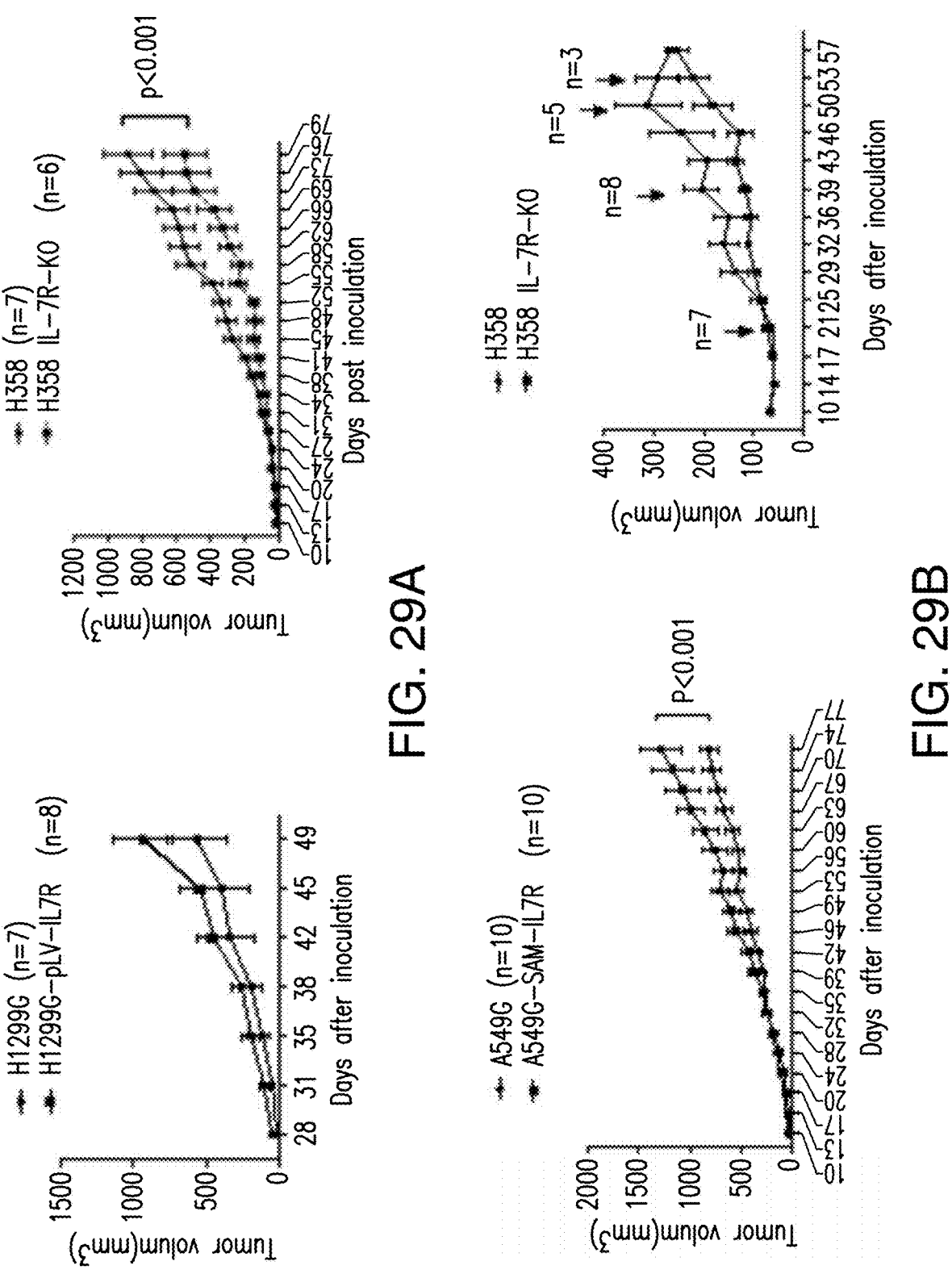

FIGS. 29A-28B depict the tumor growth in mice receiving IL-7R overexpressing or knockout tumor cells. Tumor growth was monitored in SCID mice receiving H1299G-pLV-IL7R or H358 IL-7R-KO cells (FIG. 29A) or nude mice receiving A549G-SAM-IL-7R or H358 IL-7R-KO (FIG. 29B).

Figure 30:
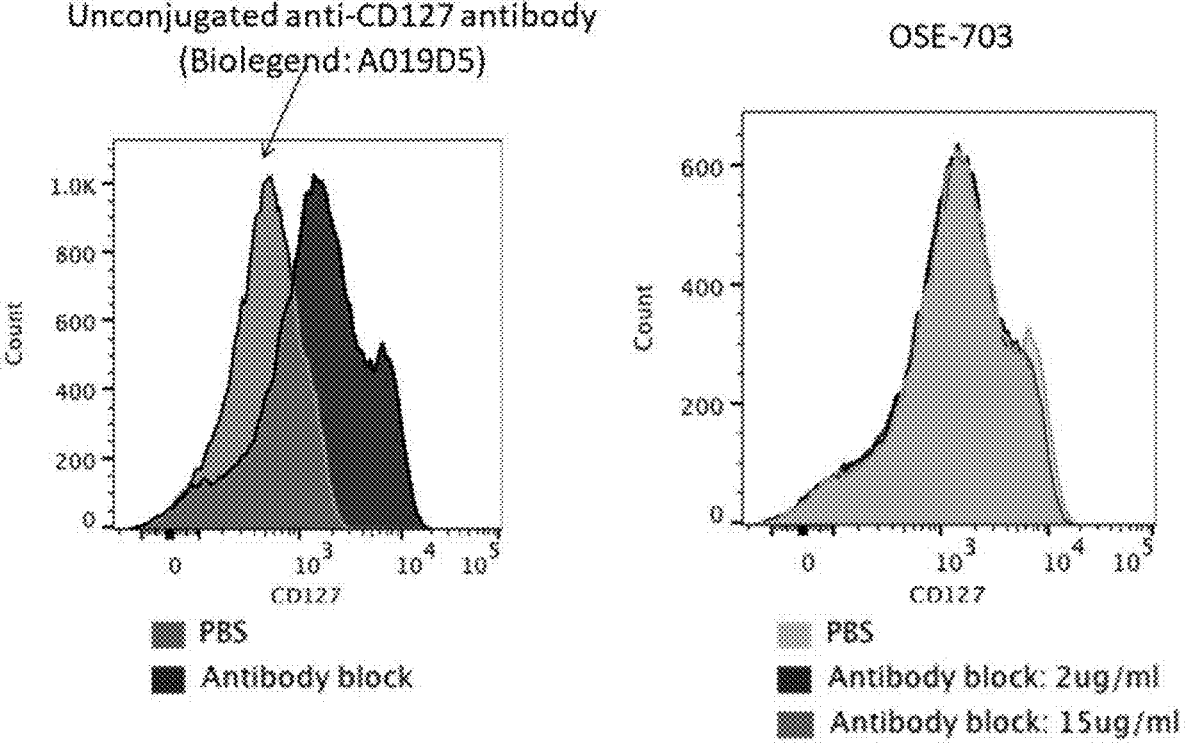

FIG. 30 shows that OSE703 treatment did not block IL-7R staining in CD4$^+$ T-cells. A549G-SAM-IL-7R cells were underwent antibody block for 1 hour, then stained with eBioRDR5.

Figure 31:
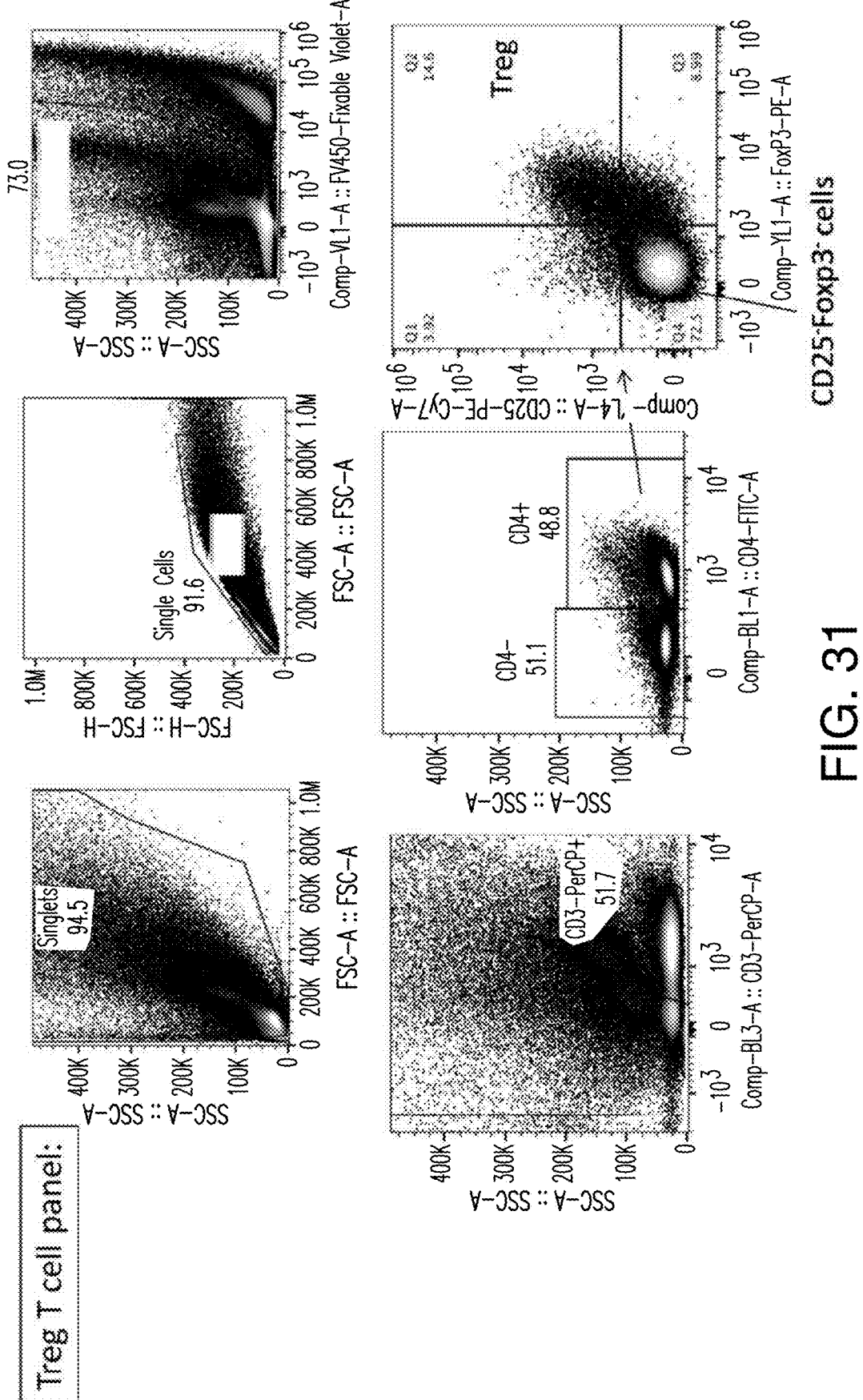

FIG. 31 depicts the FACS gating strategy for Treg T cells.

Figure 32:
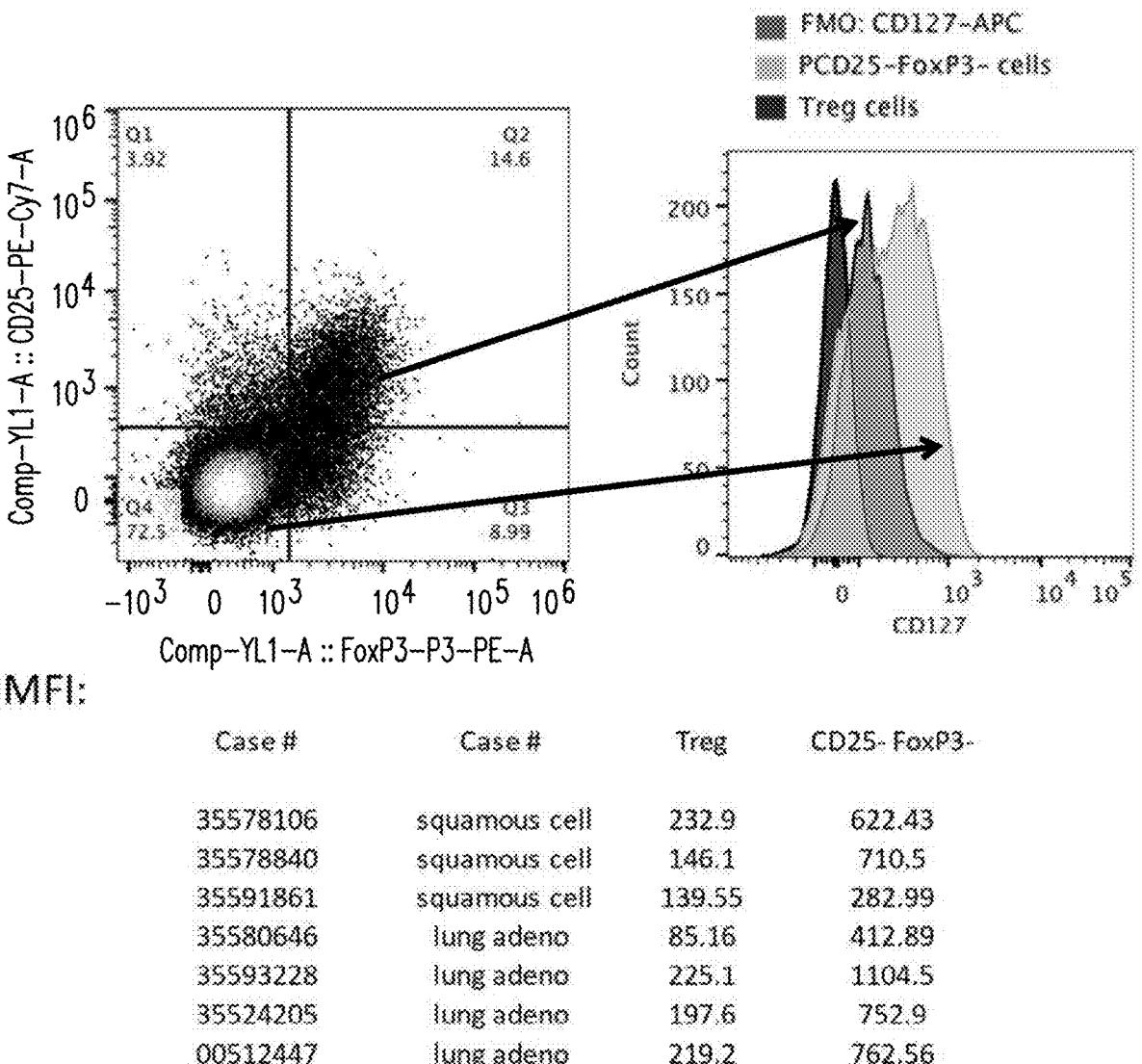

FIG. 32 depicts the FACS analysis showing that Treg cells had lower cell surface IL-7R expression than CD25-Foxp3-T-cells.

Figure 33:
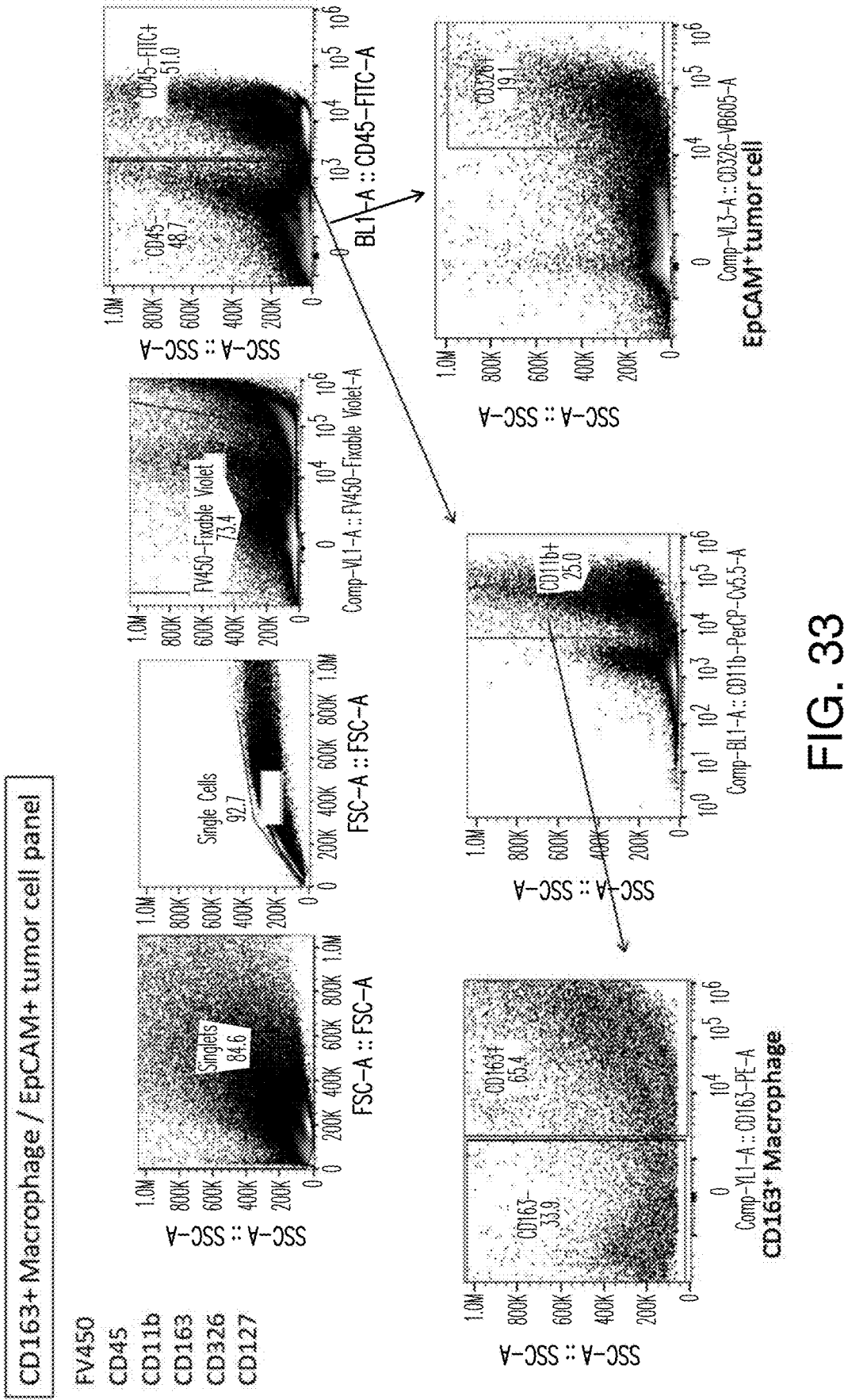

FIG. 33 depicts the FACS gating strategy for CD163+ macrophages and EpCAM+ tumor cells.

Figure 34:
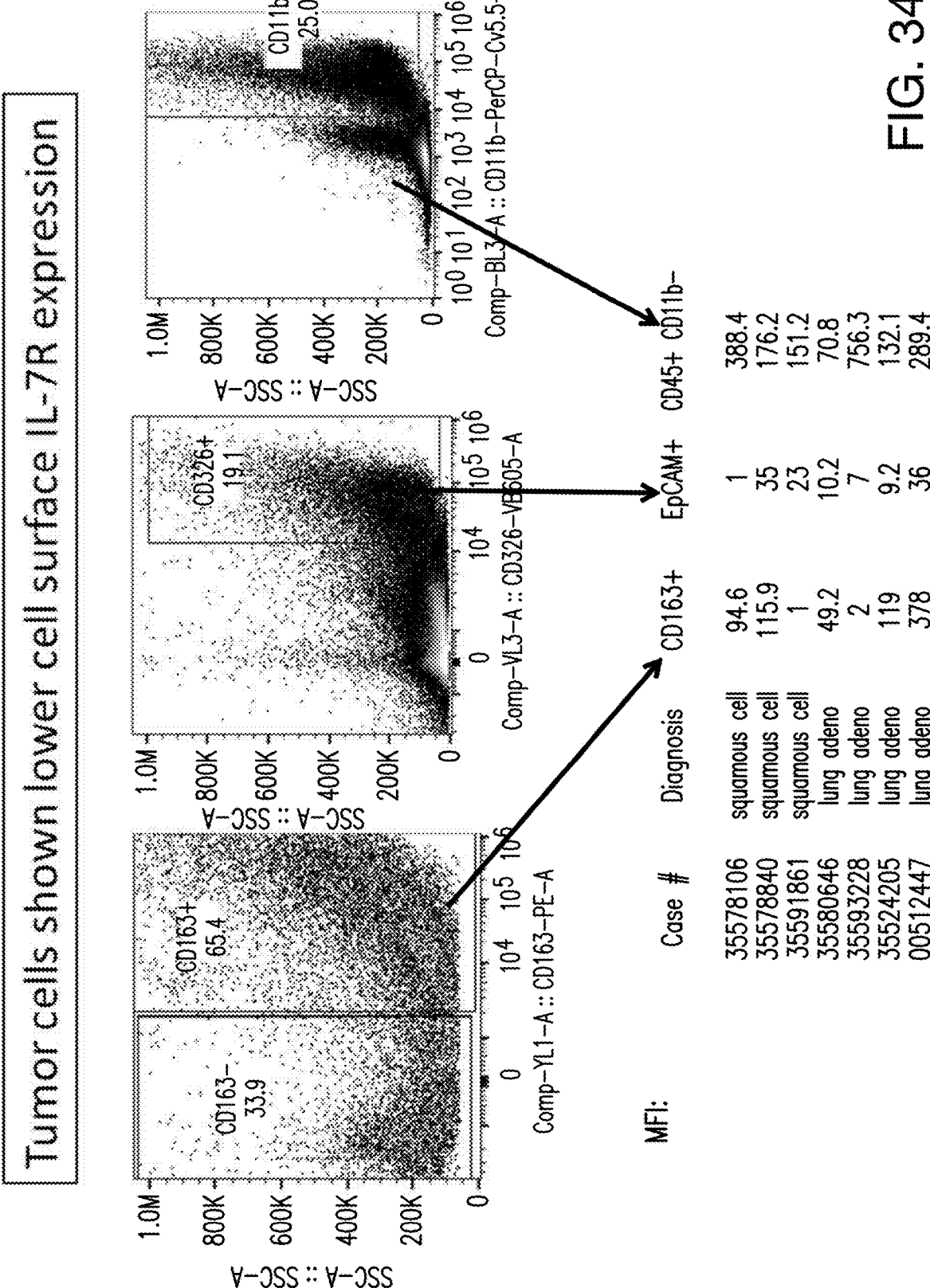

FIG. 34 depicts the FACS analysis showing that tumor cells had lower cell surface IL-7R expression.

Figure 35:
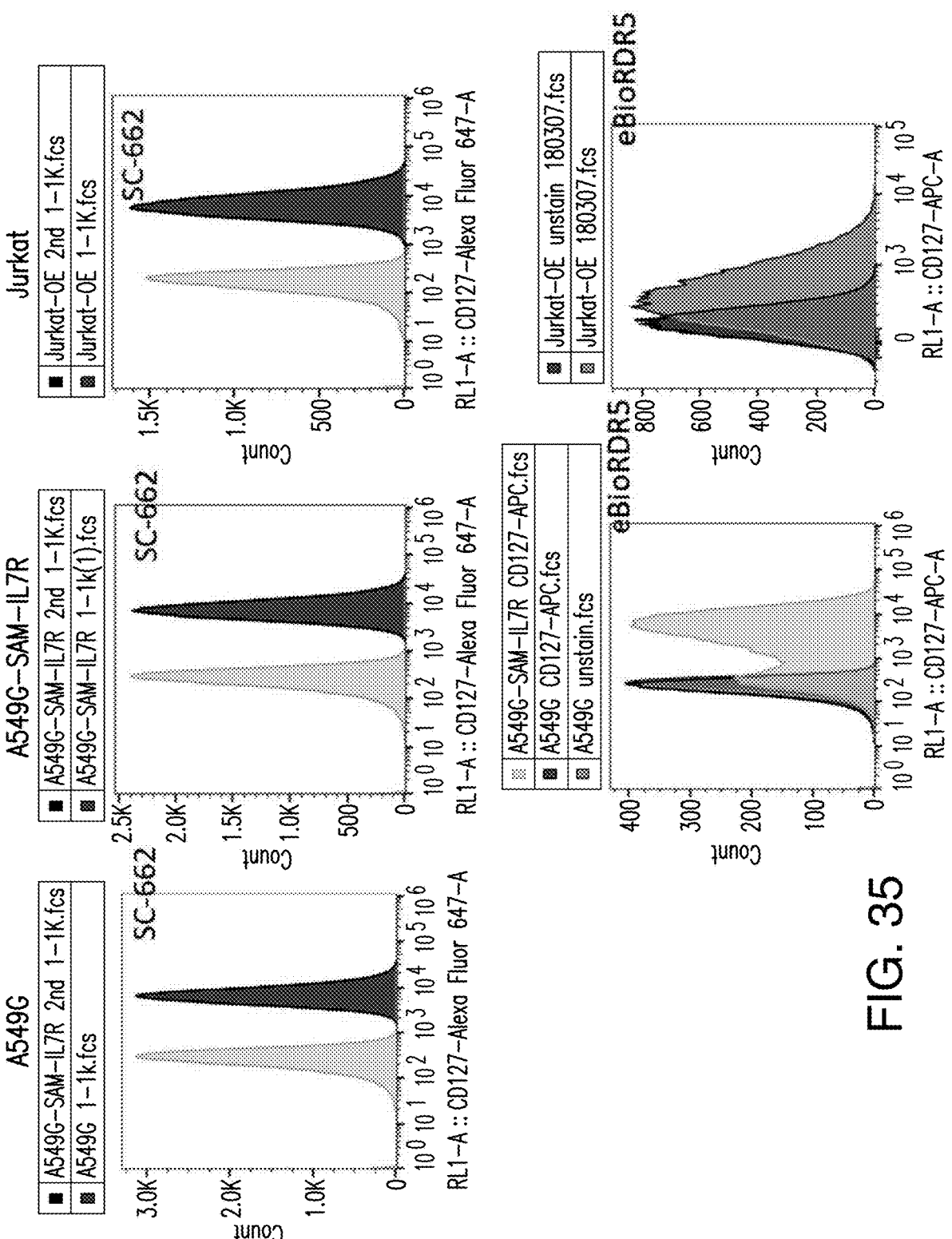

FIG. 35 depicts the IL-7R levels in A549G, A549G-SAM-IL7R and Jurkat cell lines using anti-CD127 antibodies, including eBioRDR5 and sc-662.

Figure 36:
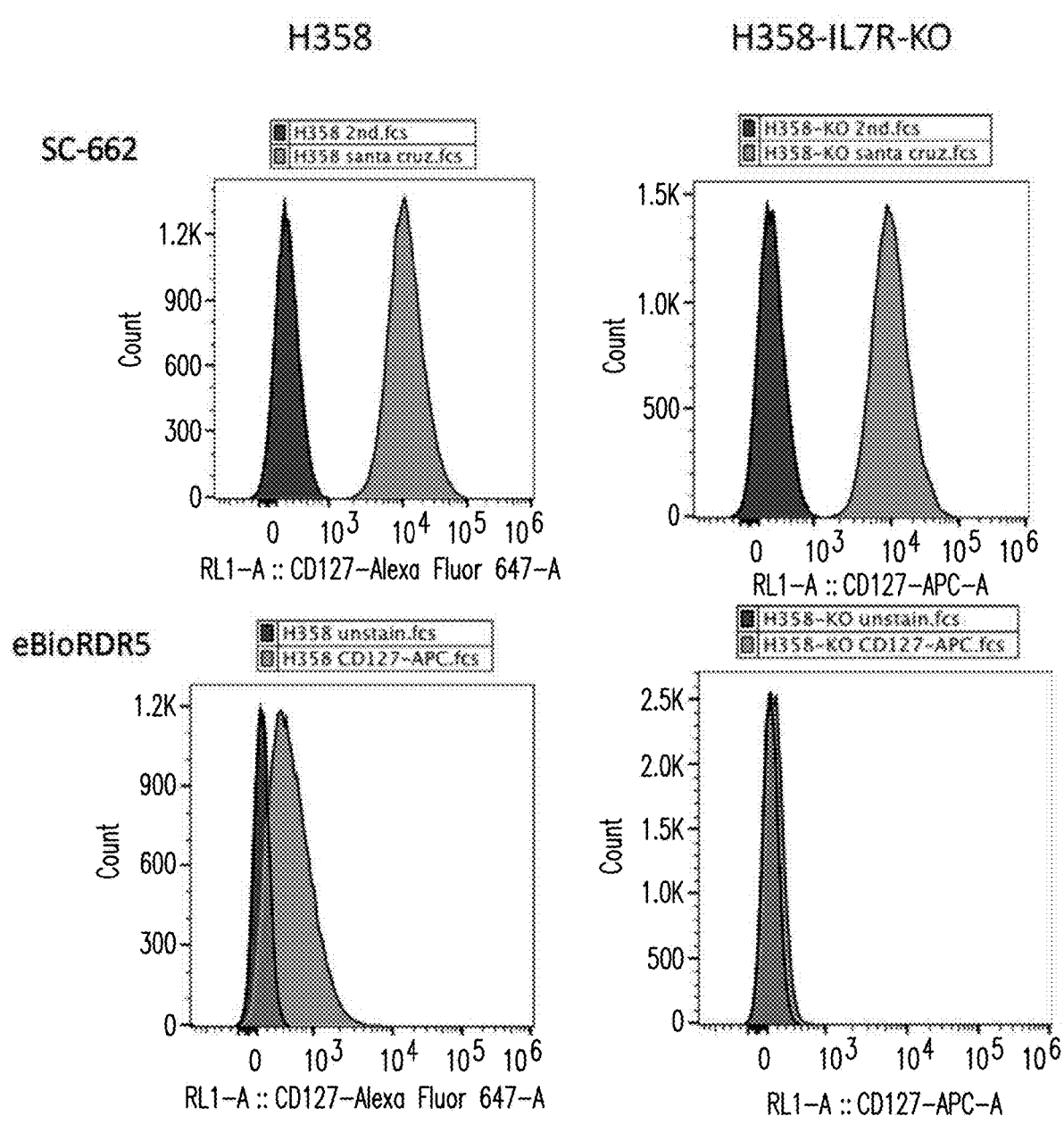

FIG. 36 depicts the IL-7R levels in H358 and H358-IL7-KO cell lines using eBioRDR5 and sc-662 antibodies.

Figure 37:
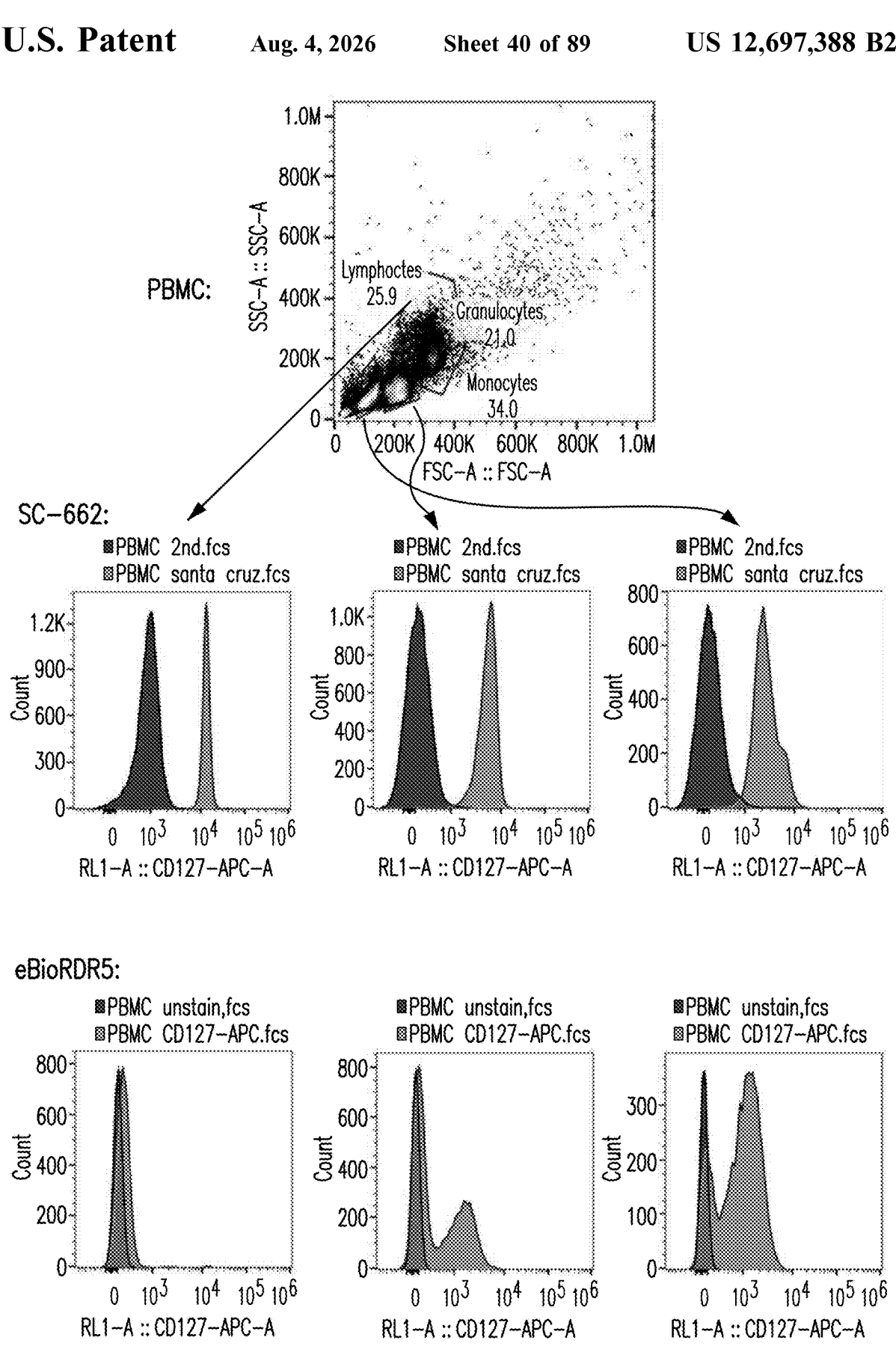

FIG. 37 depicts the FACS analysis showing IL-7R levels in PBMCs using eBioRDR5 and sc-662 antibodies.

Figure 38:
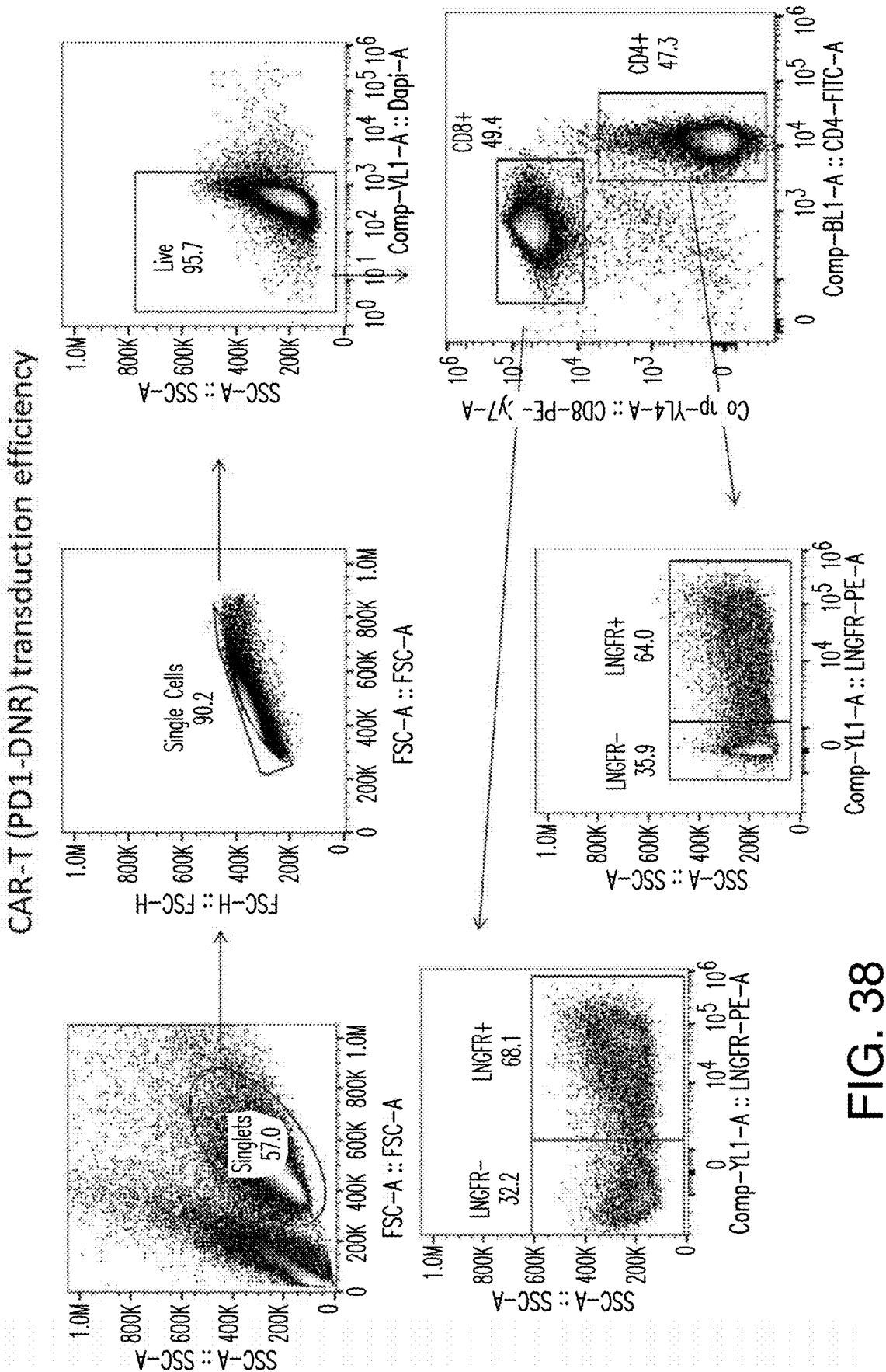

FIG. 38 depicts the FACS analysis of CAR-T (PD1-DNR), illustrating the transduction efficiency.

Figure 39:
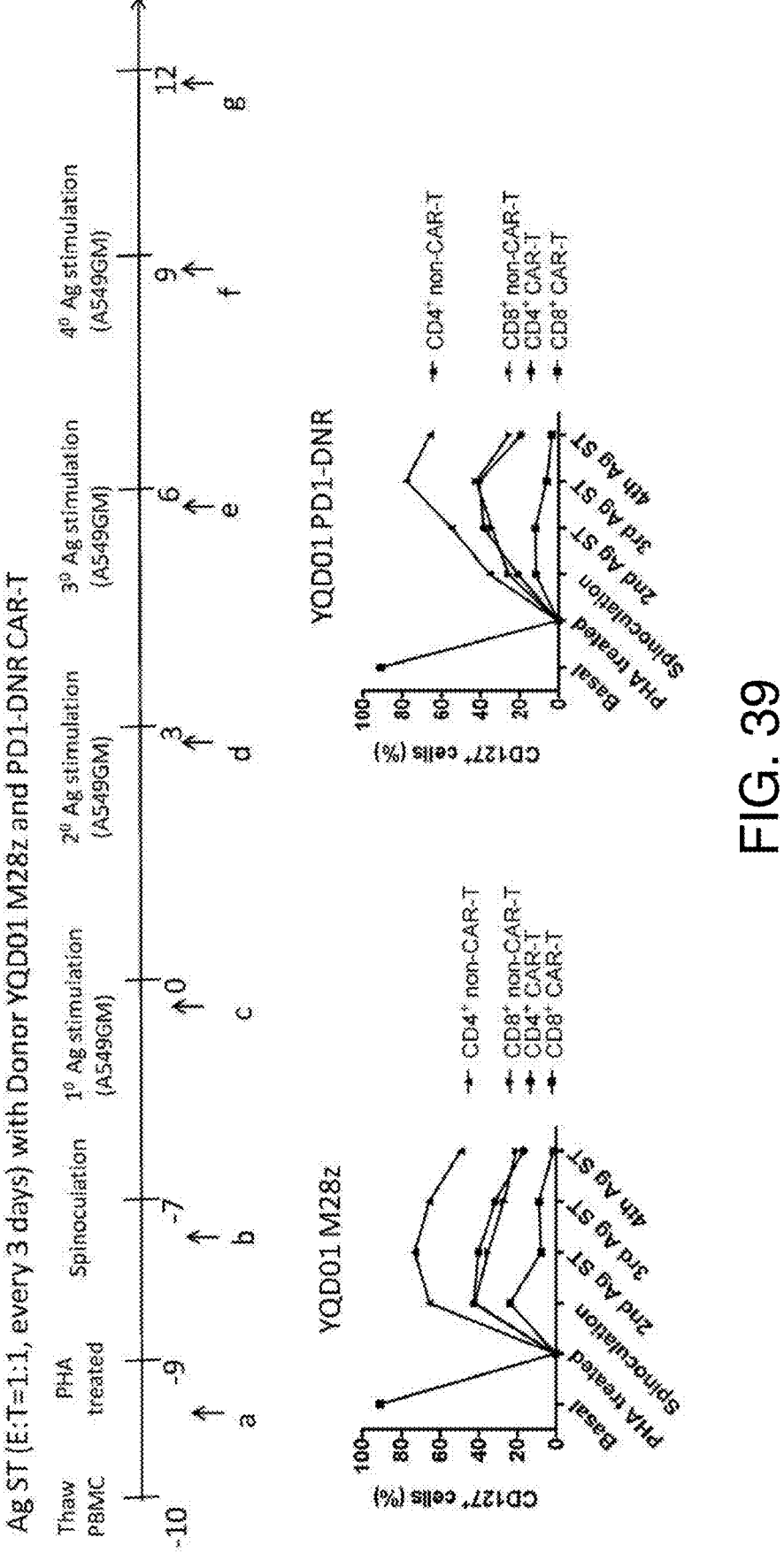

FIG. 39 depicts the reduced expression levels of CD127 in M28z and PD1-DNR CAR-T cells from donor YQD01 compared to non-transduced cells.

Figure 40:
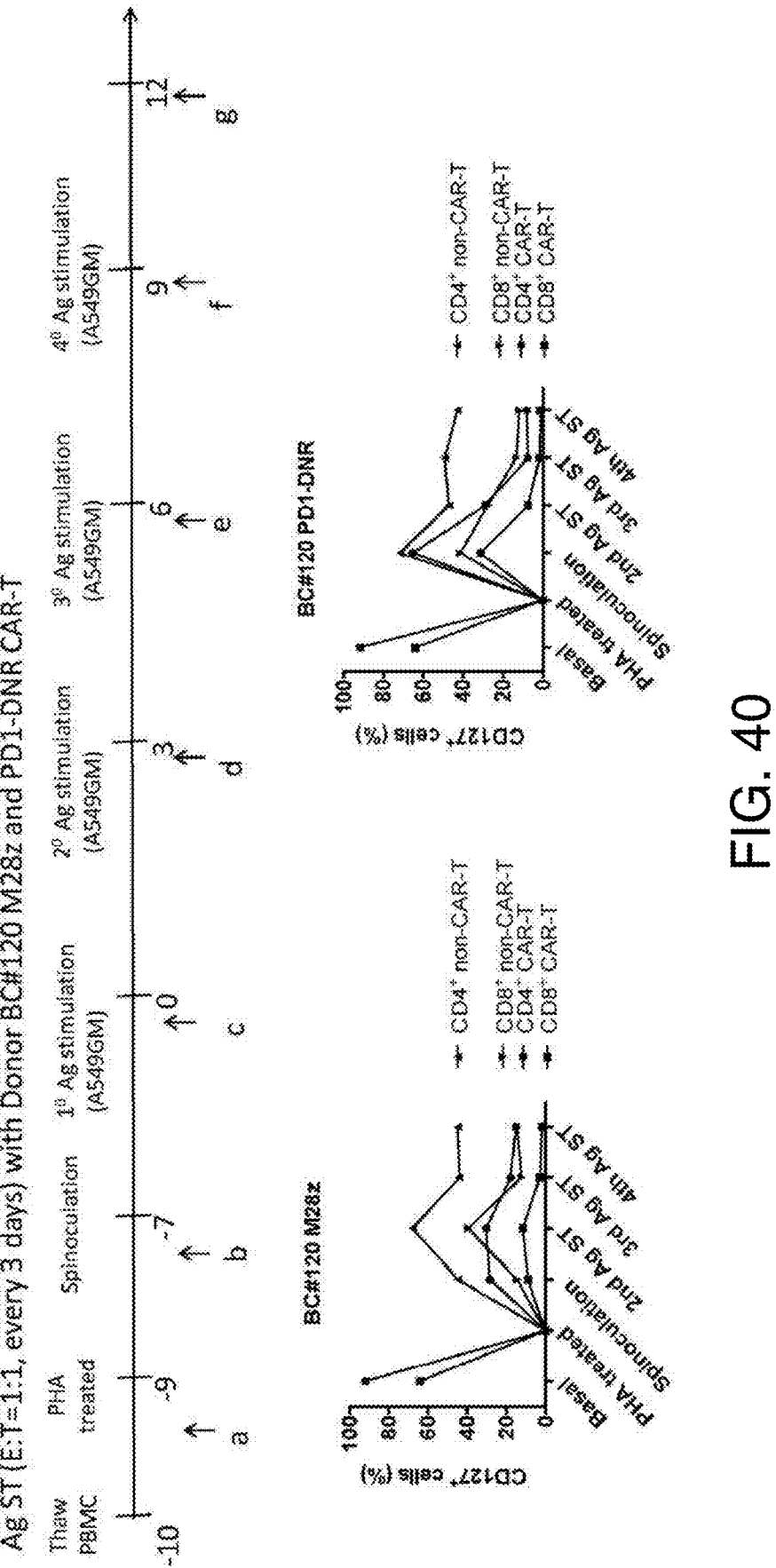

FIG. 40 depicts the reduced expression levels CD127 in M28z and PD1-DNR CAR-T cells from donor BC #120 compared to non-transduced cells.

Figure 41:
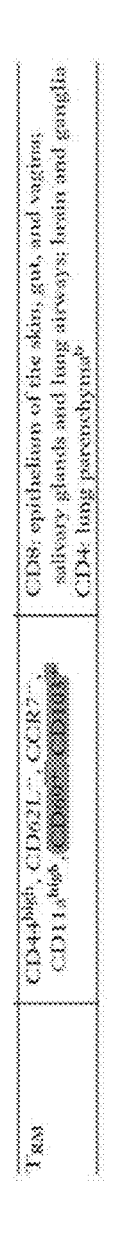
Figure 41:
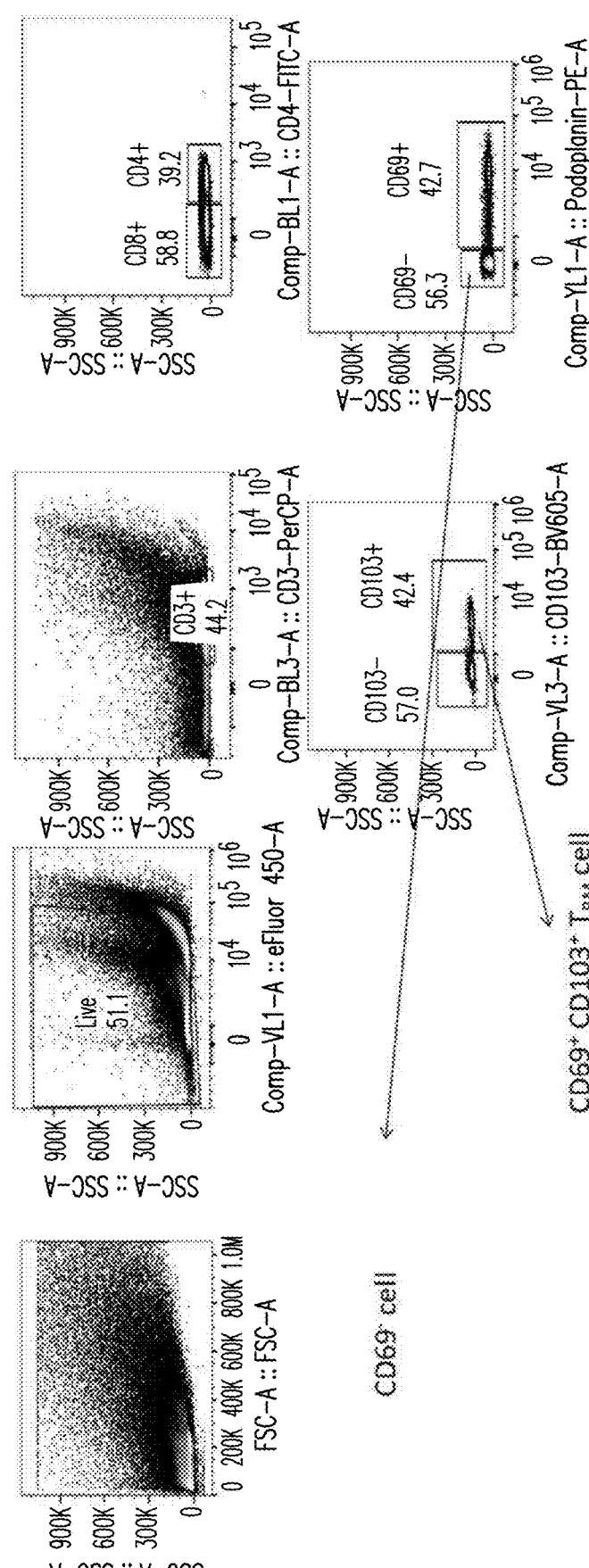

FIG. 41 shows the gating strategy for CD69$^+$ CD103$^+$ tissue-resident memory T cells (T$_{RM}$) in lung cancer.

Figure 42:
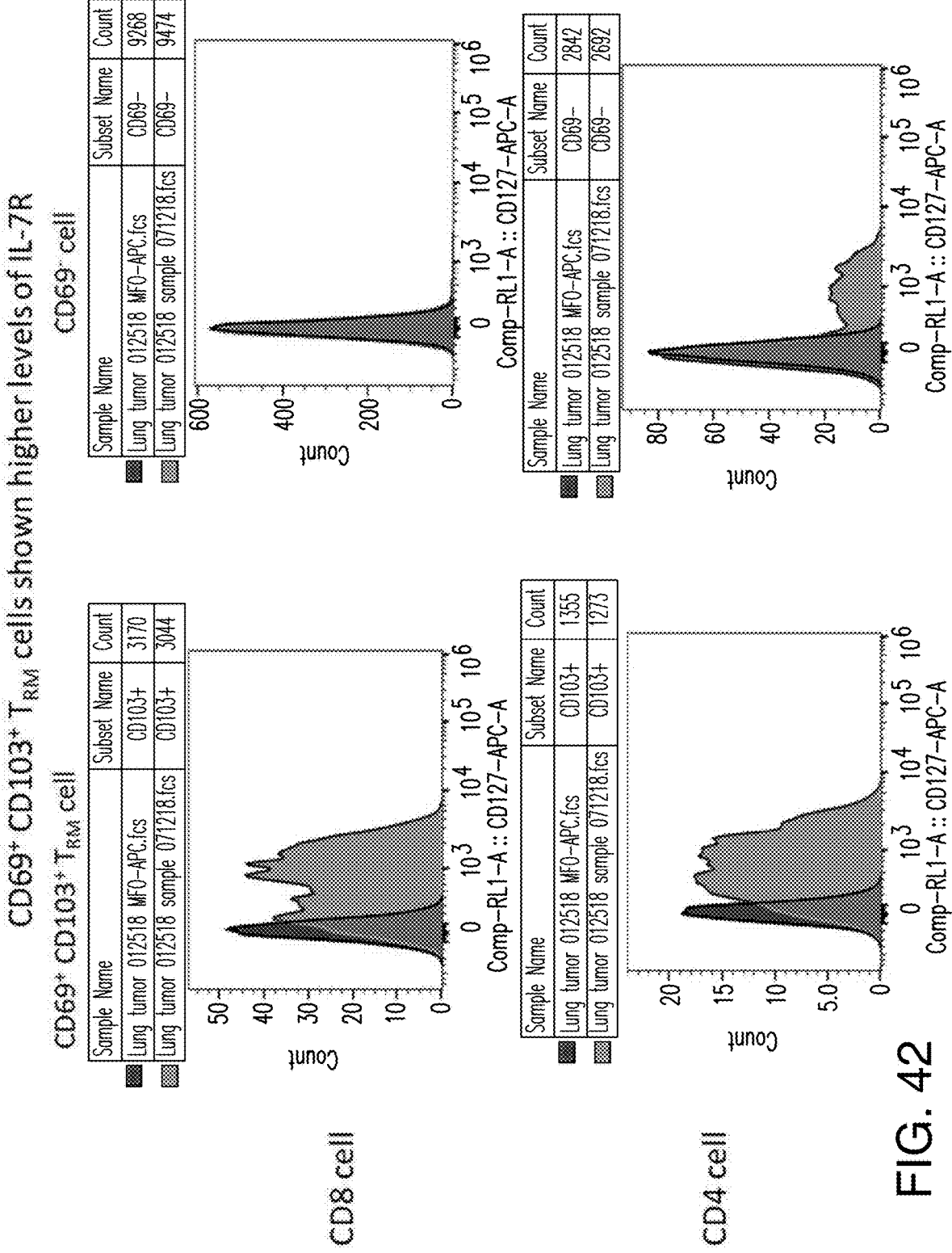

FIG. 42 shows that CD69$^+$ CD103$^+$ tissue-resident memory T cells (T$_{RM}$) in lung cancer from donor 1 had higher levels of IL-7R.

Figure 43:
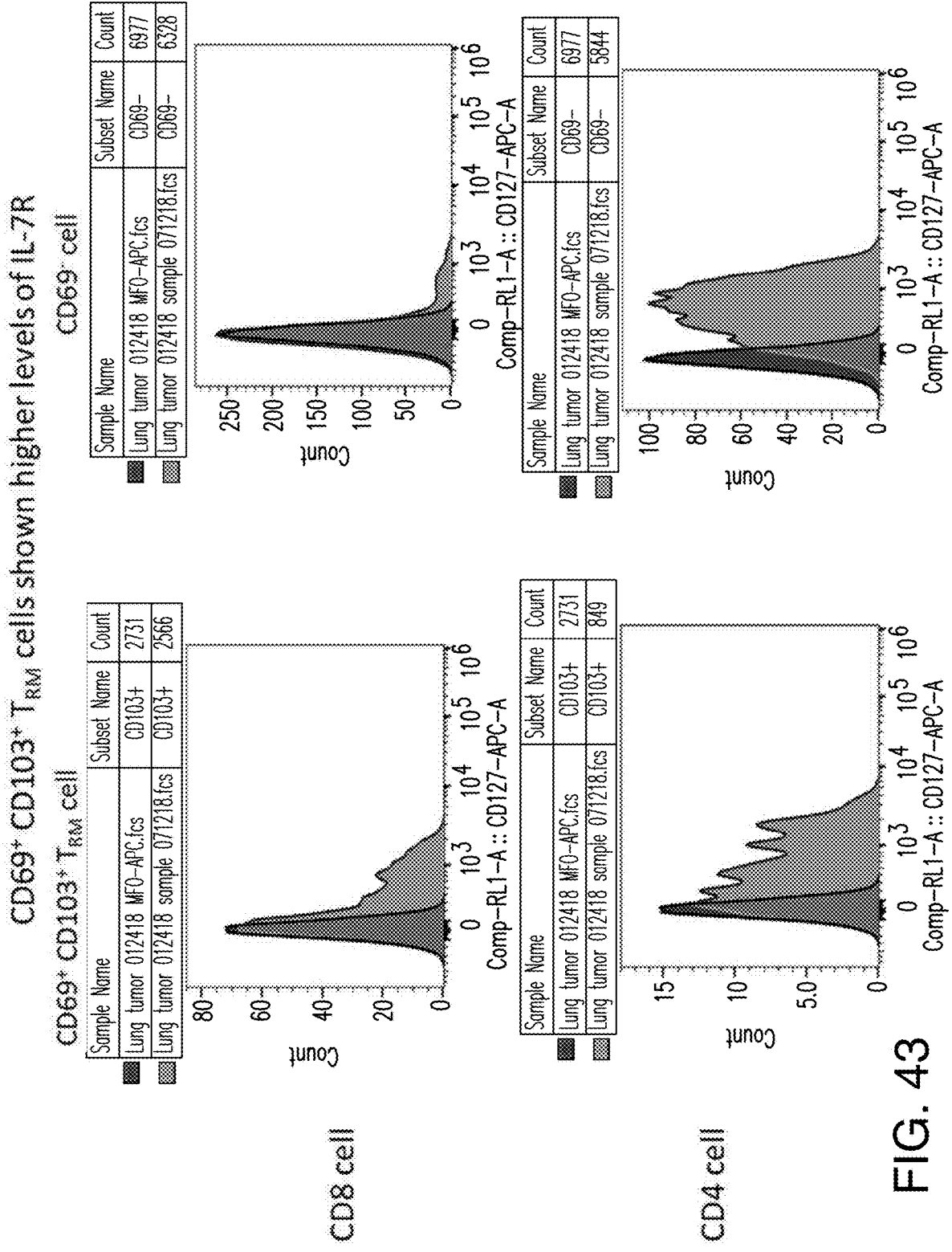

FIG. 43 shows that CD69$^+$ CD103$^+$ tissue-resident memory T cells (T$_{RM}$) in lung cancer from donor 2 had higher levels of IL-7R.

Figure 44:
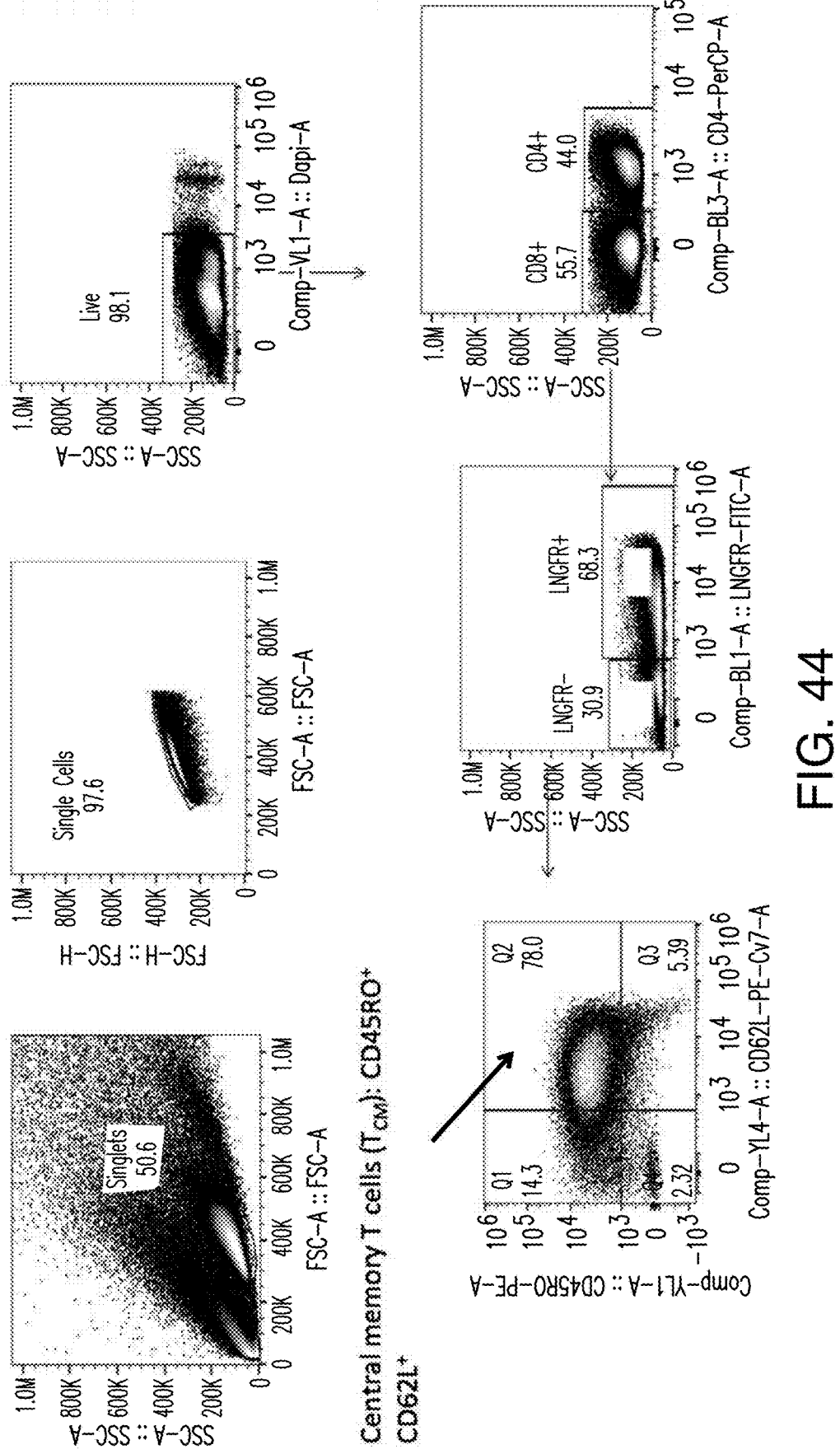

FIG. 44 shows the gating strategy for central memory T cells (T$_{CM}$, CD45RO$^+$ CD62L$^+$).

Figure 45:
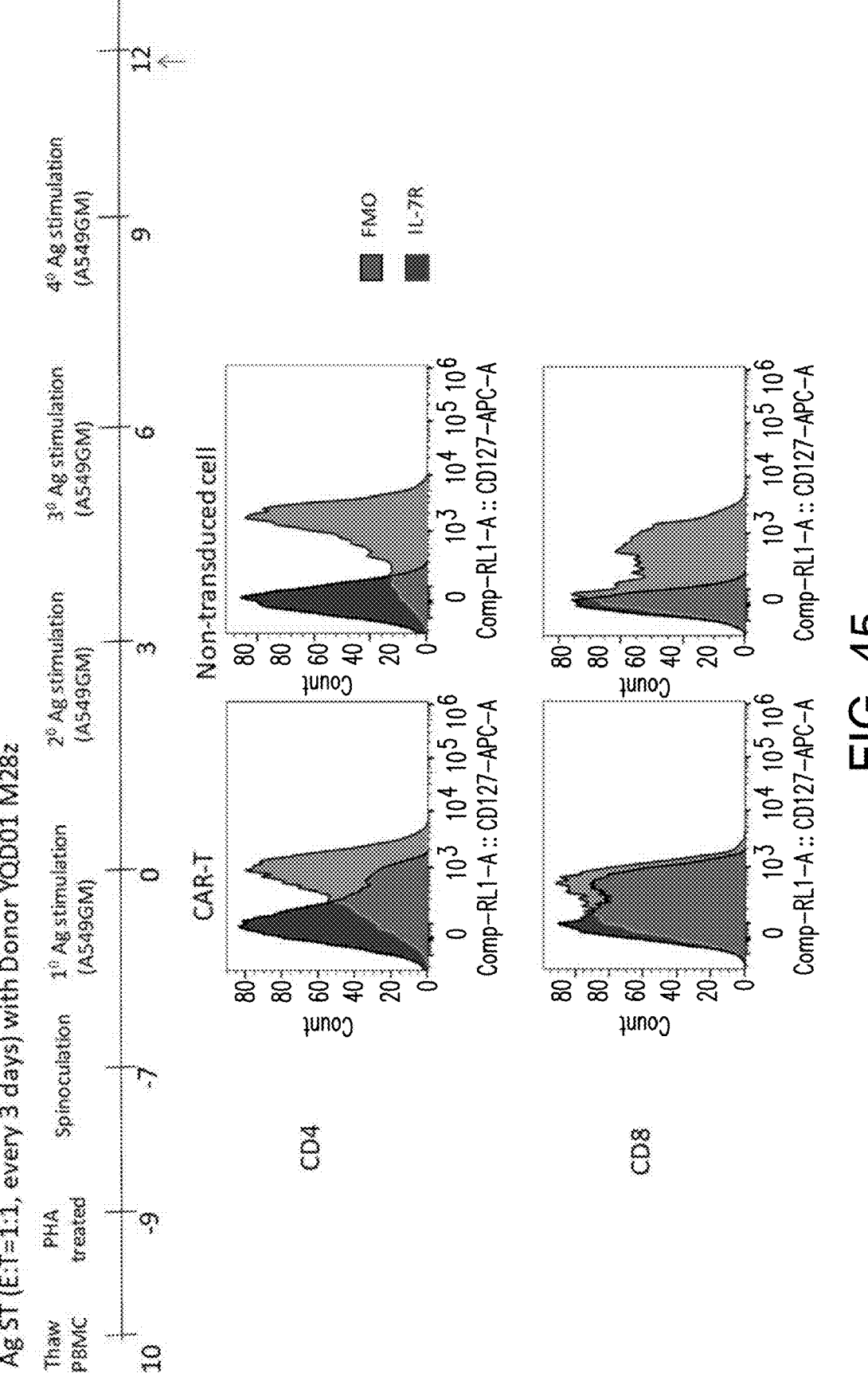

FIG. 45 shows that IL-7R was reduced in T$_C$M CAR-T cells as compared to non-transduced cells.

Figure 46:
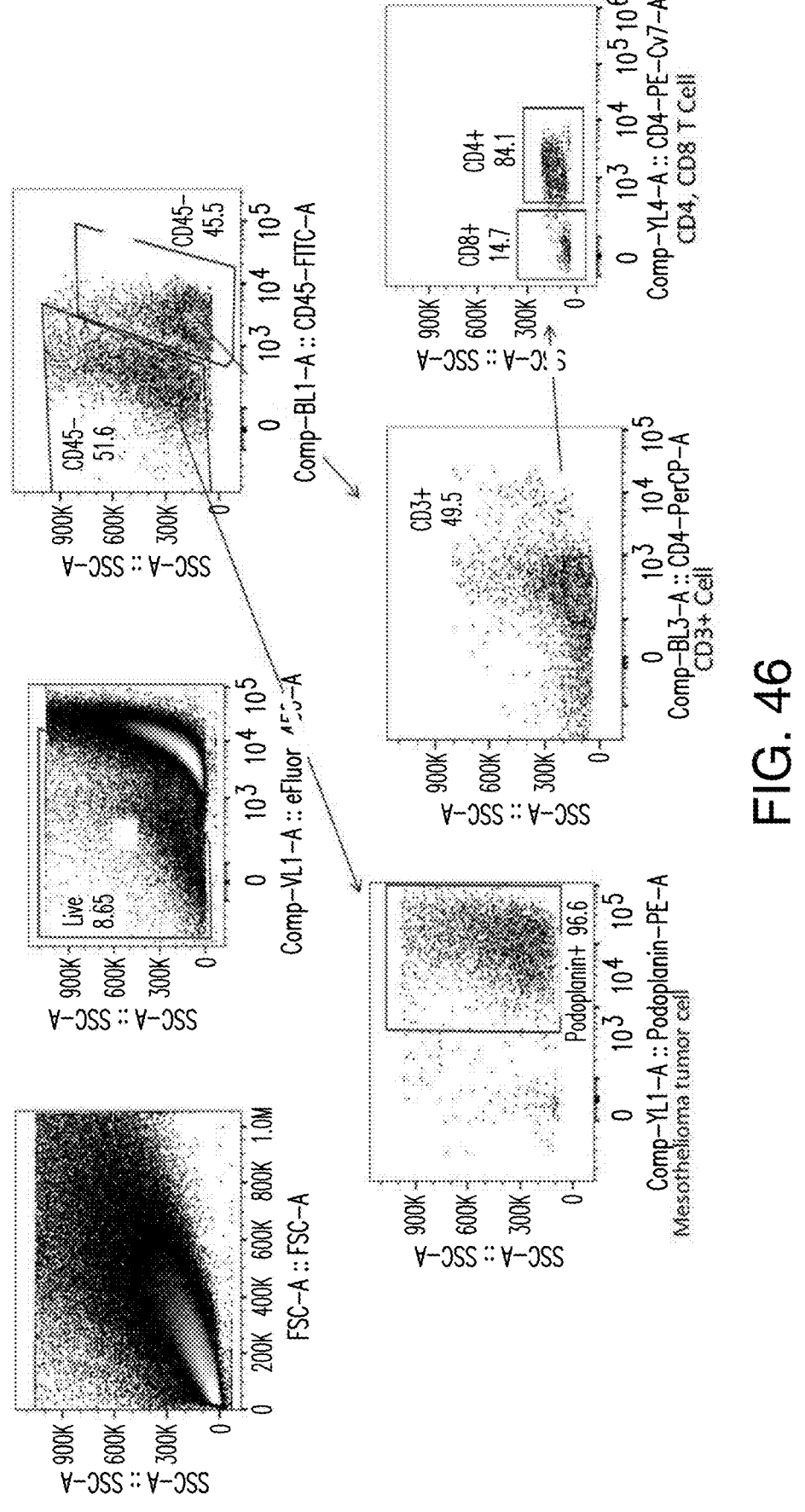

FIG. 46 shows the gating strategy for mesothelioma tumor cells.

Figure 47:
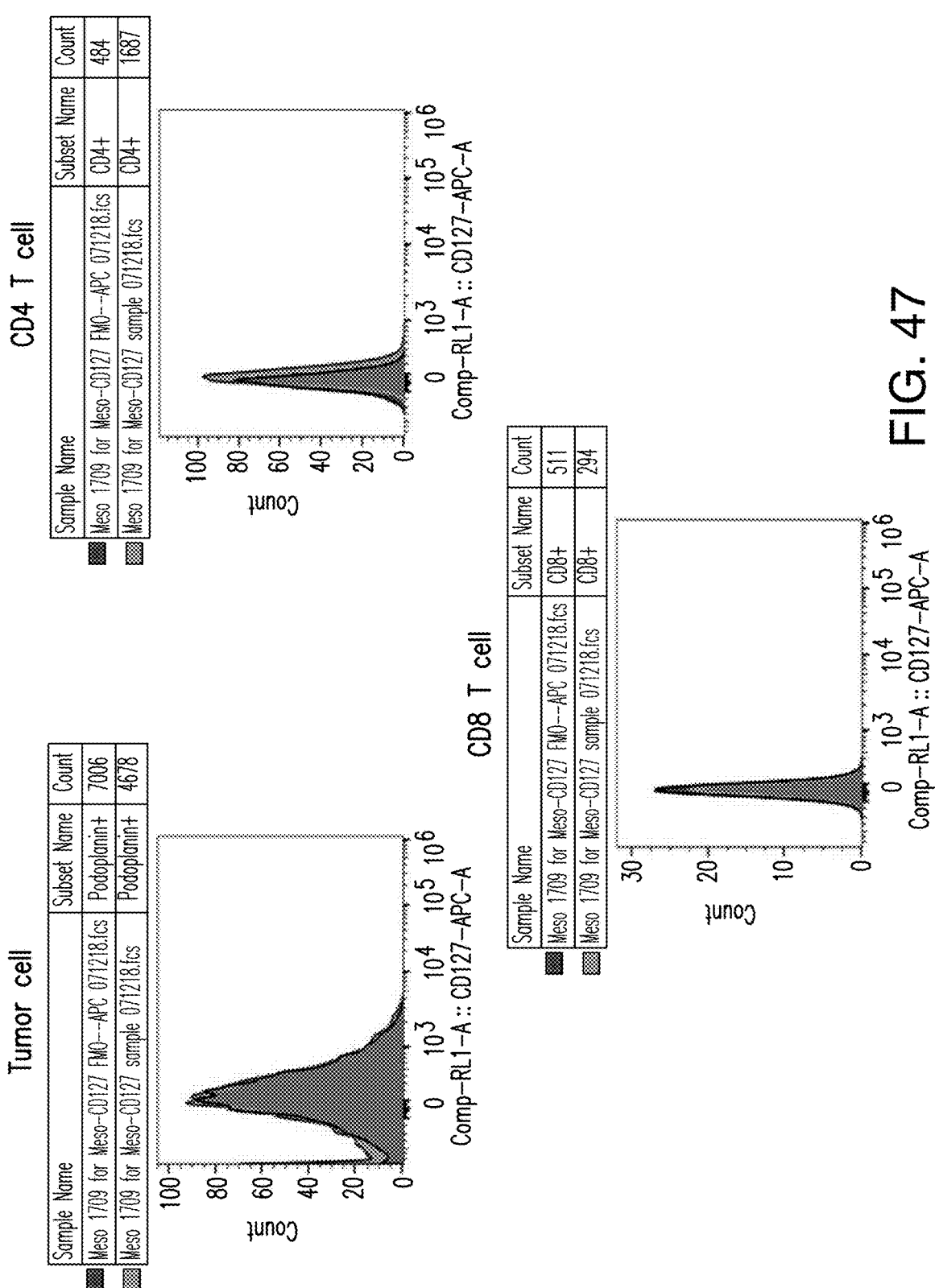
Figure 47:
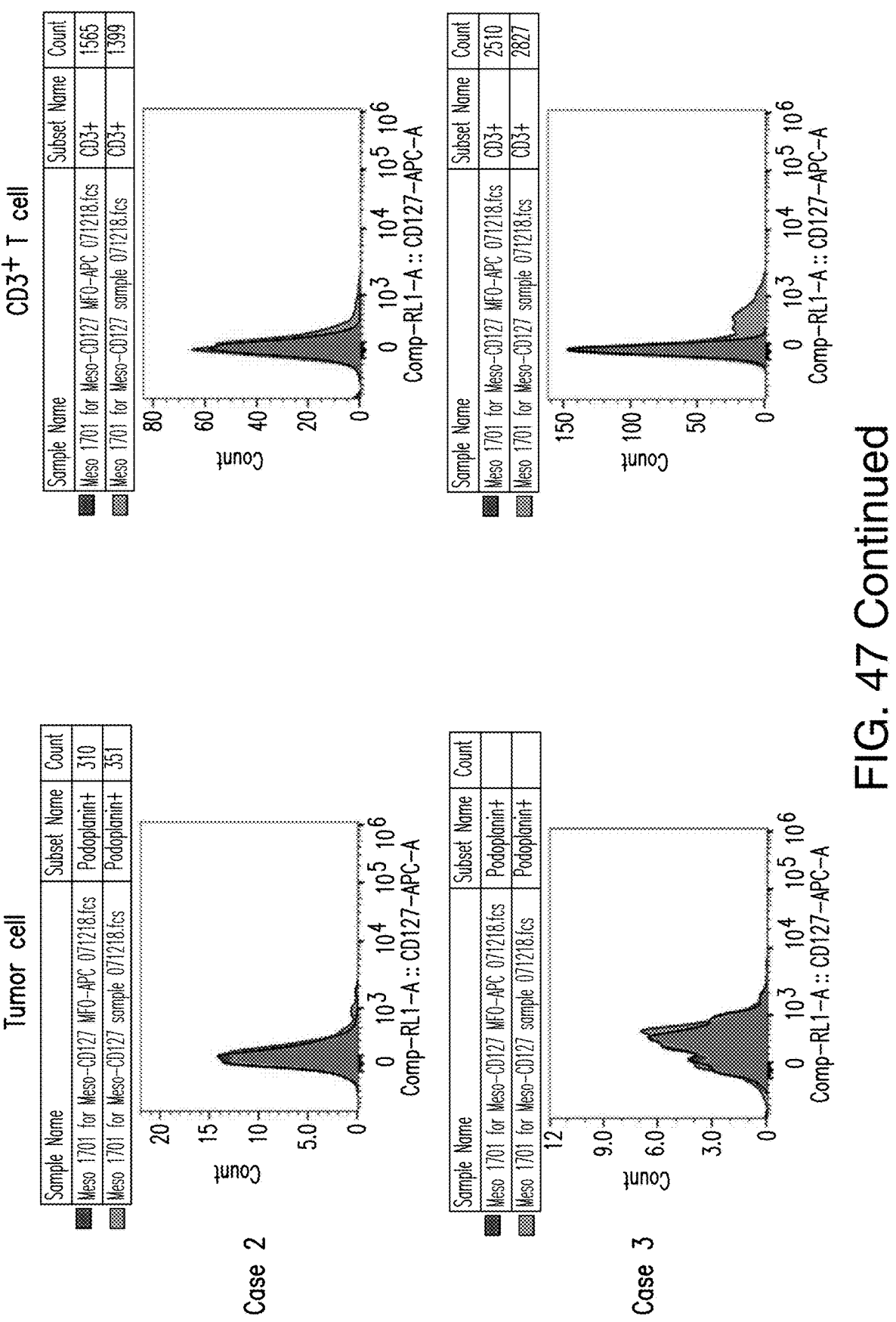

FIG. 47 shows IL-7R levels in mesothelioma tumor cells, CD4$^+$ T cells, CD8$^+$ T cells, and CD3$^+$ T cells.

Figure 48:
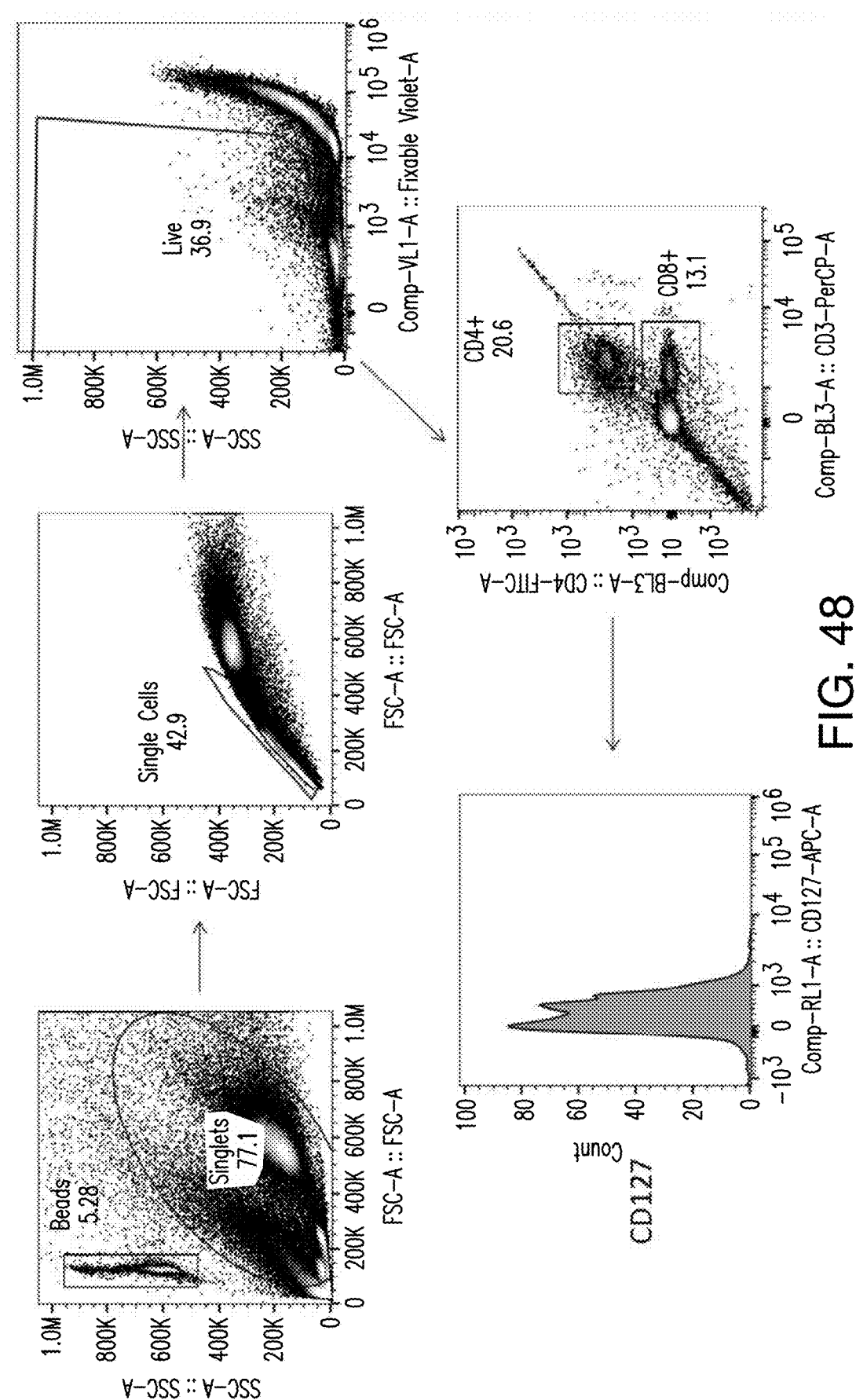

FIG. 48 shows gating strategy for T cells.

Figure 49:
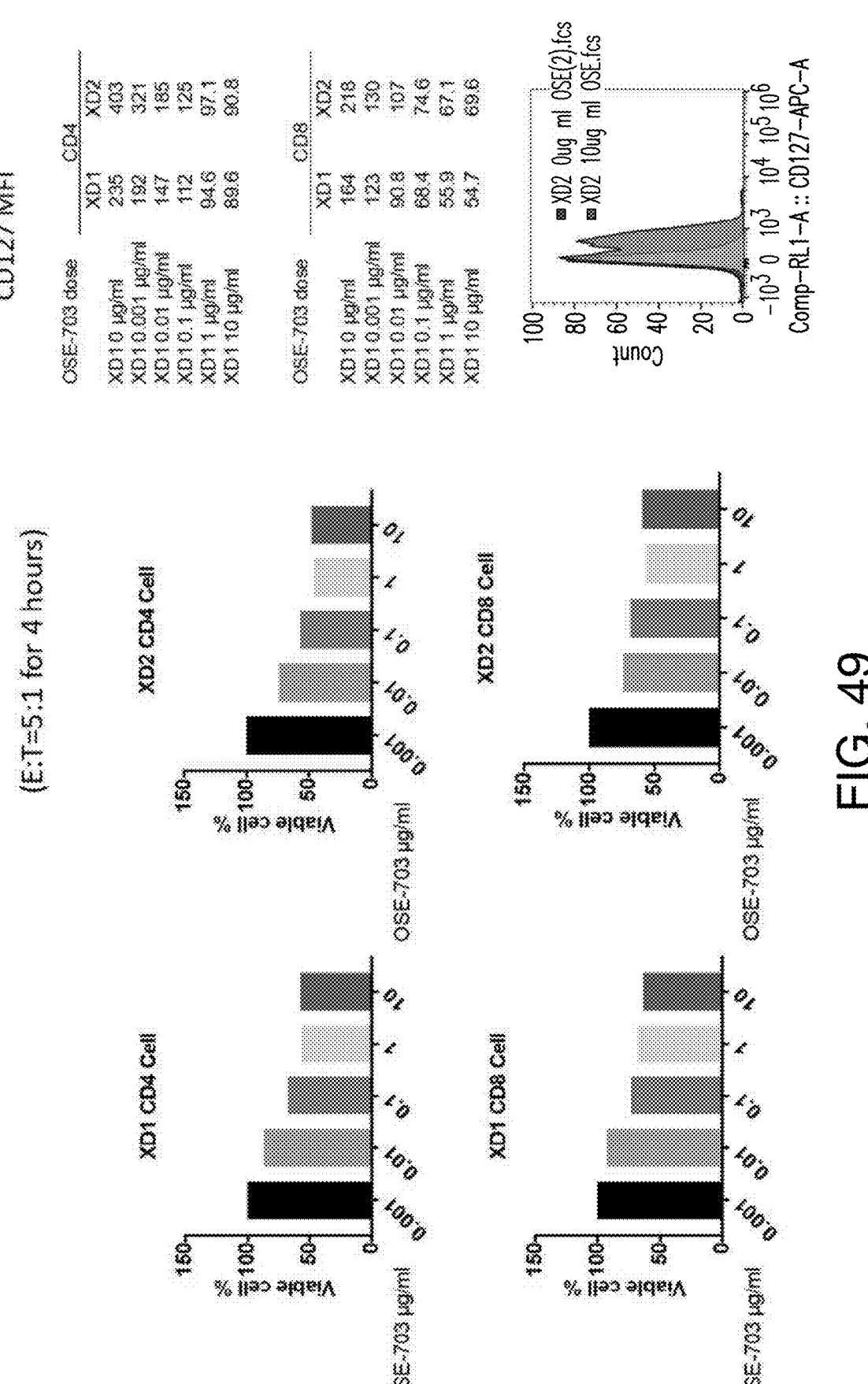

FIG. 49 shows the percentage of viable CD4$^+$ and CD8 cells after incubation with OSE-703 and NK92-176V cells.

Figure 50:
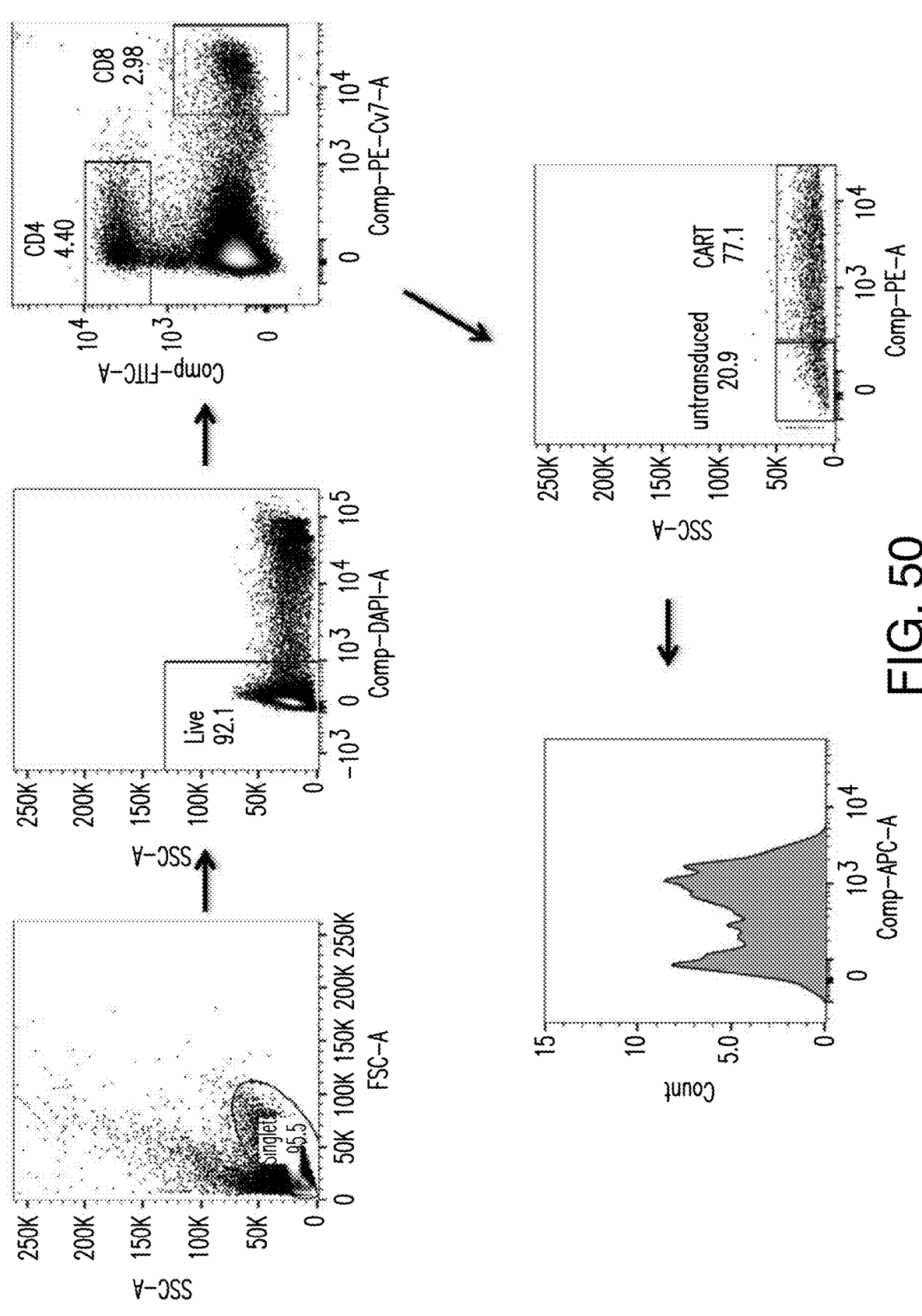

FIG. 50 shows the gating strategy for Ag ST CAR-T cells. "Ag ST" represents "antigen-stimulated".

Figure 51:
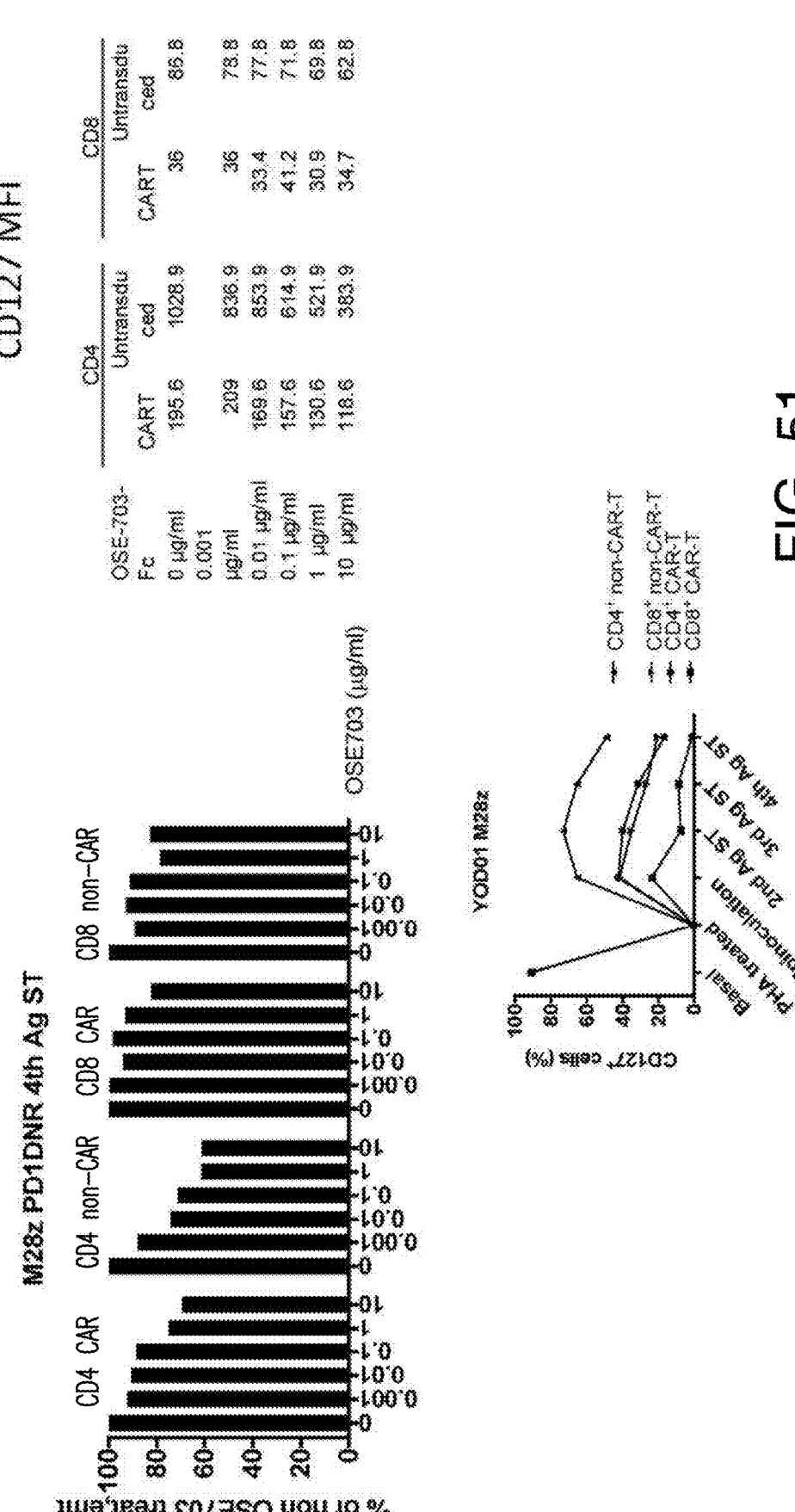
Figure 52:
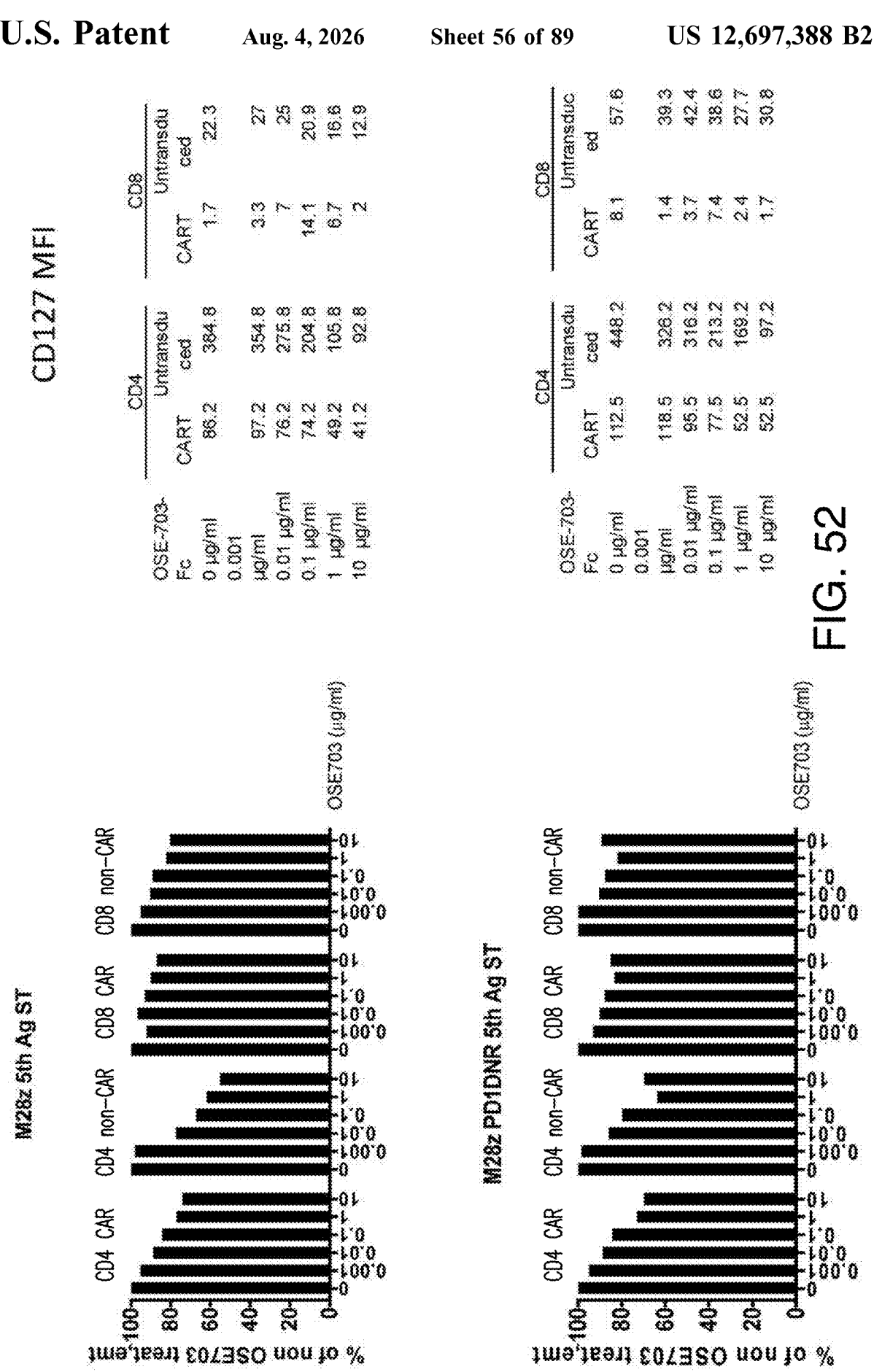
Figure 53:
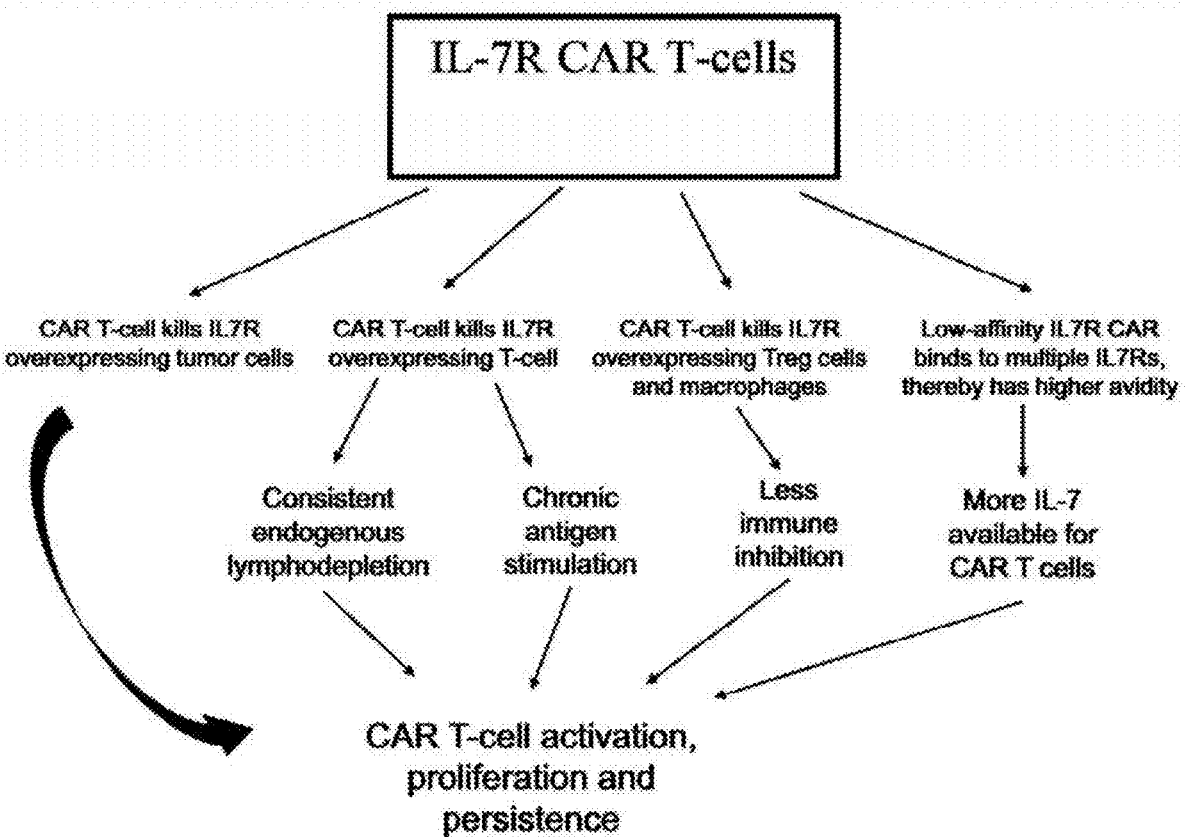

FIG. 51 shows that the cytotoxicity of OSE-703 is IL-7R expression-dependent in M28z PD1DNR CAR T cells following 4 antigen stimulations FIG. 52 shows the cytotoxicity of OSE-703 in CD4$^+$ T cells and CD8$^+$ T cells CAR and bib-transduced cells following multiple antigen stimulations FIG. 53 provides a schematic showing of possible multiple mechanisms of the presently disclosed CD127-targeted CAR T-cells in enhancing the anti-tumor efficacy and persistence.

Figure 54:
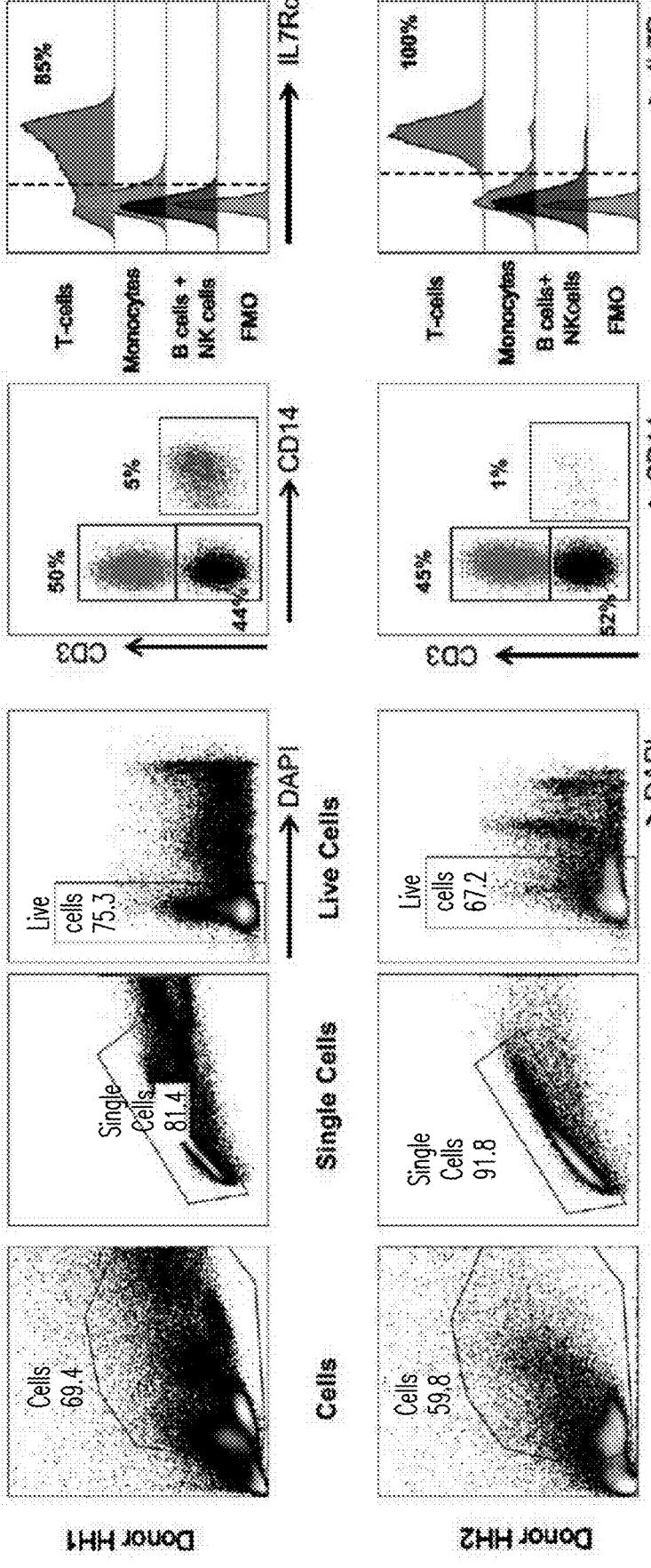

FIG. 54 shows CD127 expression in two healthy PBMC donor cells.

Figure 55:
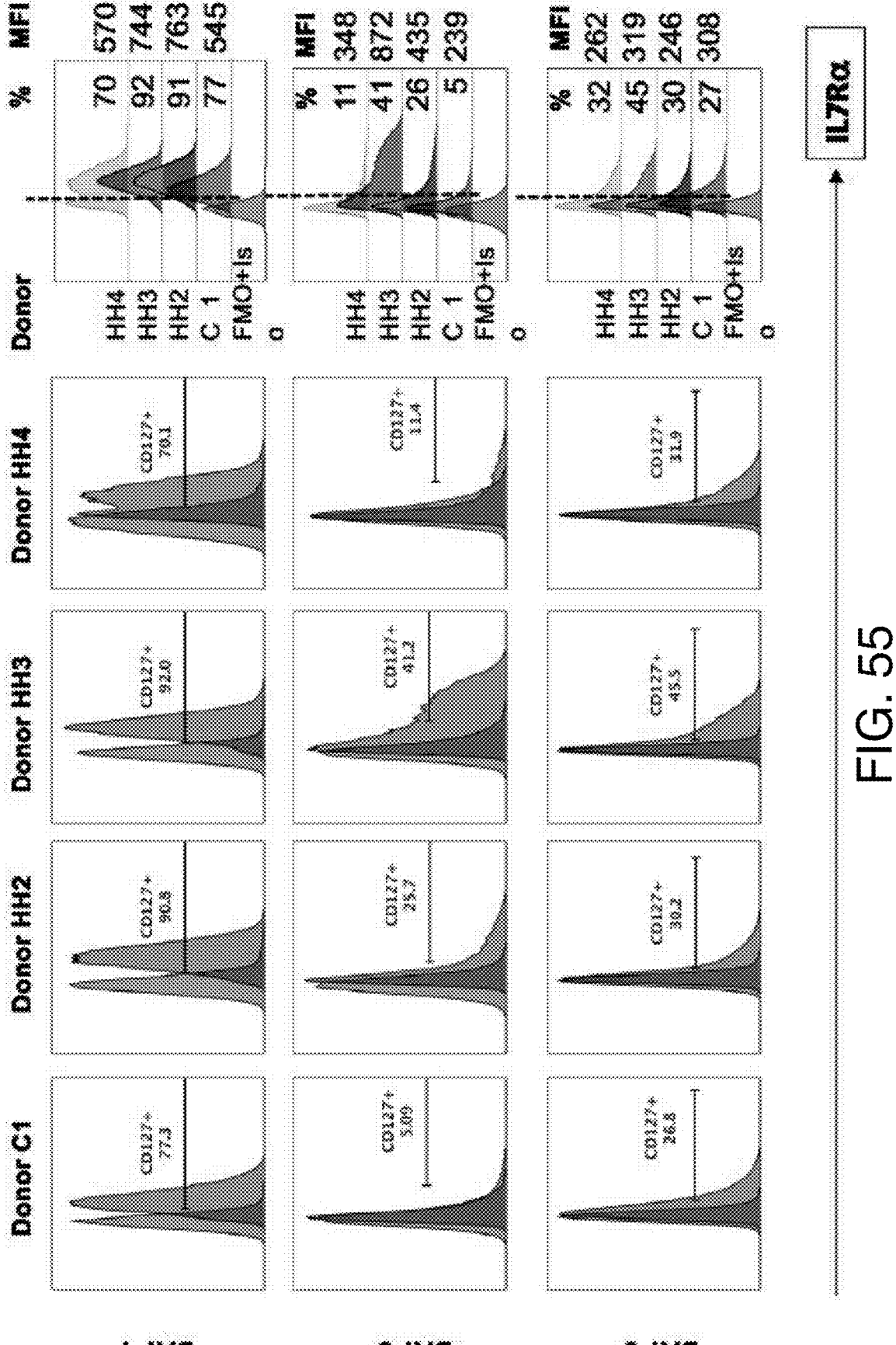

FIG. 55 shows CD127 expression in T cells of four healthy donors before and after phytohaemagglutinin P (PHA) activation on day 1, 3 and 6

Figure 56:
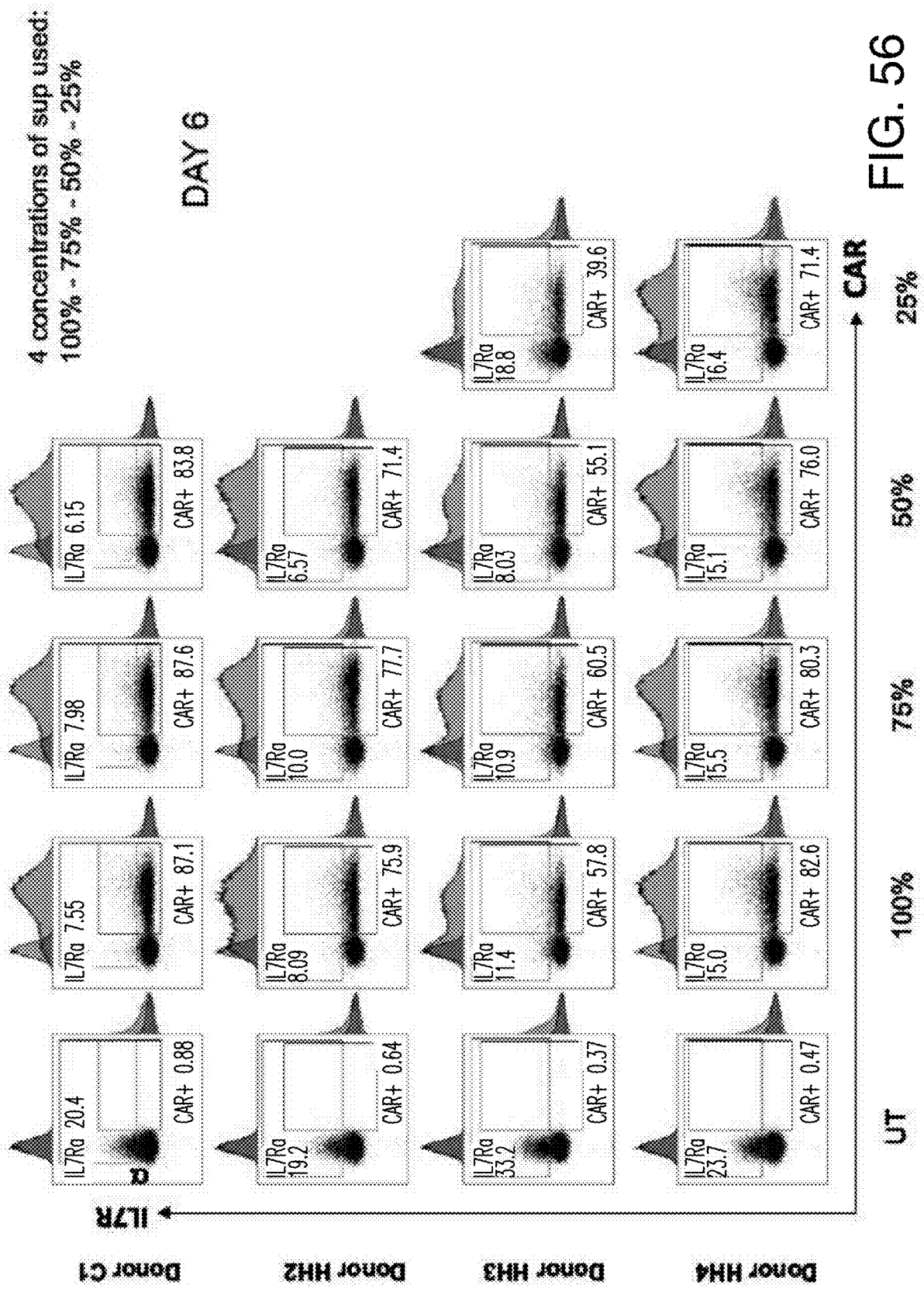
Figure 57:
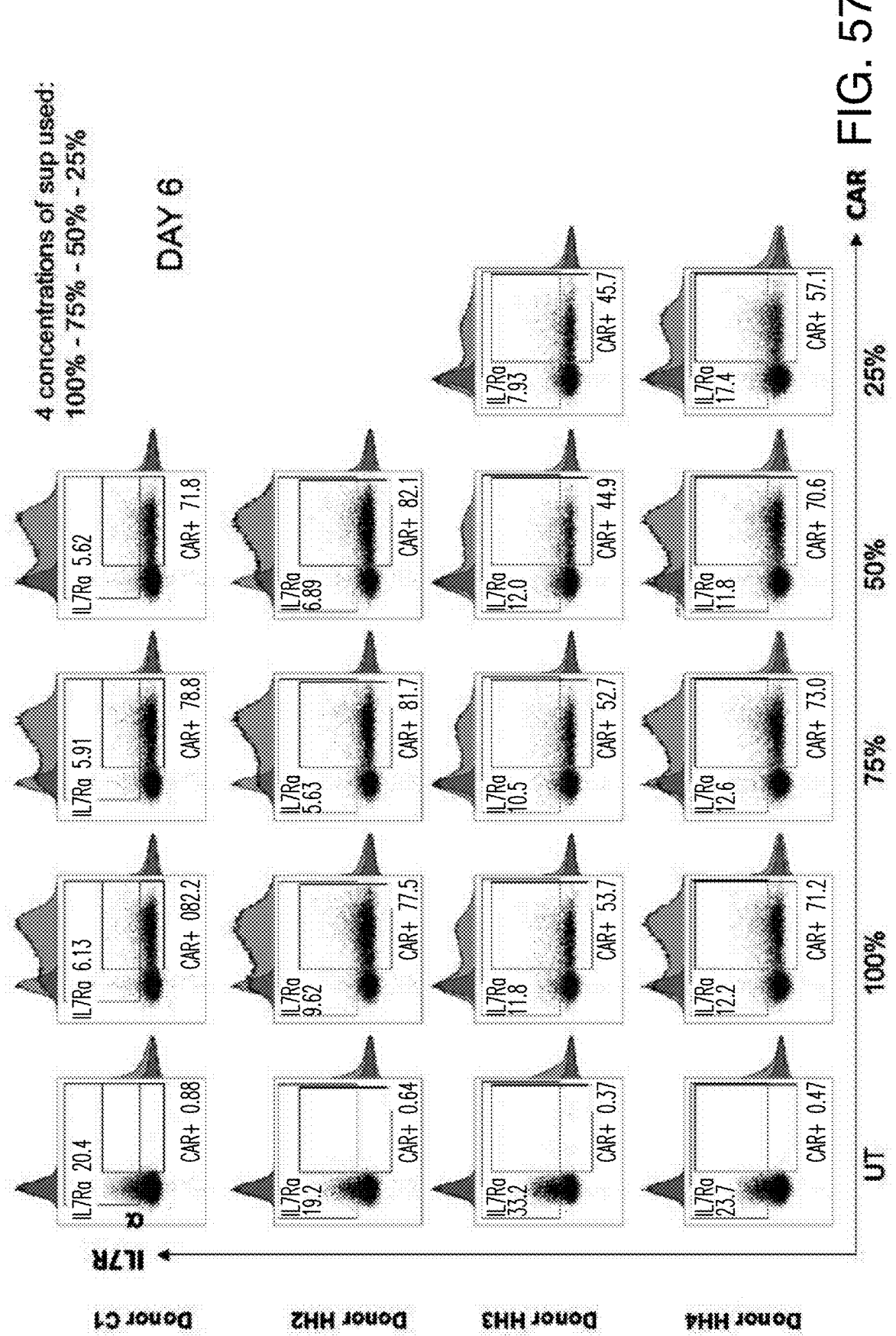
Figure 58:
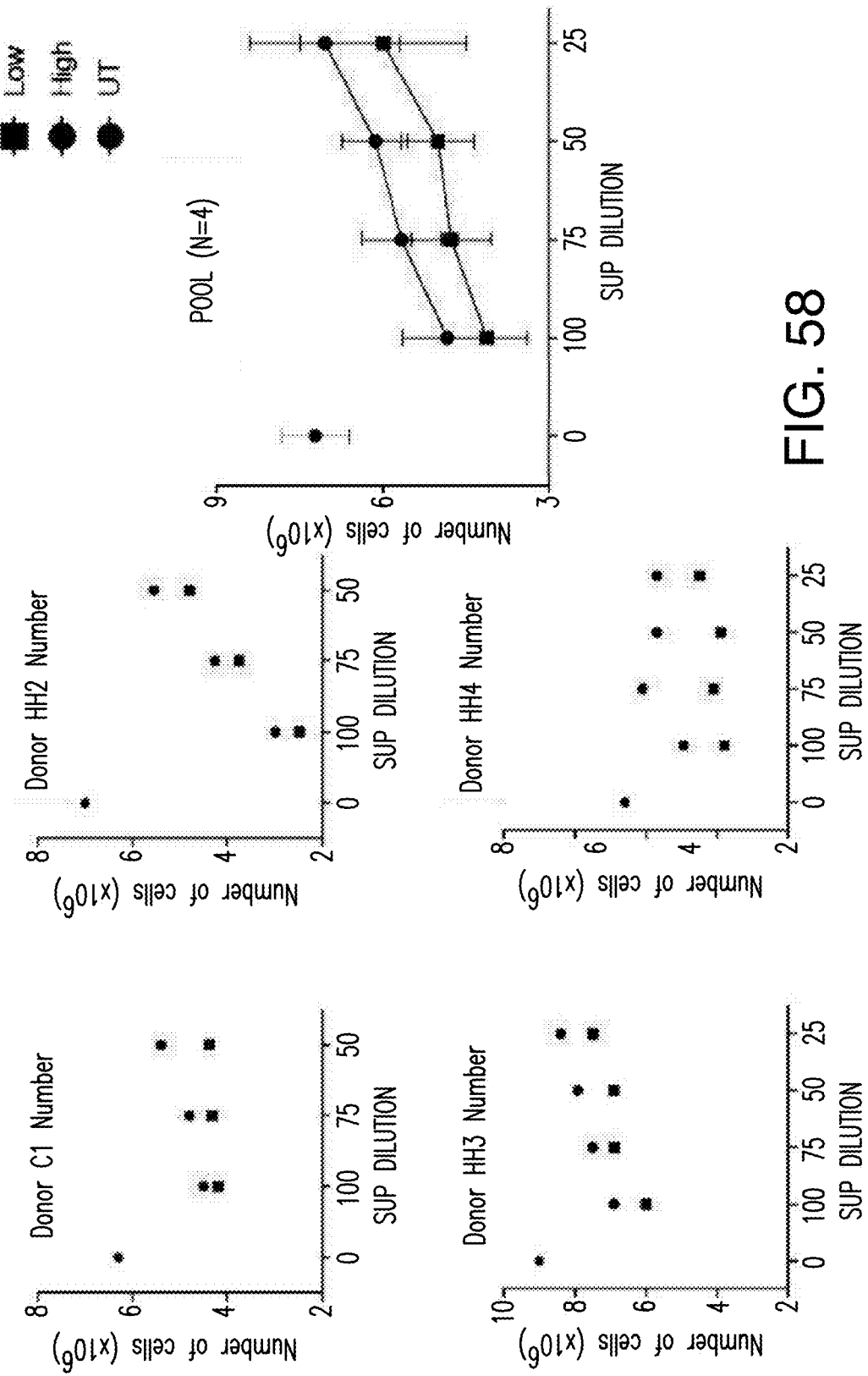

FIG. 56 shows vector sup titration in low-affinity CAR T cells to achieve optimal CAR expression and limited fratricide FIG. 57 shows vector sup titration in high-affinity CAR T cells to achieve optimal CAR expression and limited fratricide FIG. 58 shows the total number of T cells after spinoculation with different dilutions of vector supernatant used for CAR transduction.

Figure 59:
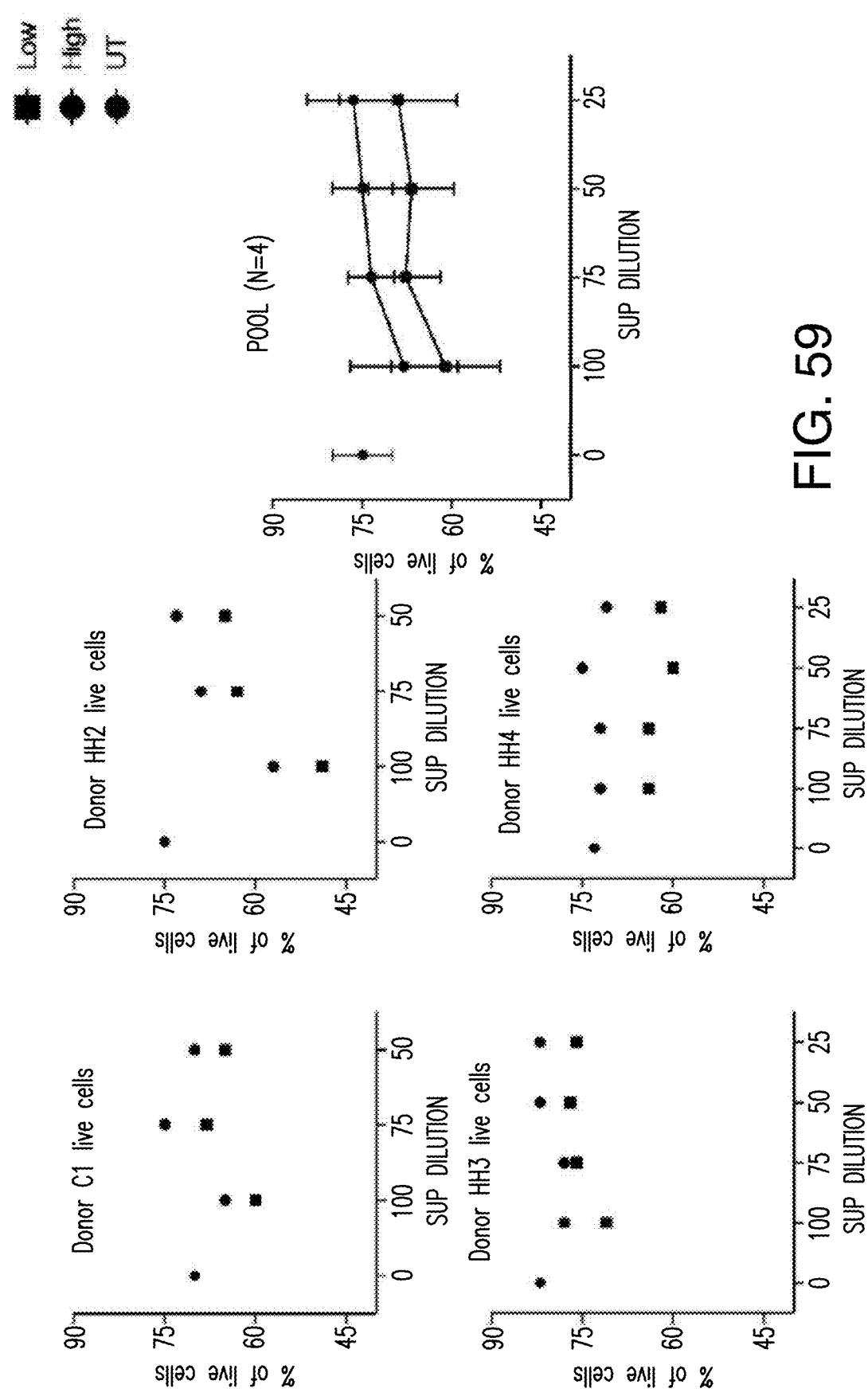

FIG. 59 shows the percentage of live cells after spinoculation with different dilutions of vector supernatant used for CAR transduction.

Figure 60:
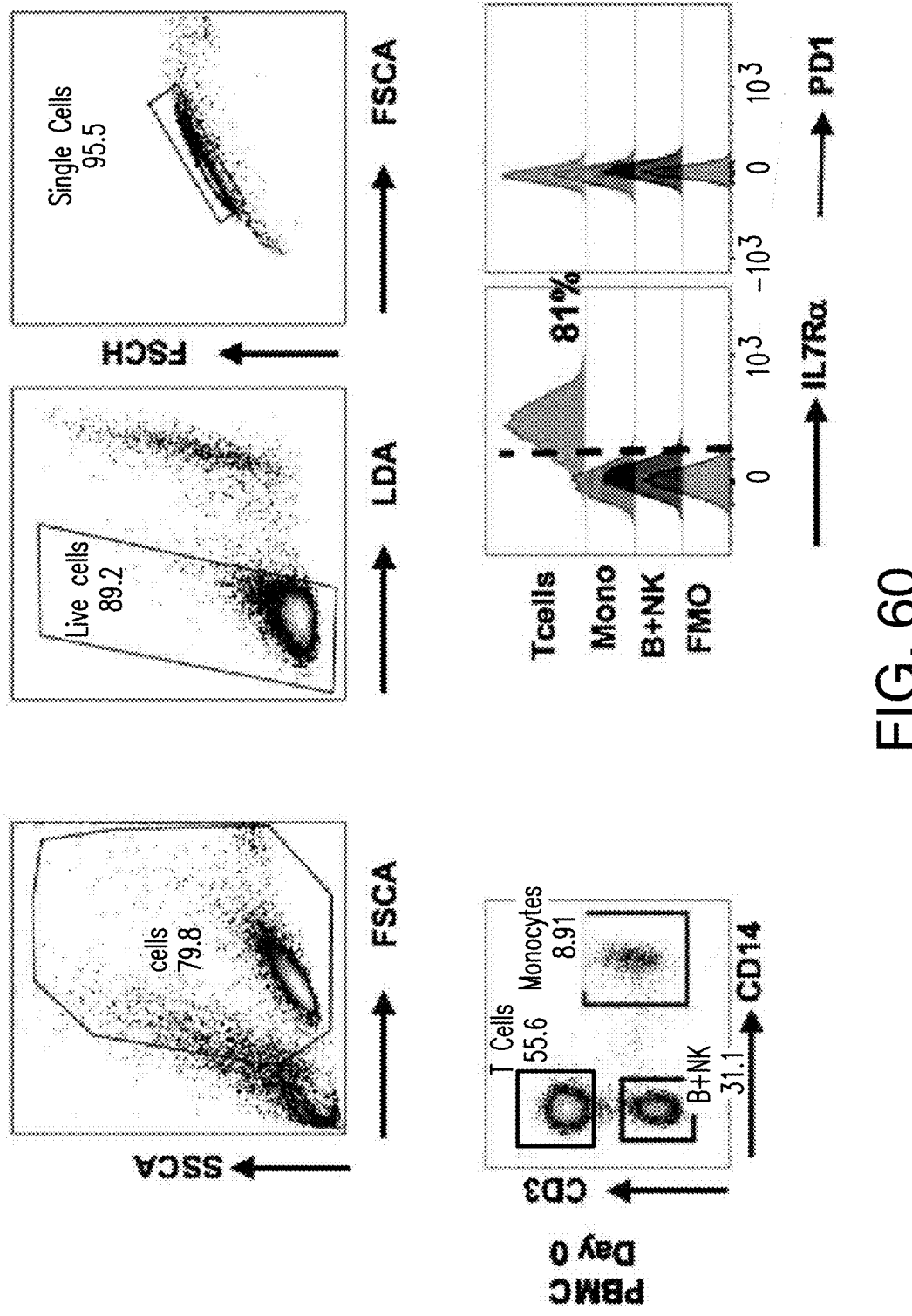
Figure 60:
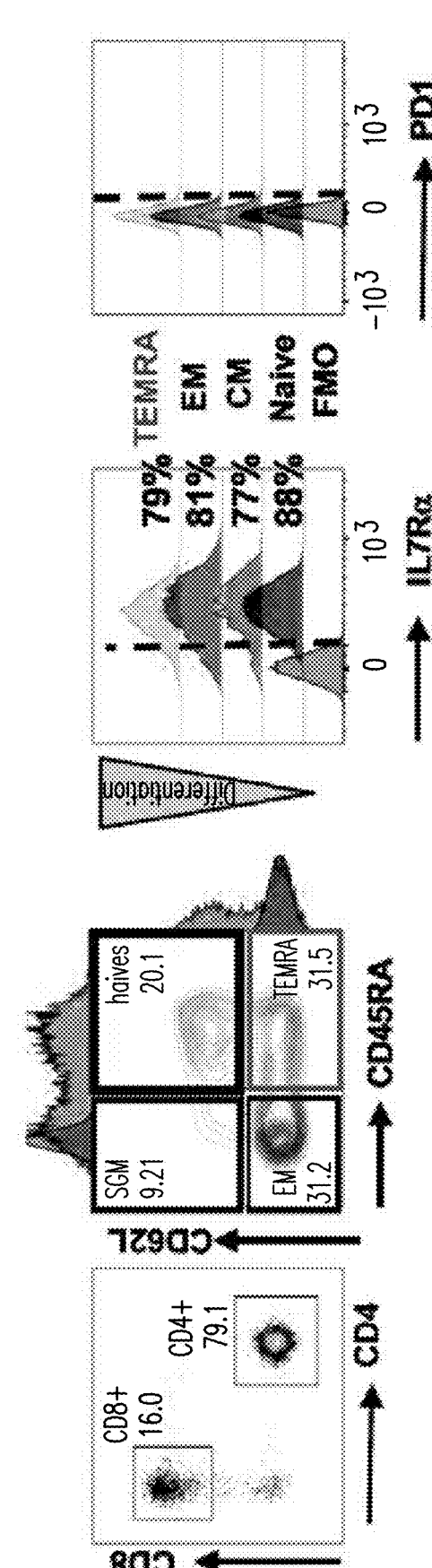
Figure 60:
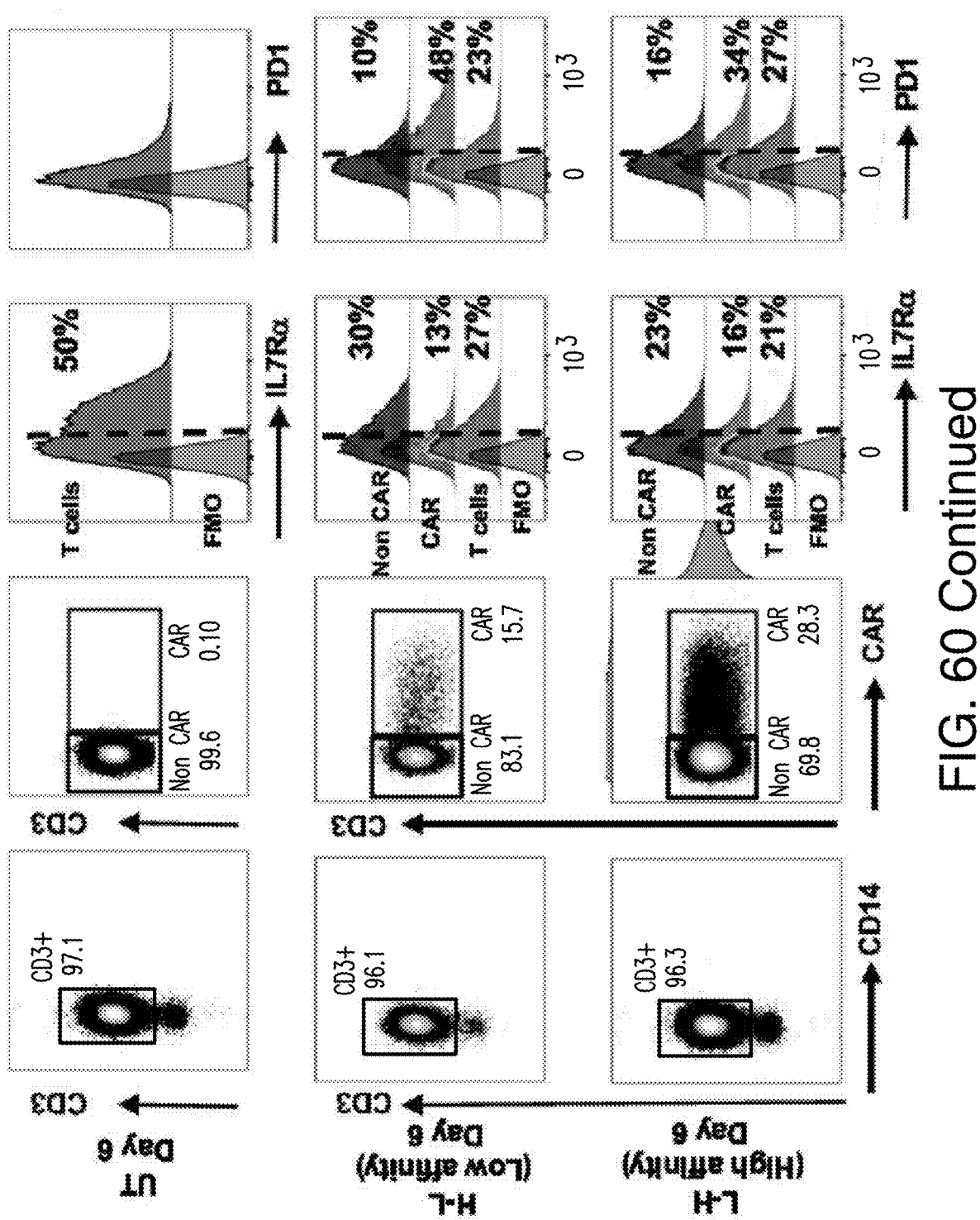
Figure 60:
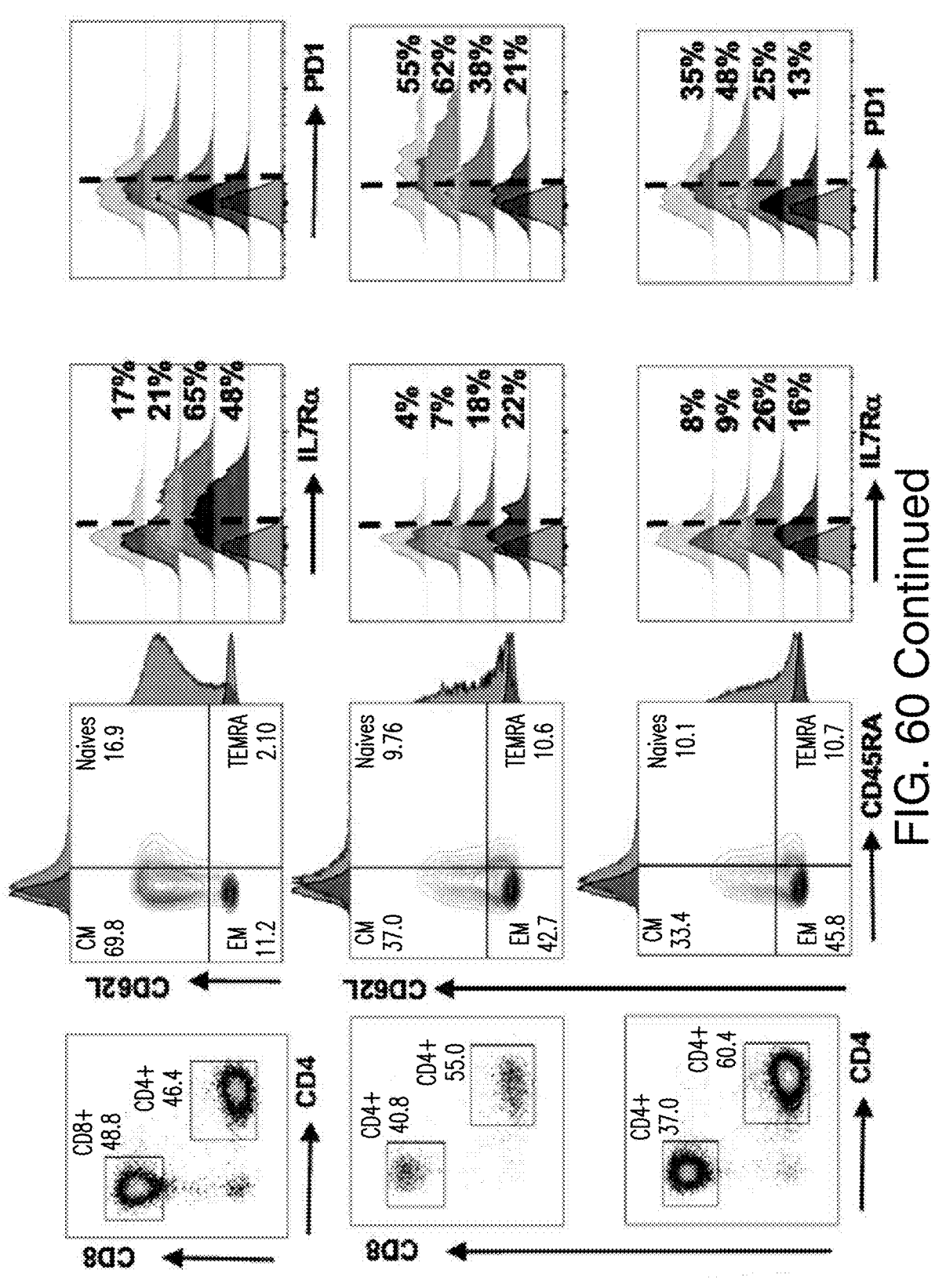

FIG. 60 shows donor H3 T cells CAR transduction percentage, IL7R expression percentage, PD1 expression percentage in CD4 and CD8 T cells on day 6 in donor T cells transduced with low- and high-affinity CARs.

Figure 61:
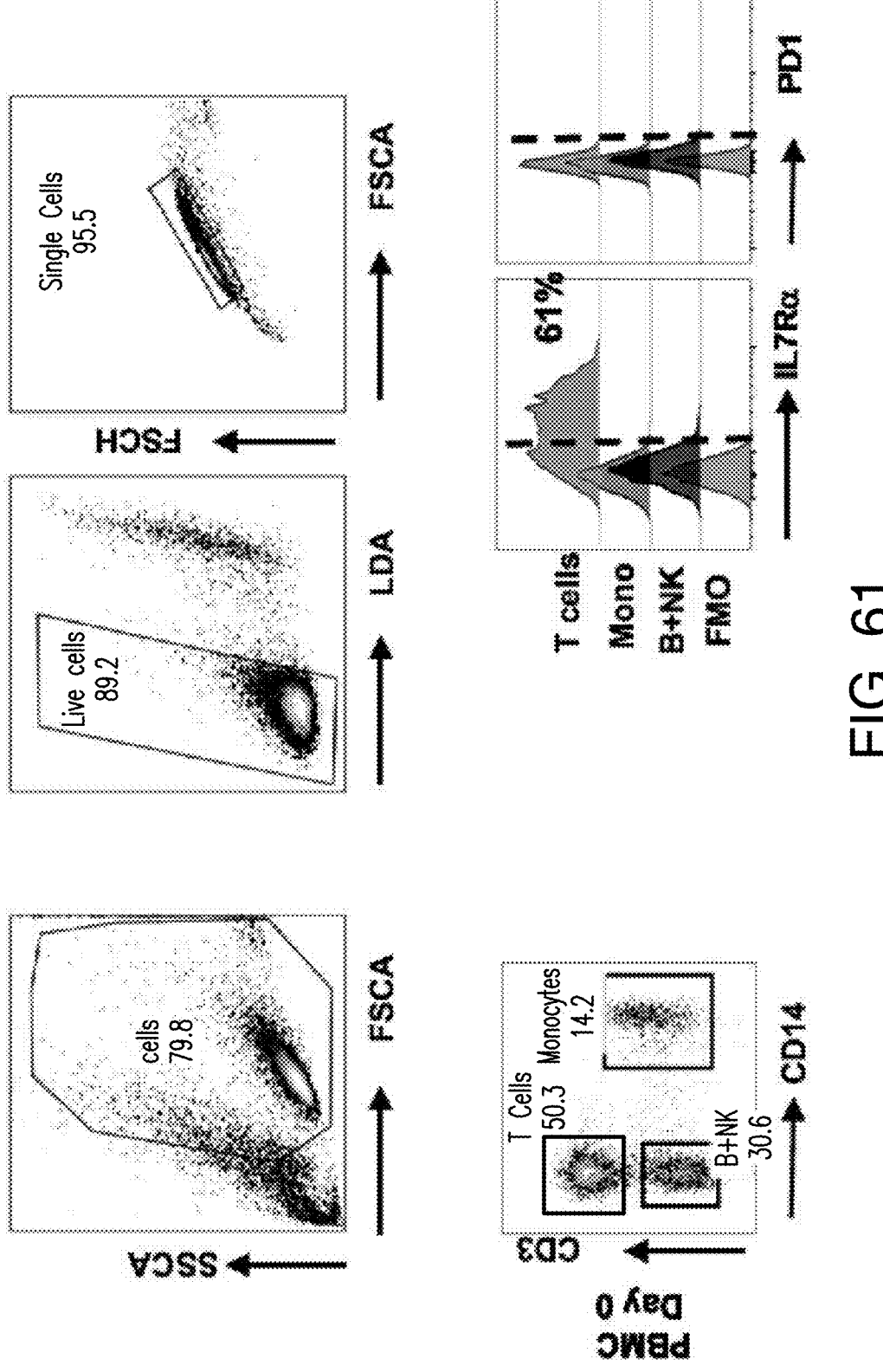
Figure 61:
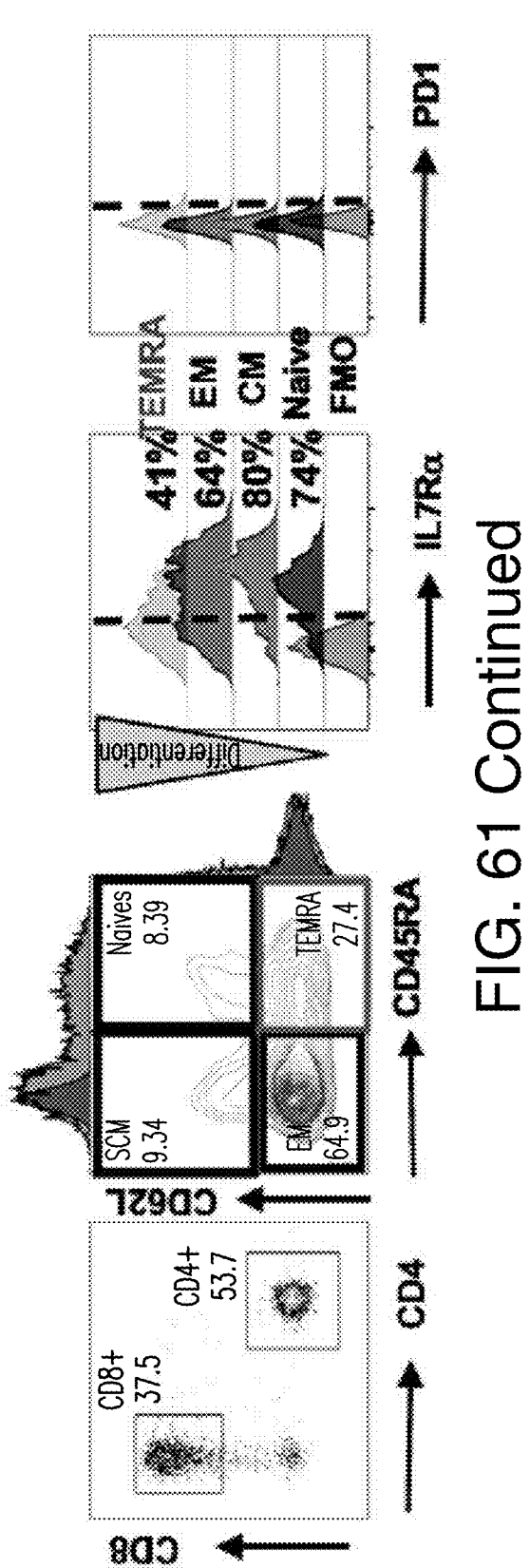
Figure 61:
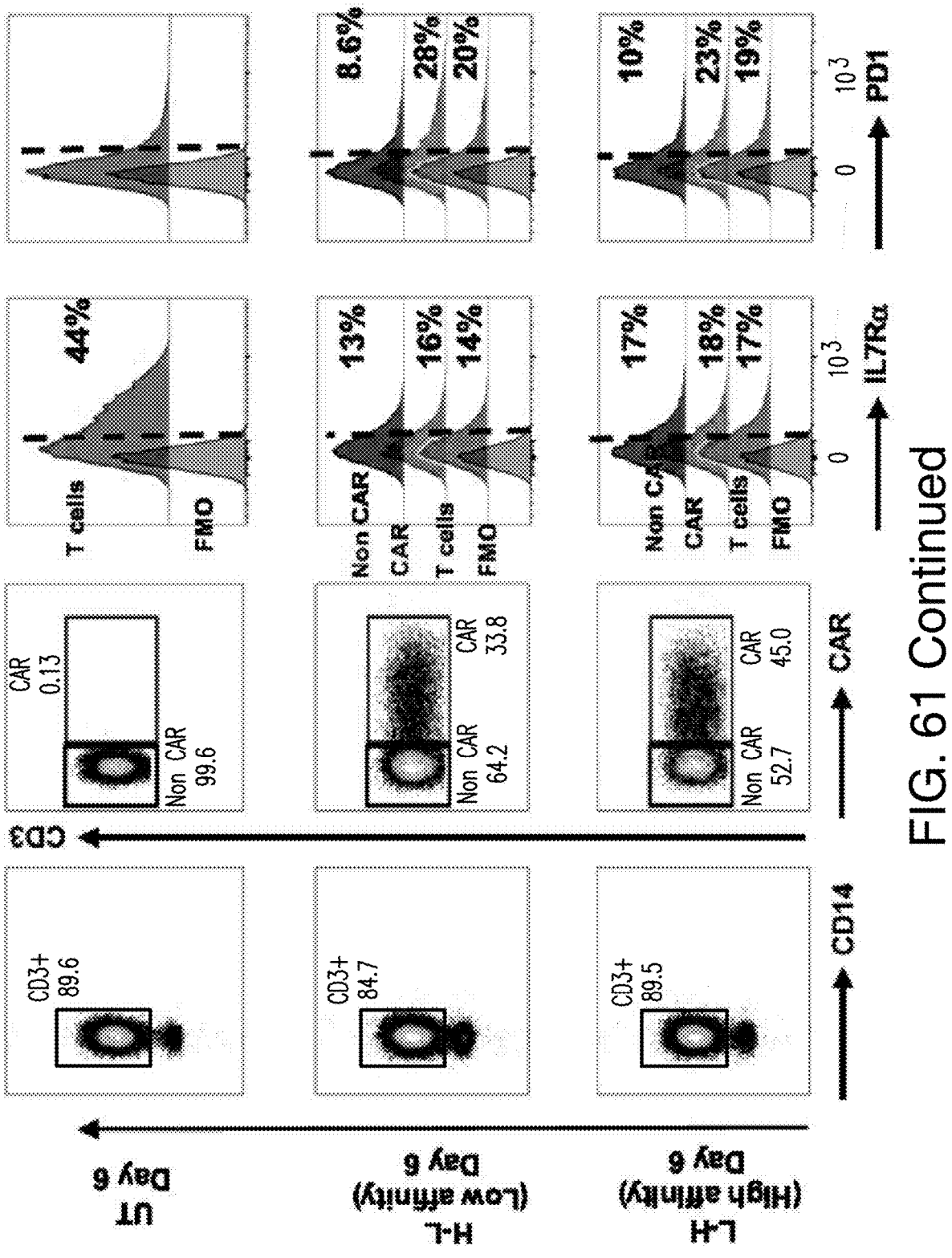
Figure 61:
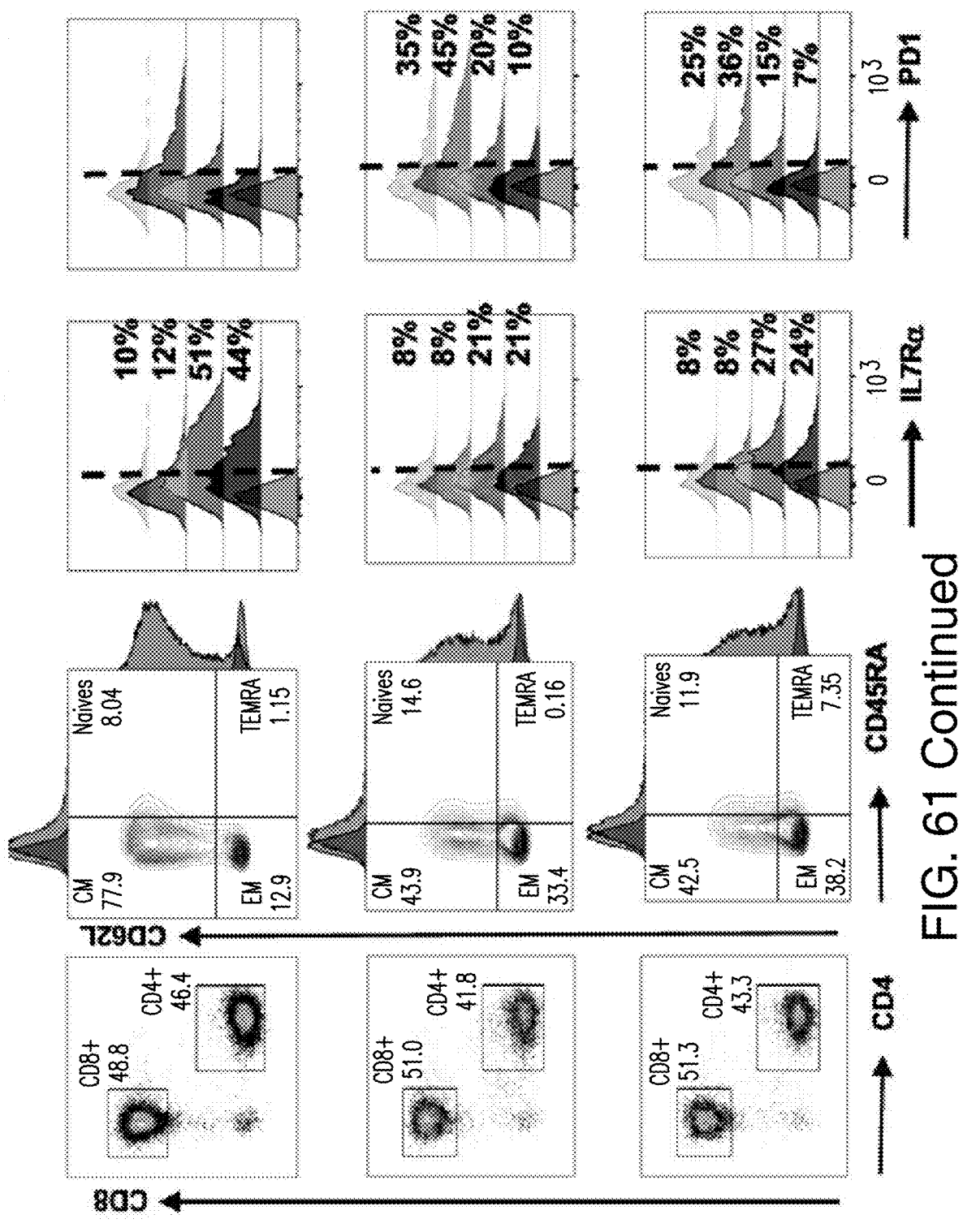

FIG. 61 shows donor H4 T cells CAR transduction percentage, IL7R expression percentage, PD1 expression percentage in CD4 and CD8 T cells on day 6 in donor T cells transduced with low- and high-affinity CARs.

Figure 62:
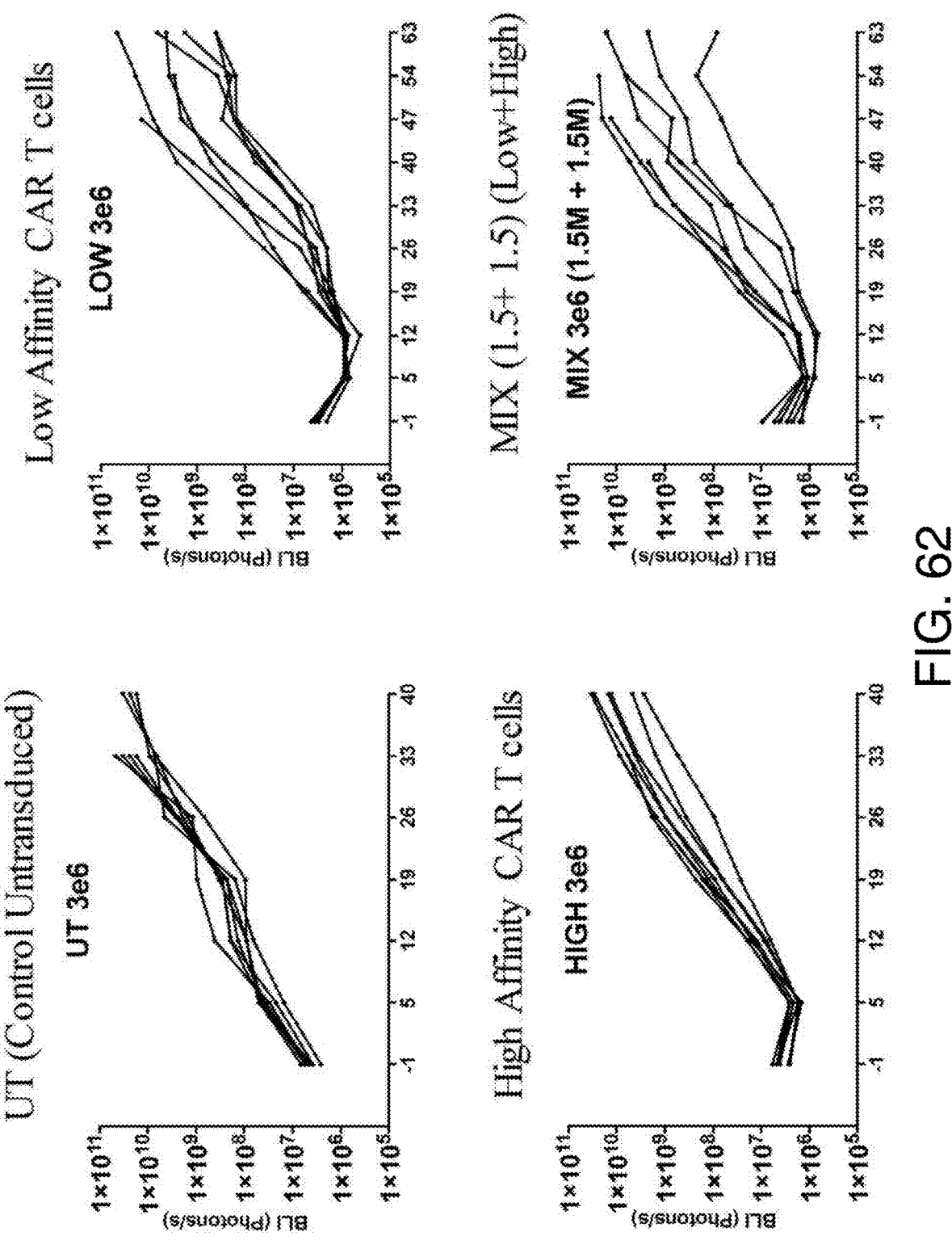

FIG. 62 shows tumor bioluminescence imaging (BLI) data of mice having T-ALL and received CAR T cell treatment. T-ALL was established in mice using DND-41 cancer cells that were administered by tail vein. Mice having established T-ALL were treated with a single dose of either control untransduced (UT) 3×10$^6$ T cells, 3×10$^6$ high-affinity IL7R CAR T cells (HIGH), 3×10$^6$ low-affinity IL7R CAR T cells (LOW), or a mixture of high (1.5×10$^6$) and low (1.5×10$^6$) affinity CAR T cells (MIX). Tumor burden progression or regression was monitored by tumor bioluminescence imaging (BLI).

Figure 63:
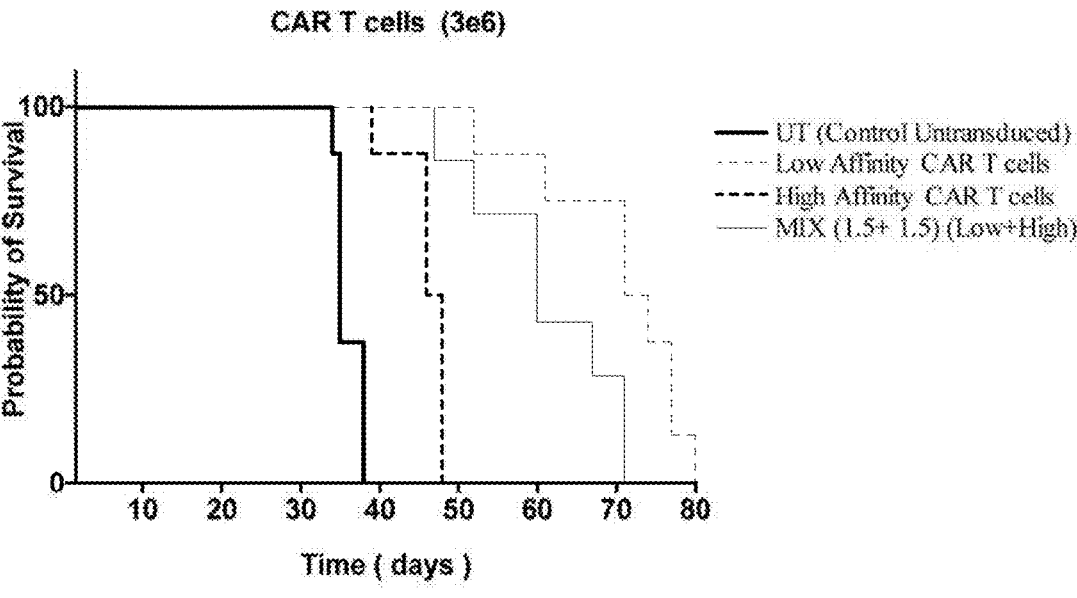

FIG. 63 shows that mice treated with 3×10$^6$ low-affinity CAR T cells, the mixture of high and low binding affinity CAR T cells, and high-affinity CAR T cells had longer median survival as compared to control mice.

Figure 64:
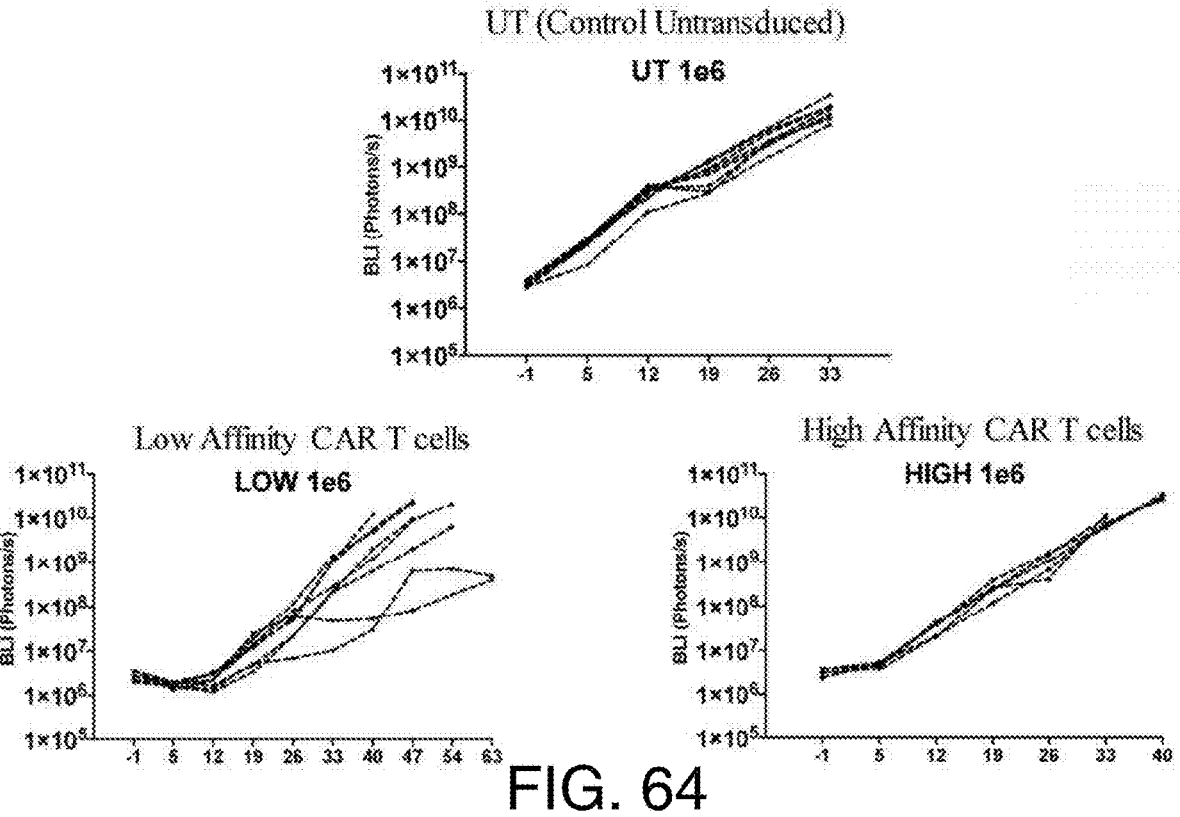

FIG. 64 shows tumor bioluminescence imaging (BLI) data of mice having T-ALL and received CAR T cell treatment. T-ALL was established in mice using DND-41 cancer cells that were administered by tail vein. Mice having established T-ALL were treated with a single dose of either control untransduced (UT) 1×10$^6$ T cells, 1×10$^6$ high-affinity IL7R CAR T cells (HIGH), or 1×10$^6$ low-affinity IL7R CAR T cells (LOW). Tumor burden progression or regression was monitored by tumor bioluminescence imaging (BLI).

Figure 65:
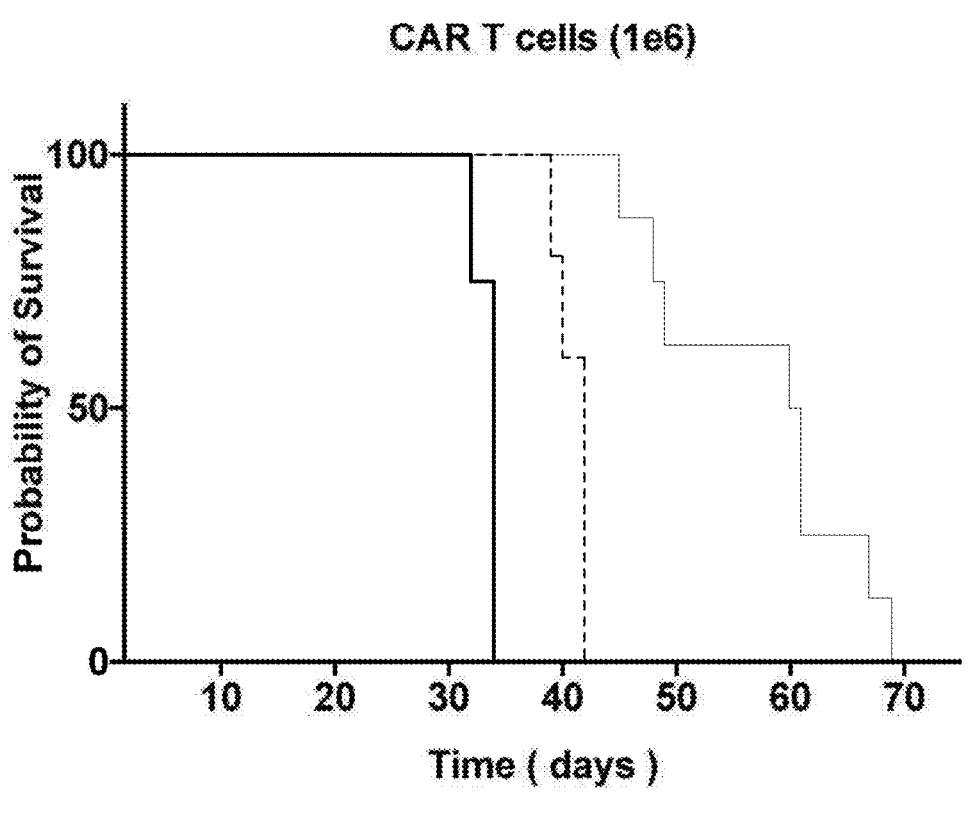

FIG. 65 shows that mice treated with 1×10$^6$ low-affinity CAR T cells or high-affinity CAR T cells had longer median survival compared to mice treated with UT control T cells.

Figure 66:
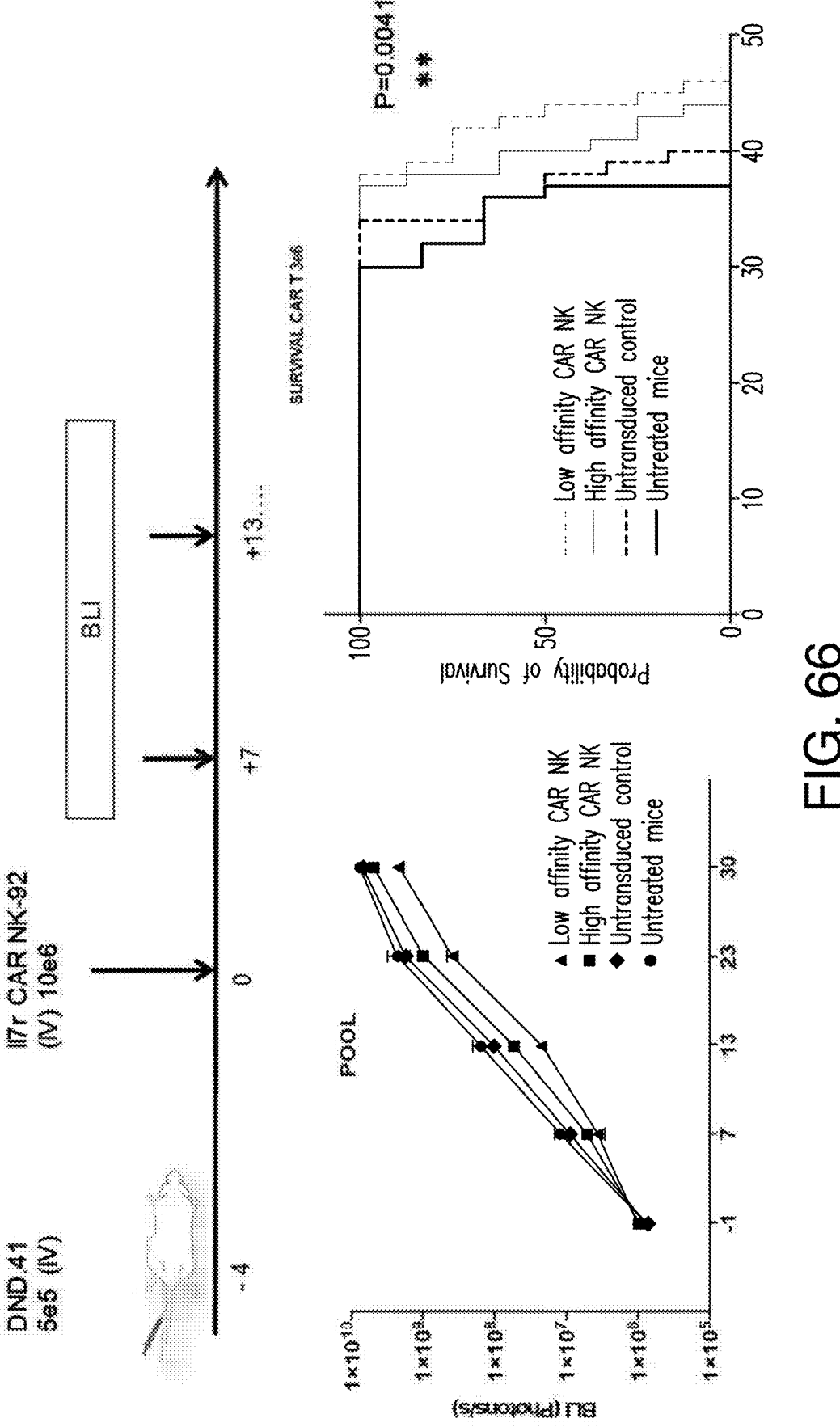

FIG. 66 shows the survival curve and BLI measurements of mice having T-ALL and received CAR NK cell treatment. T-ALL was established in mice using DND-41 cancer cells that were administered by tail vein. Mice with established T-ALL were treated with a single dose of CAR NK cells with either 1×10$^7$ control untransduced (UT) NK cells, 1×10$^7$ high-affinity IL7R CAR NK cells, or 1×10$^7$ low-affinity IL7R CAR NK cells. Tumor burden progression or regression is followed by tumor bioluminescence imaging (BLI). Mice treated with Car-NK cells showed prolongation of median survival compared to control mice.

Figure 67A:
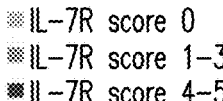
Figure 67A:
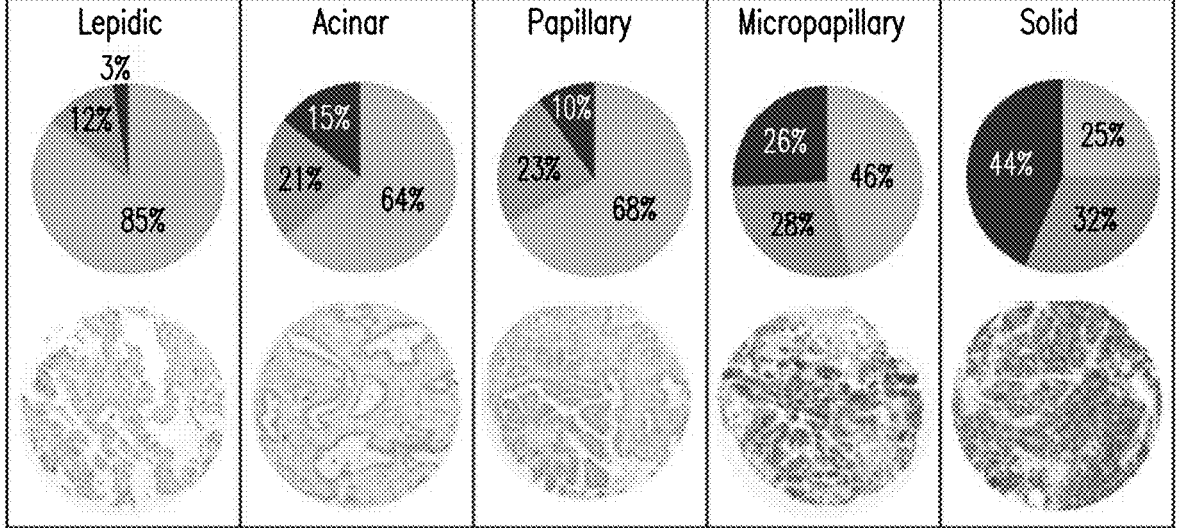
Figure 67B:
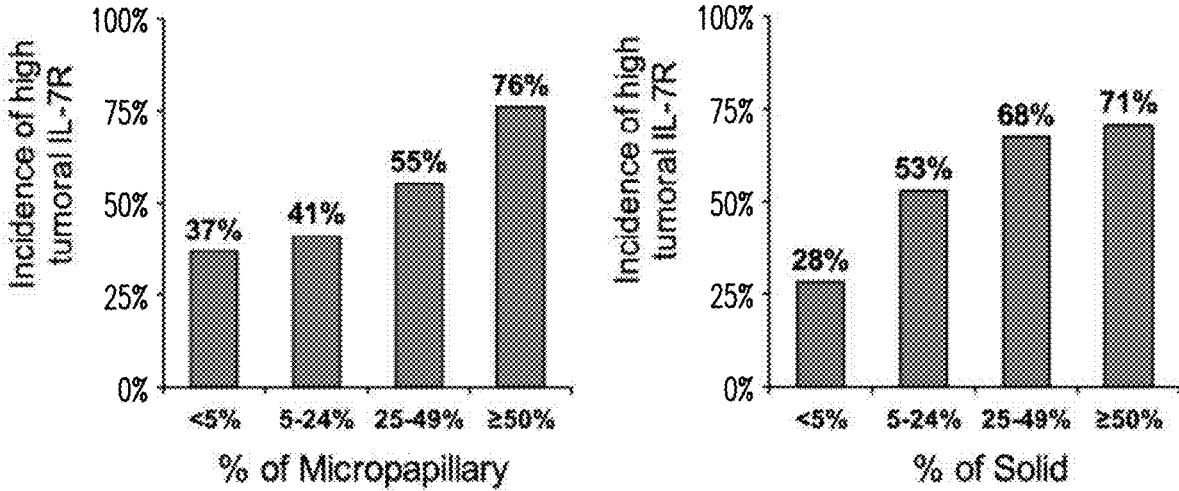
Figure 67C:
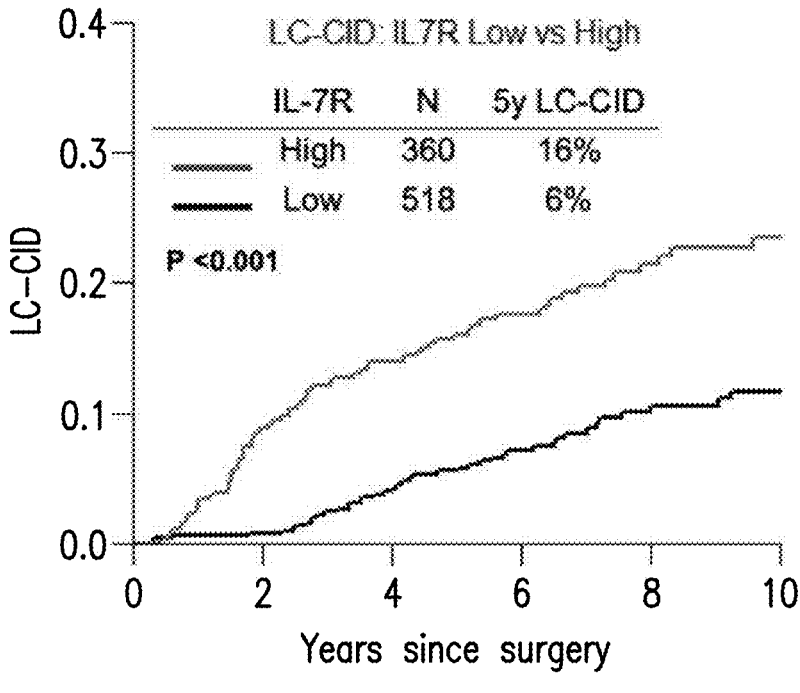
Figure 67D:
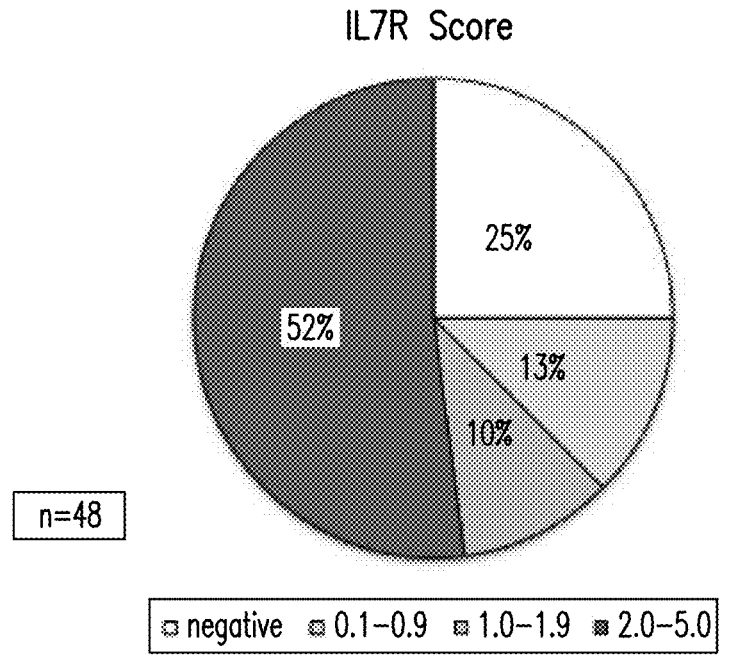

FIGS. 67A-67D show that Patients with high tumoral IL-7R expression were associated with high-grade histologic patterns and worse outcome. FIG. 67A represents IHC staining result of lung cancer tissues. FIG. 67B shows that the percentage of patients with high tumoral IL-7R expression increased as micropapillary pattern's percentage or solid pattern's percentage increased. FIG. 67C shows that patients with high tumoral IL-7R expression had higher risk of LC-CID compared with those with low tumoral IL-7R expression. FIG. 67D shows that tumoral high IL-7R expression was confirmed in biphasic and sarcomatoid mesothelioma patients.

Figure 68A:
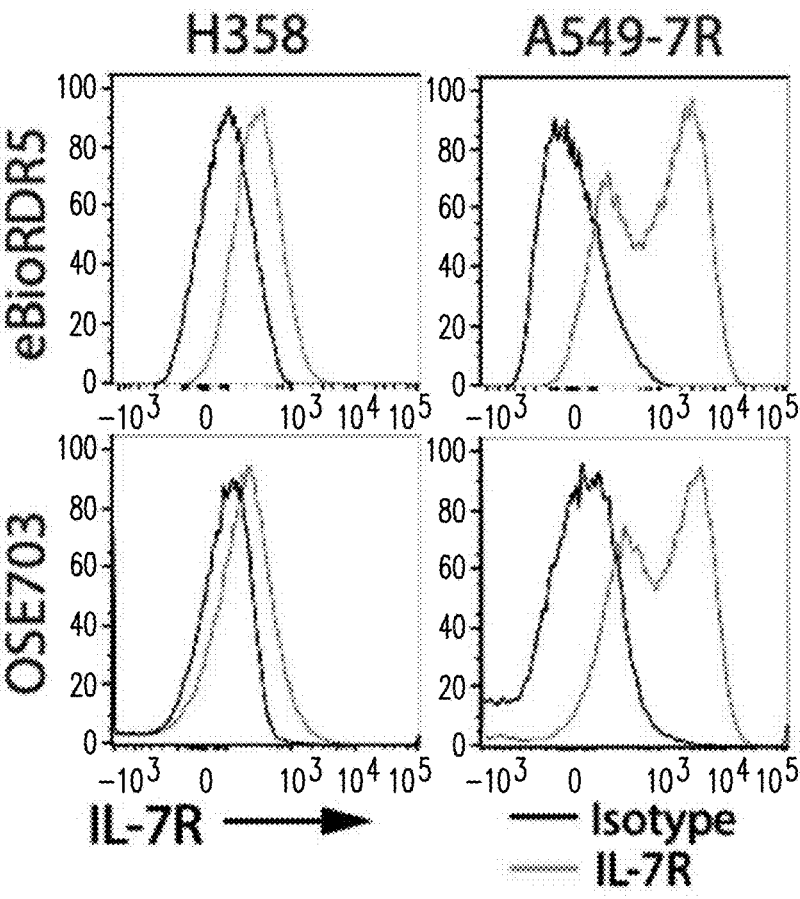
Figure 68B:
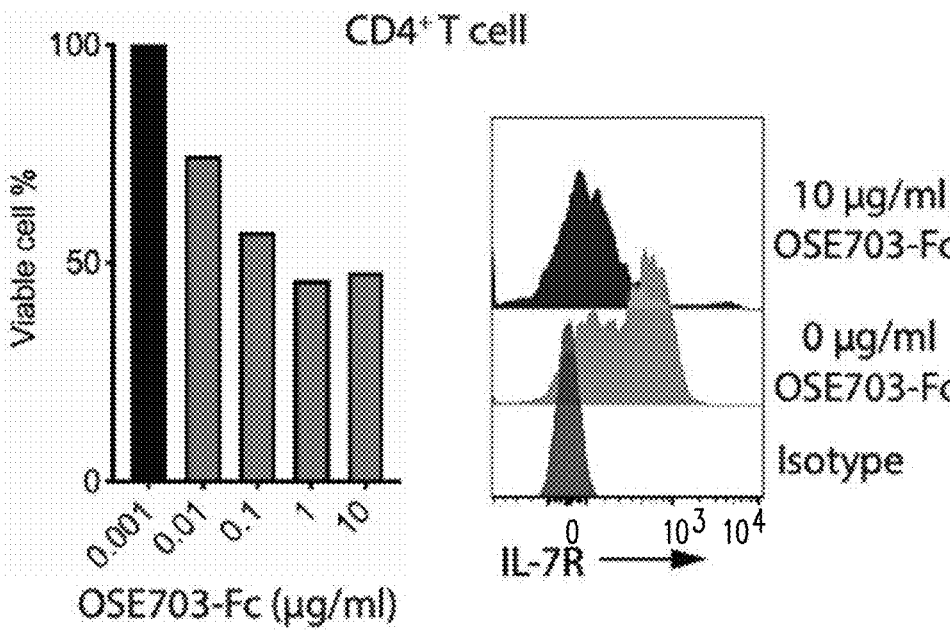
Figures 68C, 68D:
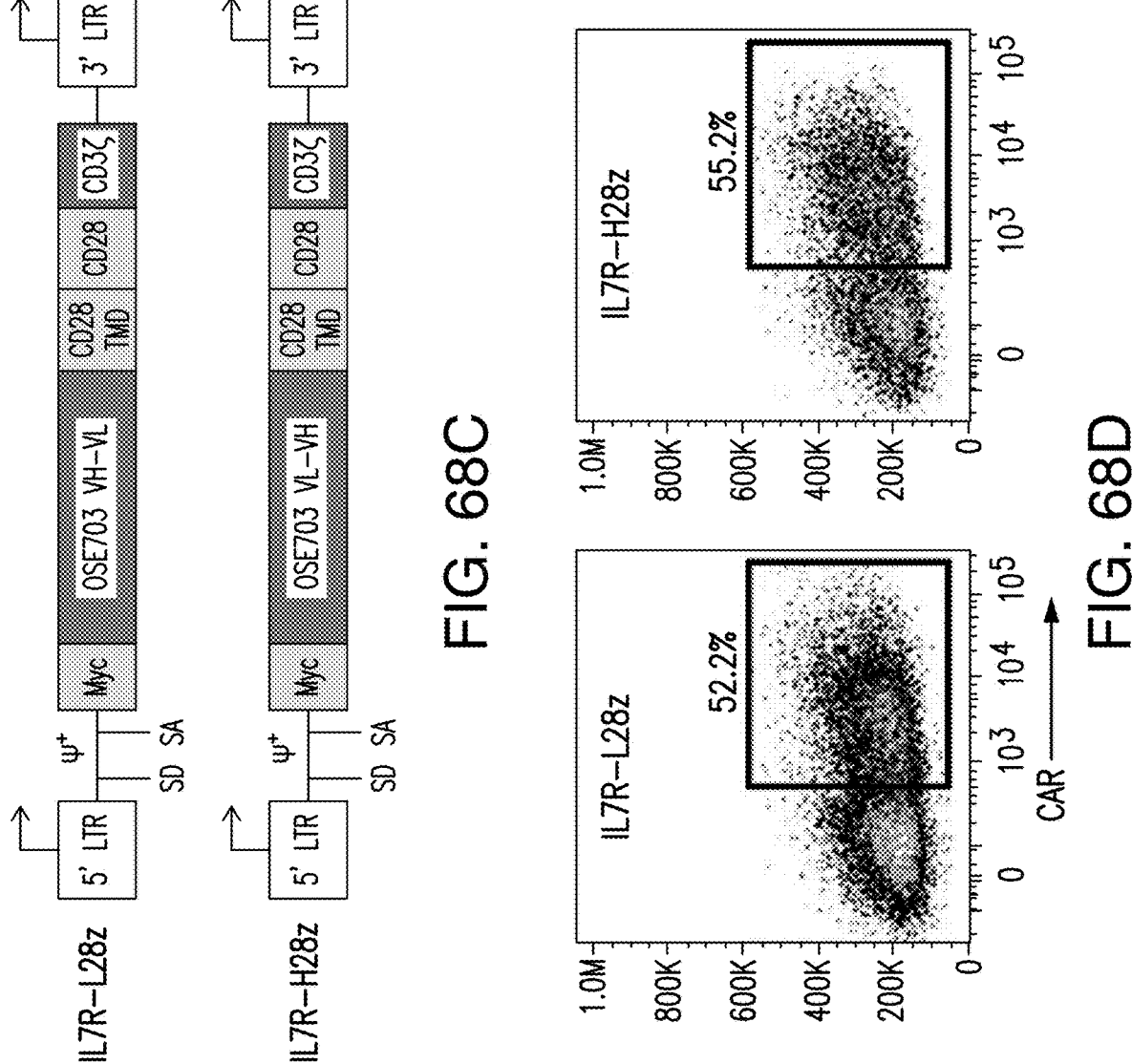
Figure 68E:
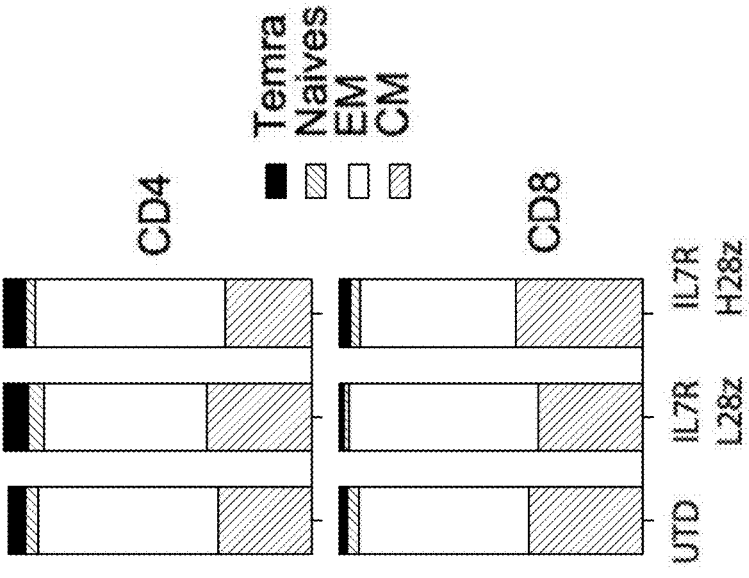
Figure 68E:
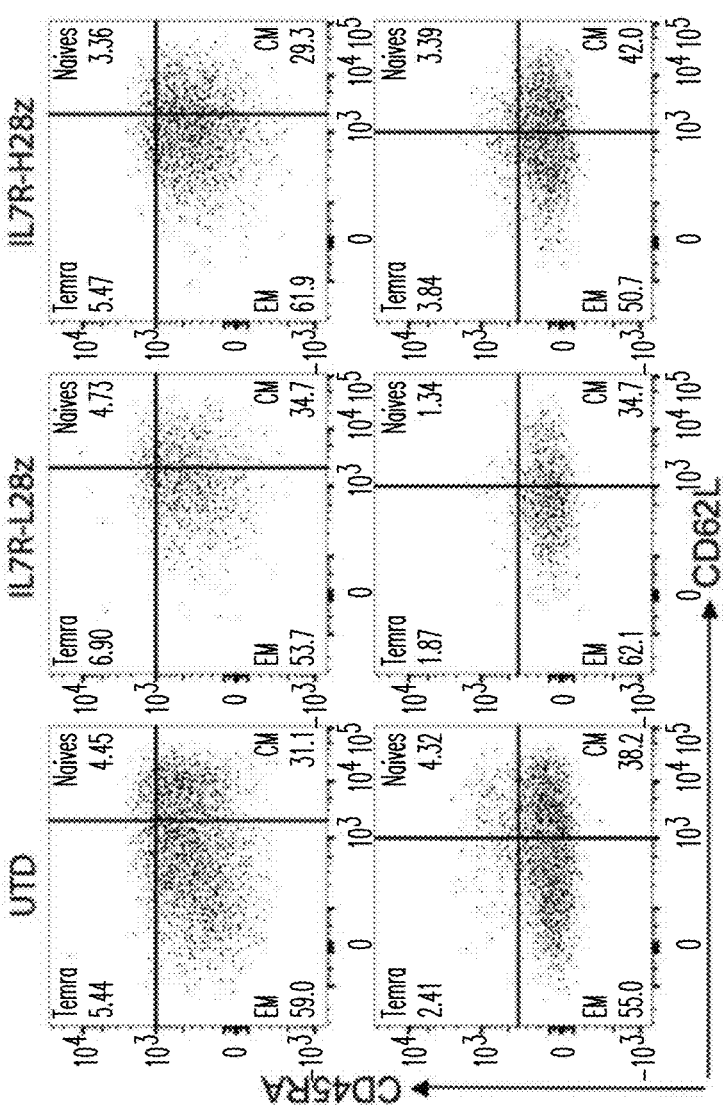

FIGS. 68A-68E show the generation of IL7R CAR T cells. FIG. 68A shows that both OSE703 antibody and commercial IL-7R antibody detected same expression levels of Endogenous IL-7R in H358 cells and overexpressed IL-7R in A549 cells. FIG. 68B shows that after incubation of 4 hours, OSE703-IgG1 induce ADCC against IL-7R+ cells by NK 92-176V cells (E:T=5:1) in a dose-dependent manner. In OSE703-IgG1 treated groups, the viable cell numbers reduced (left) and IL-7R levels decreased (right). FIG. 68C shows the schematic structure of the retroviral vectors SFG encoding the IL7R-L28z and IL7R-H28z CARs. FIG. 68D shows the representative expression of the IL7R-L28z and IL7R-H28z CARs in transduced human T cells. FIG. 68E shows that IL7R-L28z and IL7R-H28z CAR T cells contained central-memory, effector-memory, and T stem cell memory, without significant differences. UTD, untransduced. Data represent from at least two independent experiments with two different donors.

Figures 69A, 69B:
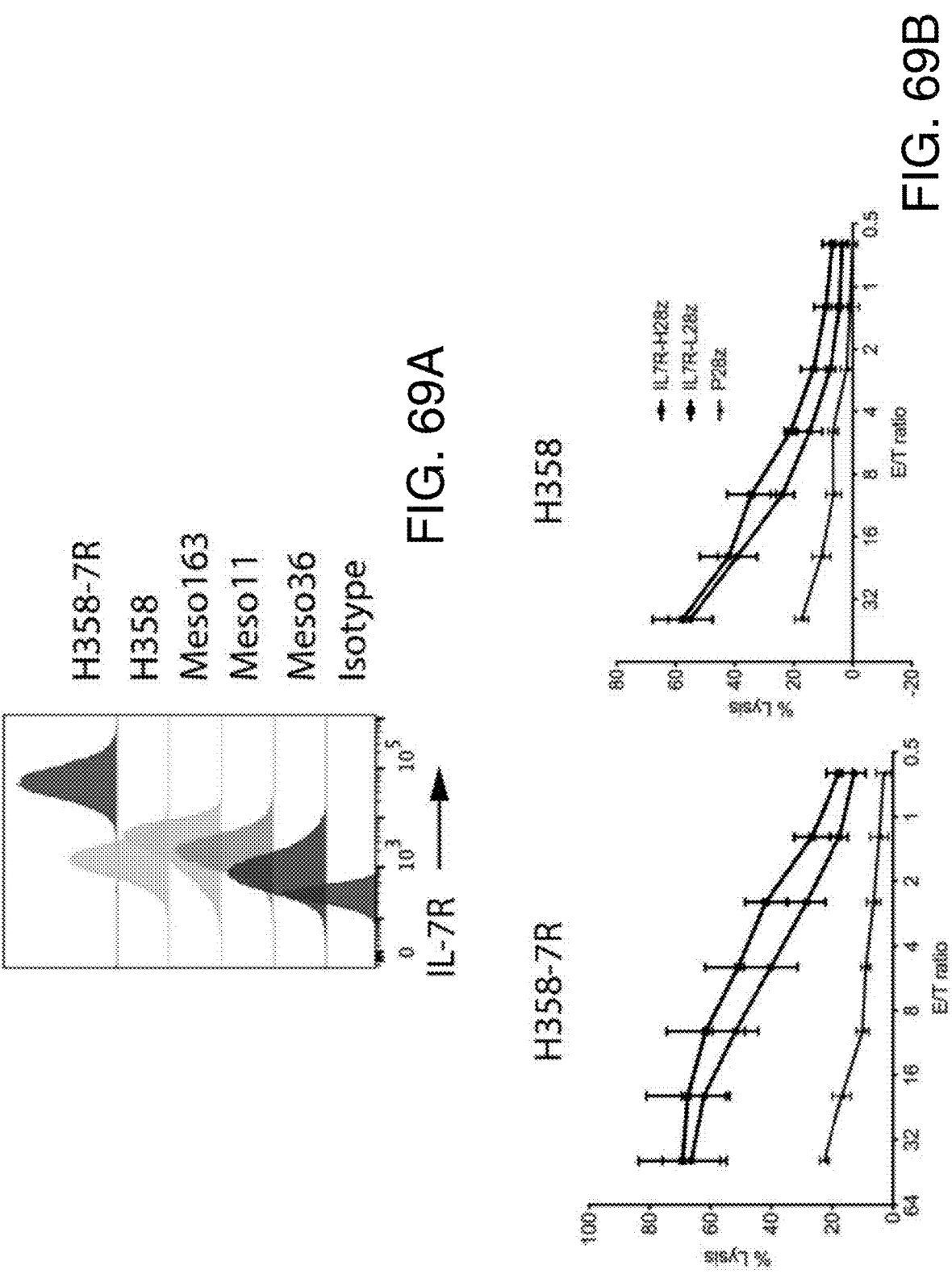
Figure 69C:
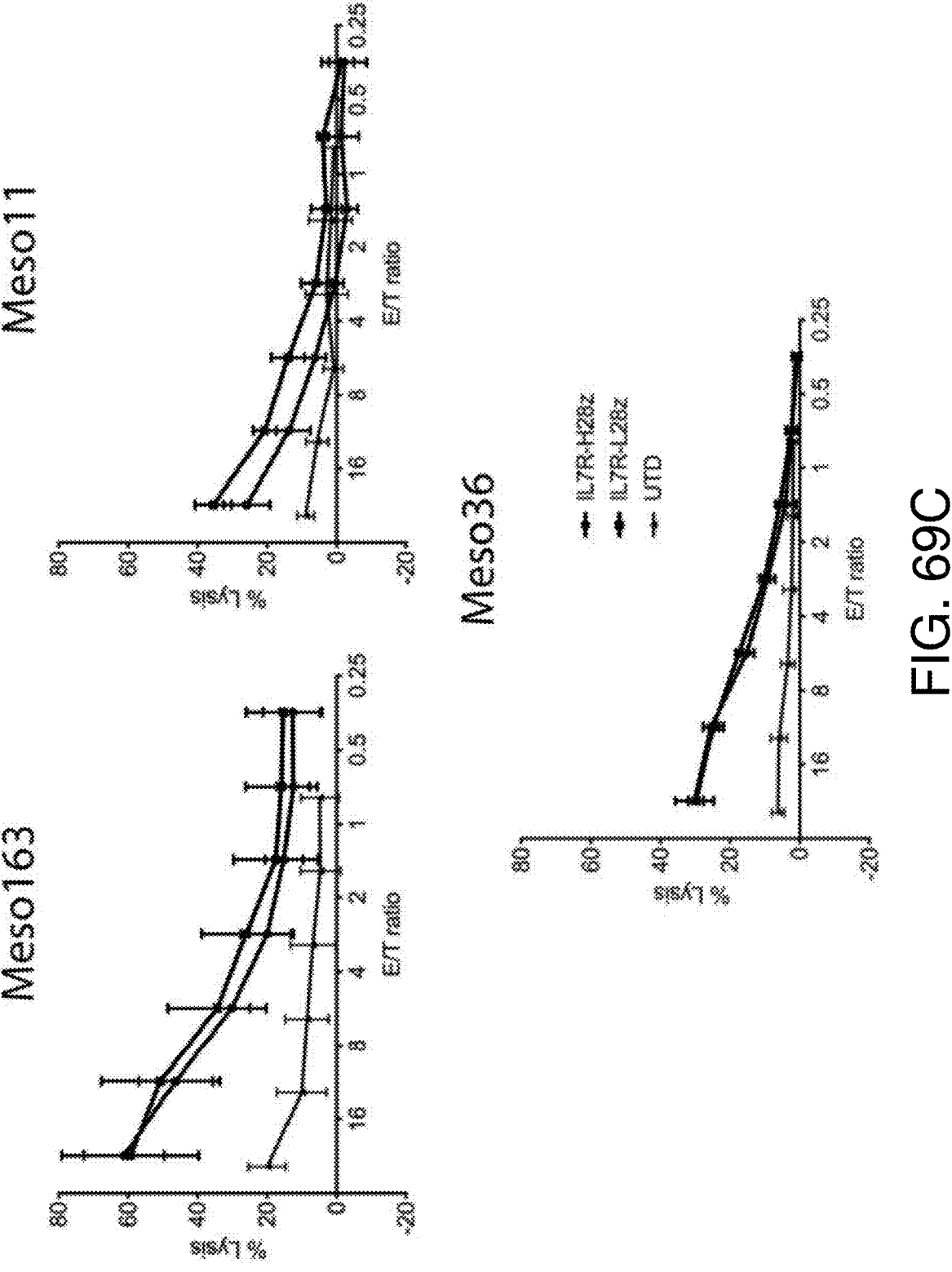
Figures 69D, 69E:
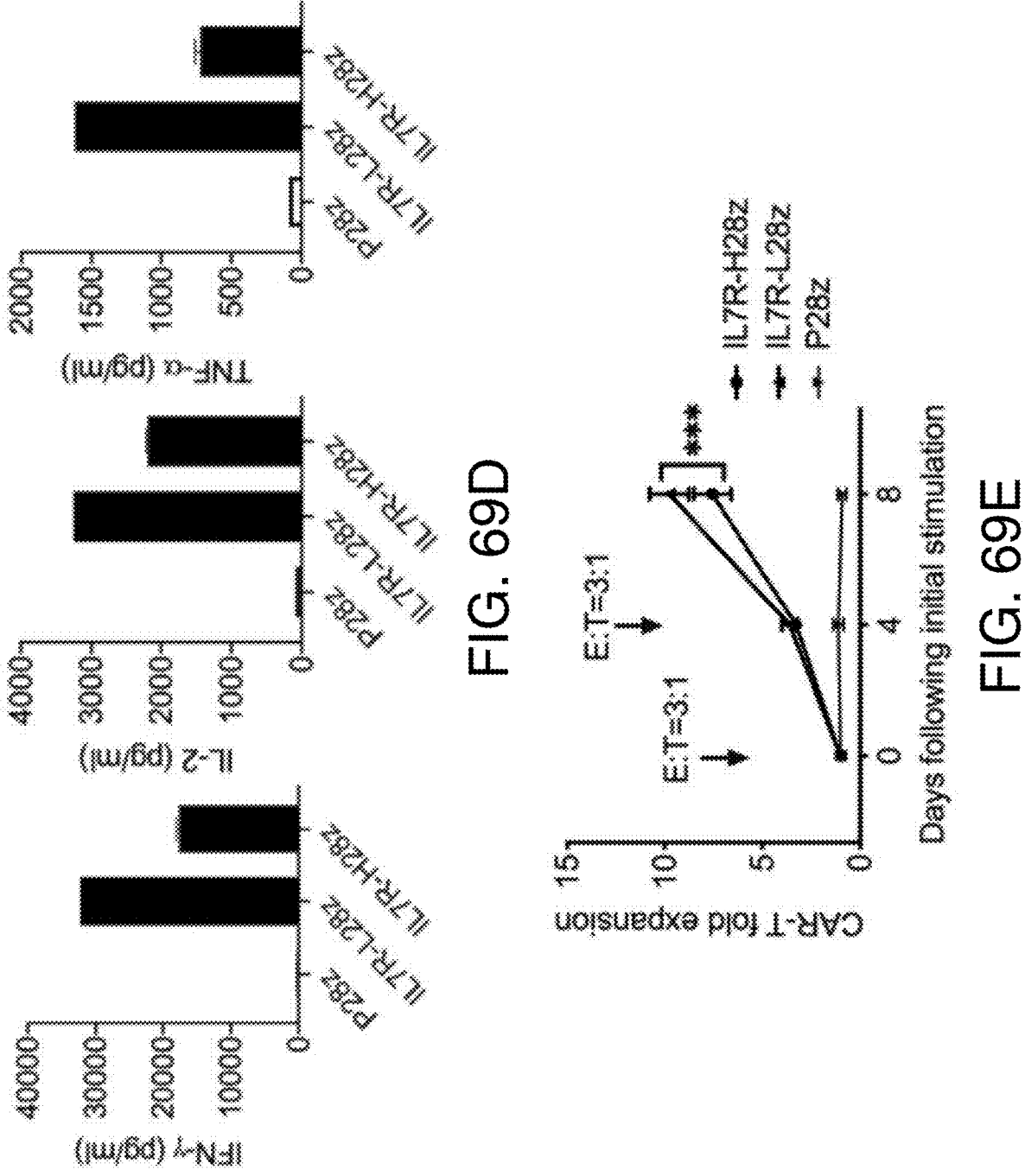

FIGS. 69A-69E show characteristics and specificity of IL7R CAR T cells. FIG. 69A shows IL-7R expression levels in H358 and H358-7R lung cancer cells, and in Meso163, Meso11 and Meso36 mesothelioma cells. FIGS. 69B and 69C show that both IL7R-L28z and IL7R-H28z CAR T cells had cytotoxic activity to lung cancer cells and mesothelioma cells with different IL-7R level, as measured by chromium-release assays. FIG. 69D shows the summary of released TNF-α, IFN-γ and IL-2 assessed by Luminex assay, after 18 hours co-culture of CAR T cells with IL-7R[+] cells. FIG. 69E shows that cumulative cell counts indicated IL7R-L28z and IL7R-H28z CARs facilitate robust T cell accumulation upon stimulation with IL-7R[+] target cells for every 4 days. UTD, untransduced. All data are means±SD. Data represent from at least two independent experiments with two different donors. Two-way ANOVA, ***p<0.001.

Figure 70A:
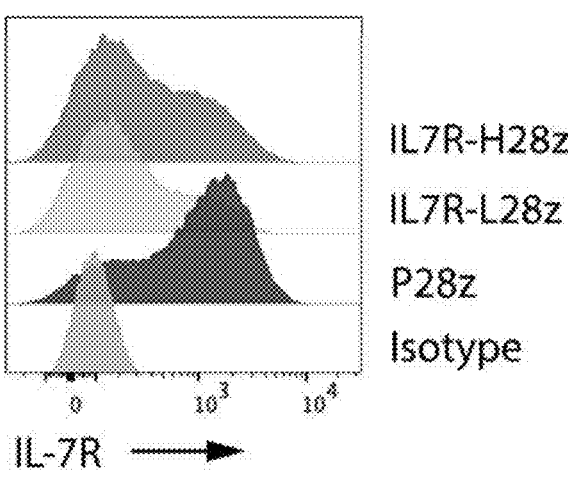
Figure 70B:
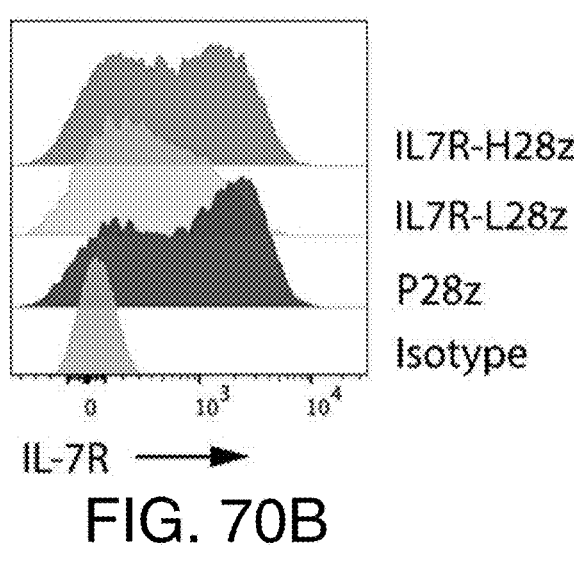
Figure 70C:
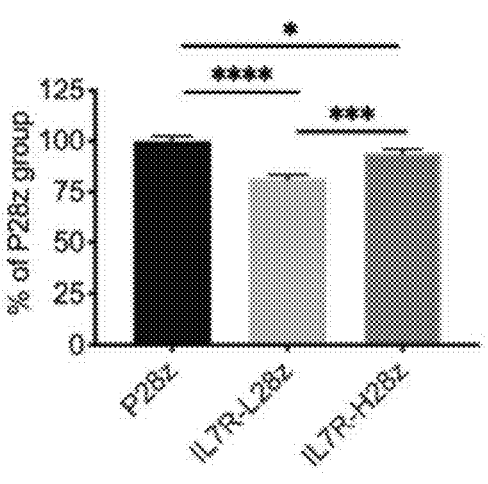
Figure 70D:
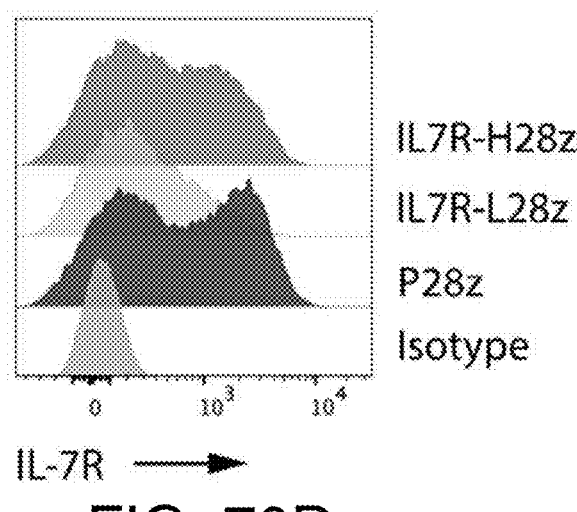
Figure 70E:
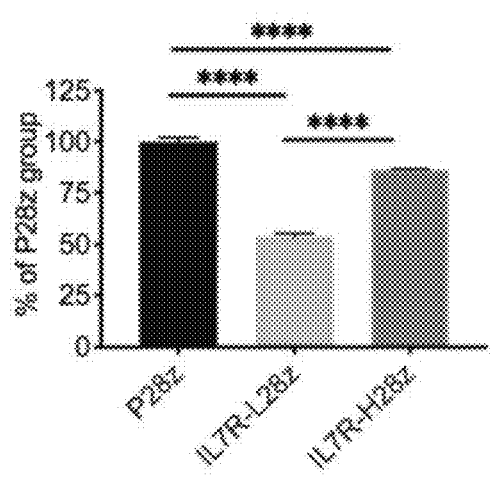

FIGS. 70A-70E show that IL7R-L28z and IL7R-H28z CAR T cells produced limited fratricide to high IL-7R T cells. FIG. 79A shows that as compared with P28z control, IL-7R levels in IL7R-L28z and IL7R-H28z CAR T cells were decreased. FIGS. 70B and 70C show that CellTrace labeled autologous T cell were co-cultured with different CAR T cells for 4 hours, then the cell numbers (FIG. 70B) and IL-7R (FIG. 70C) levels of labeled autologous T were investigated (n=3). FIGS. 70D and 70E show that CellTrace labeled autologous T cell were co-cultured with different CAR T cells for 18 hours, then the cell numbers (FIG. 70D) and IL-7R (FIG. 70E) levels of labeled autologous T were investigated (n=3). As compared with P28z group, the high IL-7R autologous T cells were eradiated in IL7R-L28z and IL7R-H28z CAR T groups. All data are means±SD. Data represent from at least three independent experiments with three different donors. Two-way ANOVA, *p<0.05, *p<0.001, **p<0.0001.

Figures 71A, 71B:
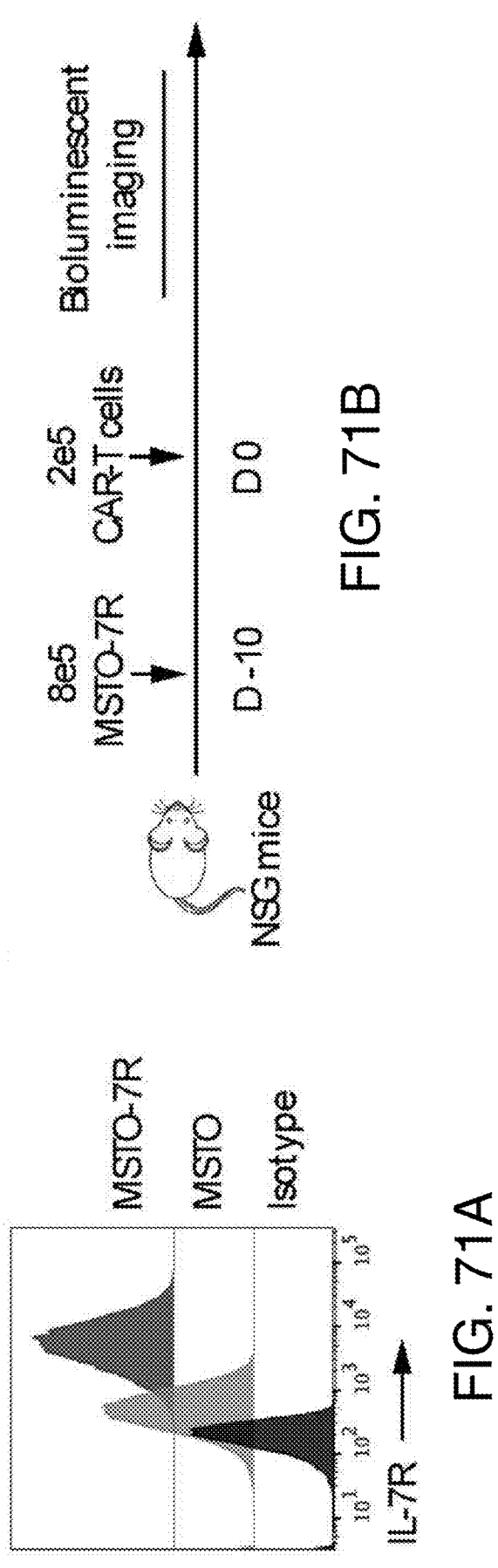
Figures 71C, 71D:
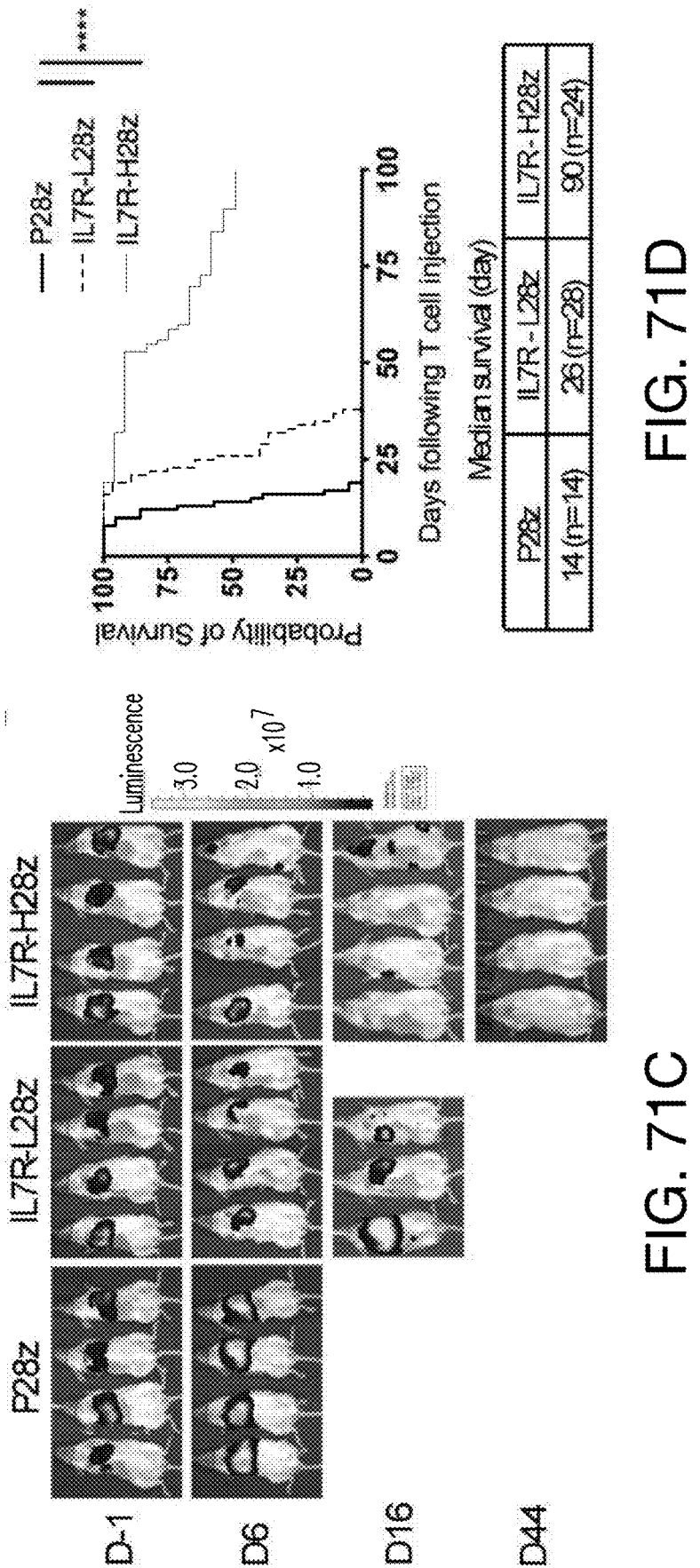
Figures 71E, 71F:
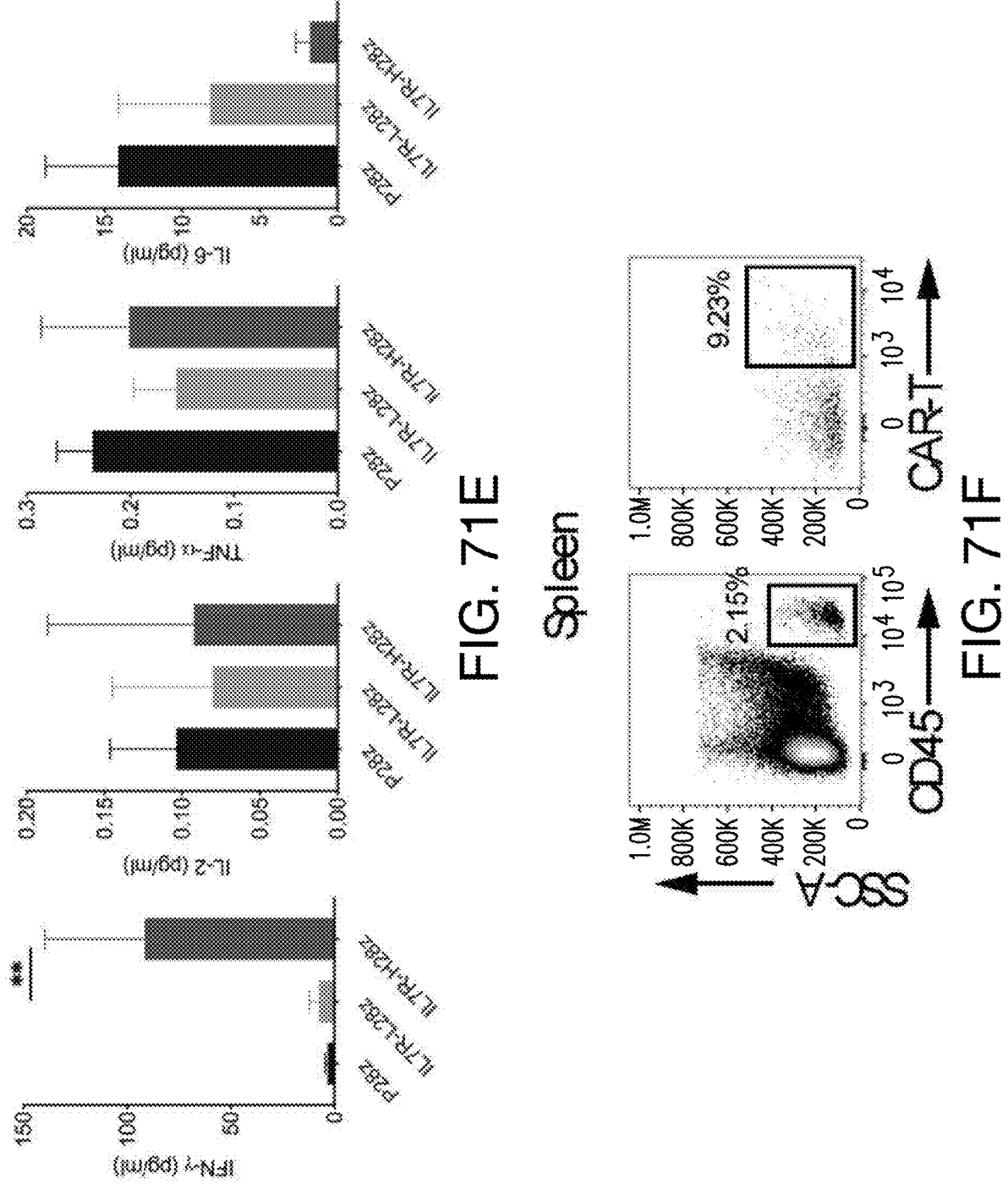

FIGS. 71A-71F show in vivo antitumor activity of IL7R CAR T cells in orthotopic mesothelioma mouse model. FIG. 71A shows IL-7R expression levels in MSTO cells and IL-7R over-expressed MSTO-7R cells. FIG. 71B shows the schema of the MPM orthotopic xenograft model, where tumor cells and CAR T cells were administered by pleural injection. FIG. 71C shows bioluminescence flux of mice at representative time points, indicating tumor burden. FIG. 71D shows that mice with established pleural tumor were treated with a single dose of 2×10[5] CAR T cells. Kaplan-Meier survival analysis comparing the in vivo efficacy of P28z, IL7R-L28z and IL7R-H28z CAR T cells. Statistical significance was determined by Mantel-Cox test, **P<0.0001. FIG. 71E shows that 10 days post CAR T cell administration, plasma was collected to measure cytokine concentrations of IFN-γ, IL-2, TNF-α and IL-6. N=4 mice for each group, error bar indicate means±SD. One-way ANOVA, p<0.01. FIG. 71F shows that 100 days post CAR T cell administration, IL7R-H28z CAR T cells were persistent in the spleen of mouse without any tumor burden.

Figures 72A, 72B:
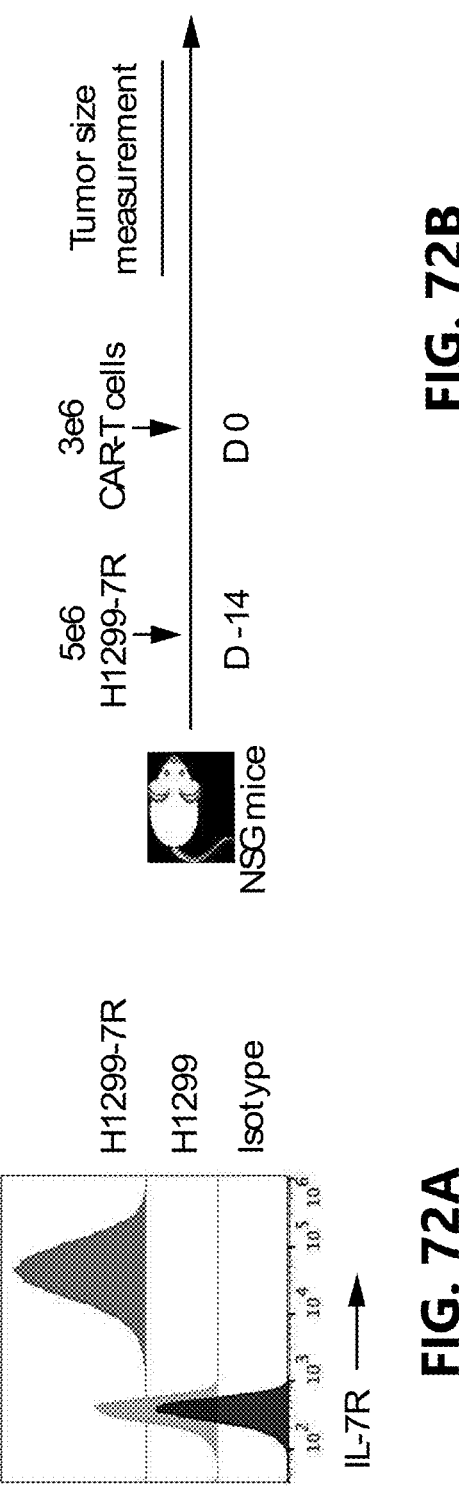
Figures 72C, 72D:
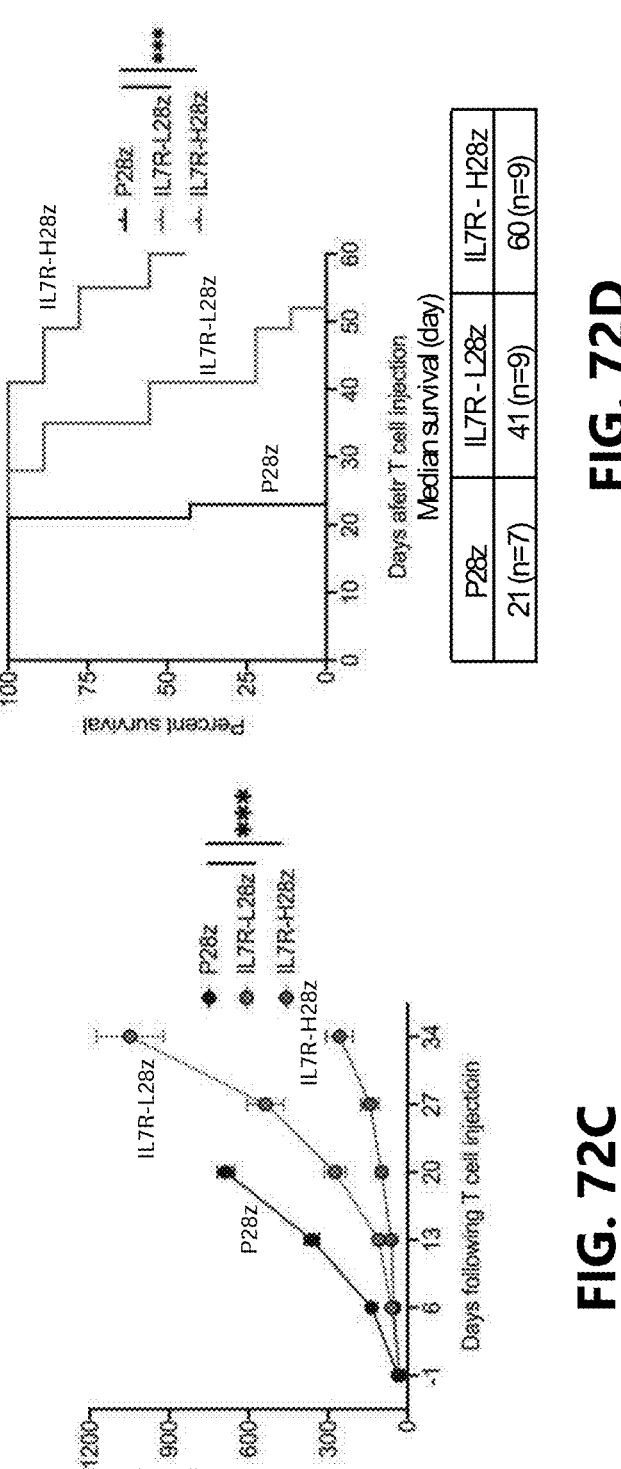

FIGS. 72A-72D show in vivo antitumor activity of IL7R CAR T cells in lung cancer xenograft mouse model. FIG. 72A shows IL-7R expression levels in H1299 cells and IL-7R over-expressed H1299-7R cells. FIG. 72B shows schema of the lung cancer xenograft model, where tumor cells were administered by subcutaneous injection (s.c) and CAR T cells were administered by tail vein injection (i.v). FIG. 72C shows that mice with established subcutaneous tumor were treated with a single dose of 3×10[6] CAR T cells. Tumor size were measured weekly after tumor engraftment. Data are shown as means±SD. N=14-18 per group. Two-way ANOVA, *p<0.001. FIG. 72D shows mice with established pleural tumor were treated with a single dose of 3×10[6] CAR T cells. Kaplan-Meier survival analysis comparing the in vivo efficacy of P28z, IL7R-L28z and IL7R-H28z CAR T cells. Statistical significance was determined by Mantel-Cox test, *P<0.001.

5. DETAILED DESCRIPTION

The present disclosure provides uses of cells comprising an antigen-recognizing receptor (e.g., a chimeric antigen receptor (CAR)) that specifically targets CD127 for treatments, e.g., for treating neoplasia. The cells can be immunoresponsive cells, e.g., genetically modified immunoresponsive cells (e.g., T-cells or NK cells).

Non-limiting embodiments of the present disclosure are described by the present specification and Examples.

For purposes of clarity of disclosure and not by way of limitation, the detailed description is divided into the following subsections:

5.1. Definitions;
    5.2. CD127;
    5.3. Antigen-Recognizing Receptors;
    5.4. Cells;
    5.5. Compositions and Vectors;
    5.6. Polypeptides;
    5.7. Formulations and Administration; and
    5.8. Methods of Treatment.

5.1 Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

By "immunoresponsive cell" is meant a cell that functions in an immune response or a progenitor, or progeny thereof. In certain embodiments, the immunoresponsive cell is a cell of lymphoid lineage. Non-limiting examples of cells of lymphoid lineage include T-cells, Natural Killer (NK) cells, B cells, and stem cells from which lymphoid cells may be differentiated. In certain embodiments, the immunoresponsive cell is a cell of myeloid lineage.

By "activates an immunoresponsive cell" is meant induction of signal transduction or changes in protein expression in the cell resulting in initiation of an immune response. For example, when CD3 Chains cluster in response to ligand binding and immunoreceptor tyrosine-based inhibition motifs (ITAMs) a signal transduction cascade is produced. In certain embodiments, when an endogenous TCR or an exogenous CAR binds to an antigen, a formation of an immunological synapse occurs that includes clustering of many molecules near the bound receptor (e.g. CD4 or CD8, CD3γ/δ/ε/ζ, etc.). This clustering of membrane bound signaling molecules allows for ITAM motifs contained within the CD3 chains to become phosphorylated. This phosphorylation in turn initiates a T-cell activation pathway ultimately activating transcription factors, such as NF-κB and AP-1. These transcription factors induce global gene expression of the T-cell to increase IL-2 production for proliferation and expression of master regulator T-cell proteins in order to initiate a T-cell mediated immune response.

By "stimulates an immunoresponsive cell" is meant a signal that results in a robust and sustained immune response. In various embodiments, this occurs after immune cell (e.g., T-cell) activation or concomitantly mediated through receptors including, but not limited to, CD28, CD137 (4-1BB), OX40, CD40 and ICOS. Receiving multiple stimulatory signals can be important to mount a robust and long-term T-cell mediated immune response. T-cells can quickly become inhibited and unresponsive to antigen. While the effects of these co-stimulatory signals may vary, they generally result in increased gene expression in order to generate long lived, proliferative, and anti-apoptotic T-cells that robustly respond to antigen for complete and sustained eradication.

The term "antigen-recognizing receptor" as used herein refers to a receptor that is capable of recognizing a target antigen (e.g., CD127). In certain embodiments, the antigen-recognizing receptor is capable of activating an immune or immunoresponsive cell (e.g., a T-cell) upon its binding to the target antigen.

As used herein, "complementarity determining regions" or "CDRs" are defined as the complementarity determining region amino acid sequences of an antibody which are the hypervariable regions of immunoglobulin heavy and light chains. See, e.g., Kabat et al., Sequences of Proteins of Immunological Interest, 4th U. S. Department of Health and Human Services, National Institutes of Health (1987), or IMGT numbering system (Lefranc, *The Immunologist* (1999); 7:132-136; Lefranc et al., *Dev. Comp. Immunol.* (2003); 27:55-77). Generally, antibodies comprise three heavy chain and three light chain CDRs or CDR regions in the variable region. CDRs provide the majority of contact residues for the binding of the antibody to the antigen or epitope. In certain embodiments, the CDRs regions are delineated using the Kabat numbering system.

As used herein, the term "single-chain variable fragment" or "scFv" is a fusion protein of the variable regions of the heavy ($V_H$) and light chains ($V_L$) of an immunoglobulin (e.g., mouse or human) covalently linked to form a $V_H$::VL heterodimer. The heavy ($V_H$) and light chains ($V_L$) are either joined directly or joined by a peptide-encoding linker (e.g., 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910-1917 (2008) and WO 2014/087010, the contents of which are hereby incorporated by reference in their entireties. In certain embodiments, the linker is a G45 linker.

In certain embodiments, the linker comprises the amino acid sequence set forth in SEQ ID NO: 1, which is provided below:

```
                                          [SEQ ID NO: 1]
                    GGGGSGGGGSGGGGS
```

In certain embodiments, the linker comprises the amino acid sequence set forth in SEQ ID NO: 2, which is provided below:

```
                                          [SEQ ID NO: 2]
               GGGGSGGGGSGGGGSGGGGS
```

In certain embodiments, the linker comprises the amino acid sequence set forth in SEQ ID NO: 3, which is provided below:

```
                                          [SEQ ID NO: 3]
            GGGGSGGGGSGGGGSGGGGSGGGGS
```

In certain embodiments, the linker comprises the amino acid sequence set forth in SEQ ID NO: 4, which is provided below:

```
                                          [SEQ ID NO: 4]
         GGGGSGGGGSGGGGSGGGGSGGGGSGGGGS
```

Despite removal of the constant regions and the introduction of a linker, scFv proteins retain the specificity of the original immunoglobulin. Single chain Fv polypeptide antibodies can be expressed from a nucleic acid comprising $V_H$- and $V_L$ encoding sequences as described by Huston, et al. Proc. Nat. Acad. Sci. USA, (1988); 85:5879-5883; U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) (2008); 27(6): 455-51; Peter et al., *J Cachexia Sarcopenia Muscle* (2012); August 12; Shieh et al., *J Imunol* (2009); 183(4):2277-85; Giomarelli et al., *Thromb Haemost* (2007); 97(6):955-63; Fife eta., *J Clin Invst* (2006); 116(8):2252-61; Brocks et al., Immunotechnology 1997 3(3):173-84; Moosmayer et al., Ther Immunol 1995 2(10:31-40). Agonistic scFvs having stimulatory activity have been described (Peter et al., *J Biol Chem* (2003); 25278(38):36740-7; Xie et al., Nat Biotech 1997 15(8):768-71; Ledbetter et al., *Crit Rev Immunol* (1997); 17(5-6):427-55; Ho et al., *BioChim Biophys Acta* (2003); 1638(3):257-66).

The term "chimeric antigen receptor" or "CAR" as used herein refers to a molecule comprising an extracellular antigen-binding domain that is fused to an intracellular signaling domain that is capable of activating or stimulating an immunoresponsive cell, and a transmembrane domain. In certain embodiments, the extracellular antigen-binding domain of a CAR comprises an scFv. The scFv can be derived from fusing the variable heavy and light regions of an antibody. Alternatively or additionally, the scFv may be derived from Fab's (instead of from an antibody, e.g., obtained from Fab libraries). In certain embodiments, the scFv is fused to the transmembrane domain, which is fused to the intracellular signaling domain.

By "substantially identical" or "substantially homologous" is meant a polypeptide or nucleic acid molecule exhibiting at least about 50% homologous or identical to a reference amino acid sequence (for example, any of the amino acid sequences described herein) or a reference nucleotide sequence (for example, any of the nucleotide sequences described herein). In certain embodiments, such a sequence is at least about 60%, at least about 65%, at least about 70%, at least about 75%, at least about 80%, at least about 85%, at least about 90%, at least about 95%, at least about 99%, or at least about 100% homologous or identical to the amino acid sequence or the nucleotide sequence used for comparison.

Sequence identity can be measured by using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, iso-leucine, leucine; aspartic acid, glutamic acid, asparagine, glutamine; serine, threonine; lysine, arginine; and phenyl-alanine, tyrosine. In an exemplary approach to determining the degree of identity, a BLAST program may be used, with a probability score between e−3 and e−100 indicating a closely related sequence.

The percent homology between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent homology between two amino acid sequences can be deter-mined using the Needleman and Wunsch (J. Mol. Biol. 48:444-453 (1970)) algorithm which has been incorporated into the GAP program in the GCG software package (avail-able at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the amino acids sequences of the presently disclosed subject matter can further be used as a "query sequence" to perform a search against public databases to, for example, identify related sequences. Such searches can be performed using the XBLAST program (version 2.0) of Altschul, et al. (1990) J. Mol. Biol. 215: 403-10. BLAST protein searches can be performed with the XBLAST program, score=50, wordlength=3 to obtain amino acid sequences homologous to the specified sequences (e.g., heavy and light chain variable region sequences of scFv703) disclosed herein. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

An "effective amount" is an amount sufficient to affect a beneficial or desired clinical result upon treatment. An effective amount can be administered to a subject in one or more doses. In certain embodiments, an effective amount can be an amount that is sufficient to palliate, ameliorate, stabilize, reverse or slow the progression of the disease, or otherwise reduce the pathological consequences of the dis-ease. The effective amount can be determined by a physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the cells administered.

By "modulate" is meant positively or negatively alter. Exemplary modulations include a about 1%, about 2%, about 5%, about 10%, about 25%, about 50%, about 75%, or about 100% change.

By "increase" is meant to alter positively by at least about 5%. An alteration may be by about 5%, about 10%, about 25%, about 30%, about 50%, about 75%, about 100% or more.

By "reduce" is meant to alter negatively by at least about 5%. An alteration may be by about 5%, about 10%, about 25%, about 30%, about 50%, about 75%, or even by about 100%.

The terms "isolated," "purified," or "biologically pure" refer to material that is free to varying degrees from com-ponents which normally accompany it as found in its native state. "Isolate" denotes a degree of separation from original source or surroundings. "Purify" denotes a degree of sepa-ration that is higher than isolation. A "purified" or "biologi-cally pure" protein is sufficiently free of other materials such that any impurities do not materially affect the biological properties of the protein or cause other adverse conse-quences. That is, a nucleic acid or peptide is purified if it is substantially free of cellular material, viral material, or culture medium when produced by recombinant DNA tech-niques, or chemical precursors or other chemicals when chemically synthesized. Purity and homogeneity are typi-cally determined using analytical chemistry techniques, for example, polyacrylamide gel electrophoresis or high-perfor-mance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to dif-ferent isolated proteins, which can be separately purified.

By "isolated cell" is meant a cell that is separated from the molecular and/or cellular components that naturally accom-pany the cell.

The term "antigen-binding domain" as used herein refers to a domain capable of specifically binding a particular antigenic determinant or set of antigenic determinants pres-ent on a cell.

By "neoplasia" is meant a disease characterized by the pathological proliferation of a cell or tissue and its subse-quent migration to or invasion of other tissues or organs. Neoplasia growth is typically uncontrolled and progressive, and occurs under conditions that would not elicit, or would cause cessation of, multiplication of normal cells. Neoplasia can affect a variety of cell types, tissues, or organs, including but not limited to an organ selected from the group consist-ing of bladder, bone, brain, breast, cartilage, glia, esophagus, fallopian tube, gallbladder, heart, intestines, kidney, liver, lung, lymph node, nervous tissue, ovaries, pancreas, pros-tate, skeletal muscle, skin, spinal cord, spleen, stomach, testes, thymus, thyroid, trachea, urogenital tract, ureter, urethra, uterus, and vagina, or a tissue or cell type thereof. Neoplasia include cancers, such as sarcomas, carcinomas, or plasmacytomas (malignant tumor of the plasma cells). The neoplasia can a primary tumor or primary cancer. In addi-tion, the neoplasia can be in metastatic status.

By "receptor" is meant a polypeptide, or portion thereof, present on a cell membrane that selectively binds one or more ligand.

By "recognize" is meant selectively binds to a target. A T-cell that recognizes a tumor can expresses a receptor (e.g., a TCR or CAR) that binds to a tumor antigen.

By "reference" or "control" is meant a standard of com-parison. For example, the level of scFv-antigen binding by a cell expressing a CAR and an scFv may be compared to the level of scFv-antigen binding in a corresponding cell expressing CAR alone.

By "signal sequence" or "leader sequence" is meant a peptide sequence (e.g., 5, 10, 15, 20, 25 or 30 amino acids) present at the N-terminus of newly synthesized proteins that directs their entry to the secretory pathway.

By "specifically binds" or "specifically binds to" or "specifically target" is meant a polypeptide or a fragment thereof that recognizes and/or binds to a biological molecule of interest (e.g., a polypeptide, e.g., a CD127 polypeptide), but which does not substantially recognize and/or bind to other molecules in a sample, for example, a biological sample, which naturally includes a presently disclosed polypeptide (e.g., a CD127 polypeptide).

The terms "comprises", "comprising", and are intended to have the broad meaning ascribed to them in U.S. Patent Law and can mean "includes", "including" and the like.

As used herein, "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

An "individual" or "subject" herein is a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

Other aspects of the presently disclosed subject matter are described in the following disclosure and are within the ambit of the presently disclosed subject matter.

5.2. CD127

CD127, also known as interleukin-7 receptor subunit alpha, IL7RA, IL-7Ralpha, is a 51 KD cytokine receptor, which is a subunit of the functional Interleukin-7 receptor (IL-7R) and Thymic Stromal Lymphopoietin (TSLP) receptors. Interleukin-7 receptor (IL-7R) is expressed on various cell types, including naive and memory T-cells and many others. IL-7 and its receptor IL-7R, which is a heterodimer of IL-7Rα and γc, are essential for normal lymphoid development (Jacobs et al., *J Immunol.* 2010; 184(7):3461-3469). Defects in IL-7R may be associated with severe combined immunodeficiency (SCID).

In certain embodiments, the presently disclosed antigen-recognizing receptor binds to a human CD127. In certain embodiments, the human CD127 comprises or consists of the amino acid sequence with a NCBI Reference No: NP_002176.2 (SEQ ID NO: 5), or a fragment thereof.

SEQ ID NO: 5 is provided below:

```
                                              [SEQ ID NO: 5]
MTILGTTFGMVFSLLQVVSGESGYAQNGDLEDAELDDYSF

SCYSQLEVNGSQHSLTCAFEDPDVNITNLEFEICGALVEV

KCLNFRKLQEIYFIETKKFLLIGKSNICVKVGEKSLTCKK

IDLTTIVKPEAPFDLSVVYREGANDFVVTFNTSHLQKKYV

KVLMHDVAYRQEKDENKWTHVNLSSTKLTLLQRKLQPAAM

YEIKVRSIPDHYFKGFWSEWSPSYYFRTPEINNSSGEMDP

ILLTISILSFFSVALLVILACVLWKKRIKPIVWPSLPDHK

KTLEHLCKKPRKNLNVSFNPESFLDCQIHRVDDIQARDEV

EGFLQDTFPQQLEESEKQRLGGDVQSPNCPSEDVVITPES

FGRDSSLTCLAGNVSACDAPILSSSRSLDCRESGKNGPHV

YQDLLLSLGTTNSTLPPPFSLQSGILTLNPVAQGQPILTS

LGSNQEEAYVTMSSFYQNQ
```

In certain embodiments, the CD127 comprises or consists of an amino acid sequence that is at least about 80%, at least about 85%, at least about 90%, at least about 95%, at least about 96%, at least about 97%, at least about 98%, at least about 99%, or at least about 100% identical to the amino acid sequence set forth in SEQ ID NO: 5 or a portion thereof.

5.3. Antigen-Recognizing Receptors

The presently disclosed antigen-recognizing receptors specifically target or bind to CD127. In certain embodiments, the antigen-recognizing receptor is a chimeric antigen receptor (CAR). In certain embodiments, the antigen-recognizing receptor is a T-cell receptor (TCR).

The presently disclosed subject matter also provides nucleic acid molecules that encode the presently disclosed antigen-recognizing receptors.

5.3.1. T-Cell Receptor (TCR)

In certain embodiments, the antigen-recognizing receptor is a TCR. A TCR is a disulfide-linked heterodimeric protein consisting of two variable chains expressed as part of a complex with the invariant CD3 chain molecules. A TCR found on the surface of T-cells is responsible for recognizing antigens as peptides bound to major histocompatibility complex (MHC) molecules. In certain embodiments, a TCR comprises an alpha chain and a beta chain (encoded by TRA and TRB, respectively). In certain embodiments, a TCR comprises a gamma chain and a delta chain (encoded by TRG and TRD, respectively).

Each chain of a TCR is composed of two extracellular domains: Variable (V) region and a Constant (C) region. The Constant region is proximal to the cell membrane, followed by a transmembrane region and a short cytoplasmic tail. The Variable region binds to the peptide/MHC complex. The variable domain of both chains each consist of three complementarity determining regions (CDRs).

In certain embodiments, a TCR can form a receptor complex with three dimeric signaling modules CD3δ/ε, CD3γ/ε and CD247 ζ/ζ or ζ/η. When a TCR complex engages with its antigen and MHC (peptide/MHC), the T-cell expressing the TCR complex is activated.

In certain embodiments, the TCR is an endogenous TCR. In certain embodiments, the antigen-recognizing receptor is naturally occurring TCR.

In certain embodiments, the antigen-recognizing receptor is an exogenous TCR. In certain embodiments, the antigen-recognizing receptor is a recombinant TCR. In certain embodiments, the antigen-recognizing receptor is a recombinant TCR. In certain embodiments, the recombinant TCR differs from any naturally occurring TCR by at least one amino acid residue. In certain embodiments, the recombinant TCR differs from any naturally occurring TCR by at least about 2, about 3, about 4, about 5, about 6, about 7, about 8, about 9, about 10, about 11, about 12, about 13, about 14, about 15, about 20, about 25, about 30, about 40, about 50, about 60, about 70, about 80, about 90, about 100 or more amino acid residues. In certain embodiments, the recombinant TCR is modified from a naturally occurring TCR by at least one amino acid residue. In certain embodiments, the recombinant TCR is modified from a naturally occurring TCR by at least about 2, about 3, about 4, about 5, about 6, about 7, about 8, about 9, about 10, about 11, about 12, about 13, about 14, about 15, about 20, about 25, about 30, about 40, about 50, about 60, about 70, about 80, about 90, about 100 or more amino acid residues.

5.3.2. Chimeric Antigen Receptor (CAR)

In certain embodiments, the antigen-recognizing receptor is a CAR. CARs are engineered receptors, which graft or confer a specificity of interest onto an immune effector cell. CARs can be used to graft the specificity of a monoclonal antibody onto a T-cell; with transferring of their coding sequence facilitated by retroviral vectors.

There are three generations of CARs. "First generation" CARs are typically composed of an extracellular antigen-binding domain (e.g., an scFv), which is fused to a trans-membrane domain, which is fused to cytoplasmic/intracellular signaling domain. "First generation" CARs can provide de novo antigen recognition and cause activation of both $CD4^+$ and $CD8^+$ T-cells through their $CD3\zeta$ chain signaling domain in a single fusion molecule, independent of HLA-mediated antigen presentation. "Second generation" CARs add intracellular signaling domains from various co-stimulatory molecules (e.g., CD28, 4-1BB, ICOS, OX40) to the cytoplasmic tail of the CAR to provide additional signals to the T-cell. "Second generation" CARs comprise those that provide both co-stimulation (e.g., CD28 or 4-1BB) and activation ($CD3\zeta$). "Third generation" CARs comprise those that provide multiple co-stimulation (e.g., CD28 and 4-1BB) and activation (CD3). In certain embodiments, the antigen-recognizing receptor is a first-generation CAR. In certain embodiments, the antigen-recognizing receptor is a CAR that does not comprise an intracellular signaling domain of a co-stimulatory molecule. In certain embodiments, the antigen-recognizing receptor is a second-generation CAR.

In certain embodiments, the CAR comprises an extracellular antigen-binding domain that specifically binds to CD127, a transmembrane domain, and an intracellular signaling domain.

5.3.2.1. Extracellular Antigen-Binding Domain of A CAR

In certain embodiments, the extracellular antigen-binding domain is an scFv. The scFv can be a human scFv, a humanized scFv, or a murine scFv. In certain embodiments, the scFv is a humanized scFv.

In certain embodiments, the extracellular antigen-binding domain is a Fab. In certain embodiments, the Fab is cross-linked. In certain embodiments, the extracellular antigen-binding domain is a $F(ab)_2$.

Any of the foregoing molecules may be comprised in a fusion protein with a heterologous sequence to form the extracellular antigen-binding domain.

The present disclosure is at least based on the discovery that cells (e.g., T cells) comprising a low-binding CD127-specific CAR (e.g., binds to human CD127 with an $ED_{50}$ of about 3300 ng/ml) showed higher cytotoxicity and proliferative capacity than cells (e.g., T cells) comprising a high-binding CD127-specific CAR (e.g., binds to human CD127 with an $ED_{50}$ of about 500 ng/ml). This can be due to that endogenous T-cells with high IL-7R expression provide chronic stimulation to IL-7R CAR T-cells, thereby promoting CAR T-cell persistence and providing continued immune surveillance. In addition, lysis of IL-7R positive T-cells can result in partial endogenous lymphodepletion, which facilitates the expansion of CAR T-cells (See FIG. 53). Furthermore, the different cytotoxicity activities of the low- and high-binding CD127-specific CARs can relate to the differential immune inhibitory receptor expression kinetics (e.g., expression of PD1, TIM3, LAG3 and CTLA4) between low- and high-binding CD127-specific CAR T cells following their antigen activation.

In certain embodiments, the extracellular antigen-binding domain of the CAR (embodied, for example, an scFv or an analog thereof) binds to CD127 (e.g., human CD127) with a low binding affinity. In certain embodiments, the variable regions within the extracellular antigen-binding domain of the CAR have to be linked one after another such that at the N-terminus of the extracellular antigen-binding domain, a heavy chain variable region ($V_H$) is positioned. In certain embodiments, the extracellular antigen-binding domain of the CAR is an scFv, and the variable regions are positioned from the N- to the C-terminus: $V_H$-$V_L$.

In certain embodiments, the extracellular antigen-binding domain of the CAR binds to CD127 (e.g., human CD127) with a dissociation constant ($K_d$) of about greater than $1\times10^{-8}$M, $1\times10^{-7}$M or more, $1\times10^{-6}$ M or more, or $1\times10^{-5}$M or more.

In certain embodiments, the extracellular antigen-binding domain of the CAR (embodied, for example, an scFv or an analog thereof) binds to CD127 (e.g., human CD127) with an $ED_{50}$ of greater than 500 ng/ml, greater than 1000 ng/ml, greater 1500 ng/ml, greater than 2000 ng/ml, greater than 2500 ng/ml, 3000 ng/ml or more, or 3500 ng/ml or more. In certain embodiments, the extracellular antigen-binding domain of the CAR binds to CD127 (e.g., human CD127) with an $ED_{50}$ of greater than about 2000 ng/ml. In certain embodiments, the extracellular antigen-binding domain of the CAR binds to CD127 (e.g., human CD127) with an $ED_{50}$ of about 3000 ng/ml or more. In certain embodiments, the extracellular antigen-binding domain of the CAR binds to CD127 (e.g., human CD127) with an $ED_{50}$ of between about 3000 ng/ml and about 3500 ng/ml. In certain embodiments, the extracellular antigen-binding domain of the CAR binds to CD127 (e.g., human CD127) with an $ED_{50}$ of about 3000 ng/ml, about 3300 ng/ml, or about 3500 ng/ml.

In certain embodiments, the extracellular antigen-binding domain of the CAR (embodied, for example, an scFv or an analog thereof) binds to CD127 (e.g., human CD127) with a high binding affinity. In certain embodiments, the variable regions within the extracellular antigen-binding domain of the CAR have to be linked one after another such that at the N-terminus of the extracellular antigen-binding domain, a light chain variable region ($V_L$) is positioned. In certain embodiments, the extracellular antigen-binding domain of the CAR is an scFv, and the variable regions are positioned from the N- to the C-terminus: $V_L$-$V_H$. In certain embodiments, the extracellular antigen-binding domain of the CAR binds to CD127 (e.g., human CD127) with a dissociation constant ($K_D$) of about $1\times10^{-8}$M or less, $1\times10^{-7}$M or less, $1\times10^{-6}$ M or less, or $1\times10^{-5}$M or less.

In certain embodiments, the extracellular antigen-binding domain of the CAR (embodied, for example, an scFv or an analog thereof) binds to CD127 (e.g., human CD127) with an $ED_{50}$ of 1000 ng/ml or less, 1500 ng/ml or less, 2000 ng/ml or less, 2500 ng/ml or less, less than 3000 ng/ml, or less than 3500 ng/ml. In certain embodiments, the extracellular antigen-binding domain of the CAR binds to CD127 (e.g., human CD127) with an $ED_{50}$ of about 2000 ng/ml or less. In certain embodiments, the extracellular antigen-binding domain of the CAR binds to CD127 (e.g., human CD127) with an $ED_{50}$ of about 1000 ng/ml or less. In certain embodiments, the extracellular antigen-binding domain of the CAR binds to CD127 (e.g., human CD127) with an $ED_{50}$ of between about 500 ng/ml and about 550 ng/ml. In certain embodiments, the extracellular antigen-binding domain of the CAR binds to CD127 (e.g., human CD127) with an $ED_{50}$ of about 500 ng/ml, or about 550 ng/ml.

Binding of the extracellular antigen-binding domain of the CAR can be confirmed by, for example, enzyme-linked immunosorbent assay (ELISA), radioimmunoassay (RIA), FACS analysis, bioassay (e.g., growth inhibition), or Western Blot assay. Each of these assays generally detect the presence of protein-antibody complexes of particular interest by employing a labeled reagent (e.g., an antibody, or an scFv) specific for the complex of interest. For example, the scFv can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a $\gamma$ counter or a scintillation counter or by autoradiography. In certain embodiments, the CD127-targeted extracellular antigen-binding domain is labeled with a fluorescent marker. Non-limiting examples of fluorescent markers include green fluorescent protein (GFP), blue fluorescent protein (e.g., EBFP, EBFP2, Azurite, and mKalama1), cyan fluorescent protein (e.g., ECFP, Cerulean, and CyPet), and yellow fluorescent protein (e.g., YFP, Citrine, Venus, and YPet). In one embodiment, the CD127-targeted human scFv is labeled with GFP.

In certain embodiments, the extracellular antigen-binding domain of the CAR (e.g., an scFv) comprises a $V_H$ CDR1 comprising the amino acid sequence set forth in SEQ ID NO: 6 or a conservative modification thereof, a $V_H$ CDR2 comprising the amino acid sequence set forth in SEQ ID NO: 7 or a conservative modification thereof, and a $V_H$ CDR3 comprising the amino acid sequence set forth in SEQ ID NO: 8 or a conservative modification thereof. SEQ ID NOs: 6-8 are provided in Table 1.

In certain embodiments, the extracellular antigen-binding domain of the CAR (e.g., an scFv) comprises a $V_L$ CDR1 comprising the amino acid sequence set forth in SEQ ID NO: 9 or a conservative modification thereof, a $V_L$ CDR2 comprising the amino acid sequence set forth in SEQ ID NO: 10 or a conservative modification thereof, and a $V_L$ CDR3 comprising the amino acid sequence set forth in SEQ ID NO: 11 or a conservative modification thereof. SEQ ID NOs: 9-11 are provided in Table 1.

In certain embodiments, the extracellular antigen-binding domain of the CAR (e.g., an scFv) comprises a $V_H$ CDR1 comprising the amino acid sequence set forth in SEQ ID NO: 6 or a conservative modification thereof, a $V_H$ CDR2 comprising the amino acid sequence set forth in SEQ ID NO: 7 or a conservative modification thereof, a $V_H$ CDR3 comprising the amino acid sequence set forth in SEQ ID NO: 8 or a conservative modification thereof, a $V_L$ CDR1 comprising the amino acid sequence set forth in SEQ ID NO: 9 or a conservative modification thereof, a $V_L$ CDR2 comprising the amino acid sequence set forth in SEQ ID NO: 10 or a conservative modification, and a $V_L$ CDR3 comprising the amino acid sequence set forth in SEQ ID NO: 11 or a conservative modification thereof.

In certain embodiments, the extracellular antigen-binding domain of the CAR (e.g., an scFv) comprises a $V_H$ CDR1 comprising the amino acid sequence set forth in SEQ ID NO: 6, a $V_H$ CDR2 comprising the amino acid sequence set forth in SEQ ID NO: 7, a $V_H$ CDR3 comprising the amino acid sequence set forth in SEQ ID NO: 8, a $V_L$ CDR1 comprising the amino acid sequence set forth in SEQ ID NO: 9, a $V_L$ CDR2 comprising the amino acid sequence set forth in SEQ ID NO: 10, and a $V_L$ CDR3 comprising the amino acid sequence set forth in SEQ ID NO: 11.

In certain embodiments, the extracellular antigen-binding domain of the CAR (e.g., an scFv) comprises a $V_H$ comprising an amino acid sequence that is at least about 80% (e.g., at least about 85%, at least about 90%, or at least about 95%) homologous or identical to the amino acid sequence set forth in SEQ ID NO: 12. For example, the extracellular antigen-binding domain of the CAR (e.g., an scFv) comprises a $V_H$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to the amino acid sequence set forth in SEQ ID NO: 12. In certain embodiments, the extracellular antigen-binding domain comprises a $V_H$ comprising the amino acid sequence set forth in SEQ ID NO: 12. SEQ ID NO: 12 is provided in Table 1 below.

In certain embodiments, the extracellular antigen-binding domain of the CAR (e.g., an scFv) comprises a $V_L$ comprising an amino acid sequence that is at least about 80% (e.g., at least about 85%, at least about 90%, or at least about 95%) homologous or identical to the amino acid sequence set forth in SEQ ID NO: 13. For example, the extracellular antigen-binding domain of the CAR (e.g., an scFv) comprises a $V_L$ comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% homologous or identical to the amino acid sequence set forth in SEQ ID NO: 13. In certain embodiments, the extracellular antigen-binding domain comprises a $V_L$ comprising the amino acid sequence set forth in SEQ ID NO: 13. SEQ ID NO: 13 is provided in Table 1 below.

In certain embodiments, the extracellular antigen-binding domain of the CAR (e.g., an scFv) comprises a $V_H$ comprising the amino acid sequence set forth in SEQ ID NO: 12, and a $V_L$ comprising the amino acid sequence set forth in SEQ ID NO: 13.

In certain embodiments, the $V_H$ and $V_L$ are linked via a linker. In certain embodiments, the linker comprises or consists of the amino acid sequence set forth in SEQ ID NO: 1, SEQ ID NO: 2, SEQ ID NO: 3, or SEQ ID NO: 4. In certain embodiments, the linker comprises or consists of the amino acid sequence set forth in SEQ ID NO: 1.

In certain embodiments, the variable regions within the extracellular antigen-binding domain of the CAR have to be linked one after another such that at the N-terminus of the extracellular antigen-binding domain, a heavy chain variable region ($V_H$) is positioned. In certain embodiments, the extracellular antigen-binding domain of the CAR is an scFv, and the variable regions are positioned from the N- to the C-terminus: $V_H$-$V_L$.

In certain embodiments, the extracellular antigen-binding domain of the CAR (e.g., an scFv) comprises or consists of the amino acid sequence set forth in SEQ ID NO: 14 and specifically binds to a CD127 polypeptide (e.g., a human CD127 polypeptide). In certain embodiments, the anti-CD127 scFv is designated as "scFv703HL". SEQ ID NO: 14 is provided in Table 1 below.

In certain embodiments, the variable regions within the extracellular antigen-binding domain of the CAR have to be linked one after another such that at the N-terminus of the extracellular antigen-binding domain, a light chain variable region ($V_L$) is positioned. In certain embodiments, the extracellular antigen-binding domain of the CAR is an scFv, and the variable regions are positioned from the N- to the C-terminus: $V_L$-$V_H$.

In certain embodiments, the extracellular antigen-binding domain of the CAR (e.g., an scFv) comprises or consists of the amino acid sequence set forth in SEQ ID NO: 15 and specifically binds to a CD127 polypeptide (e.g., a human CD127 polypeptide). In certain embodiments, the anti-CD127 scFv is designated as "scFv703LH". SEQ ID NO: 15 is provided in Table 1 below.

TABLE 1

| CDRs | 1 | 2 | 3 |
|---|---|---|---|
| $V_H$ | FTFTNAAMY [SEQ ID NO: 6] | RIRTKANNY ATYYADSVK G [SEQ ID NO: 7] | VVLTTTRD YFDY [SEQ ID NO: 8] |
| $V_L$ | RSSQSLLTV KGITSLY [SEQ ID NO: 9] | RMSNRDS [SEQ ID NO: 10] | AQFLEYPHT [SEQ ID NO: 11] |
| Full $V_H$ | AVQLVESGGGLVQPGGSLKITCAASGFTFT NAAMYWVRQAPGKGLEWVARIRTKANNYAT YYADSVKGRFTISRDDSKSTVYLQMDSVKT EDTATYYCIVVVLTTTRDYFDYWGQGVLVT VSS [SEQ ID NO: 12] | | |
| Full $V_L$ | DIVLTQSPSSLPVTPGEPASISCRSSQSLL TVKGITSLYWFLQKPGQSPKLLIYRMSNRD SGVPDRFSGSGSETDFTLKISRVEAEDVGT YYCAQFLEYPHTFGAGTKLELK [SEQ ID NO: 13] | | |
| scFv70 3HL | MLVLQWVLVTALFQGVHCAVQLVESGGGLV QPGGSLKITCAASGFTFTNAAMYWVRQAPG KGLEWVARIRTKANNYATYYADSVKGRFTI SRDDSKSTVYLQMDSVKTEDTATYYCIVVV LTTTRDYFDYWGQGVLVTVSSGGGGSGGGG SGGGGSDIVLTQSPSSLPVTPGEPASISCR SSQSLLTVKGITSLYWFLQKPGQSPKLLIY RMSNRDSGVPDRFSGSGSETDFTLKISRVE AEDVGTYYCAQFLEYPHTFGAGTKLELK [SEQ ID NO: 14] | | |
| scFv70 3LH | MKFPAQFLGLIVLCIPGATGDIVLTQSPSS LPVTPGEPASISCRSSQSLLTVKGITSLYW FLQKPGQSPKLLIYRMSNRDSGVPDRFSGS GSETDFTLKISRVEAEDVGTYYCAQFLEYP HTFGAGTKLELKGGGGSGGGGSGGGGSAVQ LVESGGGLVQPGGSLKITCAASGFTFTNAA MYWVRQAPGKGLEWVARIRTKANNYATYYA DSVKGRFTISRDDSKSTVYLQMDSVKTEDT ATYYCIVVVLTTTRDYFDYWGQGVLVTVSS [SEQ ID NO: 15] | | |

As used herein, the term "a conservative sequence modification" refers to an amino acid modification that does not significantly affect or alter the binding characteristics of the presently disclosed mesothelin-targeted CAR (e.g., the extracellular antigen-binding domain of the CAR) comprising the amino acid sequence. Conservative modifications can include amino acid substitutions, additions and deletions. Modifications can be introduced into the extracellular antigen-binding domain of the presently disclosed CAR by standard techniques known in the art, such as site-directed mutagenesis and PCR-mediated mutagenesis. Amino acids can be classified into groups according to their physico-chemical properties such as charge and polarity. Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered antibody can be tested for retained function (i.e., the functions set forth in (c) through (1) above) using the functional assays described herein. In certain embodiments, no more than one, no more than two, no more than three, no more than four, no more than five residues within a specified sequence or a CDR region are altered.

The $V_H$ and/or $V_L$ amino acid sequences having at least about 80%, at least about 80%, at least about 85%, at least about 90%, or at least about 95% (e.g., about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%) homology or identity to a specific sequence (e.g., SEQ ID NO: 12 or SEQ ID NO: 13) may contain substitutions (e.g., conservative substitutions), insertions, or deletions relative to the specified sequence(s), but retain the ability to bind to a target antigen (e.g., mesothelin). In certain embodiments, a total of 1 to 10 amino acids are substituted, inserted and/or deleted in a specific sequence (e.g., SEQ ID NO: 12 or SEQ ID NO: 13). In certain embodiments, substitutions, insertions, or deletions occur in regions outside the CDRs (e.g., in the FRs) of the extracellular antigen-binding domain. In certain embodiments, the extracellular antigen-binding domain comprises $V_H$ and/or $V_L$ sequence selected from SEQ ID NOs: 12 and 13, including post-translational modifications of SEQ ID NO: 12 or SEQ ID NO: 13.

In addition, the extracellular antigen-binding domain can comprise a leader or a signal peptide that directs the nascent protein into the endoplasmic reticulum. Signal peptide or leader can be essential if the CAR is to be glycosylated and anchored in the cell membrane. The signal sequence or leader can be a peptide sequence (about 5, about 10, about 15, about 20, about 25, or about 30 amino acids long) present at the N-terminus of newly synthesized proteins that directs their entry to the secretory pathway. In certain embodiments, the signal peptide is covalently joined to the 5' terminus of the extracellular antigen-binding domain. In certain embodiments, the signal peptide comprises a CD8 polypeptide, e.g., the CAR comprises a truncated CD8 signal peptide.

5.3.2.2. Transmembrane Domain of a CAR

In certain non-limiting embodiments, the transmembrane domain of the CAR comprises a hydrophobic alpha helix that spans at least a portion of the membrane. Different transmembrane domains result in different receptor stability. After antigen recognition, receptors cluster and a signal are transmitted to the cell. In accordance with the presently disclosed subject matter, the transmembrane domain of the CAR can comprise a native or modified transmembrane domain of CD8, CD28, CD3ζ, CD4, 4-1BB, OX40, ICOS, CD84, CD166, CD8a, CD8b, ICAM-1, CTLA-4, CD27, CD40, NKGD2, or a combination thereof.

In certain embodiments, the transmembrane domain of the CAR comprises a CD28 polypeptide (e.g., a transmembrane domain of CD28 or a portion thereof). In certain embodiments, the transmembrane domain of the CAR comprises a transmembrane domain of human CD28 or a portion thereof. In certain embodiments, the CD28 polypeptide comprises or consists of an amino acid sequence that is at least about 85%, about 90%, about 95%, about 96%, about 97%, about 98%, about 99% or 100% homologous or identical to the sequence having a NCBI Reference No: NP_006130 (SEQ ID NO: 16), or a fragment thereof, and/or may optionally comprise up to one or up to two or up to three conservative amino acid substitutions. In certain embodiments, the CD28 polypeptide comprises or consists of an amino acid sequence that is a consecutive portion of SEQ ID NO: 16 which is at least 20, or at least 30, or at least 40, or at least 50, and up to 220 amino acids in length. Alternatively or additionally, in certain embodiments, the CD28 polypeptide comprises or consists of an amino acid sequence of amino acids 1 to 220, 1 to 50, 50 to 100, 100 to 150, 150 to 200, 153 to 179, or 200 to 220 of SEQ ID NO: 16. In certain embodiments, the transmembrane domain of the CAR comprises a CD28 polypeptide comprising or consisting of amino acids 153 to 179 of SEQ ID NO: 16. SEQ ID NO: 16 is provided below.

```
                                            [SEQ ID NO: 16]
  1 MLRLLLALNL FPSIQVTGNK ILVKQSPMLV

AYDNAVNLSC KYSYNLFSRE FRASLHKGLD

61 SAVEVCVVYG NYSQQLQVYS KTGFNCDGKL

GNESVTFYLQ NLYVNQTDIY FCKIEVMYPP

121 PYLDNEKSNG TIIHVKGKHL CPSPLFPGPS

KPFWVLVVVG GVLACYSLLV TVAFIIFWVR

181 SKRSRLLHSD YMNMTPRRPG PTRKHYQPYA

PPRDFAAYRS
```

An exemplary nucleotide sequence encoding the amino acids 153 to 179 of SEQ ID NO: 16 is set forth in SEQ ID NO: 17, which is provided below.

```
                                            [SEQ ID NO: 17]
    TTTTGGGTGCTGGTGGTGGTTGGTGGAGTCCTGGCTTGCTA

TAGCTTGCTAGTAACAGTGGCCTTTATTATTTTCTGGGTG
```

In certain embodiments, the transmembrane domain of the CAR comprises a transmembrane domain of mouse CD28 or a portion thereof. In certain embodiments, the CD28 polypeptide comprises or consists of an amino acid sequence that is at least about 85%, about 90%, about 95%, about 96%, about 97%, about 98%, about 99% or 100% homologous or identical to the sequence having a NCBI Reference No: NP_031668.3 (SEQ ID No: 18), or a fragment thereof, and/or may optionally comprise up to one or up to two or up to three conservative amino acid substitutions. In certain embodiments, the CD28 polypeptide comprises or consists of an amino acid sequence that is a consecutive portion of SEQ ID NO: 18 which is at least 20, or at least 30, or at least 40, or at least 50, and up to 218 amino acids in length. Alternatively or additionally, in certain embodiments, the CD28 polypeptide comprises or consists of an amino acid sequence of amino acids 1 to 220, 1 to 50, 50 to 100, 100 to 150, 150 to 200, 151 to 177, or 200 to 218 of SEQ ID NO: 18. In certain embodiments, the transmembrane domain of the CAR comprises a CD28 polypeptide comprising or consisting of amino acids 151 to 177 of SEQ ID NO: 18. SEQ ID NO: 18 is provided below:

```
                                            [SEQ ID NO: 18]
  1 MTLRLLLFLAL NFFSVQVTEN KILVKQSPLL

VVDSNEVSLS CRYSYNLLAK EFRASLYKGV

61 NSDVEVCVGN GNFTYQPQFR SNAEFNCDGD

FDNETVTFRL WNLHVNHTDI YFCKIEFMYP

121 PPYLDNERSN GTIIHIKEKH LCHTQSSPKL

FWALVVVAGV LFCYGLLVTV ALCVIWTNSR

181 RNRLLQSDYM NMTPRRPGLT RKPYQPYAPA

RDFAAYRP
```

In certain embodiments, the transmembrane domain of the CAR comprises a CD8 polypeptide (e.g., a transmembrane domain of CD8 or a portion thereof). In certain embodiments, the transmembrane domain of the CAR comprises a transmembrane domain of human CD8 or a portion thereof. In certain embodiments, the CD8 polypeptide comprises or consists of an amino acid sequence that is at least about 85%, about 90%, about 95%, about 96%, about 97%, about 98%, about 99% or about 100% homologous or identical to the sequence having a NCBI Reference No: NP_001139345.1 (SEQ ID NO: 19) or a fragment thereof, and/or may optionally comprise up to one or up to two or up to three conservative amino acid substitutions. In certain embodiments, the CD8 polypeptide comprises or consists of an amino acid sequence that is a consecutive portion of SEQ ID NO: 19, which is at least 20, or at least 30, or at least 40, or at least 50, and up to 235 amino acids in length. Alternatively or additionally, in certain embodiments, the CD8 polypeptide comprises or consists of an amino acid sequence of amino acids 1 to 235, 1 to 50, 50 to 100, 100 to 150, 150 to 200, 137 to 209 or 200 to 235 of SEQ ID NO: 19. In certain embodiments, the transmembrane domain of the CAR comprises a CD8 polypeptide comprising or consisting of amino acids 137 to 209 of SEQ ID NO: 19. SEQ ID NO: 19 is provided below.

```
                                            [SEQ ID NO: 19]
    MALPVTALLLPLALLLHAARPSQFRVSPLDRTWNLGETVE

LKCQVLLSNPTSGCSWLFQPRGAAASPTFLLYLSQNKPKA

AEGLDTQRFSGKRLGDTFVLTLSDFRRENEGYYFCSALSN

SIMYFSHFVPVFLPAKPTTTPAPRPPTPAPTIASQPLSLR
```

-continued

```
PEACRPAAGGAVHTRGLDFACDIYIWAPLAGTCGVLLLSL

VITLYCNHRNRRRVCKCPRPVVKSGDKPSLSARYV
```

In certain embodiments, the transmembrane domain of the CAR comprises a transmembrane domain of mouse CD8 or a portion thereof. In certain embodiments, the CD8 polypeptide comprises or consists of an amino acid sequence that is at least about 85%, about 90%, about 95%, about 96%, about 97%, about 98%, about 99% or about 100% homologous or identical to the sequence having a NCBI Reference No: AAA92533.1 (SEQ ID NO: 20) or a fragment thereof, and/or may optionally comprise up to one or up to two or up to three conservative amino acid substitutions. In certain embodiments, the CD8 polypeptide comprises or consists of an amino acid sequence that is a consecutive portion of SEQ ID NO: 20, which is at least about 20, or at least about 30, or at least about 40, or at least about 50, or at least about 60, or at least about 70, or at least about 100, or at least about 200, and up to 247 amino acids in length. Alternatively or additionally, in certain embodiments, the CD8 polypeptide comprises or consists of an amino acid sequence of amino acids 1 to 247, 1 to 50, 50 to 100, 100 to 150, 150 to 200, 151 to 219, or 200 to 247 of SEQ ID NO: 20. In certain embodiments, the transmembrane domain of the CAR comprises a CD8 polypeptide comprising or consisting of amino acids 151 to 219 of SEQ ID NO: 20. SEQ ID NO: 20 is provided below.

```
                                    [SEQ ID NO: 20]
  1 MASPLTRFLS LNLLLMGESI ILGSGEAKPQ

APELRIFPKK MDAELGQKVD LVCEVLGSVS

61 QGCSWLFQNS SSKLPQPTFV VYMASSHNKI

TWDEKLNSSK LFSAVRDTNN KYVLTLNKFS

121 KENEGYYFCS VISNSVMYFS SVVPVLQKVN

STTTKPVLRT PSPVHPTGTS QPQRPEDCRP

181 RGSVKGTGLD FACDIYIWAP LAGICVAPLL

SLIITLICYH RSRKRVCKCP RPLVRQEGKP

241 RPSEKIV
```

In certain non-limiting embodiments, the CAR further comprises a spacer region that links the extracellular antigen-binding domain to the transmembrane domain. The spacer region can be flexible enough to allow the antigen binding domain to orient in different directions to facilitate antigen recognition while preserving the activating activity of the CAR.

In certain embodiments, the hinge/spacer region of the CAR comprises a native or modified hinge region of CD8, CD28, CD3ζ, CD40, 4-1BB, OX40, CD84, CD166, CD8a, CD8b, ICOS, ICAM-1, CTLA-4, CD27, CD40, NKGD2, a synthetic polypeptide (not based on a protein associated with the immune response), or a combination thereof. The hinge/spacer region can be the hinge region from IgG1, or the CH₂CH₃ region of immunoglobulin and portions of CD3, a portion of a CD28 polypeptide (e.g., a portion of SEQ ID NO: 16 or SEQ ID NO: 18), a portion of a CD8 polypeptide (e.g., a portion of SEQ ID NO: 19 or SEQ ID NO: 20), a variation of any of the foregoing which is at least about 80%, at least about 85%, at least about 90%, at least about 95%, or at least about 100% homologous or identical thereto, or a synthetic spacer sequence.

In certain embodiments, the hinge domain of the CAR comprises a native or modified hinge region of CD28. In certain embodiments, the hinge domain of the CAR comprises a native hinge region of CD28. In certain embodiments, the hinge domain of the CAR comprises the amino acid sequence of amino acids 114 to 152 of SEQ ID NO: 16.

5.3.2.3. Intracellular Signaling Domain of a CAR

In certain embodiments, the CAR comprises an intracellular signaling domain. In certain non-limiting embodiments, the intracellular signaling domain of the CAR comprises a CD3ζ polypeptide. CD3ζ can activate or stimulate a cell (e.g., a cell of the lymphoid lineage, e.g., a T-cell). Wild type ("native") CD3ζ comprises three functional immunoreceptor tyrosine-based activation motifs (ITAMs), three functional basic-rich stretch (BRS) regions (BRS1, BRS2 and BRS3). CD3 transmits an activation signal to the cell (e.g., a cell of the lymphoid lineage, e.g., a T-cell) after antigen is bound. The intracellular signaling domain of the CD3-chain is the primary transmitter of signals from endogenous TCRs.

In certain embodiments, the intracellular signaling domain of the CAR comprises a native CD3ζ. In certain embodiments, the CD3ζ polypeptide comprises or consists of an amino acid sequence that is at least about 85%, about 90%, about 95%, about 96%, about 97%, about 98%, about 99% or about 100% homologous or identical to the sequence having a NCBI Reference No: NP_932170 (SEQ ID NO: 21), or a fragment thereof, and/or may optionally comprise up to one or up to two or up to three conservative amino acid substitutions. In certain embodiments, the CD3ζ polypeptide comprises or consists of an amino acid sequence that is a consecutive portion of SEQ ID NO: 21, which is at least 20, or at least 30, or at least 40, or at least 50, and up to 164 amino acids in length. Alternatively or additionally, in non-limiting various embodiments, the CD3ζ polypeptide comprises or consists of an amino acid sequence of amino acids 1 to 164, 1 to 50, 50 to 100, 52 to 164, 100 to 150, or 150 to 164 of SEQ ID NO: 21. In certain embodiments, the intracellular signaling domain of the CAR comprises a CD3ζ polypeptide comprising or consisting of amino acids 52 to 164 of SEQ ID NO: 21. SEQ ID NO: 21 is provided below:

```
                                    [SEQ ID NO: 21]
  1 MKWKALFTAA ILQAQLPITE AQSFGLLDPK

LCYLLDGILF IYGVILTALF LRVKFSRSAD

61 APAYQQGQNQ LYNELNLGRR EEYDVLDKRR

GRDPEMGGKP QRRKNPQEGL YNELQKDKMA

121 EAYSEIGMKG ERRRGKGHDG LYQGLSTATK

DTYDALHMQA LPPR
```

In certain embodiments, the intracellular signaling domain of the CAR comprises a CD3 polypeptide comprising or consisting of the amino acid sequence set forth in SEQ ID NO: 22. SEQ ID NO: 22 is provided below.

[SEQ ID NO: 22]
RVKFSRSADAPAYQQGQNQLYNELNLGRREEYDVLDKRRG

RDPEMGGKPRRKNPQEGLYNELQKDKMAEAYSEIGMKGER

RRGKGHDGLYQGLSTATKDTYDALHMQALPPR

An exemplary nucleotide sequence encoding the amino acid sequence of SEQ ID NO: 22 is set forth in SEQ ID NO: 23, which is as provided below.

[SEQ ID NO: 23]
AGAGTGAAGTTCAGCAGGAGCGCAGACGCCCCCGCGTACC

AGCAGGGCCAGAACCAGCTCTATAACGAGCTCAATCTAGG

ACGAAGAGAGGAGTACGATGTTTTGGACAAGAGACGTGGC

CGGGACCCTGAGATGGGGGGAAAGCCGAGAAGGAAGAACC

CTCAGGAAGGCCTGTACAATGAACTGCAGAAAGATAAGAT

GGCGGAGGCCTACAGTGAGATTGGGATGAAAGGCGAGCGC

CGGAGGGGCAAGGGGCACGATGGCCTTTACCAGGGTCTCA

GTACAGCCACCAAGGACACCTACGACGCCCTTCACATGCA

GGCCCTGCCCCCTCGC

In certain non-limiting embodiments, the intracellular signaling domain of the CAR further comprises at least one co-stimulatory signaling region. In certain embodiments, the at least one co-stimulatory region comprises a co-stimulatory molecule or a portion thereof. In certain embodiments, the at least one co-stimulatory region comprises an intracellular domain of at least one co-stimulatory molecule or a portion thereof.

As used herein, a "co-stimulatory molecule" refers to a cell surface molecule other than antigen receptor or its ligand that can provide an efficient response of lymphocytes to an antigen. In certain embodiments, a co-stimulatory molecule can provide optimal lymphocyte activation. Non-limiting examples of co-stimulatory molecules include CD28, 4-1BB, OX40, ICOS, and DAP-10, and combinations thereof. The co-stimulatory molecule can bind to a co-stimulatory ligand, which is a protein expressed on cell surface that upon binding to its receptor produces a co-stimulatory response, i.e., an intracellular response that effects the stimulation provided when an antigen-recognizing receptor (e.g., a chimeric antigen receptor (CAR)) binds to its target antigen. As one example, a 4-1BB ligand (i.e., 4-1BBL) may bind to 4-1BB for providing an intracellular signal that in combination with a CAR signal induces an effector cell function of the CAR' T-cell.

In certain embodiments, the intracellular signaling domain of the CAR comprises a co-stimulatory signaling region that comprises a CD28 polypeptide, e.g., an intracellular domain of CD28 or a portion thereof. In certain embodiments, the intracellular signaling domain of the CAR comprises a co-stimulatory signaling region that comprises an intracellular domain of human CD28 or a portion thereof. In certain embodiments, the intracellular signaling domain of the CAR comprises a co-stimulatory signaling region comprising a CD28 polypeptide that comprises or consists of an amino acid sequence that is at least about 80%, at least about 85%, at least about 90%, at least about 95%, at least about 96%, at least about 97%, at least about 98%, or at least about 99%, at least about 100% homologous or identical to the amino acid sequence set forth in SEQ ID NO: 16, or a fragment thereof, and/or may optionally comprise up to one or up to two or up to three conservative amino acid substitutions. In certain embodiments, the CD28 polypeptide comprised in the co-stimulatory signaling region comprises or consists of an amino acid sequence that is a consecutive portion of SEQ ID NO: 16, which is at least 20, or at least 30, or at least 40, or at least 50, and up to 220 amino acids in length. Alternatively or additionally, in non-limiting various embodiments, the intracellular signaling domain of the CAR comprises a co-stimulatory signaling region comprising a CD28 polypeptide that comprises or consists of amino acids 1 to 220, 1 to 50, 50 to 100, 100 to 150, 114 to 220, 150 to 200, 180 to 220, or 200 to 220 of SEQ ID NO: 16. In certain embodiments, the intracellular signaling domain of the CAR comprises a co-stimulatory signaling region that comprises a CD28 polypeptide comprising or consisting of amino acids 180 to 220 of SEQ ID NO: 16.

An exemplary nucleotide sequence encoding amino acids 180 to 220 of SEQ ID NO: 16 is set forth in SEQ ID NO: 24, which is provided below.

[SEQ ID NO: 24]
AGGAGTAAGAGGAGCAGGCTCCTGCACAGTGACTACATGA

ACATGACTCCCCGCCGCCCCGGGCCCACCCGCAAGCATTA

CCAGCCCTATGCCCCACCACGCGACTTCGCAGCCTATCGC

TCC

In certain embodiments, the intracellular signaling domain of the CAR comprises a co-stimulatory signaling region comprising a CD28 polypeptide that comprises or consists of an amino acid sequence that is at least about 80%, at least about 85%, at least about 90%, at least about 95%, at least about 96%, at least about 97%, at least about 98%, or at least about 99%, at least about 100% homologous or identical to the amino acid sequence set forth in SEQ ID NO: 18, or a fragment thereof, and/or may optionally comprise up to one or up to two or up to three conservative amino acid substitutions. In certain embodiments, the intracellular signaling domain of the CAR comprises a co-stimulatory signaling region comprising a CD28 polypeptide that comprises or consists of an amino acid sequence that is a consecutive portion of SEQ ID NO: 18 which is at least about 20, or at least about 30, or at least about 40, or at least about 50, and up to 218 amino acids in length. Alternatively or additionally, in non-limiting various embodiments, the intracellular signaling domain of the CAR comprises a co-stimulatory signaling region comprising a CD28 polypeptide that comprises or consists of amino acids 1 to 218, 1 to 50, 50 to 100, 100 to 150, 150 to 218, 178 to 218, or 200 to 218 of SEQ ID NO: 18. In certain embodiments, the co-stimulatory signaling region of a presently disclosed CAR comprises a CD28 polypeptide that comprises or consists of amino acids 178 to 218 of SEQ ID NO: 18.

In certain embodiments, the intracellular signaling domain of the CAR comprises a co-stimulatory signaling region that comprises a 4-1BB polypeptide, e.g., an intracellular domain of 4-1BB or a portion thereof. In certain embodiments, the 4-1BB polypeptide comprises or consists of an amino acid sequence that is at least about 80%, at least about 85%, at least about 90%, at least about 95%, at least about 96%, at least about 97%, at least about 98%, or at least about 99%, at least about 100% homologous or identical to the sequence having a NCBI Ref. No.: NP_001552 (SEQ ID NO: 25) or a fragment thereof, and/or may optionally comprise up to one or up to two or up to three conservative amino acid substitutions. In certain embodiments, the 4-1BB polypeptide comprises or consists of an amino acid sequence that is a consecutive portion of SEQ ID NO: 25, which is at least 20, or at least 30, or at least 40, or at least 50, or at least 100, or at least 150, or at least 150, and up to 255 amino acids in length. Alternatively or additionally, in certain embodiments, the 4-1BB polypeptide comprises or consists of an amino acid sequence of amino acids 1 to 255, 1 to 50, 50 to 100, 100 to 150, 150 to 200, or 200 to 255 of SEQ ID NO: 25. In certain embodiments, the intracellular signaling domain of the CAR comprises a co-stimulatory signaling region that comprises a 4-1BB polypeptide comprising or consisting of amino acids 214 to 255 of SEQ ID NO: 25. SEQ ID NO: 25 is provided below.

```
                                    [SEQ ID NO: 25]
    MGNSCYNIVA  TLLLVLNFER  TRSLQDPCSN

CPAGTFCDNN  RNQICSPCPP  NSFSSAGGQR

TCDICRQCKG  VFRTRKECSS  TSNAECDCTP

GFHCLGAGCS

MCEQDCKQGQ  ELTKKGCKDC  CFGTFNDQKR

GICRPWTNCS  LDGKSVLVNG  TKERDVVCGP

SPADLSPGAS  SVTPPAPARE  PGHSPQIISF

FLALTSTALL  FLLFFLTLRF  SVVKRGRKKL

LYIFKQPFMR  PVQTTQEEDG  CSCRFPEEEE

GGCEL
```

An exemplary nucleotide sequence encoding amino acids 214 to 255 of SEQ ID NO: 25 is set forth in SEQ ID NO: 26, which is provided below.

```
                                    [SEQ ID NO: 26]
    AAACGGGGCAGAAAGAAACTCCTGTATATATTCAAACAACCA

TTTATGAGACCAGTACAAACTACTCAAGAGGAAGATGGCTGT

AGCTGCCGATTTCCAGAAGAAGAAGAAGGAGGATGTGAACTG
```

In certain embodiments, the intracellular signaling domain of the CAR comprises a co-stimulatory signaling region that comprises intracellular domains of two or more co-stimulatory molecules or portions thereof, e.g., intracellular domains of CD28 and 4-1BB, or intracellular domains of CD28 and OX40.

5.3.2.4. Exemplified CARs

In certain embodiments, the CAR comprises (a) an extracellular antigen-binding domain comprising (i) a $V_H$ that comprises a CDR1 comprising the amino acid sequence set forth in SEQ ID NO: 6, a CDR2 comprising the amino acid sequence set forth in SEQ ID NO: 7, and a $V_H$ CDR3 comprising the amino acid sequence set forth in SEQ ID NO: 8, and (ii) a $V_L$ that comprises a CDR1 comprising the amino acid sequence set forth in SEQ ID NO: 9, a CDR2 comprising the amino acid sequence set forth in SEQ ID NO: 10, and a $V_L$ CDR3 comprising the amino acid sequence set forth in SEQ ID NO: 11; (b) a transmembrane domain comprising a CD28 polypeptide (e.g., a transmembrane domain of human CD28 or a portion thereof), and (c) an intracellular signaling domain comprising (i) a CD3ζ polypeptide, and (ii) a co-stimulatory signaling region comprising a CD28 polypeptide (e.g., an intracellular domain of human CD28 or a portion thereof). In certain embodiments, the $V_H$ and $V_L$ are linked via a linker consisting of the amino acid sequence set forth in SEQ ID NO: 1. In certain embodiments, the $V_H$ and $V_L$ are positioned from the N- to the C-terminus: $V_H$-$V_L$. In certain embodiments, the CAR is designated as "OSE703HL-28z". In certain embodiments, the CAR comprises the amino acid sequence set forth in SEQ ID NO: 27, which is provided below.

```
                                    [SEQ ID NO: 27]
    AVQLVESGGGLVQPGGSLKITCAASGFTETNAAMYWVRQA

PGKGLEWVARIRTKANNYATYYADSVKGRFTISRDDSKST

VYLQMDSVKTEDTATYYCIVVVLTTTRDYFDYWGQGVLVT

VSSGGGGSGGGGSGGGGSDIVLTQSPSSLPVTPGEPASIS

CRSSQSLLTVKGITSLYWFLQKPGQSPKLLIYRMSNRDSG

VPDRFSGSGSETDFTLKISRVEAEDVGTYYCAQFLEYPHT

FGAGTKLELKAAAIEVMYPPPYLDNEKSNGTIIHVKGKHL

CPSPLFPGPSKPFWVLVVVGGVLACYSLLVTVAFIIFWVR

SKRSRLLHSDYMNMTPRRPGPTRKHYQPYAPPRDFAAYRS

RVKFSRSADAPAYQQGQNQLYNELNLGRREEYDVLDKRRG

RDPEMGGKPRRKNPQEGLYNELQKDKMAEAYSEIGMKGER

RRGKGHDGLYQGLSTATKDTYDALHMQALPPR
```

In certain embodiments, the CAR comprises a Myc-tag attached to the N-terminus of the scFv. In certain embodiments, the CAR comprises two Myc-tags attached to the N-terminus of the scFv. In certain embodiments, the Myc-tag consists of the amino acid sequence set forth in SEQ ID NO: 31, which is provided below.

```
                                    [SEQ ID NO: 31]
        EQKLISEEDL
```

An exemplary nucleotide sequence encoding the amino acid sequence of SEQ ID NO: 27 is set forth in SEQ ID NO: 28, which is provided below.

```
                                    [SEQ ID NO: 28]
    GATGAACGAAATAGACAGATCGCTGAGATAGGTGCCTCAC

TGATTAAGCATTGGTAACTGTCAGACCAAGTTTACTCATA

TATACTTTAGATTGATTTAAAACTTCATTTTTAATTTAAA

AGGATCTAGGTGAAGATCCTTTTTGATAATCTCATGACCA

AAATCCCTTAACGTGAGTTTTCGTTCCACTGAGCGTCAGA

CCCCGTAGAAAAGATCAAAGGATCTTCTTGAGATCCTTTT

TTTCTGCGCGTAATCTGCTGCTTGCAAACAAAAAAACCAC

CGCTACCAGCGGTGGTTTGTTTGCCGGATCAAGAGCTACC

AACTCTTTTTCCGAAGGTAACTGGCTTCAGCAGAGCGCAG

ATACCAAATACTGTCCTTCTAGTGTAGCCGTAGTTAGGCC

ACCACTTCAAGAACTCTGTAGCACCGCCTACATACCTCGC

TCTGCTAATCCTGTTACCAGTGGCTGCTGCCAGTGGCGAT

AAGTCGTGTCTTACCGGGTTGGACTCAAGACGATAGTTAC
```

-continued

```
CGGATAAGGCGCAGCGGTCGGGCTGAACGGGGGGTTCGTG

CACACAGCCCAGCTTGGAGCGAACGACCTACACCGAACTG

AGATACCTACAGCGTGAGCATTGAGAAAGCGCCACGCTTC

CCGAAGGGAGAAAGGCGGACAGGTATCCGGTAAGCGGCAG

GGTCGGAACAGGAGAGCGCACGAGGGAGCTTCCAGGGGGA

AACGCCTGGTATCTTTATAGTCCTGTCGGGTTTCGCCACC

TCTGACTTGAGCGTCGATTTTTGTGATGCTCGTCAGGGGG

GCGGAGCCTATGGAAAAACGCCAGCAACGCGGCCTTTTTA

CGGTTCCTGGCCTTTTGCTGGCCTTTTGCTCACATGTTCT

TTCCTGCGTTATCCCCTGATTCTGTGGATAACCGTATTAC

CGCCTTTGAGTGAGCTGATACCGCTCGCCGCAGCCGAACG

ACCGAGCGCAGCGAGTCAGTGAGCGAGGAAGCGGAAGAGC

GCCCAATACGCAAACCGCCTCTCCCCGCGCGTTGGCCGAT

TCATTAATGCAGCTGGCACGACAGGTTTCCCGACTGGAAA

GCGGGCAGTGAGCGCAACGCAATTAATGTGAGTTAGCTCA

CTCATTAGGCACCCCAGGCTTTACACTTTATGCTTCCGGC

TCGTATGTTGTGTGGAATTGTGAGCGGATAACAATTTCAC

ACAGGAAACAGCTATGACCATGATTACGCCAAGCTTTGCT

CTTAGGAGTTTCCTAATACATCCCAAACTCAAATATATAA

AGCATTTGACTTGTTCTATGCCCTAGGGGGCGGGGGGAAG

CTAAGCCAGCTTTTTTTAACATTTAAAATGTTAATTCCAT

TTTAAATGCACAGATGTTTTTATTTCATAAGGGTTTCAAT

GTGCATGAATGCTGCAATATTCCTGTTACCAAAGCTAGTA

TAAATAAAAATAGATAAACGTGGAAATTACTTAGAGTTTC

TGTCATTAACGTTTCCTTCCTCAGTTGACAACATAAATGC

GCTGCTGAGCAAGCCAGTTTGCATCTGTCAGGATCAATTT

CCCATTATGCCAGTCATATTAATTACTAGTCAATTAGTTG

ATTTTTATTTTTGACATATACATGTGAATGAAAGACCCCA

CCTGTAGGTTTGGCAAGCTAGCTTAAGTAACGCCATTTTG

CAAGGCATGGAAAAATACATAACTGAGAATAGAAAAGTTC

AGATCAAGGTCAGGAACAGATGGAACAGCTGAATATGGGC

CAAACAGGATATCTGTGGTAAGCAGTTCCTGCCCCGGCTC

AGGGCCAAGAACAGATGGAACAGCTGAATATGGGCCAAAC

AGGATATCTGTGGTAAGCAGTTCCTGCCCCGGCTCAGGGC

CAAGAACAGATGGTCCCCAGATGCGGTCCAGCCCTCAGCA

GTTTCTAGAGAACCATCAGATGTTTCCAGGGTGCCCCAAG

GACCTGAAATGACCCTGTGCCTTATTTGAACTAACCAATC

AGTTCGCTTCTCGCTTCTGTTCGCGCGCTTATGCTCCCCG

AGCTCAATAAAAGAGCCCACAACCCCTCACTCGGGGCGCC

AGTCCTCCGATTGACTGAGTCGCCCGGGTACCCGTGTATC
```

-continued

```
CAATAAACCCTCTTGCAGTTGCATCCGACTTGTGGTCTCG

CTGTTCCTTGGGAGGGTCTCCTCTGAGTGATTGACTACCC

GTCAGCGGGGGTCTTTCATTTGGGGGCTCGTCCGGGATCG

GGAGACCCCTGCCCAGGGACCACCGACCCACCACCGGGAG

GTAAGCTGGCCAGCAACTTATCTGTGTCTGTCCGATTGTC

TAGTGTCTATGACTGATTTTATGCGCCTGCGTCGGTACTA

GTTAGCTAACTAGCTCTGTATCTGGCGGACCCGTGGTGGA

ACTGACGAGTTCGGAACACCCGGCCGCAACCCTGGGAGAC

GTCCCAGGGACTTCGGGGGCCGTTTTTGTGGCCCGACCTG

AGTCCTAAAATCCCGATCGTTTAGGACTCTTTGGTGCACC

CCCCCTTAGAGGAGGGATATGTGGTTCTGGTAGGAGACGAG

AACCTAAAACAGTTCCCGCCTCCGTCTGAATTTTTGCTTT

CGGTTTGGGACCGAAGCCGCGCCGCGCGTCTTGTCTGCTG

CAGCATCGTTCTGTGTTGTCTCTGTCTGACTGTGTTTCTG

TATTTGTCTGAAAATATGGGCCCGGGCTAGACTGTTACCA

CTCCCTTAAGTTTGACCTTAGGTCACTGGAAAGATGTCGA

GCGGATCGCTCACAACCAGTCGGTAGATGTCAAGAAGAGA

CGTTGGGTTACCTTCTGCTCTGCAGAATGGCCAACCTTTA

ACGTCGGATGGCCGCGAGACGGCACCTTTAACCGAGACCT

CATCACCCAGGTTAAGATCAAGGTCTTTTCACCTGGCCCG

CATGGACACCCAGACCAGGTCCCCTACATCGTGACCTGGG

AAGCCTTGGCTTTTGACCCCCCTCCCTGGGTCAAGCCCTT

TGTACACCCTAAGCCTCCGCCTCCTCTTCCTCCATCCGCC

CCGTCTCTCCCCCTTGAACCTCCTCGTTCGACCCCGCCTC

GATCCTCCCTTTATCCAGCCCTCACTCCTTCTCTAGGCGC

CCCCATATGGCCATATGAGATCTTATATGGGGCACCCCCG

CCCCTTGTAAACTTCCCTGACCCTGACATGACAAGAGTTA

CTAACAGCCCCTCTCTCCAAGCTCACTTACAGGCTCTCTA

CTTAGTCCAGCACGAAGTCTGGAGACCTCTGGCGGCAGCC

TACCAAGAACAACTGGACCGACCGGTGGTACCTCACCCTT

ACCGAGTCGGCGACACAGTGTGGGTCCGCCGACACCAGAC

TAAGAACCTAGAACCTCGCTGGAAAGGACCTTACACAGTC

CTGCTGACCACCCCCACCGCCCTCAAAGTAGACGGCATCG

CAGCTTGGATACACGCCGCCCACGTGAAGGCTGCCGACCC

CGGGGGGTGGACCATCCTCTAGACTGCCATGGCCCTGCCAG

TAACGGCTCTGCTGCTGCCACTTGCTCTGCTCCTCCATGC

AGCCAGGCCTGAGCAGAAGCTGATCTCAGAGGAGGACCTG

GAGCAGAAGCTGATCTCAGAGGAGGACCTGGCCGTTCAAC

TTGTTGAATCTGGTGGTGGCCTCGTTCAGCCGGGGGGCTC

CCTTAAAATTACTTGTGCAGCTAGCGGATTCACATTCACC

AATGCCGCAATGTACTGGGTTAGACAAGCTCCTGGCAAAG
```

-continued

```
GACTGGAATGGGTAGCTAGAATTAGAACTAAAGCTAATAA

CTATGCAACATACTATGGTGATTCCGTCAAAGGACGATTC

ACTATCAGCAGAGATGATAGCAAGTCAACTGTGTACCTGC

AGATGGACTCCGTTAAGACAGAGGATACAGCTACATACTA

TTGTATCGTAGTTGTGCTGACAACTACCAGAGATTACTTT

GATTATTGGGGCCAAGGTGTTCTGGTAACAGTGAGTAGTG

GAGGTGGAGGATCAGGCGGTGGAGGATCCGGTGGCGGAGG

AAGCGATATAGTCCTCACACAGTCCCCTAGTTCACTGCCA

GTCACTCCAGGAGAACCTGCTTCCATATCATGTAGATCAA

GTCAAAGTTTGCTTACAGTAAAAGGAATTACAAGCCTCTA

TTGGTTCTTGCAAAAACCTGGTCAGAGCCCAAAGTTGCTG

ATCTATAGAATGTCCAACAGAGACTCCGGAGTCCCTGATA

GATTCAGCGGCTCAGGATCAGAAACGGACTTCACCCTTAA

AATATCAAGAGTAGAAGCCGAAGATGTTGGCACCTACTAT

TGTGCTCAGTTTCTGGAATACCCTCATACGTTTGGAGCAG

GTACCAAGCTCGAACTCAAGGCGGCCGCAATTGAAGTTAT

GTATCCTCCTCCTTACCTAGACAATGAGAAGAGCAATGGA

ACCATTATCCATGTGAAAGGGAAACACCTTTGTCCAAGTC

CCCTATTTCCCGGACCTTCTAAGCCCTTTTGGGTGCTGGT

GGTGGTTGGTGGAGTCCTGGCTTGCTATAGCTTGCTAGTA

ACAGTGGCCTTTATTATTTTCTGGGTGAGGAGTAAGAGGA

GCAGGCTCCTGCACAGTGACTACATGAACATGACTCCCCG

CCGCCCCGGGCCCACCCGCAAGCATTACCAGCCCTATGCC

CCACCACGCGACTTCGCAGCCTATCGCTCCAGAGTGAAGT

TCAGCAGGAGCGCAGACGCCCCCGCGTACCAGCAGGGCCA

GAACCAGCTCTATAACGAGCTCAATCTAGGACGAAGAGAG

GAGTACGATGTTTTGGACAAGAGACGTGGCCGGGACCCTG

AGATGGGGGGAAAGCCGAGAAGGAAGAACCCTCAGGAAGG

CCTGTACAATGAACTGCAGAAAGATAAGATGGCGGAGGCC

TACAGTGAGATTGGGATGAAAGGCGAGCGCCGGAGGGGCA

AGGGGCACGATGGCCTTTACCAGGGTCTCAGTACAGCCAC

CAAGGACACCTACGACGCCCTTCACATGCAGGCCCTGCCC

CCTCGCTGAGTCGACGGATCCGGATTAGTCCAATTTGTTA

AAGACAGGATATCAGTGGTCCAGGCTCTAGTTTTGACTCA

ACAATATCACCAGCTGAAGCCTATAGAGTACGAGCCATAG

ATAAAATAAAAGATTTTATTTAGTCTCCAGAAAAAGGGGG

GAATGAAAGACCCCACCTGTAGGTTTGGCAAGCTAGCTTA

AGTAACGCCATTTTGCAAGGCATGGAAAAATACATAACTG

AGAATAGAGAAGTTCAGATCAAGGTCAGGAACAGATGGAA

CAGCTGAATATGGGCCAAACAGGATATCTGTGGTAAGCAG
```

-continued

```
TTCCTGCCCCGGCTCAGGGCCAAGAACAGATGGAACAGCT

GAATATGGGCCAAACAGGATATCTGTGGTAAGCAGTTCCT

GCCCCGGCTCAGGGCCAAGAACAGATGGTCCCCAGATGCG

GTCCAGCCCTCAGCAGTTTCTAGAGAACCATCAGATGTTT

CCAGGGTGCCCCAAGGACCTGAAATGACCCTGTGCCTTAT

TTGAACTAACCAATCAGTTCGCTTCTCGCTTCTGTTCGCG

CGCTTCTGCTCCCCGAGCTCAATAAAAGAGCCCACAACCC

CTCACTCGGGGCGCCAGTCCTCCGATTGACTGAGTCGCCC

GGGTACCCGTGTATCCAATAAACCCTCTTGCAGTTGCATC

CGACTTGTGGTCTCGCTGTTCCTTGGGAGGGTCTCCTCTG

AGTGATTGACTACCCGTCAGCGGGGGTCTTTCACACATGC

AGCATGTATCAAAATTAATTTGGTTTTTTTTCTTAAGTAT

TTACATTAAATGGCCATAGTACTTAAAGTTACATTGGCTT

CCTTGAAATAAACATGGAGTATTCAGAATGTGTCATAAAT

ATTTCTAATTTTAAGATAGTATCTCCATTGGCTTTCTACT

TTTTCTTTTATTTTTTTTTGTCCTCTGTCTTCCATTTGTT

GTTGTTGTTGTTTGTTTGTTTGTTGGTTGGTTGGTT

AATTTTTTTTTAAAGATCCTACACTATAGTTCAAGCTAGA

CTATTAGCTACTCTGTAACCCAGGGTGACCTTGAAGTCAT

GGGTAGCCTGCTGTTTTAGCCTTCCCACATCTAAGATTAC

AGGTATGAGCTATCATTTTTGGTATATTGATTGATTGATT

GATTGATGTGTGTGTGTGTGATTGTGTTTGTGTGTGTGAC

TGTGAAATGTGTGTATGGGTGTGTGTGAATGTGTGTATG

TATGTGTGTGTGTGAGTGTGTGTGTGTGTGTGTGCATGTG

TGTGTGTGTGACTGTGTCTATGTGTATGACTGTGTGTGTG

TGTGTGTGTGTGTGTGTGTGTGTGTGTGTGTGTGTGTTGT

GAAAAAATATTCTATGGTAGTGAGAGCCAACGCTCCGGCT

CAGGTGTCAGGTTGGTTTTTGAGACAGAGTCTTTCACTTA

GCTTGGAATTCACTGGCCGTCGTTTTACAACGTCGTGACT

GGGAAAACCCTGGCGTTACCCAACTTAATCGCCTTGCAGC

ACATCCCCCTTTCGCCAGCTGGCGTAATAGCGAAGAGGCC

CGCACCGATCGCCCTTCCCAACAGTTGCGCAGCCTGAATG

GCGAATGGCGCCTGATGCGGTATTTTCTCCTTACGCATCT

GTGCGGTATTTCACACCGCATATGGTGCACTCTCAGTACA

ATCTGCTCTGATGCCGCATAGTTAAGCCAGCCCCGACACC

CGCCAACACCCGCTGACGCGCCCTGACGGGCTTGTCTGCT

CCCGGCATCCGCTTACAGACAAGCTGTGACCGTCTCCGGG

AGCTGCATGTGTCAGAGGTTTTCACCGTCATCACCGAAAC

GCGCGATGACGAAAGGGCCTCGTGATACGCCTATTTTTAT

AGGTTAATGTCATGATAATAATGGTTTCTTAGACGTCAGG

TGGCACTTTTCGGGGAAATGTGCGCGGAACCCCTATTTGT
```

-continued

```
TTATTTTTCTAAATACATTCAAATATGTATCCGCTCATGA

GACAATAACCCTGATAAATGCTTCAATAATATTGAAAAAG

GAAGAGTATGAGTATTCAACATTTCCGTGTCGCCCTTATT

CCCTTTTTTGCGGCATTTTGCCTTCCTGTTTTTGCTCACC

CAGAAACGCTGGTGAAAGTAAAAGATGCTGAAGATCAGTT

GGGTGCACGAGTGGGTTACATCGAACTGGATCTCAACAGC

GGTAAGATCCTTGAGAGTTTTCGCCCCGAAGAACGTTTTC

CAATGATGAGCACTTTTAAAGTTCTGCTATGTGGCGCGGT

ATTATCCCGTATTGACGCCGGGCAAGAGCAACTCGGTCGC

CGCATACACTATTCTCAGAATGACTTGGTTGAGTACTCAC

CAGTCACAGAAAAGCATCTTACGGATGGCATGACAGTAAG

AGAATTATGCAGTGCTGCCATAACCATGAGTGATAACACT

GCGGCCAACTTACTTCTGACAACGATCGGAGGACCGAAGG

AGCTAACCGCTTTTTTGCACAACATGGGGGATCATGTAAC

TCGCCTTGATCGTTGGGAACCGGAGCTGAATGAAGCCATA

CCAAACGACGAGCGTGACACCACGATGCCTGTAGCAATGG

CAACAACGTTGCGCAAACTATTAACTGGCGAACTACTTAC

TCTAGCTTCCCGGCAACAATTAATAGACTGGATGGAGGCG

GATAAAGTTGCAGGACCACTTCTGCGCTCGGCCCTTCCGG

CTGGCTGGTTTATTGCTGATAAATCTGGAGCCGGTGAGCG

TGGGTCTCGCGGTATCATTGCAGCACTGGGGCCAGATGGT

AAGCCCTCCCGTATCGTAGTTATCTACACGACGGGGAGTC

AGGCAACTATG
```

In certain embodiments, the CAR comprises (a) an extracellular antigen-binding domain comprising (i) a $V_H$ that comprises a CDR1 comprising the amino acid sequence set forth in SEQ ID NO: 6, a CDR2 comprising the amino acid sequence set forth in SEQ ID NO: 7, and a $V_H$ CDR3 comprising the amino acid sequence set forth in SEQ ID NO: 8, and (ii) a $V_L$ that comprises a CDR1 comprising the amino acid sequence set forth in SEQ ID NO: 9, a CDR2 comprising the amino acid sequence set forth in SEQ ID NO: 10, and a $V_L$ CDR3 comprising the amino acid sequence set forth in SEQ ID NO: 11; (b) a transmembrane domain comprising a CD28 polypeptide (e.g., a transmembrane domain of human CD28 or a portion thereof), and (c) an intracellular signaling domain comprising (i) a CD3ζ polypeptide, and (ii) a co-stimulatory signaling region comprising a CD28 polypeptide (e.g., an intracellular domain of human CD28 or a portion thereof). In certain embodiments, the $V_H$ and $V_L$ are linked via a linker consisting of the amino acid sequence set forth in SEQ ID NO: 13. In certain embodiments, the $V_H$ and $V_L$ are positioned from the N- to the C-terminus: $V_L$-$V_H$. In certain embodiments, the CAR is designated as "OSE703LH-28z". In certain embodiments, the CAR comprises the amino acid sequence set forth in SEQ ID NO: 29, which is provided below.

```
                                  [SEQ ID NO: 29]
DIVLTQSPSSLPVTPGEPASISCRSSQSLLTVKGITSLYW

FLQKPGQSPKLLIYRMSNRDSGVPDRFSGSGSETDFTLKI

SRVEAEDVGTYYCAQFLEYPHTFGAGTKLELKGGGGSGGG

GSGGGGSAVQLVESGGGLVQPGGSLKITCAASGFTFTNAA

MYWVRQAPGKGLEWVARIRTKANNYATYYADSVKGRFTIS

RDDSKSTVYLQMDSVKTEDTATYYCIVVVLTTTRDYFDYW

GQGVLVTVSSAAAIEVMYPPPYLDNEKSNGTIIHVKGKHL

CPSPLFPGPSKPFWVLVVVGGVLACYSLLVTVAFIIFWVR

SKRSRLLHSDYMNMTPRRPGPTRKHYQPYAPPRDFAAYRS

RVKFSRSADAPAYQQGQNQLYNELNLGRREEYDVLDKRRG

RDPEMGGKPRRKNPQEGLYNELQKDKMAEAYSEIGMKGER

RRGKGHDGLYQGLSTATKDTYDALHMQALPPR
```

In certain embodiments, the CAR comprises a Myc-tag attached to the N-terminus of the scFv. In certain embodiments, the CAR comprises two Myc-tags attached to the N-terminus of the scFv. In certain embodiments, the Myc-tag consists of the amino acid sequence set forth in SEQ ID NO: 31.

An exemplary nucleotide sequence encoding the amino acid sequence of SEQ ID NO: 29 is set forth in SEQ ID NO: 30, which is provided below.

```
                                  [SEQ ID NO: 30]
GATGAACGAAATAGACAGATCGCTGAGATAGGTGCCTCAC

TGATTAAGCATTGGTAACTGTCAGACCAAGTTTACTCATA

TATACTTTAGATTGATTTAAAACTTCATTTTTAATTTAAA

AGGATCTAGGTGAAGATCCTTTTTGATAATCTCATGACCA

AAATCCCTTAACGTGAGTTTTCGTTCCACTGAGCGTCAGA

CCCCGTAGAAAAGATCAAAGGATCTTCTTGAGATCCTTTT

TTTCTGCGCGTAATCTGCTGCTTGCAAACAAAAAAACCAC

CGCTACCAGCGGTGGTTTGTTTGCCGGATCAAGAGCTACC

AACTCTTTTTCCGAAGGTAACTGGCTTCAGCAGAGCGCAG

ATACCAAATACTGTCCTTCTAGTGTAGCCGTAGTTAGGCC

ACCACTTCAAGAACTCTGTAGCACCGCCTACATACCTCGC

TCTGCTAATCCTGTTACCAGTGGCTGCTGCCAGTGGCGAT

AAGTCGTGTCTTACCGGGTTGGACTCAAGACGATAGTTAC

CGGATAAGGCGCAGCGGTCGGGCTGAACGGGGGGTTCGTG

CACACAGCCCAGCTTGGAGCGAACGACCTACACCGAACTG

AGATACCTACAGCGTGAGCATTGAGAAAGCGCCACGCTTC

CCGAAGGGAGAAAGGCGGACAGGTATCCGGTAAGCGGCAG

GGTCGGAACAGGAGAGCGCACGAGGGAGCTTCCAGGGGGA

AACGCCTGGTATCTTTATAGTCCTGTCGGGTTTCGCCACC

TCTGACTTGAGCGTCGATTTTTGTGATGCTCGTCAGGGGG

GCGGAGCCTATGGAAAAACGCCAGCAACGCGGCCTTTTTA

CGGTTCCTGGCCTTTTGCTGGCCTTTTGCTCACATGTTCT
```

TTCCTGCGTTATCCCCTGATTCTGTGGATAACCGTATTAC

CGCCTTTGAGTGAGCTGATACCGCTCGCCGCAGCCGAACG

ACCGAGCGCAGCGAGTCAGTGAGCGAGGAAGCGGAAGAGC

GCCCAATACGCAAACCGCCTCTCCCCGCGCGTTGGCCGAT

TCATTAATGCAGCTGGCACGACAGGTTTCCCGACTGGAAA

GCGGGCAGTGAGCGCAACGCAATTAATGTGAGTTAGCTCA

CTCATTAGGCACCCCAGGCTTTACACTTTATGCTTCCGGC

TCGTATGTTGTGTGGAATTGTGAGCGGATAACAATTTCAC

ACAGGAAACAGCTATGACCATGATTACGCCAAGCTTTGCT

CTTAGGAGTTTCCTAATACATCCCAAACTCAAATATATAA

AGCATTTGACTTGTTCTATGCCCTAGGGGGCGGGGGGAAG

CTAAGCCAGCTTTTTTTAACATTTAAAATGTTAATTCCAT

TTTAAATGCACAGATGTTTTTATTTCATAAGGGTTTCAAT

GTGCATGAATGCTGCAATATTCCTGTTACCAAAGCTAGTA

TAAATAAAAATAGATAAACGTGGAAATTACTTAGAGTTTC

TGTCATTAACGTTTCCTTCCTCAGTTGACAACATAAATGC

GCTGCTGAGCAAGCCAGTTTGCATCTGTCAGGATCAATTT

CCCATTATGCCAGTCATATTAATTACTAGTCAATTAGTTG

ATTTTTATTTTTGACATATACATGTGAATGAAAGACCCCA

CCTGTAGGTTTGGCAAGCTAGCTTAAGTAACGCCATTTTG

CAAGGCATGGAAAAATACATAACTGAGAATAGAAAAGTTC

AGATCAAGGTCAGGAACAGATGGAACAGCTGAATATGGGC

CAAACAGGATATCTGTGGTAAGCAGTTCCTGCCCCGGCTC

AGGGCCAAGAACAGATGGAACAGCTGAATATGGGCCAAAC

AGGATATCTGTGGTAAGCAGTTCCTGCCCCGGCTCAGGGC

CAAGAACAGATGGTCCCCAGATGCGGTCCAGCCCTCAGCA

GTTTCTAGAGAACCATCAGATGTTTCCAGGGTGCCCCAAG

GACCTGAAATGACCCTGTGCCTTATTTGAACTAACCAATC

AGTTCGCTTCTCGCTTCTGTTCGCGCGCTTATGCTCCCCG

AGCTCAATAAAAGAGCCCACAACCCCTCACTCGGGGCGCC

AGTCCTCCGATTGACTGAGTCGCCCGGGTACCCGTGTATC

CAATAAACCCTCTTGCAGTTGCATCCGACTTGTGGTCTCG

CTGTTCCTTGGGAGGGTCTCCTCTGAGTGATTGACTACCC

GTCAGCGGGGGTCTTTCATTTGGGGGCTCGTCCGGGATCG

GGAGACCCCTGCCCAGGGACCACCGACCCACCACCGGGAG

GTAAGCTGGCCAGCAACTTATCTGTGTCTGTCCGATTGTC

TAGTGTCTATGACTGATTTTATGCGCCTGCGTCGGTACTA

GTTAGCTAACTAGCTCTGTATCTGGCGGACCCGTGGTGGA

ACTGACGAGTTCGGAACACCCGGCCGCAACCCTGGGAGAC

GTCCCAGGGACTTCGGGGGCCGTTTTTGTGGCCCGACCTG

AGTCCTAAAATCCCGATCGTTTAGGACTCTTTGGTGCACC

CCCCTTAGAGGAGGGATATGTGGTTCTGGTAGGAGACGAG

AACCTAAAACAGTTCCCGCCTCCGTCTGAATTTTTGCTTT

CGGTTTGGGACCGAAGCCGCGCCGCGCGTCTTGTCTGCTG

CAGCATCGTTCTGTGTTGTCTCTGTCTGACTGTGTTTCTG

TATTTGTCTGAAAATATGGGCCCGGGCTAGACTGTTACCA

CTCCCTTAAGTTTGACCTTAGGTCACTGGAAAGATGTCGA

GCGGATCGCTCACAACCAGTCGGTAGATGTCAAGAAGAGA

CGTTGGGTTACCTTCTGCTCTGCAGAATGGCCAACCTTTA

ACGTCGGATGGCCGCGAGACGGCACCTTTAACCGAGACCT

CATCACCCAGGTTAAGATCAAGGTCTTTTCACCTGGCCCG

CATGGACACCCAGACCAGGTCCCCTACATCGTGACCTGGG

AAGCCTTGGCTTTTGACCCCCCTCCCTGGGTCAAGCCCTT

TGTACACCCTAAGCCTCCGCCTCCTCTTCCTCCATCCGCC

CCGTCTCTCCCCCTTGAACCTCCTCGTTCGACCCCGCCTC

GATCCTCCCTTTATCCAGCCCTCACTCCTTCTCTAGGCGC

CCCCATATGGCCATATGAGATCTTATATGGGCCACCCCCG

CCCCTTGTAAACTTCCCTGACCCTGACATGACAAGAGTTA

CTAACAGCCCCTCTCTCCAAGCTCACTTACAGGCTCTCTA

CTTAGTCCAGCACGAAGTCTGGAGACCTCTGGCGGCAGCC

TACCAAGAACAACTGGACCGACCGGTGGTACCTCACCCTT

ACCGAGTCGGCGACACAGTGTGGGTCCGCCGACACCAGAC

TAAGAACCTAGAACCTCGCTGGAAAGGACCTTACACAGTC

CTGCTGACCACCCCCACCGCCCTCAAAGTAGACGGCATCG

CAGCTTGGATACACGCCGCCCACGTGAAGGCTGCCGACCC

CGGGGGTGGACCATCCTCTAGACTGCCATGGCCCTGCCAG

TAACGGCTCTGCTGCTGCCACTTGCTCTGCTCCTCCATGC

AGCCAGGCCTGAGCAGAAGCTGATCTCAGAGGAGGACCTG

GAGCAGAAGCTGATCTCAGAGGAGGACCTGGATATAGTCC

TCACACAGTCCCCTAGTTCACTGCCAGTCACTCCAGGAGA

ACCTGCTTCCATATCATGTAGATCAAGTCAAAGTTTGCTT

ACAGTAAAAGGAATTACAAGCCTCTATTGGTTCTTGCAAA

AACCTGGTCAGAGCCCAAAGTTGCTGATCTATAGAATGTC

CAACAGAGACTCCGGAGTCCCTGATAGATTCAGCGGCTCA

GGATCAGAAACGGACTTCACCCTTAAAATATCAAGAGTAG

AAGCCGAAGATGTTGGCACCTACTATTGTGCTCAGTTTCT

GGAATACCCTCATACGTTTGGAGCAGGTACCAAGCTCGAA

CTCAAGGGAGGTGGAGGATCAGGCGGTGGAGGATCCGGTG

GCGGAGGAAGCGCCGTTCAACTTGTTGAATCTGGTGGTGG

CCTCGTTCAGCCGGGGGGCTCCCTTAAAATTACTTGTGCA

GCTAGCGGATTCACATTCACCAATGCCGCAATGTACTGGG

-continued

```
TTAGACAAGCTCCTGGCAAAGGACTGGAATGGGTAGCTAG

AATTAGAACTAAAGCTAATAACTATGCAACATACTATGCT

GATTCCGTCAAAGGACGATTCACTATCAGCAGAGATGATA

GCAAGTCAACTGTGTACCTGCAGATGGACTCCGTTAAGAC

AGAGGATACAGCTACATACTATTGTATCGTAGTTGTGCTG

ACAACTACCAGAGATTACTTTGATTATTGGGGCCAAGGTG

TTCTGGTAACAGTGAGTAGTGCGGCCGCAATTGAAGTTAT

GTATCCTCCTCCTTACCTAGACAATGAGAAGAGCAATGGA

ACCATTATCCATGTGAAAGGGAAACACCTTTGTCCAAGTC

CCCTATTTCCCGGACCTTCTAAGCCCCTTTTGGGTGCTGGT

GGTGGTTGGTGGAGTCCTGGCTTGCTATAGCTTGCTAGTA

ACAGTGGCCTTTATTATTTTCTGGGTGAGGAGTAAGAGGA

GCAGGCTCCTGCACAGTGACTACATGAACATGACTCCCCG

CCGCCCCGGGCCCACCCGCAAGCATTACCAGCCCTATGCC

CCACCACGCGACTTCGCAGCCTATCGCTCCAGAGTGAAGT

TCAGCAGGAGCGCAGAcgCCCCCGCGTACCAGCAGGGCCA

GAACCAGCTCTATAACGA

GCTCAATCTAGGACGAAGAGAGGAGTACGATGTTTTGGAC

AAGAGACGTGGCCGGGACCCTGAGATGGGGGGAAAGCCGA

GAAGGAAGAACCCTCAGGAAGGCCTGTACAATGAACTGCA

GAAAGATAAGATGGCGGAGGCCTACAGTGAGATTGGGATG

AAAGGCGAGCGCCGGAGGGGCAAGGGGCACGATGGCCTTT

ACCAGGGTCTCAGTACAGCCACCAAGGACACCTACGACGC

CCTTCACATGCAGGCCCTGCCCCCTCGCTGAGTCGACGGA

TCCGGATTAGTCCAATTTGTTAAAGACAGGATATCAGTGG

TCCAGGCTCTAGTTTTGACTCAACAATATCACCAGCTGAA

GCCTATAGAGTACGAGCCATAGATAAAATAAAAGATTTTA

TTTAGTCTCCAGAAAAAGGGGGGAATGAAAGACCCCACCT

GTAGGTTTGGCAAGCTAGCTTAAGTAACGCCATTTTGCAA

GGCATGGAAAAATACATAACTGAGAATAGAGAAGTTCAGA

TCAAGGTCAGGAACAGATGGAACAGCTGAATATGGGCCAA

ACAGGATATCTGTGGTAAGCAGTTCCTGCCCCGGCTCAGG

GCCAAGAACAGATGGAACAGCTGAATATGGGCCAAACAGG

ATATCTGTGGTAAGCAGTTCCTGCCCCGGCTCAGGGCCAA

GAACAGATGGTCCCCAGATGCGGTCCAGCCCTCAGCAGTT

TCTAGAGAACCATCAGATGTTTCCAGGGTGCCCCAAGGAC

CTGAAATGACCCTGTGCCTTATTTGAACTAACCAATCAGT

TCGCTTCTCGCTTCTGTTCGCGCGCTTCTGCTCCCCGAGC

TCAATAAAAGAGCCCACAACCCCTCACTCGGGGCGCCAGT

CCTCCGATTGACTGAGTCGCCCGGGTACCCGTGTATCCAA
```

-continued

```
TAAACCCTCTTGCAGTTGCATCCGACTTGTGGTCTCGCTG

TTCCTTGGGAGGGTCTCCTCTGAGTGATTGACTACCCGTC

AGCGGGGGTCTTTCACACATGCAGCATGTATCAAAATTAA

TTTGGTTTTTTTTCTTAAGTATTTACATTAAATGGCCATA

GTACTTAAAGTTACATTGGCTTCCTTGAAATAAACATGGA

GTATTCAGAATGTGTCATAAATATTTCTAATTTTAAGATA

GTATCTCCATTGGCTTTCTACTTTTTCTTTTATTTTTTTT

TGTCCTCTGTCTTCCATTTGTTGTTGTTGTTGTTTGTTTG

TTTGTTTGTTGGTTGGTTGGTTAATTTTTTTTTAAAGATC

CTACACTATAGTTCAAGCTAGACTATTAGCTACTCTGTAA

CCCAGGGTGACCTTGAAGTCATGGGTAGCCTGCTGTTTTA

GCCTTCCCACATCTAAGATTACAGGTATGAGCTATCATTT

TTGGTATATTGATTGATTGATTGATTGATGTGTGTGTGTG

TGATTGTGTTTGTGTGTGTGACTGTGAAAATGTGTGTATG

GGTGTGTGTGAATGTGTGTATGTATGTGTGTGTGTGAGTG

TGTGTGTGTGTGTGTGCATGTGTGTGTGTGACTGTGTC

TATGTGTATGACTGTGTGTGTGTGTGTGTGTGTGTGTGTG

TGTGTGTGTGTGTGTGTGTTGTGAAAAAATATTCTATGGT

AGTGAGAGCCAACGCTCCGGCTCAGGTGTCAGGTTGGTTT

TTGAGACAGAGTCTTTCACTTAGCTTGGAATTCACTGGCC

GTCGTTTTACAACGTCGTGACTGGGAAAACCCTGGCGTTA

CCCAACTTAATCGCCTTGCAGCACATCCCCCTTTCGCCAG

CTGGCGTAATAGCGAAGAGGCCCGCACCGATCGCCCTTCC

CAACAGTTGCGCAGCCTGAATGGCGAATGGCGCCTGATGC

GGTATTTTCTCCTTACGCATCTGTGCGGTATTTCACACCG

CATATGGTGCACTCTCAGTACAATCTGCTCTGATGCCGCA

TAGTTAAGCCAGCCCCGACACCCGCCAACACCCGCTGACG

CGCCCTGACGGGCTTGTCTGCTCCCGGCATCCGCTTACAG

ACAAGCTGTGACCGTCTCCGGGAGCTGCATGTGTCAGAGG

TTTTCACCGTCATCACCGAAACGCGCGATGACGAAAGGGC

CTCGTGATACGCCTATTTTTATAGGTTAATGTCATGATAA

TAATGGTTTCTTAGACGTCAGGTGGCACTTTTCGGGGAAA

TGTGCGCGGAACCCCTATTTGTTTATTTTTCTAAATACAT

TCAAATATGTATCCGCTCATGAGACAATAACCCTGATAAA

TGCTTCAATAATATTGAAAAAGGAAGAGTATGAGTATTCA

ACATTTCCGTGTCGCCCTTATTCCCTTTTTTGCGGCATTT

TGCCTTCCTGTTTTTGCTCACCCAGAAACGCTGGTGAAAG

TAAAAGATGCTGAAGATCAGTTGGGTGCACGAGTGGGTTA

CATCGAACTGGATCTCAACAGCGGTAAGATCCTTGAGAGT

TTTCGCCCCGAAGAACGTTTTCCAATGATGAGCACTTTTA

AAGTTCTGCTATGTGGCGCGGTATTATCCCGTATTGACGC
```

-continued

```
CGGGCAAGAGCAACTCGGTCGCCGCATACACTATTCTCAG

AATGACTTGGTTGAGTACTCACCAGTCACAGAAAAGCATC

TTACGGATGGCATGACAGTAAGAGAATTATGCAGTGCTGC

CATAACCATGAGTGATAACACTGCGGCCAACTTACTTCTG

ACAACGATCGGAGGACCGAAGGAGCTAACCGCTTTTTTGC

ACAACATGGGGGATCATGTAACTCGCCTTGATCGTTGGGA

ACCGGAGCTGAATGAAGCCATACCAAACGACGAGCGTGAC

ACCACGATGCCTGTAGCAATGGCAACAACGTTGCGCAAAC

TATTAACTGGCGAACTACTTACTCTAGCTTCCCGGCAACA

ATTAATAGACTGGATGGAGGCGGATAAAGTTGCAGGACCA

CTTCTGCGCTCGGCCCTTCCGGCTGGCTGGTTTATTGCTG

ATAAATCTGGAGCCGGTGAGCGTGGGTCTCGCGGTATCAT

TGCAGCACTGGGGCCAGATGGTAAGCCCTCCCGTATCGTA

GTTATCTACACGACGGGGAGTCAGGCAACTATG
```

In certain embodiments, a presently disclosed CAR further comprises an inducible promoter, for expressing nucleotide sequences in human cells. Promoters for use in expressing CAR genes can be a constitutive promoter, such as ubiquitin C (UbiC) promoter

5.4. Cells

The presently disclosed subject matter provides cells comprising a presently disclosed CD127-targeted antigen-recognizing receptor (e.g., one disclosed in Section 5.3). In certain embodiments, the cell is selected from the group consisting of cells of lymphoid lineage and cells of myeloid lineage. In certain embodiments, the cell is an immunoresponsive cell. In certain embodiments, the immunoresponsive cell is a cell of lymphoid lineage.

In certain embodiments, the cell is a cell of the lymphoid lineage. Cells of the lymphoid lineage can provide production of antibodies, regulation of cellular immune system, detection of foreign agents in the blood, detection of cells foreign to the host, and the like. Non-limiting examples of cells of the lymphoid lineage include T-cells, Natural Killer (NK) cells, B cells, dendritic cells, stem cells from which lymphoid cells may be differentiated. In certain embodiments, the stem cell is a pluripotent stem cell (e.g., embryonic stem cell).

In certain embodiments, the cell is a T-cell. T-cells can be lymphocytes that mature in the thymus and are chiefly responsible for cell-mediated immunity. T-cells are involved in the adaptive immune system. The T-cells of the presently disclosed subject matter can be any type of T-cells, including, but not limited to, helper T-cells, cytotoxic T-cells, memory T-cells (including central memory T-cells, stem-cell-like memory T-cells (or stem-like memory T-cells), and two types of effector memory T-cells: e.g., TEM cells and TEMRA cells, Regulatory T-cells (also known as suppressor T-cells), tumor-infiltrating lymphocyte (TIL), Natural killer T-cells, Mucosal associated invariant T-cells, and γδ T-cells. Cytotoxic T-cells (CTL or killer T-cells) are a subset of T lymphocytes capable of inducing the death of infected somatic or tumor cells. A patient's own T-cells may be genetically modified to target specific antigens through the introduction of an antigen-recognizing receptor, e.g., a CAR or a TCR. In certain embodiments, the immunoresponsive cell is a T-cell. The T-cell can be a CD4$^+$ T-cell or a CD8$^+$ T-cell. In certain embodiments, the T-cell is a CD4$^+$ T-cell. In certain embodiments, the T-cell is a CD8$^+$ T-cell.

In certain embodiments, the cell is a NK cell. Natural killer (NK) cells can be lymphocytes that are part of cell-mediated immunity and act during the innate immune response. NK cells do not require prior activation in order to perform their cytotoxic effect on target cells.

Types of human lymphocytes of the presently disclosed subject matter include, without limitation, peripheral donor lymphocytes. e.g., those disclosed in Sadelain et al., *Nat Rev Cancer* (2003); 3:35-45 (disclosing peripheral donor lymphocytes genetically modified to express CARs), in Morgan, R. A., et al. 2006 *Science* 314:126-129 (disclosing peripheral donor lymphocytes genetically modified to express a full-length tumor antigen-recognizing T-cell receptor complex comprising the a and f3 heterodimer), in Panelli et al., *J Immunol* (2000); 164:495-504; Panelli et al., *J Immunol* (2000); 164:4382-4392 (disclosing lymphocyte cultures derived from tumor infiltrating lymphocytes (TILs) in tumor biopsies), and in Dupont et al., Cancer Res (2005); 65:5417-5427; Papanicolaou et al., *Blood* (2003); 102:2498-2505 (disclosing selectively in vitro-expanded antigen-specific peripheral blood leukocytes employing artificial antigen-presenting cells (AAPCs) or pulsed dendritic cells).

The cells (e.g., T-cells) can be autologous, non-autologous (e.g., allogeneic), or derived in vitro from engineered progenitor or stem cells.

The cells of the presently disclosed subject matter can be cells of the myeloid lineage. Non-limiting examples of cells of the myeloid lineage include monocytes, macrophages, neutrophils, dendritic cells, basophils, neutrophils, eosinophils, megakaryocytes, mast cell, erythrocyte, thrombocytes, and stem cells from which myeloid cells may be differentiated. In certain embodiments, the stem cell is a pluripotent stem cell (e.g., an embryonic stem cell or an induced pluripotent stem cell).

In certain embodiments, the cells can be transduced with the presently disclosed CD127-targeted antigen-recognizing receptor such that the cells express the antigen-recognizing receptor.

5.5. Compositions and Vectors

The presently disclosed subject matter provides compositions comprising a presently disclosed CD127-targeted antigen-recognizing receptor (e.g., one disclosed in Section 5.3). Also provided are cells comprising such compositions.

In certain embodiments, the presently disclosed CD127-targeted antigen-recognizing receptor is operably linked to a promoter.

Furthermore, the present discloses subject matter provides nucleic acid compositions comprising a polynucleotide encoding a presently disclosed CD127-targeted antigen-recognizing receptor (e.g., one disclosed in Section 5.3). Also provided are cells comprising such nucleic acid compositions.

In certain embodiments, the nucleic acid composition further comprises a promoter that is operably linked to the presently disclosed CD127-targeted antigen-recognizing receptor.

In certain embodiments, the promoter is endogenous or exogenous. In certain embodiments, the exogenous promoter is selected from an elongation factor (EF)-1 promoter, a cytomegalovirus immediate-early promoter (CMV) promoter, a simian virus 40 early promoter (SV40) promoter, a phosphoglycerate kinase (PGK) promoter, and a metallothionein promoter. In certain embodiments, the promoter is an inducible promoter. In certain embodiment, the inducible promoter is selected from a NFAT transcriptional response element (TRE) promoter, a CD69 promoter, a CD25 promoter, and an IL-2 promoter.

The compositions and nucleic acid compositions can be administered to subjects or and/delivered into cells by art-known methods or as described herein. Genetic modification of a cell (e.g., a T-cell or a NK cell) can be accomplished by transducing a substantially homogeneous cell composition with a recombinant DNA construct. In certain embodiments, a retroviral vector (e.g., gammaretroviral vector or lentiviral vector) is employed for the introduction of the DNA construct into the cell. For example, a polynucleotide encoding an antigen-recognizing receptor can be cloned into a retroviral vector and expression can be driven from its endogenous promoter, from the retroviral long terminal repeat, or from a promoter specific for a target cell type of interest. Non-viral vectors may be used as well.

For initial genetic modification of a cell to include a presently disclosed CD127-targeted antigen-recognizing receptor (e.g., a CAR or a TCR), a retroviral vector can be employed for transduction, however any other suitable viral vector or non-viral delivery system can be used. The antigen-recognizing receptor can be constructed in a single, multicistronic expression cassette, in multiple expression cassettes of a single vector, or in multiple vectors. Examples of elements that create polycistronic expression cassette include, but is not limited to, various viral and non-viral Internal Ribosome Entry Sites (IRES, e.g., FGF-1 IRES, FGF-2 IRES, VEGF IRES, IGF-II IRES, NF-κB IRES, RUNX1 IRES, p53 IRES, hepatitis A IRES, hepatitis C IRES, pestivirus IRES, aphthovirus IRES, picornavirus IRES, poliovirus IRES and encephalomyocarditis virus IRES) and cleavable linkers (e.g., 2A peptides, e.g., P2A, T2A, E2A and F2A peptides). Combinations of retroviral vector and an appropriate packaging line are also suitable, where the capsid proteins will be functional for infecting human cells. Various amphotropic virus-producing cell lines are known, including, but not limited to, PA12 (Miller et al., (1985) Mol Cell Biol (1985); 5:431-437); PA317 (Miller., et al., Mol Cell Biol (1986); 6:2895-2902); and CRIP (Danos et al., Proc Natl Acad Sci USA (1988); 85:6460-6464). Non-amphotropic particles are suitable too, e.g., particles pseudotyped with VSVG, RD114 or GALV envelope and any other known in the art.

Possible methods of transduction also include direct co-culture of the cells with producer cells (Bregni et al., Blood (1992); 80:1418-1422), or culturing with viral supernatant alone or concentrated vector stocks with or without appropriate growth factors and polycations (Xu et al., Exp Hemat (1994); 22:223-230; and Hughes et al. J Clin Invest (1992); 89:1817).

Other transducing viral vectors can be used to modify a cell. In certain embodiments, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). Other viral vectors that can be used include, for example, adeno-viral, lentiviral, and adena-associated viral vectors, vaccinia virus, a bovine papilloma virus, or a herpes virus, such as Epstein-Barr Virus (also see, for example, the vectors of Miller, Human Gene Thera (1990); 15-14; Friedman, Science 244:1275-1281, 1989; Eglitis et al., BioTechniques (1988); 6:608-614; Tolstoshev et al., Cur Opin Biotechnol (1990); 1:55-61; Sharp, The Lancet (1991); 337:1277-78; Cornetta et al., Nucleic Acid Research and Molecular Biology 36:311-22, 1987; Anderson, Science (1984); 226:401-409; Moen, Blood Cells 17:407-16, 1991; Miller et al., Biotechnol (1989); 7:980-90; LeGal La Salle et al., Science (1993); 259:988-90; and Johnson, Chest (1995)107:77S-83S). Retroviral vectors are particularly well developed and have been used in clinical settings (Rosenberg et al., N Engl J Med (1990); 323:370, 1990; Anderson et al., U.S. Pat. No. 5,399,346).

Non-viral approaches can also be employed for genetic modification of a cell. For example, a nucleic acid molecule can be introduced into a cell by administering the nucleic acid in the presence of lipofection (Feigner et al., Proc Natl Acad Sci U.S.A. (1987); 84:7413; Ono et al., Neurosci Lett (1990); 17:259; Brigham et al., Am J Med Sci (1989); 298:278; Staubinger et al., Methods in Enzymol (1983); 101:512, Wu et al., J Biol Chem (1988); 263:14621; Wu et al., J Biol Chem (1989); 264:16985), or by micro-injection under surgical conditions (Wolff et al., Science (1990); 247:1465). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g. Zinc finger nucleases, meganucleases, or TALE nucleases, CRISPR). Transient expression may be obtained by RNA electroporation.

Any targeted genome editing methods can also be used to deliver a presently disclosed antigen-recognizing receptor to a cell or a subject. In certain embodiments, a CRISPR system is used to deliver a presently disclosed antigen-recognizing receptor disclosed herein. In certain embodiments, zinc-finger nucleases are used to deliver the antigen-recognizing receptor. In certain embodiments, a TALEN system is used to deliver a presently disclosed antigen-recognizing receptor.

Clustered regularly-interspaced short palindromic repeats (CRISPR) system is a genome editing tool discovered in prokaryotic cells. When utilized for genome editing, the system includes Cas9 (a protein able to modify DNA utilizing crRNA as its guide), CRISPR RNA (crRNA, contains the RNA used by Cas9 to guide it to the correct section of host DNA along with a region that binds to tracrRNA (generally in a hairpin loop form) forming an active complex with Cas9), trans-activating crRNA (tracrRNA, binds to crRNA and forms an active complex with Cas9), and an optional section of DNA repair template (DNA that guides the cellular repair process allowing insertion of a specific DNA sequence). CRISPR/Cas9 often employs a plasmid to transfect the target cells. The crRNA needs to be designed for each application as this is the sequence that Cas9 uses to identify and directly bind to the target DNA in a cell. The repair template carrying CAR expression cassette need also be designed for each application, as it must overlap with the sequences on either side of the cut and code for the insertion sequence. Multiple crRNA's and the tracrRNA can be packaged together to form a single-guide RNA (sgRNA).

This sgRNA can be joined together with the Cas9 gene and made into a plasmid in order to be transfected into cells.

A zinc-finger nuclease (ZFN) is an artificial restriction enzyme, which is generated by combining a zinc finger DNA-binding domain with a DNA-cleavage domain. A zinc finger domain can be engineered to target specific DNA sequences which allows a zinc-finger nuclease to target desired sequences within genomes. The DNA-binding domains of individual ZFNs typically contain a plurality of individual zinc finger repeats and can each recognize a plurality of base pairs. The most common method to generate new zinc-finger domain is to combine smaller zinc-finger "modules" of known specificity. The most common cleavage domain in ZFNs is the non-specific cleavage domain from the type IIs restriction endonuclease FokI. Using the endogenous homologous recombination (HR) machinery and a homologous DNA template carrying CAR expression cassette, ZFNs can be used to insert the CAR expression cassette into genome. When the targeted sequence is cleaved by ZFNs, the HR machinery searches for homology between the damaged chromosome and the homologous DNA template, and then copies the sequence of the template between the two broken ends of the chromosome, whereby the homologous DNA template is integrated into the genome.

Transcription activator-like effector nucleases (TALEN) are restriction enzymes that can be engineered to cut specific sequences of DNA. TALEN system operates on almost the same principle as ZFNs. They are generated by combining a transcription activator-like effectors DNA-binding domain with a DNA cleavage domain. Transcription activator-like effectors (TALEs) are composed of 33-34 amino acid repeating motifs with two variable positions that have a strong recognition for specific nucleotides. By assembling arrays of these TALEs, the TALE DNA-binding domain can be engineered to bind desired DNA sequence, and thereby guide the nuclease to cut at specific locations in genome.cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g. the elongation factor 1a enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Methods for delivering the genome editing agents/systems can vary depending on the need. In certain embodiments, the components of a selected genome editing method are delivered as DNA constructs in one or more plasmids. In certain embodiments, the components are delivered via viral vectors. Common delivery methods include but is not limited to, electroporation, microinjection, gene gun, impalefection, hydrostatic pressure, continuous infusion, sonication, magnetofection, adeno-associated viruses, envelope protein pseudotyping of viral vectors, replication-competent vectors cis and trans-acting elements, herpes simplex virus, and chemical vehicles (e.g., oligonucleotides, lipoplexes, polymersomes, polyplexes, dendrimers, inorganic Nanoparticles, and cell-penetrating peptides).

5.6. Polypeptides

The presently disclosed subject matter provides methods for optimizing an amino acid sequence or a nucleotide sequence by producing an alteration in the sequence. Such alterations may include certain mutations, deletions, insertions, or post-translational modifications. The presently disclosed subject matter further includes analogs of any naturally-occurring polypeptides disclosed herein (including, but not limited to, CD127, CD8, CD28, 4-1BB, and CD3ζ). Analogs can differ from a naturally-occurring polypeptide disclosed herein by amino acid sequence differences, by post-translational modifications, or by both. Analogs can exhibit at least about 85%, about 90%, about 91%, about 92%, about 93%, about 94%, about 95%, about 96%, about 97%, about 98%, about 99% or more homologous or identical to all or part of a naturally-occurring amino, acid sequence of the presently disclosed subject matter. The length of sequence comparison is at least 5, 10, 15 or 20 amino acid residues, e.g., at least 25, 50, or 75 amino acid residues, or more than 100 amino acid residues. Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

In addition to full-length polypeptides, the presently disclosed subject matter also provides fragments of any of the polypeptides disclosed herein. As used herein, the term "a fragment" means at least 5, 10, 13, or 15 amino acids. In certain embodiments, a fragment comprises at least 20 contiguous amino acids, at least 30 contiguous amino acids, or at least 50 contiguous amino acids. In certain embodiments, a fragment comprises at least 60 to 80, 100, 200, 300 or more contiguous amino acids. Fragments can be generated by methods known to those skilled in the art or may result from normal protein processing (e.g., removal of amino acids from the nascent polypeptide that are not required for biological activity or removal of amino acids by alternative mRNA splicing or alternative protein processing events).

5.7. Formulations and Administration

The presently disclosed subject matter also provides compositions comprising the presently disclosed cells. Compositions comprising the presently disclosed cells can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are some-what more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the genetically modified cells in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the presently disclosed subject matter, however, any vehicle, diluent, or additive used would have to be compatible with the genetically modified cells.

The compositions can be isotonic, i.e., they can have the same osmotic pressure as blood and lacrimal fluid. The desired isotonicity of the compositions may be accomplished using sodium chloride, or other pharmaceutically acceptable agents such as dextrose, boric acid, sodium tartrate, propylene glycol or other inorganic or organic solutes. Sodium chloride can be particularly for buffers containing sodium ions.

Viscosity of the compositions, if desired, can be maintained at the selected level using a pharmaceutically acceptable thickening agent. For example, methylcellulose is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Compositions comprising the presently disclosed cells can be provided systemically or directly to a subject for inducing and/or enhancing an immune response to an antigen and/or treating and/or preventing a neoplasia. In certain embodiments, the presently disclosed cells or compositions comprising thereof are directly injected into an organ of interest (e.g., an organ affected by a neoplasia). Alternatively, the presently disclosed cells or compositions comprising thereof are provided indirectly to the organ of interest, for example, by administration into the circulatory system (e.g., the tumor vasculature). Expansion and differentiation agents can be provided prior to, during or after administration of the cells or compositions to increase production of cells (e.g., T-cells or NK cells) in vitro or in vivo.

The presently disclosed cells can be administered in any physiologically acceptable vehicle, normally intravascularly, although they may also be introduced into bone or other convenient site where the cells may find an appropriate site for regeneration and differentiation (e.g., thymus).

The quantity of cells to be administered can vary for the subject being treated. In certain embodiments, between about $10^4$ and about $10^{10}$, between about $10^4$ and about $10^7$, between about $10^5$ and about $10^7$, between about $10^5$ and about $10^9$, or between about $10^6$ and about $10^8$ of the presently disclosed cells are administered to a subject. More effective cells may be administered in even smaller numbers. Usually, at least about $1\times10^5$ cells will be administered, eventually reaching about $1\times10^{10}$ or more. In certain embodiments, at least about $1\times10^5$, at least about $5\times10^5$, at least about $1\times10^6$, at least about $5\times10^6$, at least about $1\times10^7$, at least about $5\times10^7$, at least about $1\times10^8$, or at least about $5\times10^8$ of the presently disclosed cells are administered to a subject. In certain embodiments, between about $1\times10^5$ and about $5\times10^5$ of the presently disclosed cells are administered to a subject. In certain embodiments, about $2\times10^5$ of the presently disclosed cells are administered to a subject. In certain embodiments, between about $1\times10^6$ and about $5\times10^6$ of the presently disclosed cells are administered to a subject. In certain embodiments, about $1\times10^6$ of the presently disclosed cells are administered to a subject. In certain embodiments, about $3\times10^6$ of the presently disclosed cells are administered to a subject. In certain embodiments, between about $1\times10^7$ and about $5\times10^7$ of the presently disclosed cells are administered to a subject. In certain embodiments, about $1\times10^7$ of the presently disclosed cells are administered to a subject. The precise determination of what would be considered an effective dose can be based on factors individual to each subject, including their size, age, sex, weight, and condition of the particular subject. Dosages can be readily ascertained by those skilled in the art from this disclosure and the knowledge in the art.

The presently disclosed cells can comprise a purified population of cells. Those skilled in the art can readily determine the percentage of the presently disclosed cells in a population using various well-known methods, such as fluorescence activated cell sorting (FACS). Suitable ranges of purity in populations comprising the presently disclosed immunoresponsive cells are about 50% to about 55%, about 5% to about 60%, and about 65% to about 70%. In certain embodiments, the purity is about 70% to about 75%, about 75% to about 80%, or about 80% to about 85%. In certain embodiments, the purity is about 85% to about 90%, about 90% to about 95%, and about 95% to about 100%. Dosages can be readily adjusted by those skilled in the art (e.g., a decrease in purity may require an increase in dosage). The cells can be introduced by injection, catheter, or the like.

The skilled artisan can readily determine the amount of cells and optional additives, vehicles, and/or carrier in compositions and to be administered in methods. Typically, any additives (in addition to the active cell(s) and/or agent(s)) are present in an amount of 0.001 to 50% (weight) solution in phosphate buffered saline, and the active ingredient is present in the order of micrograms to milligrams, such as about 0.0001 to about 5 wt %, about 0.0001 to about 1 wt %, about 0.0001 to about 0.05 wt % or about 0.001 to about 20 wt %, about 0.01 to about 10 wt %, or about 0.05 to about 5 wt %. For any composition to be administered to an animal or human, the followings can be determined: toxicity such as by determining the lethal dose (LD) and LD50 in a suitable animal model e.g., rodent such as mouse; the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

In certain embodiments, the composition is a pharmaceutical composition comprising the presently disclosed cells and a pharmaceutically acceptable carrier.

Administration of the compositions can be autologous or heterologous. For example, cells can be obtained from one subject, and administered to the same subject or a different, compatible subject. Peripheral blood derived cells or their progeny (e.g., in vivo, ex vivo or in vitro derived) can be administered. When administering a presently disclosed composition (e.g., a pharmaceutical composition comprising presently disclosed cells), it can be formulated in a unit dosage injectable form (solution, suspension, emulsion).

The presently disclosed cells and compositions can be administered by any method known in the art including, but not limited to, oral administration, intravenous administration, subcutaneous administration, intranodal administration, intratumoral administration, intrathecal administration, intrapleural administration, intraosseous administration, intraperitoneal administration, pleural administration, and direct administration to the subject.

5.8. Methods of Treatment

The presently disclosed cells and compositions comprising thereof can be used for treating and/or preventing a tumor or a neoplasia. In certain embodiments, the tumor or neoplasia can be treated by the presently disclosed cells and compositions include leukemia (e.g., acute lymphoblastic leukemia, e.g. T-cell acute lymphoblastic leukemia (T-ALL) or B-cell acute lymphoblastic leukemia (B-ALL)), lymphoma (e.g., Hodgkin's lymphoma, and non-Hodgkin's lymphoma), breast cancer associated with CD127$^+$ cells, renal cancer, bladder cancer, lung cancer, pancreatic cancer, T-cell cutaneous lymphoma (e.g., Sezary lymphoma), or acute lymphoblastoid leukemia with gain-mutation of the IL7-R/TSLP pathway, and mesothelioma. In certain embodiments, the cell is a T-cell. The T-cell can be a CD4$^+$ T-cell or a CD8$^+$ T-cell. In certain embodiments, the T-cell is a CD4$^+$ T-cell.

The presently disclosed subject matter provides methods for inducing and/or increasing an immune response in a subject in need thereof. The presently disclosed cells and compositions comprising thereof can be used in a therapy or medicament. The presently disclosed subject matter provides various methods of using the cells (e.g., T-cells) or compositions comprising thereof. For example, the presently disclosed cells and compositions comprising thereof can be used for reducing tumor burden in a subject. The presently disclosed cell can reduce the number of tumor cells, reduce tumor size, and/or eradicate the tumor in the subject. The presently disclosed cells and compositions comprising thereof can be used for treating and/or preventing a neoplasia in a subject. The presently disclosed cells and compositions comprising thereof can be used for prolonging the survival of a subject suffering from a neoplasia. Such methods comprise administering the presently disclosed cells or a composition (e.g., a pharmaceutical composition) comprising thereof to achieve the desired effect, e.g., palliation of an existing condition or prevention of recurrence. For treatment, the amount administered is an amount effective in producing the desired effect. An effective amount can be provided in one or a series of administrations. An effective amount can be provided in a bolus or by continuous perfusion.

The presently disclosed subject matter provides various methods of using the cells (e.g., T-cells) or compositions comprising thereof. For example, the presently disclosed subject matter provides methods of reducing tumor burden in a subject. In certain embodiments, the method of reducing tumor burden comprises administering the presently disclosed cells or a composition comprising thereof to the subject. The presently disclosed cell can reduce the number of tumor cells, reduce tumor size, and/or eradicate the tumor in the subject.

The presently disclosed subject matter also provides methods of increasing or lengthening survival of a subject having a neoplasia. In certain embodiments, the method of increasing or lengthening survival of a subject having neoplasia comprises administering the presently disclosed immunoresponsive cells or a composition comprising thereof to the subject. The method can reduce or eradicate tumor burden in the subject. Additionally, the presently disclosed subject matter provides methods for increasing an immune response in a subject, comprising administering the presently disclosed cell or a composition comprising thereof to the subject. The presently disclosed subject matter further provides methods for treating and/or preventing a neoplasia in a subject, comprising administering the presently disclosed cells or a composition comprising thereof to the subject.

In certain embodiments, the tumor or neoplasia is associated with CD127. In certain embodiments, the tumor or neoplasia expresses CD127. In certain embodiments, the tumor is cancer.

In certain embodiments, the tumor or neoplasia is a solid tumor. In such certain embodiments, the cells used in the above-noted various methods comprise a CD127-targeted antigen-recognizing receptor (e.g., a CAR) that has a high binding affinity to CD127, e.g., one disclosed in Section 5.3. In certain embodiments, the cells comprise a CD127-targeted CAR comprising an extracellular antigen-binding domain that binds to human CD127 with an ED$_{50}$ of less than about 3000 ng/ml. In certain embodiments, the cells comprise a CD127-targeted CAR comprising an extracellular antigen-binding domain that binds to human CD127 with an ED$_{50}$ of about 2000 ng/ml or less. In certain embodiments, the cells comprise a CD127-targeted CAR comprising an extracellular antigen-binding domain that binds to human CD127 with an ED$_{50}$ of about 1000 ng/ml or less. In certain embodiments, the cells comprise a CD127-targeted CAR comprising an extracellular antigen-binding domain that binds to human CD127 with an ED$_{50}$ of about 500 ng/ml. In certain embodiments, the cells comprise a CD127-targeted CAR comprising an extracellular antigen-binding domain that binds to human CD127 with an ED$_{50}$ of about 550 ng/ml.

Non-limiting examples of solid tumors include mesothelioma, renal cancer, bladder cancer, lung cancer, pancreatic cancer, ovarian cancer, breast cancer, colon cancer, pleural tumor, glioblastoma, esophageal cancer, gastric cancer, synovial sarcoma, thymic carcinoma, endometrial carcinoma, stomach cancer, and cholangiocarcinoma.

In certain embodiments, the tumor or neoplasia is a hematological tumor. In certain embodiments, the tumor or neoplasia is a hematological malignancy (e.g., hematological cancer). In such certain embodiments, the cells used in the above-noted various methods comprise a CD127-targeted antigen-recognizing receptor (e.g., a CAR) that has a low binding affinity to CD127, e.g., one disclosed in Section 5.3. In certain embodiments, the cells comprise a CD127-targeted CAR comprising an extracellular antigen-binding domain that binds to human CD127 with an $ED_{50}$ of about 3000 ng/ml or more. In certain embodiments, the cells comprise a CD127-targeted CAR comprising an extracellular antigen-binding domain that binds to human CD127 with an $ED_{50}$ of about 3000 ng/ml. In certain embodiments, the cells comprise a CD127-targeted CAR comprising an extracellular antigen-binding domain that binds to human CD127 with an $ED_{50}$ of about 3300 ng/ml.

Non-limiting examples of hematological tumors include acute lymphoblastic leukemia (e.g. T-cell acute lymphoblastic leukemia (T-ALL), and B-cell acute lymphoblastic leukemia (B-ALL), and acute lymphoblastoid leukemia with gain-mutation of the IL7-R/TSLP pathway), lymphoma (e.g., Hodgkin lymphoma and non-Hodgkin's lymphoma), and T-cell cutaneous lymphoma (e.g., Sezary lymphoma). In certain embodiments, the hematological tumor is T-cell acute lymphoblastic leukemia (T-ALL).

The subjects can have an advanced form of disease, in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

As a consequence of surface expression of a presently disclosed CD127-targeted antigen-recognizing receptor, adoptively transferred cells (e.g., immunoresponsive cells, e.g., T-cells or NK cells) are endowed with augmented and selective cytolytic activity at the tumor site. Furthermore, subsequent to their localization to tumor or viral infection and their proliferation, the cells turn the tumor or viral infection site into a highly conductive environment for a wide range of immune cells involved in the physiological anti-tumor or antiviral response (tumor infiltrating lymphocytes, NK—, NKT-cells, dendritic cells, and macrophages).

Further modification can be introduced to the presently disclosed cells (e.g., T-cells) to avert or minimize the risks of immunological complications (known as "malignant T-cell transformation"), e.g., graft versus-host disease (GvHD), or when healthy tissues express the same target antigens as the tumor cells, leading to outcomes similar to GvHD. A potential solution to this problem is engineering a suicide gene into the presently disclosed cells. Suitable suicide genes include, but are not limited to, Herpes simplex virus thymidine kinase (hsv-tk), inducible Caspase 9 Suicide gene (iCasp-9), and a truncated human epidermal growth factor receptor (EGFRt) polypeptide. In certain embodiments, the suicide gene is an EGFRt polypeptide. The EGFRt polypeptide can enable T-cell elimination by administering anti-EGFR monoclonal antibody (e.g., cetuximab). EGFRt can be covalently joined to the upstream of the antigen-recognizing receptor (e.g., CAR). The suicide gene can be included within the vector comprising nucleic acids encoding a presently disclosed antigen-recognizing receptor (e.g., CAR). In this way, administration of a prodrug designed to activate the suicide gene (e.g., a prodrug (e.g., AP1903 that can activate iCasp-9) during malignant T-cell transformation (e.g., GVHD) triggers apoptosis in the suicide gene-activated cells expressing the antigen-recognizing receptor (e.g., CAR). The incorporation of a suicide gene into the a presently disclosed antigen-recognizing receptor (e.g., CAR) gives an added level of safety with the ability to eliminate the majority of receptor-expressing cells within a very short time period. A presently disclosed cell (e.g., a T-cell) incorporated with a suicide gene can be pre-emptively eliminated at a given timepoint post the cell infusion, or eradicated at the earliest signs of toxicity.

6. EXAMPLE

The presently disclosed subject matter will be better understood by reference to the following Example, which is provided as exemplary of the presently disclosed subject matter, and not by way of limitation.

Figure 1A:
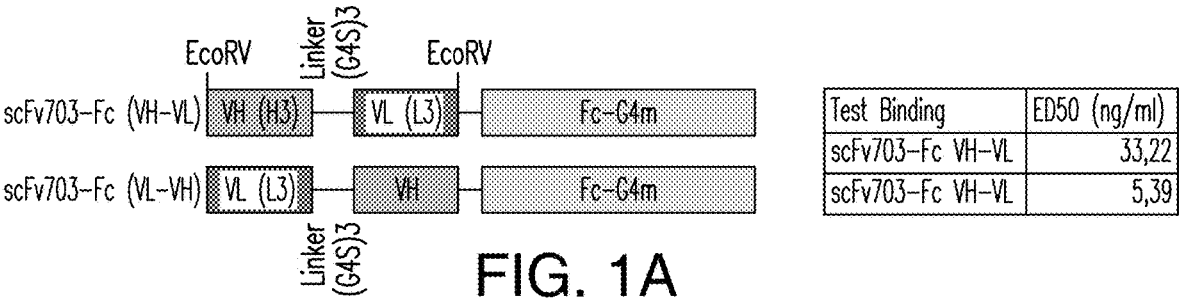

Example 1: Generation and Assessment of In Vitro Activities of CD127-Targeted CAR T-Cells Two exemplary embodiments of the presently disclosed CD127-targeted scFv were generated, scFv703-Fc (VH-VL) and scFv703-Fc (VL-VH) (FIG. 1A). scFv703-Fc (VH-VL) had lower binding affinity to IL-7R ($ED_{50}$=3322 ng/ml) than scFv703-Fc (VL-VH) ($ED_{50}$=539 ng/l) (FIG. 1A). The amino acid sequence of scFv703-Fc (VH-VL) is set forth in SEQ ID NO: 14, and the amino acid sequence of scFv703-Fc (VL-VH) is set forth in SEQ ID NO: 15.

Second generation chimeric antigen receptors (CARs) were created to target CD127. The constructs of presently disclosed exemplary CD127-targeted CARs, OSE703HL-28z and OSE703LH-28z were shown in FIG. 1B. OSE703HL-28z comprises an extracellular antigen-binding domain that comprises scFv703-Fc (VH-VL), and OSE703LH-28z comprises an extracellular antigen-binding domain that comprises scFv703-Fc (VL-VH). The amino acid sequence of OSE703HL-28z is set forth in SEQ ID NO: 27, and the amino acid sequence of scFv703-Fc (VL-VH) is set forth in SEQ ID NO: 29.

Figure 2:
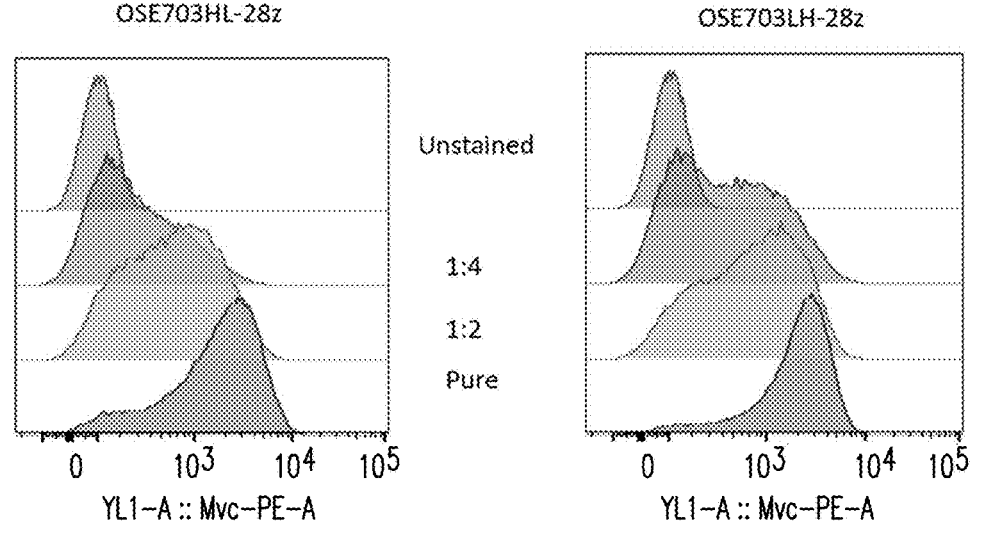
FIG. 2 shows that retroviral packaging R30 packaging cell lines expressed OSE703HL-28z CAR and OSE703LH-28z CAR.
Figure 3:
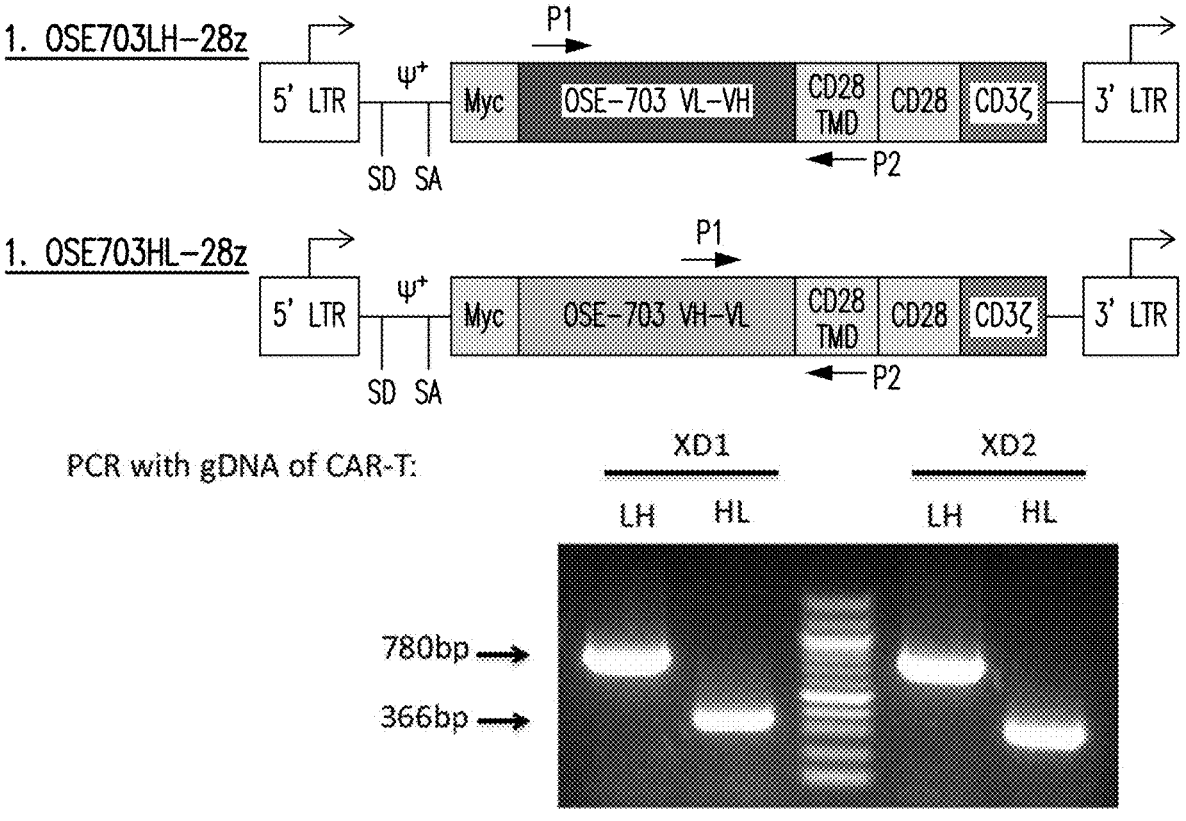
FIG. 3 shows that the transduction of OSE703HL-28z and OSE703LH-28z constructs in T-cells was verified by PCR with gDNA of transduced CAR T-cells. P1, forward primer, P2, backward primer.
Figure 4:
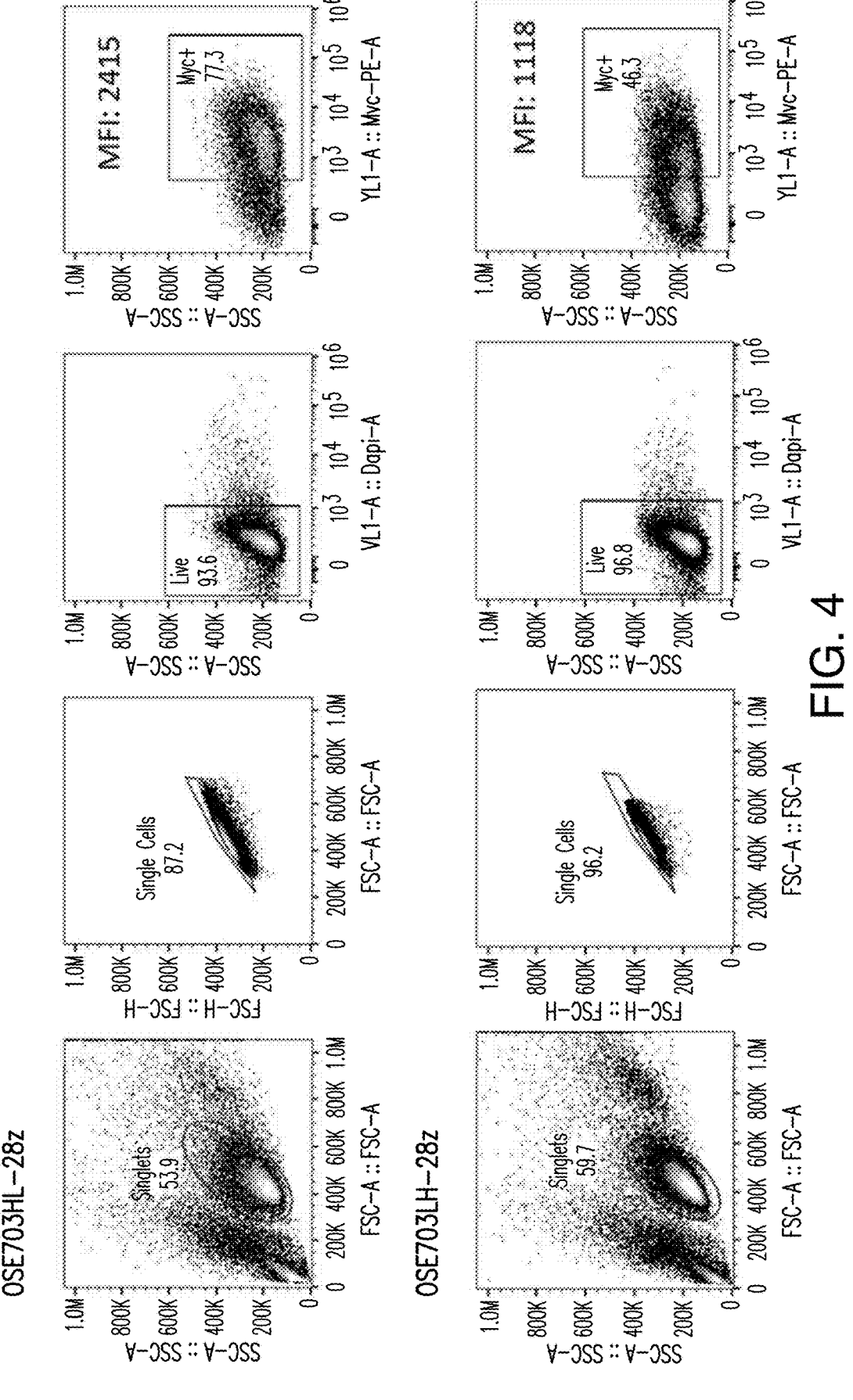
FIG. 4 depicts the FACS analysis of Donor 1-derived T-cells transduced with OSE703HL-28z and OSE703LH-28z, illustrating the transduction efficiency.
Figure 5:
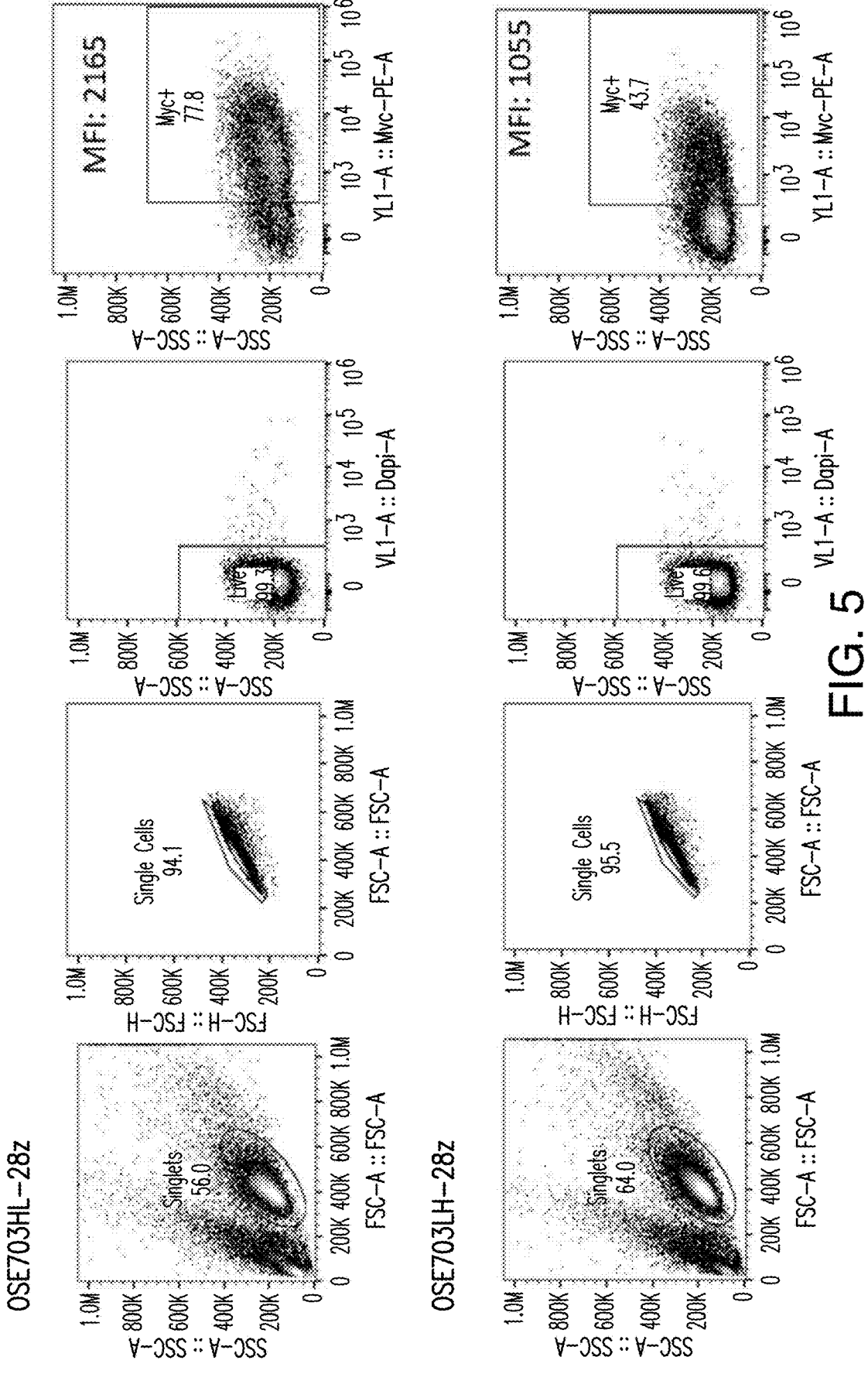
FIG. 5 depicts the FACS analysis of Donor 2-derived T-cells transduced with OSE703HL-28z and OSE703LH-28z, illustrating the transduction efficiency.

Production of retroviral particles in R30 cells expressing OSE703HL-28z CAR and OSE703LH-28z CAR was verified by FACS (FIG. 2). Donor XD1 and donor XD2 derived T-cells were transduced with lentivirus expressing the presently disclosed CARs and the transduction was verified by PCR analysis (FIG. 3). As shown in FIGS. 4 and 5, CD127-targeted CARs OSE703HL-28z and OSE703LH-28z were successfully transduced in human T-cells with sustained transduction efficiency (40%-70%) and mean fluorescence intensity (MFI).

Figure 6:
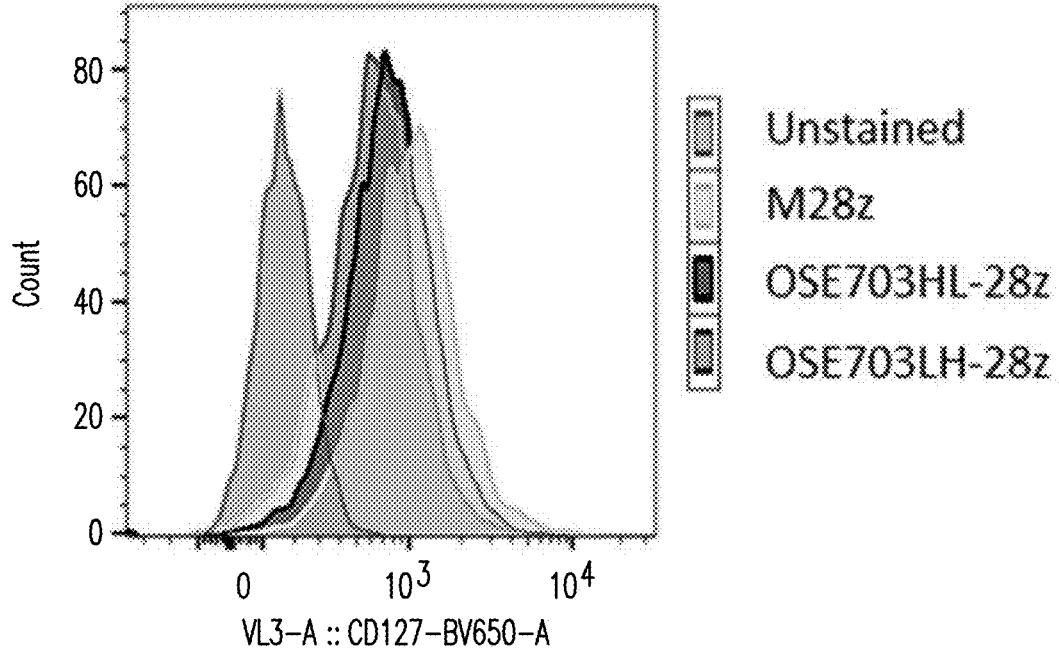
FIG. 6 depicts the FACS analysis showing that OSE703LH-28z CAR T-cells had lower CD127 expression than the OSE703HL-28z CAR T-cells.

OSE703LH-28z CAR T-cells, which had a higher binding affinity to CD127, had lower CD127 expression than the OSE703HL-28z CAR T-cells, which had a lower binding affinity to CD127 (see FIG. 6).

Figure 7:
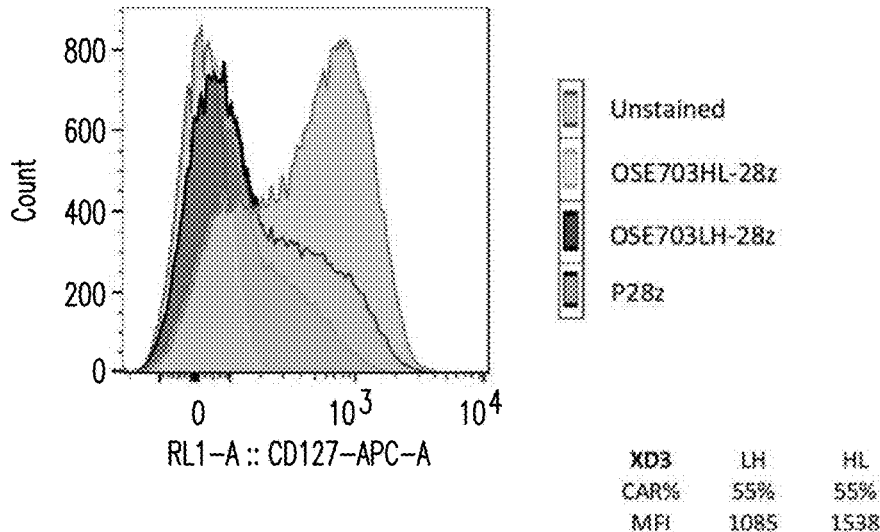
FIG. 7 shows the killing properties of the presently disclosed CAR T-cells. CAR T-cells from donors XD1 and XD3 and transduced with OSE703HL-28z or OSE703LH-28z killed lymphocytes expressing high levels of CD127.
Figure 7:
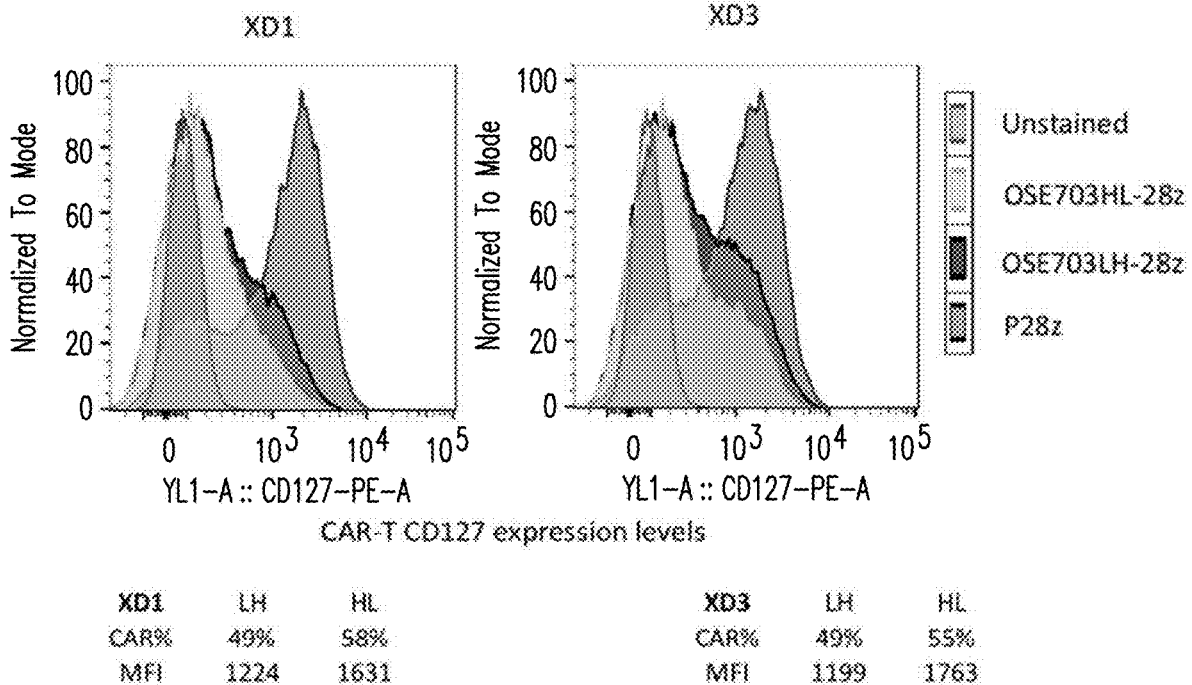
Figure 8:
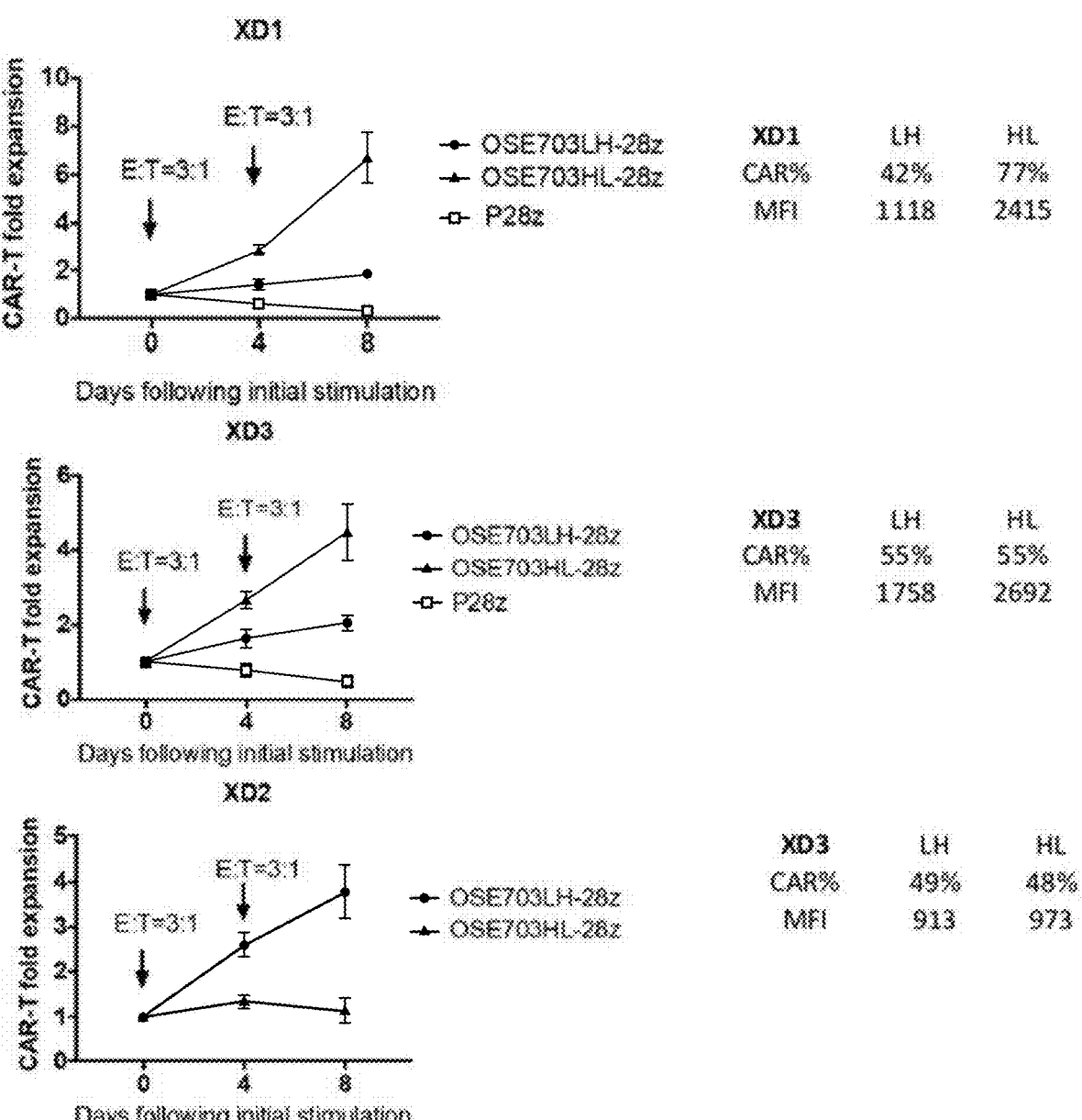
FIG. 8 shows the fold expansion of OSE703HL-28z CAR T-cells and OSE703LH-28z CAR T-cells from donors XD1, XD2, and XD3 after the initial stimulation. P28z CAR T-cells was used as a negative control.
Figure 9:
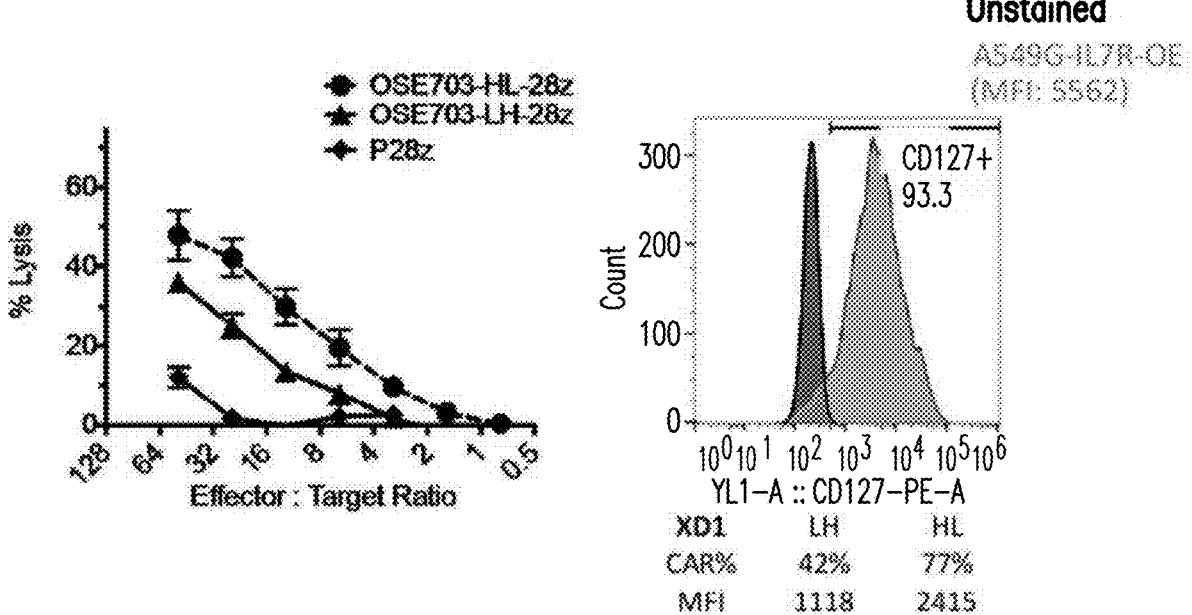
FIG. 9 shows the killing of IL-7R overexpressing A549G cells (A549G-IL7R-OE) by OSE703HL-28z or OSE703LH-28z CAR T-cells, after 18 hours of incubation.

The activities of T-cells comprising OSE703LH-28z and -cells comprising OSE703HL-28z were evaluated. The OSE703LH-28z and OSE703HL-28z CAR T-cells effectively killed lymphocytes expressing high levels of CD127 (see FIG. 7). Notably, as shown in FIG. 8, T-cell transduced with the OSE703HL-28z CAR had a higher expansion capability than the ones transduced with the OSE703-LH-28z CAR, when co-cultured with A549G cells overexpressing IL-7 receptor. Further, OSE703HL-28z CAR T-cells also exhibited higher cytotoxic capability than OSE703LH-28z CAR T-cells, when incubated for 18 h with A549G cells overexpressing IL-7R (see FIG. 9).

Figure 10:
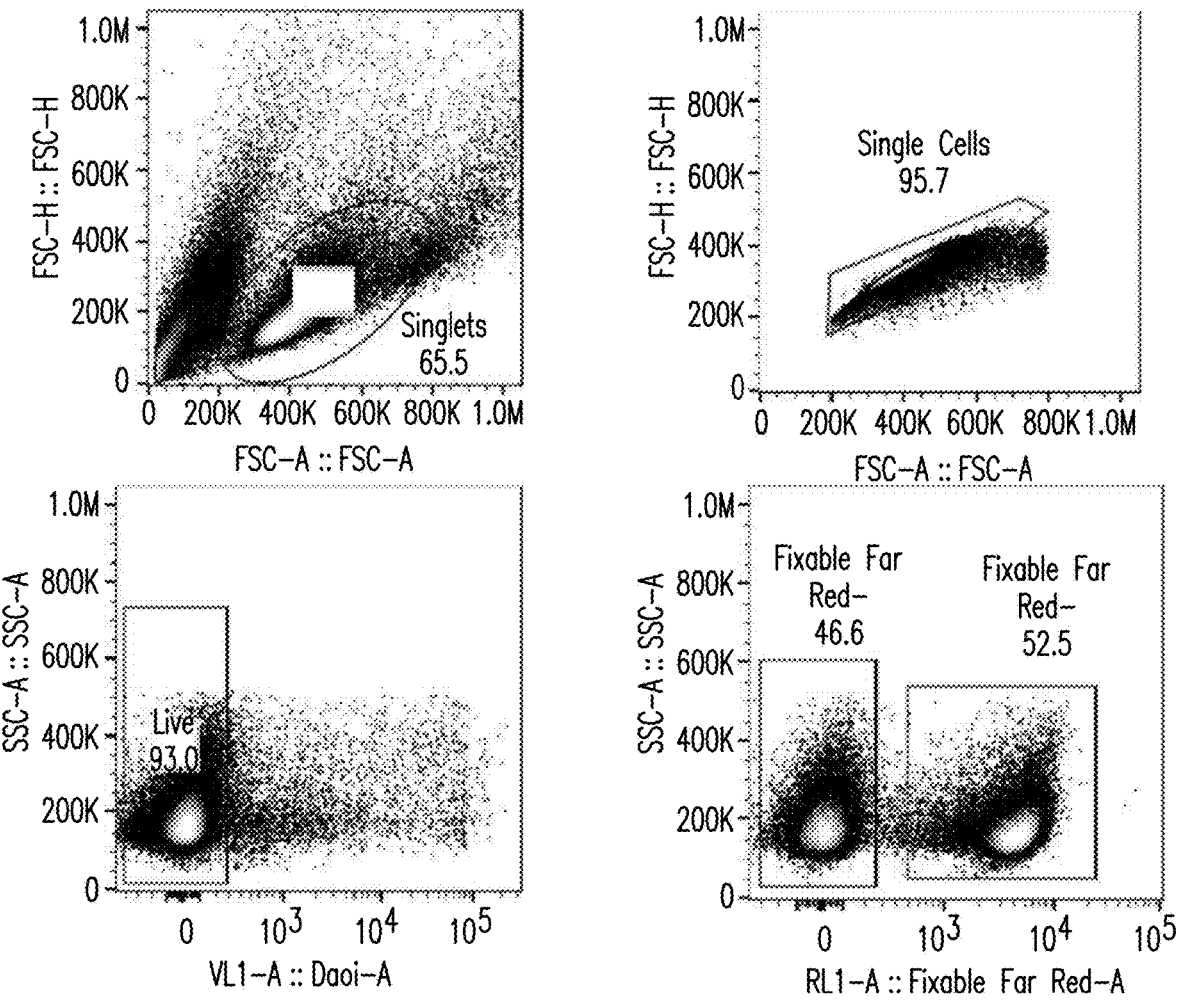
FIG. 10 depicts the FACS gating strategy for FACS analysis of cell-tracer labeled PBMCs when co-cultured with CAR-T cells.

To confirm that IL-7R-targeted CAR T-cells did not result in a high fratricide leading to non-feasibility of CAR T-cell manufacturing and expansion and to confirm that IL-7R CAR T-cells did not cause complete lymphodepletion, CD127-targeted CAR T-cells were co-cultured with cell-tracer labeled peripheral blood mononuclear cells (PBMC) for three days, 4 hours, or 18 hours (1:1 or 4:1) (see FIG. 10). As shown in FIG. 12, OSE703LH-28z T-cells and OSE703HL-28z CAR T-cells killed CD127$^{high}$ PBMC. Further, the low-binding CD127 CAR T-cells (OSE703-L28z in FIGS. 11A and 11B) killed more CD127$^{high}$ PBMCs as compared to the high-binding CD127 CAR T cells (OSE703-H28z in FIGS. 11A and 11B). Additionally, cytokine analysis following antigen stimulation at 18 hours (E:T=3:1) showed that low-binding CD127 CAR T-cells (OSE703-L28z) produced more cytokines, such as TNF-α, IFN-γ, and IL-2, than high-affinity CD127 CAR T cells (OSE703-H28z) (see FIG. 11C).

In summary, the presently disclosed CD127-targeted CAR T-cells induced the cytotoxicity and lysis of CD127-expressing cells. OSE703HL-28z CAR T-cells showed more expansion capability and killing activity than OSE703LH-28z. Notably, these CARs did not cause complete lymphodepletion.

Different cell lines, representing different tumor types, were screened for the expression of CD127. CD127 expression were detected in mesothelioma (meso 163, meso 11, meso 36) and lung cancer cell lines (H358) using 1.5 ul/sample of eBioRDR5 anti-CD127 antibody (see FIG. 13). The expression of IL-7R and PDL1 in these tumor cell lines was measured (see FIG. 17). The killing activity of OSE703HL-28z and OSE703LH-28z CAR T-cells against mesothelioma (meso 163, meso 11, meso 36) and lung cancer cell lines (H358) are shown in FIGS. 14A-14D, FIG. 15, and FIG. 16A-16B.

Example 2: IL-7R in Solid Tumor and the Effect of Therapeutic Function of Anti-IL-7R Antibody OSE-703

IL-7R is expressed on various cell types, including B cell, T cell, DCs, monocytes and others. IL-7R regulates lymphopoiesis and promotes B and T-cell proliferation and survival. IL-7R plays a key role in the development and remodeling of lymph nodes. IL-7R contributes to the progression of lymphoid malignancies, around 10% of T-ALL patients display IL-7R gain-of-function mutations leading (Adv Biol Regul. 2013; 53(2):211-22; Sci Rep. 2017 Sep. 6; 7(1):10735; Nat Genet. 2011 Sep. 4; 43(10):932-9). Yet, the role of IL-7R in solid tumor is not well determined yet. Tumoral IL-7R can be a potential target for lung adenocarcinoma therapy (Suzuki et al., *Journal of Clinical Oncology* (2013); 31:490-498).

Stable tumor cell lines that overexpressed (OE) or was knocked out (KO) of IL-7R (also known as CD127) were created. The detection capacity of clone A019D5 and eBioRDR5 of anti-CD127 antibodies were tested in H358 cells which had endogenous IL-7R expression. As shown in FIG. 19, clone eBioRDR5 was better than clone A019D5 in detecting IL-7R in cells. Endogenous expression levels of IL-7R in A549, H1299, H358, and EKVX cell lines were determined by FACS analysis. The results are shown in FIG. 20. As shown in FIG. 21, IL-7R was overexpressed in tumor cell lines A549, H1299 and EKVXG using pLV-IL-7R lentivirus. As shown in FIG. 22, IL-7R was knocked out in in tumor cell lines A549, H1299 and EKVXG using CRISPR-Cas9 system.

The effect of IL-7R on tumor cell proliferation was measure using cell Counting Kit-8 (Dojindo®) (www.dojindo.com). H1299G, A549G, and H358 cells were seeded 5×10$^3$/well in 96 well plate, with or without 20 ng/ml IL-7 for 3 days. As shown in FIG. 23, IL-7 had no effect on the proliferation of IL-7R OE cells. The function of IL-7 was measured by IL-7 induced IL-7R internalization and IL-7 induced p-STAT5 activity (Blood 2010; 115(16):3269-77; J Biol Chem. 2013; 288(12):8691-701). CD4$^+$ T cells were treated for 20 minutes with 20 ng/ml IL-7. As shown in FIG. 24, IL-7 activated IL-7R signaling in CD4$^+$ T cells. As shown in FIG. 25, IL-7 did not induce IL-7R signaling in tumor cells. As shown in FIG. 26, IL-7 did not induce IL-7R signaling in A549G-SAM-IL-7R cells.

Therapeutic function of anti-IL-7R antibody OSE-703 (Effi-3) was measured. OSE-703 contains human Fc IgG1, which can induce antibody-dependent cellular cytotoxicity (ADCC). The Fc region of an antibody mediates its serum half-life and effector functions, antibody-dependent cellular cytotoxicity (ADCC) and antibody-dependent cell phagocytosis (ADCP) Immunol. 2012; 189(7):3430-8). The animal model used for testing OSE-703 in the presently disclosed study was xenograft in SCID mice. SCID mice SCID mice were s.c. injected with 1×10$^6$ H358, H358-IL7R-KO cells, H1299G, or H1299G-pLV-IL7R. When the tumor grew to 50-100 mm$^3$, the mice were i.p. injected with 0.5 mg/injection OSE-703 twice per week. As shown in FIGS. 27 and 28, OSE703 did not have any effect on the tumor growth in H358 xenograft and H1299G xenograft. Moreover, as shown in FIG. 29, IL-7R-OE tumor grew bigger while IL-7R-KO tumor grew smaller. As shown in FIG. 30, treatment of CD4$^+$ T cells with OSE703 did not block IL-7R staining using eBioRDR5.

IL-7R levels in tumor and immune cells in lung cancer were evaluated. Tregs were stained with Fixable Viability Dye$^-$; CD3$^+$; CD4$^+$, CD25$^+$, Foxp3$^+$; CD163+ Macrophages were stained with Fixable Viability Dye$^-$; CD45$^+$, CD1 CD163$^+$; EpCAM+ tumor cells were stained with Fixable Viability Dye$^-$; CD45$^-$, CD326$^+$. Antibody panels for FACS included Treg T cell panel (Fixable Viability Dye; CD3; CD4; CD25; Foxp3; CD127) and CD163+ Macrophage/EpCAM+ tumor cell panel (Fixable Viability Dye; CD45; CD11b; CD163; CD326; CD127).

Treg cells had lower cell surface IL-7R expression than CD25$^-$Foxp3$^-$ T cells (FIGS. 31 and 32). Tumor cells had lower cell surface IL-7R expression (FIGS. 33 and 34)

Additional anti-IL-7R antibodies, including eBioRDR5 and sc-662 were used to detect IL-7R levels in tumor cells (see FIGS. 35 and 36) and PBMC (see FIG. 37).

IL-7R levels were determined in CAR-T cells during antigen stimulation. CAR-T (PD1-DNR) transduction efficiency is shown in FIG. 38. As shown in FIGS. 39 and 40, the expression of CD127 was reduced in CAR-T cells as compared to non-transduced cells.

Moreover, IL-7R levels were evaluated in lung cancer tissue-resident memory T cells. CD69 and CD103 are markers for tissue-resident memory T cells (Annu Rev Immunol. 2013; 31:137-61). Gating strategy for CD69$^+$ CD103$^+$ tissue-resident memory T cells (T$_{RM}$) is shown in FIG. 41. As shown in FIGS. 42 and 43, CD69$^+$ CD103$^+$ T$_{RM}$ cells had higher levels of IL-7R. Gating strategy for central memory T cells (T$_{CM}$, CD45RO$^+$ CD62L$^+$) is shown in FIG. 44. As shown in FIG. 45, IL-7R was reduced in T$_{CM}$ CAR-T cells as compare to non-transduced cell.

Gating strategy for mesothelioma tumor cells is shown in FIG. 46. Podoplanin (D2-40) was used as the marker for mesothelioma tumor cells (Arch Pathol Lab Med. 2018

January; 142(1):89-108). IL-7R levels were measured in mesothelioma tumor cells. The results are shown in FIG. 47.

Example 3: Evaluating ADCC Function of the OSE-703 Antibody

The ADCC function of the OSE-703 antibody to T cells was determined. NK92-176V cells were transduced with a retrovirus expressing a high-affinity variant of CD16 (V176), which can induce ADCC (EBioMedicine. 2016; 8:277-290; *J Immunol Methods.* 2011; 368(1-2):54-63). Gating strategy for T cells is shown in FIG. 48. Percentages of viable CD4+ and CD8+ cells after incubated with OSE-703 and NK92-176V cells are shown in FIG. 49.

Gating strategy for Ag ST CAR-T cells is shown in FIG. 50. Results were shown in FIGS. 51 and 52.

Example 4: Preclinical Evaluation and Clinical Trial

T-cell acute lymphoblastic leukemia (T-ALL) is an aggressive blood cancer, accounting for 10-15% of pediatric and 20-25% of adult ALL cases. More than 50% of adult and up to 30% of pediatric patients with T-ALL relapse, highlighting an unmet clinical need for a selective, safer, and efficient treatment. On the basis that T-ALL cells overexpress IL-7 receptor (IL-7R), which promotes chemotherapy resistance and relapse, the present disclosure developed IL-7R targeted chimeric antigen receptor (CAR) T cells and established their antitumor efficacy against cancer cells with IL-7R expression. Furthermore, data in multiple donor T cells showed that transduction of IL-7R CAR T cells did not result in complete fratricide, and IL-7R CAR T-cell manufacturing and expansion was highly feasible. In fact, the bystander cytotoxicity on a proportion of normal T cells with high IL-7R expression imparted a beneficial effect for IL-7R CAR T cells due to repeated antigen stimulation and partial endogenous lymphodepletion that in turn promoted CAR T-cell expansion and persistence. Thus, the presently disclosed subject matter can rapidly translate and fulfill an unmet clinical need to treat aggressive therapy-resistant T-ALL.

T-ALL is an aggressive hematological cancer for which current treatment options often result in suboptimal therapeutic efficacy, and the outcomes for patients who relapsed remain extremely poor (Freyer et al., *Blood.* 2011; 117(11): 3010-3015; Thomas et al., *J Clin Oncol.* 2004; 22(20):4075-4086). Significant progress has been made for the treatment of B-cell ALL with the recent approval of CD19- and CD22-targeted immunotherapy, including CD19 CAR (Tisagenlecleucel); however, no drug has been approved by FDA since 2005 for treatment of T-ALL. Thus, there is a pressing need for the development of an effective treatment for patients with relapsed and/or aggressive T-ALL.

IL-7 and its receptor (IL-7R, a heterodimer of IL-7Rα and γc) are essential for normal lymphoid development (Jacobs et al., *J Immunol.* 2010; 184(7):3461-3469). However, the IL-7/IL-7R axis also plays a significant role in leukemogenesis. IL-7 induces the survival and proliferation of T-ALL in vitro and in vivo, and mutation-induced activation of IL-7Rα, leading to constitutive activation of the JAK-STAT pathway, are common and associated with resistance to corticosteroid and chemotherapy (Shochat et al., *J Exp Med.* 2011; 208(5):901-908; Zenatti et al., *Nat Genet.* 2011; 43(10):932-939; Barata et al., *Blood.* 2001; 98(5):1524-1531; Scupoli et al., *Haematologica.* 2003; 88(11):1229-1237; Barata et al., *J Exp Med.* 2004; 200(5):659-669;

Scupoli et al., *Haematologica.* 2007; 92(2):264-266; Silva et al., *Cancer Res.* 2011; 71(14):4780-4789; Laouar et al., *Blood.* 2004; 103(6):1985-1994). More importantly, leukemic blasts from patients with T-ALL (~70%), a subset of high-risk B-ALL (~30-40%) overexpress IL-7R, and these patients tend to have worse survival rates with frequent relapses (Gianfelici et al., *Leuk Lymphoma.* 2019; 60(3): 829-832). Combined, these findings validate the role of IL-7/IL-7R in leukemogenesis and provide a strong rationale for targeting the IL-7/IL-7R axis to improve the outcome of patients with relapsed T-ALL. Although antibody studies have shown that targeting the IL-7/IL-7Rα axis may be beneficial, the lack of specificity to disease site may result in toxicity, which led to develop IL-7R CARs.

Figure 1B:
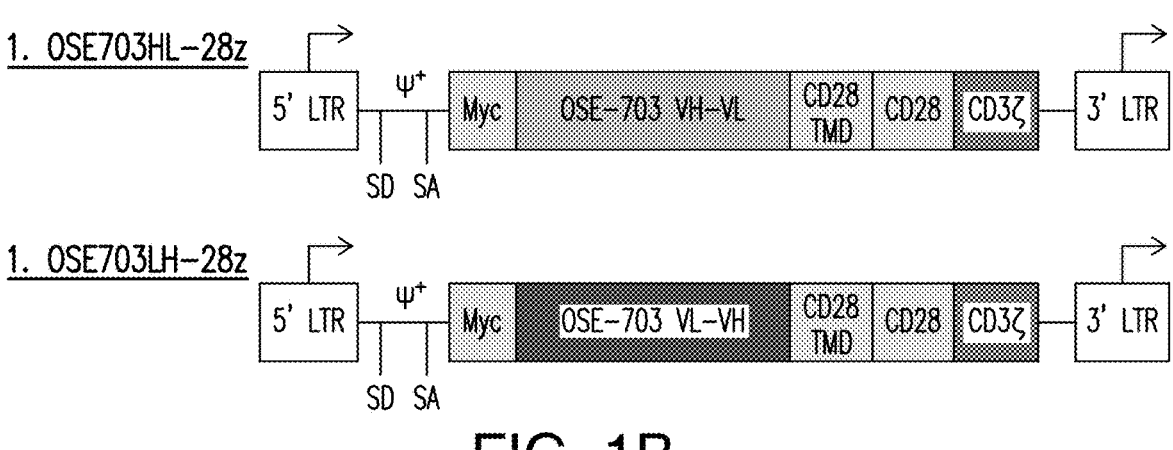

The present disclosure designed scFvs of variable affinity and with 2 scFvs with high- and low-affinity. The present disclosure designed 2$^{nd}$ generation CARs with CD28 costimulatory domain as shown in FIG. 1B. IL-7R CARs were successfully transduced in both CD4+ and CD8+ human T cells (n=6) with sustained transduction efficiency (40-70%) and mean fluorescence intensity (MFI). IL-7R-targeted CAR T cells effectively lysed (see FIG. 9) and proliferate (see FIG. 8) when co-cultured with cancer cells with variable IL-7R expression (see FIG. 13). Low-affinity IL-7R CAR T cells (OSE703HL-28z in FIGS. 8 and 9) showed higher cytotoxicity and proliferative capacity compared to high-affinity IL-7R CAR T cells (OSE703LH-28z in FIGS. 8 and 9). To confirm that IL-7R-targeted CAR T cells did not result in high fratricide leading to non-feasibility of CAR T-cell manufacturing and expansion and to confirm that IL-7R CAR T cells did not cause complete lymphodepletion, the present disclosure co-cultured IL-7R CAR T cells along with labeled control T cells. As shown in FIGS. 11A and 11B, low-affinity IL-7R CAR was highly efficient and did not cause complete fratricide. These results suggested that endogenous T cells with high IL-7R expression provide chronic stimulation to IL-7R CAR T cells, thereby promoting CAR T cell persistence and providing continued immune surveillance. In addition, lysis of IL-7R+ T cells can result in partial endogenous lymphodepletion facilitating CAR T-cell expansion.

The present disclosure verifies that low-affinity IL-7R-targeted CAR T cells eliminate IL-7R expressing T-ALL cells and achieve sustained antitumor efficacy aided by the bystander effect of endogenous lymphodepletion, and chronic antigen stimulation-induced CAR T-cell persistence.

The present disclosure investigates the antitumor efficacy of IL-7R CAR T cells against variable IL-7R expressing primary T-ALL samples in vitro and further investigates the in vivo antitumor efficacy in clinically relevant T-ALL mouse model. The present disclosure verifies that low-affinity IL-7R CAR T cells can eradicate T-ALL and prolong survival compared to high-affinity IL-7R CAR T cells due to their high proliferative and cytotoxic capacity.

The present disclosure investigates the ability of IL-7R CAR T cells in preventing T-ALL relapse aided by the bystander effect on IL-7R+ endogenous T cells resulting in CAR T-cell persistence. The present disclosure verifies that following eradication of T-ALL, sustained antigen stimulation provided by the IL-7R expressing endogenous T cells promote CAR T-cell persistence.

Primary human T-ALL cells with variable IL-7R expression levels (TAIL7, HPB-ALL, DND4.1, MOLT4, TALL1), Jurkat and murine Ba/F3 and D1 cells are subjected to human primary T cells transduced with high- and low-affinity IL-7R CAR at variable transduction percentage, MFI, E:T ratios, and tested for cytotoxicity (Cr$^{52}$ release assay), effector cytokine secretion (Luminex), proliferation (CFSE assay) following single and repeated antigen stress test. At chosen E:T ratios from these results, IL-7R CAR T cells are incubated with CFSE labeled non-CAR T cells (CD8, CD4, variable memory and effector phenotypic percentages) to investigate the bystander effect on normal T cells with variable IL-7R expression. The present disclosure obtains T-ALL patients peripheral blood samples and transduces selected IL-7R CAR to determine the manufacturing feasibility, expansion ability, and antitumor efficacy when co-cultured with patients' T-ALL cells. Flow cytometry prior to and after co-culture define the cytotoxicity on target cells as well as bystander effect on IL-7R expressing normal T cells.

Following the establishment of significant tumor burden (confirmed by bioluminescence imaging) in NOD-SCIDγC mice administered GFP-luciferase labeled T-ALL cells, at least 3 different doses of IL-7R CAR T cells (control PSMA CAR T cells) are administered intravenously to monitor tumor burden progression/regression, survival, and any toxicity. Separate cohorts of mice (with or without T-ALL) administered with IL-7R (myc-tag) and control (LNGFR-tag) CAR T cells at varying proportions (25:75, 50:50 and 75:25) are sacrificed at days 1, 5, 14, and 28; bone marrow, spleen, liver, lungs, intestine, and brain harvested and analyzed for proportion of T cells and their phenotype to assess bystander efficacy, CAR T-cell persistence and residual T-ALL. Mice with tumor eradication is re-challenged with T-ALL cells at 1 and 2 months to assess for CAR T-cell functional persistence in preventing tumor re-establishment.

Example 5: Preparation of CD127 CAR T-Cells Using Donor T-Cells

CD127 expression levels were measured in PBMCs collected from healthy donors. The results are shown in FIG. 54. CD127 was only expressed on T cells, but not B cells, NK cells, or monocytes. CD127 expressions in T cells of four healthy donors before and after phytohaemagglutinin P (PHA) activation were also measured and the results are shown in FIG. 55. Levels of CD127 low-affinity CAR T-cells and high-affinity CAR T-cells in different concentrations of sup are shown in FIGS. 56 and 57. The effects of spinoculation on the number of total cells are shown in FIG. 58. Percentage of live cells were examined (FIG. 59), and differentiation (FIGS. 60 and 61).

Example 6: Treating T-ALL with IL-7R CAR T Cells or IL-7R CAR NK Cells in Mice Hematological malignancy T-ALL was established in mice by administering DND-41 cancer cells to mice through tail vein injection. Mice having established T-ALL were treated with a single dose of either control untransduced (UT) $3\times10^6$ T cells, $3\times10^6$ high-affinity IL7R CAR T cells, $3\times10^6$ low-affinity IL7R CAR T cell, or a mixture of high ($1.5\times10^6$) and low ($1.5\times10^6$) affinity CAR T cells. Mice treated with low-affinity CAR T cells, the mixture of high and low binding affinity CAR T cells, and high-affinity CAR T cells had longer median survival and slower tumor burden progression as compared to control mice (FIGS. 62-63).

Mice having established T-ALL were also treated with a single dose of either control untransduced (UT) $1\times10^6$ T cells, $1\times10^6$ high-affinity IL7R CAR T cells, or $1\times10^6$ low-affinity IL7R CAR T cells. Mice treated with $1\times10^6$ low-affinity CAR T cells or high-affinity CAR T cells had longer median survival and slower tumor burden progression as compared to mice treated with UT control T cells (FIGS. 64-65).

Mice having established T-ALL were also treated with a single dose of CAR NK cells with either $1\times10^7$ control untransduced (UT) NK cells, $1\times10^7$ high-affinity IL7R CAR NK cells, or $1\times10^7$ low-affinity IL7R CAR NK cells. Mice treated with CAR NK cells had prolongation of median survival compared to control mice (FIG. 66).

Example 7: Treating Solid Tumor with IL-7R—Redirected CAR T Cells

The field of cancer immunotherapy has received a significant boost by the application of chimeric antigen receptor (CAR) T cell therapy in cancers. CAR T cells targeting CD19 have given remarkable success in treating hematological malignancies (Brentjens et al., Sci Transl Med 5, 177ra138 (2013); Maude et al., N Engl J Med 371, 1507-1517 (2014); Schuster et al., N Engl J Med 377, 2545-2554 (2017); Park et al., N Engl J Med 378, 449-459 (2018)), while response rates among patients with solid cancers are less favorable. One of the major challenges for CAR T cell immunotherapy in solid cancers are the identification of unique tumor target antigens (TAA) (Newick et al., *Annu Rev Med* 68, 139-152 (2017); Schmidts et al., Front Immunol 9, 2593 (2018)).

The signaling of Interleukin 7 (IL-7) and its receptor (IL-7R) is essential for the development and maintenance of the immune system. Unlike the widespread distribution of IL-7, its cognate receptor, a heterodimer composed of an IL-7R-specific alpha subunit (IL-7Rα, CD127) and the common gamma chain (γc), has a much more restricted distribution in normal human tissues (Fry et al., Trends Immunol 22, 564-571 (2001); Barata et al., Nat Immunol 20, 1584-1593 (2019)). However, IL-7R is aberrantly expressed in a high proportion of human malignancies, including T-cell acute lymphoblastic leukemia (T-ALL), breast cancer, lung cancer and mesothelioma (Silva et al., *Cancer Res* 71, 4780-4789 (2011); Al-Rawi et al., Eur J Cancer 40, 494-502 (2004); Ming et al., Cancer Immunol Immunother 61, 79-88 (2012)). In addition, high expression of tumoral IL-7R frequently correlates poor clinical outcome in lung cancer and mesothelioma (Ujiie et al., Oncoimmunology 4, e1009285 (2015); Suzuki et al., J Clin Oncol 31, 490-498 (2013)). The high expression across multiple tumor types make IL-7R an attractive target for immunotherapy. Indeed, IL-7R blockade suppresses melanoma development in a xenograft model (Li et al., Inflammation 37, 1444-1452 (2014)). And recent studies showed in pre-clinical models that anti-IL-7R antibodies chimerized with human IgG1 have therapeutic efficacy against T-ALL via antibody-dependent cell-mediated cytotoxicity (ADCC)-dependent and independent mechanisms (Akkapeddi et al., Leukemia 33, 2155-2168 (2019); Hixon et al., Leukemia 34, 35-49 (2020)).

The present disclosure discovered that patients with high tumoral IL-7R expression were associated with high-grade histologic patterns in thoracic cancers. Two CAR T cells targeting IL-7R were generated. The present disclosure discovered that these CAR T cells effectively eliminated malignant tumor lines in vitro and significantly inhibited tumor growth in an orthotopic mouse model of pleural mesothelioma and in a xenograft lung cancer mouse model.

Results

High Expression Tumoral IL-7R in Thoracic Tumor

A large, uniform cohort of patients with lung ADC was used to investigate prognostic impact of tumoral IL-7R expression on lung cancer-specific survival. Of all 913 patients, the 360 patients (39%) had high tumoral IL-7R expression. High tumoral IL-7R expression was associated with greater percentage of male patients, smokers, patients with COPD history, lower FEV1 and DLCO, larger tumor size, higher p-Stage, lymphatic invasion, vascular invasion, pleural invasion, necrosis, STAS, lower incidence of low histologic grade tumors and higher incidence of higher incidence of high histologic grade tumors, and lower incidence of EGFR mutation.

High-grade histologic patterns in lung adenocarcinoma, such as micropapillary pattern and solid pattern are reported to be associated with patient poor prognosis. The present disclosure investigated association between tumoral IL-7R expression and high-grade histologic patterns. The percentage of patients with high tumoral IL-7R expression increased as micropapillary pattern's percentage or solid pattern's percentage increased. The percentage of patients with high tumoral IL-7R expression was lowest as 37% when micropapillary pattern was <5%, and arrived highest as 76% when micropapillary pattern was >50%. The percentage of patients with high tumoral IL-7R expression was lowest as 28% when solid pattern was <5%, and arrived highest as 71% when solid pattern was >50% (FIGS. 67A and 67B). Prognostic analysis showed that patients with high tumoral IL-7R expression had higher risk of 5-year LC-CID compared with those with low tumoral IL-7R expression, as 16% vs. 6%, p<0.001 (FIG. 67C). Same as lung cancer patients, MPM patients' higher-level expression of IL-7R was associated with increased risk of death (Meybohm et al., *N Engl J Med* 373, 1397-1407 (2015).). Furthermore, high IL-7R expression was discovered in biphasic and sarcomatoid mesothelioma patients (FIG. 67D), which was the type that the most aggressive and the most difficult to treat. All these results suggested that IL-7R is a target for lung cancer and mesothelioma immunotherapy.

Generation of IL7R CAR T Cells

OSE703 (OSE Immunotherapeutics) is a humanized monoclonal antibody that is directed against the extracellular domain of the alpha-chain of IL-7R. It is a therapeutic or diagnostic antibody that can recognize the native protein. Therefore, OSE703 was tested for binding to native IL-7R associated with cell surfaces. The present disclosure used H358 cells that expressed native protein and A549-7R cells that over-expressed IL-7R protein. OSE703 detected the same IL-7R levels in H358 cells and A549-7R cells as the commercial anti-IL-7R eBioRDR5 antibody (FIG. 68A), indicating that OSE703 was highly specific to IL-7R on these cells. To further confirm the specificity, OSE703 with an engineered IgG1 Fc-tail (OSE703-IgG1) was used to test whether IL-7R$^+$ cell can be killed through antibody-dependent cell-mediated cytotoxicity (ADCC). After incubation for 18 hours, OSE-703-IgG1 induced ADCC against IL-7R positive cells by NK 92-176V cells in a dose-dependent manner (FIG. 68B), while IL-7R$^{low/-}$ cells were not affected. Therefore, the variable heavy chain ($V_H$) and variable light chain ($V_L$) of OSE703 antibody were used to design the single-chain variable fragment (scFv) of CARs to target IL-7R.

scFv binding experiments showed that both $V_H$-$V_L$ scFv and $V_L$-$V_H$ scFv of OSE703 can bind IL-7R, the ED$_{50}$ were 3322 ng/ml and 539 ng/ml respectively. Therefore, the present disclosure generated two CARs using scFv derived from OSE703 mAb linked CD28/CD3ζ domain, which were lower binding affinity $V_H$-$V_L$ scFv/CD28/CD3ζ (IL7R-L28z) and higher binding affinity $V_L$-$V_H$ scFv/CD28/CD3ζ (IL7R-H28z) (FIG. 68C). After transduction, both constructs were stably expressed by human peripheral blood T cells (FIG. 68D) and phenotypic analysis showed that both IL7R-L28z and IL7R-H28z contained central-memory, effector-memory, and T stem cell memory, without significant differences (FIG. 68E).

Characteristics and Specificity of IL7R CAR T Cells

The present disclosure next explored the efficacy and specificity of IL7R-L28z and IL7R-H28z mediated tumor cell killing using a chromium-51 release assay. Lung cancer cells and mesothelioma cells with different IL-7Rα levels were used as target cells, including H358, IL-7R overexpressed H358-7R, Meso163, Meso1 1 and Meso36 cells (FIG. 69A). Nontransduced T cells (NTD) or P28z CAR T cells that were specific for prostate-specific membrane antigen (PSMA) were used as negative controls. Results showed that both IL7R-L28z and IL7R-H28z specifically and effectively lysed IL-7R positive lung cancer cells (FIG. 69B) and mesothelioma cells (FIG. 69C) in an antigen dependent manner, and the efficacy is similar. In contrast, NTD or P28z failed to initiate the specific lysis of these tumor cell lines.

To confirm the specific cytotoxicity of CAR T cells, TH1 cytokines were assessed in the cell culture medium. Coculture of IL-7R$^+$ cells specifically induced cytokine production by IL7R-L28z and IL7R-H28z CAR T cells but not by control groups. IL7R-L28z CAR T cells secreted Th1 cytokines 1.5-2.5 folds higher than IL7R-H28z CAR T cells (FIG. 69D). Meanwhile, Both IL7R-L28z and IL7R-H28z CAR T cells achieved accumulation upon repeated exposure to IL-7R$^+$ cells, and IL7R-L28z CAR T cells presented higher proliferative capacity (FIG. 69E).

IL7R CAR T Cells Produce Limited Fratricide

After transduction, IL-7R downregulation occurred at both IL7R-L28z and IL7R-H28z CAR T cells, and IL7R-L28z CAR T cells showed lower IL-7R (FIG. 70A), which could induce fratricide that considering initial expression of IL-7R on T cells. To assess the extent of fratricide among CAR T cells against autologous T cells, the present disclosure compared cytotoxicity against autologous T cells cocultured with IL7R-L28z, IL7R-H28z, and control P28z CAR T cells for 4 and 18 hours. Autologous T cell numbers decreased in coculture with T cells transduced with either IL7R-L28z CAR or IL7R-H28z CAR, and the autologous T cells decreasing levels were consistent with IL-7R downregulation levels (FIGS. 70B-70E). On the other hand, IL-7R downregulation did not impair the cytotoxicity of CAR T cells, nor did it compromise their cytokine production or overall T-cell proliferation, therefore the fratricide was limited.

IL7R CAR T Cells Showing In Vivo Antitumor Efficacy

MSTO-211H with firefly-luciferase-transduced (ffLuc-transduced) cells were used in an orthotopic model of malignant pleural mesothelioma (MPM). These cells were transduced with human IL-7R to serve as target tumor cell for in vivo experiments (FIG. 71A). Ten days after intrapleural injection of FFluc-transduced IL-7R$^+$ tumor cell to NSG mice, 2×10$^5$ P28z, IL7R-L28z or IL7R-H28z CAR T cells were adoptively transferred into the thoracic cavity of tumor-bearing mice by direct intrapleural injection (FIG. 71B). Results showed that both IL7R-L28z or IL7R-H28z CAR T cells effectively controlled tumor growth (FIG. 71C), and mice treated with IL7R-H28z CAR T cells survived longer (median survival, 90 days) than mice treated with IL7R-L28z CAR T cells (median survival, 26 days) (FIG.

71D). Ten days post CAR T cell administration, plasma was collected to measure cytokine concentrations. The IFN-γ levels were significantly higher in IL7R-H28z group than IL7R-L28z group, while IL-2, TNF-α levels were similar between IL7R-H28z and IL7R-L28z groups (FIG. 71E). IL-6 levels were similar between P28z and IL7R-L28z groups, and higher than IL7R-H28z group. Moreover, long-term persistent of IL7R-H28z CAR T cells were confirmed in spleen 100 days after T cell infusion, when the mice have no tumor burden detected (FIG. 71F).

The present disclosure next tested the ability of IL7R CAR T cells to eradicate subcutaneous H1299 lung cancer tumor in a xenograft model. Fourteen days after tumor implantation, NSG mice bearing s.c. H1299-7R tumors were treated with 1 dose of 3×10$^6$ CAR T cells (FIGS. 72A and 72B). Same as in MPM tumor model, both IL7R-L28z and IL7R-H28z CAR T cells exerted a reduction in tumor size, while IL7R-H28z CAR cells treated mice maintained durable tumor control and survived longer than mice treated with IL7R-L28z CAR T cells (FIGS. 72C and 72D).

Discussion

Identification of unique TAA, is one of the major challenges to the success of CAR T cells for the treatment of solid malignancies. The present disclosure investigated using IL-7R as a clinically relevant target for CAR T cell-based immunotherapy in solid tumors. It was found that patients had high tumoral IL-7R expression in thoracic cancers, especially in patients of high-grade histologic patterns. The present disclosure generated two CAR T cells targeting IL-7R and found these CAR T cells effectively eliminated malignant tumor lines in vitro and significantly inhibited tumor growth in an orthotopic mouse model of pleural mesothelioma.

The ideal target epitope for CAR T cell therapy would be expressed on every tumor cell while being absent on healthy tissues. In practice, TAA that solely present on malignant but not on healthy cells has proven rare. On target, off-tumor toxicities of CARs for solid cancers were observed when targeting molecules are expressed in some normal tissues (Morgan et al., *Mol Ther* 18, 843-851 (2010); Lamers et al., Mol Ther 21, 904-912 (2013)). Therefore, it is aimed to find a target epitope of high expression on the tumor cells to avoid on-target, off-tumor toxicities to healthy tissues that express low level target epitope. The expression and distribution of IL-7R normally restricted to cells of hematopoietic lineage, primarily B and T lymphocytes as well as selected myeloid cells (Carrette et al., *Semin Immunol* 24, 209-217 (2012); Palmer et al., *Cell Mol Immunol* 5, 79-89 (2008)). However, it was found that IL-7R is aberrantly expressed in a high proportion of human malignancies, including T-cell acute lymphoblastic leukemia (T-ALL), breast cancer, lung cancer and mesothelioma; which suggest IL-7R is a useful target for immunotherapy. Moreover, the present disclosure confirmed that patients with high tumoral IL-7R expression were associated with high-grade histologic patterns in thoracic cancers. In lung cancer, the percentage of patients with high tumoral IL-7R expression increased as micropapillary pattern's percentage or solid pattern's percentage increased. In biphasic and sarcomatoid mesothelioma, 52% of patients are found high IL-7R expression. Since high-grade histologic patterns are associated with poor prognoses, and more aggressive and difficult to treat (Russell et al., *J Thorac Oncol* 6, 1496-1504 (2011); Eguchi et al., *Semin Thorac Cardiovasc Surg* 26, 210-222 (2014); Meyerhoff et al., *J Surg Res* 196, 23-32 (2015)), which make IL-7R a more attractive target for immunotherapy of solid tumors.

OSE-703 is a humanized monoclonal antibody directed against the extracellular domain of human IL-7R. Results showed that OSE-703 recognized IL-7R and IL-7R specific ADCC was mediated by OSE-703-IgG1. OSE-703 does not cross-react with murine (data not shown). Therefore, the single-chain variable fragment (scFv) derived from OSE-703 was used to design CARs of targeting IL-7R. In order to generate CARs to target cancer cells while selectively spare normal cells, both $V_H$-$V_L$ and $V_L$-$V_H$ scFv with different IL-7R biding affinity were used to generate two CARs, IL7R-L28z (lower affinity) and IL7R-H28z (higher affinity), to compare which one would present better therapeutic efficacy and less toxicity. Results showed that both IL7R-L28z and IL7R-H28z CAR T cells effectively recognized and eliminated IL-7R$^+$ malignant tumor cells in vitro. Surprisingly, low-affinity IL7R-L28z CAR T cells showed greater cytokines production and proliferative responses in vitro. It was reported that low-affinity CARs against ErbB2 and CD19 give equivalent or superior antitumor responses to high-affinity CARs (Liu et al., Cancer Res 75, 3596-3607 (2015); Ghorashian et al., Nat Med 25, 1408-1414 (2019)).

Since IL-7R is expressed in lymphoid cells and plays a role in normal T cell development and homeostasis of mature T cells, CARs targeting IL-7R induced fratricide against T cells. Both IL7R-L28z and IL7R-H28z CAR T cells achieved accumulation and antigen specific cytotoxicity upon repeated exposure to IL-7R$^+$ cells, suggesting the fratricide is limited. On the other hand, IL-7/IL-7R pathway has an important role in T cell proliferative and antiapoptotic, boosting immune system against tumor. For example, CAR T cells that engineered to express IL-7 and CCL19 showed superior anti-tumor activity as compared to conventional CAR-T cells, with improved immune cell infiltration and CAR-T cell survival in mouse pre-established solid tumors (Adachi et al., Nat Biotechnol 36, 346-351 (2018)). Constitutively active IL-7R signaling in CAR-T cells increased their persistence and antitumor activity against multiple preclinical tumor models (Shum et al., Cancer Discov 7, 1238-1247 (2017)). Moreover, in chronic inflammatory diseases, IL-7R blockade blunts the infiltration of antigen-specific memory T cell to inflammation tissues (Belarif et al., *Nat Commun* 9, 4483 (2018); Belarif et al., *J Clin Invest* 129, 1910-1925 (2019)), which suggests that reduced IL-7R expression could damage the infiltration capability of CAR T cells to tumor tissues. Therefore, in in vivo animal solid tumor models, it is more complicate to evaluate the effect of reduced IL-7R in CAR T cells and the effect of fratricide. Indeed, although in vitro experiments showed that IL7R-L28z CAR T cells had higher proliferative capacity and secreted more TH1 cytokines, the in vivo solid tumor models showed that IL7R-H28z CAR T cells had superior anti-tumor activity. This could be due to that in tumor tissues the fratricide level of IL7R-L28z CAR T cells is too high and overwhelmed their proliferation capability. It can also be due to that the lower IL-7R levels decreased IL7R-H28z CAR T cells survival capability, infiltration and immune system boosting. One option is simultaneously knockout IL-7R when generating CAR T cells by using CRISPR-Cas9 (Liu et al., *Cell Res* 27, 154-157 (2017); Eyquem et al., *Nature* 543, 113-117 (2017)). Moreover, an engineered constitutive IL-7R without extracellular domain could compensate the low IL-7R induced by fratricide (Shum et al., *Cancer Discov* 7, 1238-1247 (2017)).

On-target, off-tumor toxicity remains a possibility considering that IL-7Rα expresses in human normal tissues, while recent studies showed that anti-IL-7R IgG1 suppressed T-ALL without significant toxicities (Akkapeddi et al., *Leukemia* 33, 2155-2168 (2019); Hixon et al., *Leukemia* 34, 35-49 (2020)), suggesting on-target, off-tumor toxicity of IL-7Rα CARs is manageable. Furthermore, lymphodepletion is included in most CAR T cell therapy protocols and therefore can neutralize the on-target, off-tumor toxicity of IL-7R CAR T cells to lymphoid cells (Maus et al., *Clin Cancer Res* 22, 1875-1884 (2016)). In conclusion, the present disclosure developed IL-7R CAR T cells to target malignant IL-7R$^+$ cells with limited fratricide, and provide novel clinical application for treating solid tumors.

Materials and Methods

Cell Lines and Donor T Cells

Human lung cancer cell A549, H1299 and H358 cells, MSTO-211H human pleural mesothelioma cells and CD16-176V.NK-92 cells were obtained from ATCC. A549, H1299 and MSTO-211H cells were transduced with GFP and ffLuc fusion protein. These cells were then transduced with a lentivirus vector encoding human IL-7R to generate IL-7R overexpression tumor cells. Mesothelioma cell lines Meso 11, Meso 36 and Meso 163 were established from malignant pleural effusions of patients (Gueugnon et al., *Am J Pathol* 178, 1033-1042 (2011)). Human T cells were obtained from buffy coats prepared from whole blood collected by the New York Blood Center (New York, NY).

In Vivo Experiments

NOD/SCID/IL-2Rγ$^{null}$ (NSG) mice were purchased from The Jackson Laboratory. All animal studies were carried out under a protocol approved by the Memorial Sloan Kettering Cancer Center (MSKCC) Institutional Animal Care and Use Committee. All relevant animal use guidelines and ethical regulations were followed.

For orthotopic pleural mesothelioma animal model, mice were anesthetized using inhaled isoflurane and oxygen, with bupivacaine administered for analgesia. Direct intrapleural injection of $8\times10^5$ tumor cells in 200 μl of serum-free medium via a right thoracic incision was performed to establish orthotopic MPM tumors. In total, $2\times10^5$ transduced CAR T cells (in 200 μl of serum-free medium) were adoptively transferred into tumor-bearing mice, into the thoracic cavity by direct intrapleural injection. BLI data was analyzed using Living Image software; BLI signal was reported as total flux (photons per second), which represents the average of ventral and dorsal flux.

For subcutaneously xenograft animal model, mice were subcutaneously injected with $5\times10^6$ H1299-7R tumor cells. After 14 days, mice received $3\times10^6$ transduced CAR T cells via tail vein injection. Tumors were measured by caliper and tumor volume was calculated using the formula: Tumor volume=length×width$^2$/2, where length represents the largest tumor diameter and width represents the perpendicular tumor diameter.

Retroviral Vector Construction and Viral Production

To generate IL-7R-specific CARs, a myc tag and the variable regions of the heavy and light chains of the OSE703 mAb was synthesized as $V_H$-$V_L$ scFv or $V_L$-$V_H$ scFv fragments, then fused to a CAR backbone comprising a human CD28 transmembrane domain, CD28 costimulatory domain, and CD3z intracellular signaling domain. The control PSMA-specific CAR was generated similarly. The CAR sequence was inserted into the SFG γ-retroviral vector, then transfected into 293T H29 and 293Vec RD114 packaging cell lines to produce the retrovirus, as previously described (Cherkassky et al., *J Clin Invest* 126, 3130-3144 (2016)).

Generation of CAR T Cells

Peripheral blood mononuclear cells (PBMCs) were isolated by low-density centrifugation on Lymphoprep (Stem Cell Technology) and activated with phytohemagglutinin (2 ug/ml; Remel). Two days after isolation, PBMCs were transduced with 293VecRD114-produced retroviral particles encoding CARs by spinoculation of 1 hour at 1,800×g on plates coated with retronectin (15 μg/ml; r-Fibronectin, Takara).

Flow Cytometry

Cell staining was analyzed using an Attune (Thermo Fisher Scientific) and FlowJo analysis software (Tree Star Inc). Fluorochrome-conjugated antibodies against human cell markers were used: IL-7R (1:100, clone eBioRDR5, Thermo Fisher Scientific). CD4 (1:100; clone OKT4, BioLegend), CD8α (1:100; clone HIT8a, BioLegend), CD62L (1:100; clone DREG-56, BioLegend), CD45RA (1:100; clone HI100, BioLegend), CD62L (1:100; clone DREG-56, BioLegend), Myc (1:200; clone 9B11, Cell Signaling Technology).

T Cell Functional Assays

The cytotoxicity of T cells transduced with a CAR or vector control was determined by standard $^{51}$Cr-release assays (McCoy et al., *Natl Cancer Inst Monogr* 37, 59-67 (1973)). Cytokine-release assays were performed by coculturing T cells with target cells (E:T) at a 3:1 ratio. After 18 hours of coculture, supernatants were collected. Cytokine levels were determined using a multiplex bead Human Cytokine Detection Kit in accordance with the manufacturer's instructions (Millipore).

To analyze the proliferation, CAR T cells were re-stimulated on irradiated MSTO-211H cells expressing IL-7R every 4 days at an E:T ratio of 3:1 in triplicate. T cell numbers were counted 4 and 8 days following initial stimulation using a hemacytometer, with plotted numbers adjusted for CAR$^+$ percentage as determined by flow cytometry.

ADCC was measured by using CD16-176V.NK-92 cells (NK cell line expressing CD16) as effectors co-cultured with T cells as targets at a ratio of 5:1 with different concentration of OSE703-IgG1 antibody. After 4 hours, the percentage ADCC was determined by flow cytometric analysis of the decrease in CD4$^+$ T cells in the presence different concentration of OSE703-IgG1 compared to in 0.001 mg/ml OSE703-IgG1.

Data were analyzed using Prism software (GraphPad Software Inc) and are presented as mean±SD, as stated in the figure legends. Results were analyzed using two-tailed Student's t test or two-way ANOVA, with the Sidak-Bonferroni correction used to correct for multiple comparisons when applicable. Survival curves were analyzed using the log-rank test. Statistical significance was defined as P<0.05.

Although the presently disclosed subject matter and certain of its advantages have been described in detail, it should be understood that various changes, substitutions and alterations can be made herein without departing from the spirit and scope of the disclosure. Moreover, the scope of the present application is not intended to be limited to the particular embodiments of the process, machine, manufacture, and composition of matter, and methods described in the specification. As one of ordinary skill in the art will readily appreciate from the disclosure of the presently disclosed subject matter, processes, machines, manufacture, compositions of matter, or methods, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, or methods.

Various patents, patent applications, publications, product descriptions, protocols, and sequence accession numbers are cited throughout this application, the disclosure of which are incorporated herein by reference in their entireties for all purposes.

What is claimed is:

1. A method for reducing tumor burden in a subject having a hematological tumor, treating and/or preventing a hematological tumor in a subject, and/or increasing or lengthening survival of a subject having a hematological tumor, comprising administering to the subject a) an effective amount of cells comprising an antigen-recognizing receptor, b) a pharmaceutical composition comprising an effective amount of cells comprising an antigen-recognizing receptor; or c) a nucleic acid composition comprising a polynucleotide encoding an antigen-recognizing receptor;

wherein the antigen-recognizing receptor comprises a chimeric antigen receptor (CAR) comprising an extracellular antigen-binding domain, a transmembrane domain, and an intracellular signaling domain, wherein the extracellular antigen-binding domain specifically binds CD127 comprises a heavy chain variable region ($V_H$) and a light chain variable region ($V_L$), which are positioned from a N- to a C-terminus: $V_H$-$V_L$, and wherein the heavy chain variable region comprises a CDR1 comprising the amino acid sequence set forth in SEQ ID NO: 6, a CDR2 comprising the amino acid sequence set forth in SEQ ID NO: 7, and a CDR3 comprising the amino acid sequence set forth in SEQ ID NO: 8, and the light chain variable region comprises a CDR1 comprising the amino acid sequence set forth in SEQ ID NO: 9, a CDR2 comprising the amino acid sequence set forth in SEQ ID NO: 10, and a CDR3 comprising the amino acid sequence set forth in SEQ ID NO: 11.

2. Method of claim 1, wherein the extracellular antigen-binding domain is a single-chain variable fragment (scFv), a Fab, or a F(ab)$_2$.

3. The method of claim 1, wherein the extracellular antigen-binding domain is a humanized scFv.

4. The method of claim 1, wherein the heavy chain variable region comprises the amino acid sequence set forth in SEQ ID NO: 12 and the light chain variable region comprises the amino acid sequence set forth in SEQ ID NO: 13.

5. The method of claim 1, wherein the extracellular antigen-binding domain comprises a linker between a heavy chain variable region and a light chain variable region.

6. The method of claim 5, wherein the linker consists of the amino acid sequence set forth in SEQ ID NO: 1, SEQ ID NO: 2, SEQ ID NO: 3, or SEQ ID NO: 4.

7. The method of claim 1, wherein the extracellular antigen-binding domain comprises the amino acid sequence set forth in SEQ ID NO: 14.

8. The method of claim 1,
wherein the transmembrane domain comprises a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, a synthetic peptide (not based on a protein associated with the immune response), or a combination thereof; and/or
wherein the intracellular signaling domain comprises a CD3ζ polypeptide.

9. The method of claim 8, wherein the transmembrane domain comprises a CD28 polypeptide.

10. The method of claim 1, wherein the intracellular signaling domain further comprises at least one co-stimulatory signaling region.

11. The method of claim 10, wherein the at least one co-stimulatory signaling region comprises a CD28 polypeptide, a 4-1BB polypeptide, an OX40 polypeptide, an ICOS polypeptide, a DAP-10 polypeptide, or a combination thereof.

12. The method of claim 1, wherein the antigen-recognizing receptor comprises the amino acid sequence set forth in SEQ ID NO: 27.

13. The method of claim 1, wherein the antigen-recognizing receptor is recombinantly expressed and/or is expressed from a vector.

14. The method of claim 1, wherein the polynucleotide comprises or consists of the nucleotide acid sequence set forth in SEQ ID NO: 28.

15. The method of claim 1, wherein the nucleic acid composition is a vector.

16. The method of claim 15, wherein the vector is a γ-retroviral vector.

17. The method of claim 1, wherein the cell is transduced with the antigen-recognizing receptor.

18. The method of claim 1, wherein the cell is an immunoresponsive cells, a cell of the lymphoid lineage, or a cell of the myeloid lineage.

19. The method of claim 1, wherein the cell is selected from the group consisting of a T-cell, a Natural Killer (NK) cell, and a stem cell from which a lymphoid cell may be differentiated.

20. The method of claim 1, wherein
a) the T-cell is a cytotoxic T lymphocyte (CTL) or a regulatory T-cell; or
b) the stem cell is a pluripotent stem cell, an embryoid stem cell, or an induced pluripotent stem cell.

21. The method of claim 1, wherein the pharmaceutical composition further comprises a pharmaceutically acceptable carrier.

22. The method of claim 1, wherein the method reduces the number of tumor cells, reduces tumor size, and/or eradicates the tumor in the subject.

23. The method of claim 1, wherein the hematological tumor is selected from the group consisting of acute lymphoblastic leukemia (ALL), Hodgkin's lymphoma, non-Hodgkin's lymphoma, T-cell cutaneous lymphoma.

24. The method of claim 23, wherein the acute lymphoblastic leukemia (ALL) is associated with gain-mutation of the IL7-R/TSLP pathway.

25. The method of claim 23, wherein the acute lymphoblastic leukemia (ALL) is T-cell acute lymphoblastic leukemia (T-ALL) or B-cell acute lymphoblastic leukemia (B-ALL).

26. The method of claim 1, wherein the hematological tumor is T-cell acute lymphoblastic leukemia (T-ALL).

\* \* \* \* \*

SEQUENCE LISTING

Sequence total quantity: 31
SEQ ID NO: 1              moltype = AA   length = 15
FEATURE                   Location/Qualifiers
REGION                    1..15
                          note = Synthetic
source                    1..15
                          mol_type = protein
                          organism = synthetic construct
SEQUENCE: 1
GGGGSGGGGS GGGGS                                                   15

SEQ ID NO: 2              moltype = AA   length = 19
FEATURE                   Location/Qualifiers
REGION                    1..19
                          note = Synthetic
source                    1..19
                          mol_type = protein
                          organism = synthetic construct
SEQUENCE: 2
GGGGSGGGGS GGGSGGGGS                                               19

SEQ ID NO: 3              moltype = AA   length = 24
FEATURE                   Location/Qualifiers
REGION                    1..24
                          note = Synthetic
source                    1..24
                          mol_type = protein
                          organism = synthetic construct
SEQUENCE: 3
GGGGSGGGGS GGGGSGGGSG GGGS                                         24

SEQ ID NO: 4              moltype = AA   length = 29
FEATURE                   Location/Qualifiers
REGION                    1..29
                          note = Synthetic
source                    1..29
                          mol_type = protein
                          organism = synthetic construct
SEQUENCE: 4
GGGGSGGGGS GGGGSGGGGS GGGSGGGGS                                    29

SEQ ID NO: 5              moltype = AA   length = 459
FEATURE                   Location/Qualifiers
source                    1..459
                          mol_type = protein
                          organism = Homo sapiens
SEQUENCE: 5
MTILGTTFGM VFSLLQVVSG ESGYAQNGDL EDAELDDYSF SCYSQLEVNG SQHSLTCAFE  60
DPDVNITNLE FEICGALVEV KCLNFRKLQE IYFIETKKFL LIGKSNICVK VGEKSLTCKK  120
IDLTTIVKPE APFDLSVVYR EGANDFVVTF NTSHLQKKYV KVLMHDVAYR QEKDENKWTH  180
VNLSSTKLTL LQRKLQPAAM YEIKVRSIPD HYFKGFWSEW SPSYYFRTPE INNSSGEMDP  240
ILLTISILSF FSVALLVILA CVLWKKRIKP IVWPSLPDHK KTLEHLCKKP RKNLNVSFNP  300
ESFLDCQIHR VDDIQARDEV EGFLQDTFPQ QLEESEKQRL GGDVQSPNCP SEDVVITPES  360
FGRDSSLTCL AGNVSACDAP ILSSSRSLDC RESGKNGPHV YQDLLLSLGT TNSTLPPPFS  420
LQSGILTLNP VAQGQPILTS LGSNQEEAYV TMSSFYQNQ                         459

SEQ ID NO: 6              moltype = AA   length = 9
FEATURE                   Location/Qualifiers
REGION                    1..9
                          note = Synthetic
source                    1..9
                          mol_type = protein
                          organism = synthetic construct
SEQUENCE: 6
FTFTNAAMY                                                          9

SEQ ID NO: 7              moltype = AA   length = 19
FEATURE                   Location/Qualifiers
REGION                    1..19
                          note = Synthetic
source                    1..19
                          mol_type = protein
                          organism = synthetic construct
SEQUENCE: 7
RIRTKANNYA TYYADSVKG                                               19

SEQ ID NO: 8              moltype = AA   length = 12
FEATURE                   Location/Qualifiers

```
REGION                    1..12
                          note = Synthetic
source                    1..12
                          mol_type = protein
                          organism = synthetic construct
SEQUENCE: 8
VVLTTTRDYF DY                                                      12

SEQ ID NO: 9              moltype = AA   length = 16
FEATURE                   Location/Qualifiers
REGION                    1..16
                          note = Synthetic
source                    1..16
                          mol_type = protein
                          organism = synthetic construct
SEQUENCE: 9
RSSQSLLTVK GITSLY                                                  16

SEQ ID NO: 10             moltype = AA   length = 7
FEATURE                   Location/Qualifiers
REGION                    1..7
                          note = Synthetic
source                    1..7
                          mol_type = protein
                          organism = synthetic construct
SEQUENCE: 10
RMSNRDS                                                            7

SEQ ID NO: 11             moltype = AA   length = 9
FEATURE                   Location/Qualifiers
REGION                    1..9
                          note = Synthetic
source                    1..9
                          mol_type = protein
                          organism = synthetic construct
SEQUENCE: 11
AQFLEYPHT                                                          9

SEQ ID NO: 12             moltype = AA   length = 123
FEATURE                   Location/Qualifiers
REGION                    1..123
                          note = Synthetic
source                    1..123
                          mol_type = protein
                          organism = synthetic construct
SEQUENCE: 12
AVQLVESGGG LVQPGGSLKI TCAASGFTFT NAAMYWVRQA PGKGLEWVAR IRTKANNYAT  60
YYADSVKGRF TISRDDSKST VYLQMDSVKT EDTATYYCIV VVLTTTRDYF DYWGQGVLVT  120
VSS                                                                123

SEQ ID NO: 13             moltype = AA   length = 112
FEATURE                   Location/Qualifiers
REGION                    1..112
                          note = Synthetic
source                    1..112
                          mol_type = protein
                          organism = synthetic construct
SEQUENCE: 13
DIVLTQSPSS LPVTPGEPAS ISCRSSQSLL TVKGITSLYW FLQKPGQSPK LLIYRMSNRD  60
SGVPDRFSGS GSETDFTLKI SRVEAEDVGT YYCAQFLEYP HTFGAGTKLE LK          112

SEQ ID NO: 14             moltype = AA   length = 268
FEATURE                   Location/Qualifiers
REGION                    1..268
                          note = Synthetic
source                    1..268
                          mol_type = protein
                          organism = synthetic construct
SEQUENCE: 14
MLVLQWVLVT ALFQGVHCAV QLVESGGGLV QPGGSLKITC AASGFTFTNA AMYWVRQAPG  60
KGLEWVARIR TKANNYATYY ADSVKGRFTI SRDDSKSTVY LQMDSVKTED TATYYCIVVV  120
LTTTRDYFDY WGQGVLVTVS SGGGGSGGGG SGGGGSDIVL TQSPSSLPVT PGEPASISCR  180
SSQSLLTVKG ITSLYWFLQK PGQSPKLLIY RMSNRDSGVP DRFSGSGSET DFTLKISRVE  240
AEDVGTYYCA QFLEYPHTFG AGTKLELK                                     268

SEQ ID NO: 15             moltype = AA   length = 270
FEATURE                   Location/Qualifiers
REGION                    1..270
                          note = Synthetic
```

-continued

```
source                  1..270
                        mol_type = protein
                        organism = synthetic construct
SEQUENCE: 15
MKFPAQFLGL IVLCIPGATG DIVLTQSPSS LPVTPGEPAS ISCRSSQSLL TVKGITSLYW   60
FLQKPGQSPK LLIYRMSNRD SGVPDRFSGS GSETDFTLKI SRVEAEDVGT YYCAQFLEYP  120
HTFGAGTKLE LKGGGGSGGG GSGGGGSAVQ LVESGGGLVQ PGGSLKITCA ASGFTFTNAA  180
MYWVRQAPGK GLEWVARIRT KANNYATYYA DSVKGRFTIS RDDSKSTVYL QMDSVKTEDT  240
ATYYCIVVVL TTTRDYFDYW GQGVLVTVSS                                   270

SEQ ID NO: 16           moltype = AA   length = 220
FEATURE                 Location/Qualifiers
source                  1..220
                        mol_type = protein
                        organism = Homo sapiens
SEQUENCE: 16
MLRLLLALNL FPSIQVTGNK ILVKQSPMLV AYDNAVNLSC KYSYNLFSRE FRASLHKGLD   60
SAVEVCVVYG NYSQQLQVYS KTGFNCDGKL GNESVTFYLQ NLYVNQTDIY FCKIEVMYPP  120
PYLDNEKSNG TIIHVKGKHL CPSPLFPGPS KPFWVLVVVG GVLACYSLLV TVAFIIFWVR  180
SKRSRLLHSD YMNMTPRRPG PTRKHYQPYA PPRDFAAYRS                        220

SEQ ID NO: 17           moltype = DNA   length = 81
FEATURE                 Location/Qualifiers
misc_feature            1..81
                        note = Synthetic
source                  1..81
                        mol_type = other DNA
                        organism = synthetic construct
SEQUENCE: 17
ttttgggtgc tggtggtggt tggtggagtc ctggcttgct atagcttgct agtaacagtg   60
gcctttatta ttttctgggt g                                            81

SEQ ID NO: 18           moltype = AA   length = 218
FEATURE                 Location/Qualifiers
source                  1..218
                        mol_type = protein
                        organism = Mus musculus
SEQUENCE: 18
MTLRLLLFLAL NFFSVQVTEN KILVKQSPLL VVDSNEVSLS CRYSYNLLAK EFRASLYKGV   60
NSDVEVCVGN GNFTYQPQFR SNAEFNCDGD FDNETVTFRL WNLHVNHTDI YFCKIEFMYP  120
PPYLDNERSN GTIIHIKEKH LCHTQSSPKL FWALVVVAGV LFCYGLLVTV ALCVIWTNSR  180
RNRLLQSDYM NMTPRRPGLT RKPYQPYAPA RDFAAYRP                          218

SEQ ID NO: 19           moltype = AA   length = 235
FEATURE                 Location/Qualifiers
source                  1..235
                        mol_type = protein
                        organism = Homo sapiens
SEQUENCE: 19
MALPVTALLL PLALLLHAAR PSQFRVSPLD RTWNLGETVE LKCQVLLSNP TSGCSWLFQP   60
RGAAASPTFL LYLSQNKPKA AEGLDTQRFS GKRLGDTFVL TLSDFRRENE GYYFCSALSN  120
SIMYFSHFVP VFLPAKPTTT PAPRPPTPAP TIASQPLSLR PEACRPAAGG AVHTRGLDFA  180
CDIYIWAPLA GTCGVLLLSL VITLYCNHRN RRRVCKCPRP VVKSGDKPSL SARYV       235

SEQ ID NO: 20           moltype = AA   length = 247
FEATURE                 Location/Qualifiers
source                  1..247
                        mol_type = protein
                        organism = Mus musculus
SEQUENCE: 20
MASPLTRFLS LNLLLMGESI ILGSGEAKPQ APELRIFPKK MDAELGQKVD LVCEVLGSVS   60
QGCSWLFQNS SSKLPQPTFV VYMASSHNKI TWDEKLNSSK LFSAVRDTNN KYVLTLNKFS  120
KENEGYYFCS VISNSVMYFS SVVPVLQKVN STTTKPVLRT PSPVHPTGTS QPQRPEDCRP  180
RGSVKGTGLD FACDIYIWAP LAGICVAPLL SLIITLICYH RSRKRVCKCP RPLVRQEGKP  240
RPSEKIV                                                           247

SEQ ID NO: 21           moltype = AA   length = 164
FEATURE                 Location/Qualifiers
source                  1..164
                        mol_type = protein
                        organism = Homo sapiens
SEQUENCE: 21
MKWKALFTAA ILQAQLPITE AQSFGLLDPK LCYLLDGILF IYGVILTALF LRVKFSRSAD   60
APAYQQGQNQ LYNELNLGRR EEYDVLDKRR GRDPEMGGKP QRRKNPQEGL YNELQKDKMA  120
EAYSEIGMKG ERRRGKGHDG LYQGLSTATK DTYDALHMQA LPPR                  164

SEQ ID NO: 22           moltype = AA   length = 112
FEATURE                 Location/Qualifiers
REGION                  1..112
```

```
                                 note = Synthetic
source                           1..112
                                 mol_type = protein
                                 organism = synthetic construct
SEQUENCE: 22
RVKFSRSADA PAYQQGQNQL YNELNLGRRE EYDVLDKRRG RDPEMGGKPR RKNPQEGLYN   60
ELQKDKMAEA YSEIGMKGER RRGKGHDGLY QGLSTATKDT YDALHMQALP PR          112

SEQ ID NO: 23                    moltype = DNA   length = 336
FEATURE                          Location/Qualifiers
misc_feature                     1..336
                                 note = Synthetic
source                           1..336
                                 mol_type = other DNA
                                 organism = synthetic construct
SEQUENCE: 23
agagtgaagt tcagcaggag cgcagacgcc cccgcgtacc agcagggcca gaaccagctc   60
tataacgagc tcaatctagg acgaagagag gagtacgatg ttttggacaa gagacgtggc  120
cgggaccctg agatggggggg aaagccgaga aggaagaacc ctcaggaagg cctgtacaat  180
gaactgcaga aagataagat ggcggaggcc tacagtgaga ttgggatgaa aggcgagcgc  240
cggagggggca aggggcacga tggcctttac cagggtctca gtacagccac caaggacacc  300
tacgacgccc ttcacatgca ggccctgccc cctcgc                           336

SEQ ID NO: 24                    moltype = DNA   length = 123
FEATURE                          Location/Qualifiers
misc_feature                     1..123
                                 note = Synthetic
source                           1..123
                                 mol_type = other DNA
                                 organism = synthetic construct
SEQUENCE: 24
aggagtaaga ggagcaggct cctgcacagt gactacatga acatgactcc ccgccgcccc   60
gggcccaccc gcaagcatta ccagccctat gccccaccac gcgacttcgc agcctatcgc  120
tcc                                                               123

SEQ ID NO: 25                    moltype = AA   length = 255
FEATURE                          Location/Qualifiers
source                           1..255
                                 mol_type = protein
                                 organism = Homo sapiens
SEQUENCE: 25
MGNSCYNIVA TLLLVLNFER TRSLQDPCSN CPAGTFCDNN RNQICSPCPP NSFSSAGGQR   60
TCDICRQCKG VFRTRKECSS TSNAECDCTP GFHCLGAGCS MCEQDCKQGQ ELTKKGCKDC  120
CFGTFNDQKR GICRPWTNCS LDGKSVLVNG TKERDVVCGP SPADLSPGAS SVTPPAPARE  180
PGHSPQIISF FLALTSTALL FLLFFLTLRF SVVKRGRKKL LYIFKQPFMR PVQTTQEEDG  240
CSCRFPEEEE GGCEL                                                  255

SEQ ID NO: 26                    moltype = DNA   length = 126
FEATURE                          Location/Qualifiers
misc_feature                     1..126
                                 note = Synthetic
source                           1..126
                                 mol_type = other DNA
                                 organism = synthetic construct
SEQUENCE: 26
aaacggggca gaaagaaact cctgtatata ttcaaacaac catttatgag accagtacaa   60
actactcaag aggaagatgg ctgtagctgc cgatttccag aagaagaaga aggaggatgt  120
gaactg                                                            126

SEQ ID NO: 27                    moltype = AA   length = 472
FEATURE                          Location/Qualifiers
REGION                           1..472
                                 note = Sythetic
source                           1..472
                                 mol_type = protein
                                 organism = synthetic construct
SEQUENCE: 27
AVQLVESGGG LVQPGGSLKI TCAASGFTFT NAAMYWVRQA PGKGLEWVAR IRTKANNYAT   60
YYADSVKGRF TISRDDSKST VYLQMDSVKT EDTATYYCIV VVLTTTRDYF DYWGQGVLVT  120
VSSGGGGSGG GGSGGGGSDI VLTQSPSSLP VTPGEPASIS CRSSQSLLTV KGITSLYWFL  180
QKPGQSPKLL IYRMSNRDSG VPDRFSGSGS ETDFTLKISR VEAEDVGTYY CAQFLEYPHT  240
FGAGTKLELK AAAIEVMYPP PYLDNEKSNG TIIHVKGKHL CPSPLFPGPS KPFWVLVVVG  300
GVLACYSLLV TVAFIIFWVR SKRSRLLHSD YMNMTPRRPG PTRKHYQPYA PPRDFAAYRS  360
RVKFSRSADA PAYQQGQNQL YNELNLGRRE EYDVLDKRRG RDPEMGGKPR RKNPQEGLYN  420
ELQKDKMAEA YSEIGMKGER RRGKGHDGLY QGLSTATKDT YDALHMQALP PR          472

SEQ ID NO: 28                    moltype = DNA   length = 7891
FEATURE                          Location/Qualifiers
misc_feature                     1..7891
```

```
                          note = Synthetic
source                    1..7891
                          mol_type = other DNA
                          organism = synthetic construct
SEQUENCE: 28
gatgaacgaa  atagacagat  cgctgagata  ggtgcctcac  tgattaagca  ttggtaactg  60
tcagaccaag  tttactcata  tatactttag  attgatttaa  aacttcattt  ttaatttaaa  120
aggatctagg  tgaagatcct  ttttgataat  ctcatgacca  aaatcccttta  acgtgagttt  180
tcgttccact  gagcgtcaga  ccccgtagaa  aagatcaaag  gatcttcttg  agatcctttt  240
tttctgcgcg  taatctgctg  cttgcaaaca  aaaaaaccac  cgctaccagc  ggtggtttgt  300
ttgccggatc  aagagctacc  aactcttttt  ccgaaggtaa  ctggcttcag  cagagcgcag  360
ataccaaata  ctgtccttct  agtgtagccg  tagttaggcc  accacttcaa  gaactctgta  420
gcaccgccta  catacctcgc  tctgctaatc  ctgttaccag  tggctgctgc  cagtggcgat  480
aagtcgtgtc  ttaccgggtt  ggactcaaga  cgatagttac  cggataaggc  gcagcggtcg  540
ggctgaacgg  ggggttcgtg  cacacagccc  agcttggagc  gaacgaccta  caccgaactg  600
agatacctac  agcgtgagca  ttgagaaagc  gccacgcttc  ccgaagggag  aaaggcggac  660
aggtatccgg  taagcggcag  ggtcggaaca  ggagagcgca  cgagggagct  tccaggggga  720
aacgcctggt  atctttatag  tcctgtcggg  tttcgccacc  tctgacttga  gcgtcgattt  780
ttgtgatgct  cgtcagggg  gcggagccta  tggaaaaacg  ccagcaacgc  ggcctttttta  840
cggttcctgg  cctttttgctg  gcctttttgct  cacatgttct  ttcctgcgtt  atcccctgat  900
tctgtggata  accgtattac  cgcctttgag  tgagctgata  ccgctcgccg  cagccgaacg  960
accgagcgca  gcgagtcagt  gagcgaggaa  gcggaagagc  gcccaatacg  caaaccgcct  1020
ctccccgcgc  gttggccgat  tcattaatgc  agctggcacg  acaggtttcc  cgactggaaa  1080
gcgggcagtg  agcgcaacgc  aattaatgtg  agttagctca  ctcattaggc  accccaggct  1140
ttacacttta  tgcttccggc  tcgtatgttg  tgtggaattg  tgagcggata  acaatttcac  1200
acaggaaaca  gctatgacca  tgattacgcc  aagctttgct  cttaggagtt  tcctaataca  1260
tcccaaactc  aaatatataa  agcatttgac  ttgttctatg  ccctaggggg  cggggggaag  1320
ctaagccagc  ttttttttaac  atttaaaatg  ttaattccat  tttaaatgca  cagatgtttt  1380
tatttcataa  gggtttcaat  gtgcatgaat  gctgcaatat  tcctgttacc  aaagctagta  1440
taaataaaaa  tagataaacg  tggaaattac  ttagagtttc  tgtcattaac  gtttccttcc  1500
tcagttgaca  acataaatgc  gctgctgagc  aagccagttt  gcatctgtca  ggatcaattt  1560
cccattatgc  cagtcatatt  aattactagt  caattagttg  attttttattt  ttgacatata  1620
catgtgaatg  aaagacccca  cctgtaggtt  tggcaagcta  gcttaagtaa  cgccattttg  1680
caaggcatgg  aaaaatacat  aactgagaat  agaaaagttg  agatcaaggt  caggaacaga  1740
tggaacagct  gaatatgggc  caaacaggat  atctgtggta  agcagttcct  gccccggctc  1800
agggccaaga  acagatggaa  cagctgaata  tgggccaaac  aggatatctg  tggtaagcag  1860
ttcctgcccc  ggctcagggc  caagaacaga  tggtccccag  atgcggtcca  gccctcagca  1920
gtttctagag  aaccatcaga  tgtttccagg  gtgccccaag  gacctgaaat  gaccctgtgc  1980
cttatttgaa  ctaaccaatc  agttcgcttc  tcgcttctgt  tcgcgcgctt  atgctcccccg  2040
agctcaataa  aagagcccac  aacccctcac  tcggggcgcc  agtcctccga  ttgactgagt  2100
cgcccgggta  cccgtgtatc  caataaaccc  tcttgcagtt  gcatccgact  tgtggtctcg  2160
ctgttccttg  ggagggtctc  ctctgagtga  ttgactaccc  gtcagcgggg  gtctttcatt  2220
tgggggctcg  tccgggatcg  ggagaccccct  gcccagggac  caccgaccca  ccaccgggag  2280
gtaagctggc  cagcaactta  tctgtgtctg  tccgattgtc  tagtgtctat  gactgatttt  2340
atgcgcctgc  gtcggtacta  gttagctaac  tagctctgta  tctggcggac  ccgtggtgga  2400
actgacgagt  tcggaacacc  cggccgcaac  cctgggagac  gtcccaggga  cttcgggggc  2460
cgtttttgtg  gcccgacctg  agtcctaaaa  tcccgatcgt  ttaggactct  ttggtgcacc  2520
cccccttagag  gagggatatg  tggttctggt  aggagacgag  aacctaaaac  agttcccgcc  2580
tccgtctgaa  tttttgcttt  cggtttggga  ccgaagccgc  gccgcgcgtc  ttgtctgctg  2640
cagcatcgtt  ctgtgttgtc  tctgtctgac  tgtgtttctg  tatttgtctg  aaaatatggg  2700
cccgggctag  actgttacca  ctcccttaag  tttgacctta  ggtcactgga  aagatgtcga  2760
gcggatcgct  cacaaccagt  cggtagatgt  caagaagaga  cgttgggtta  ccttctgctc  2820
tgcagaatgg  ccaaccttta  acgtcggatg  gccgcgagac  ggcacctttta  accgagacct  2880
catcacccag  gttaagatca  aggtcttttc  acctggcccg  catggacacc  cagaccaggt  2940
cccctacatc  gtgacctggg  aagccttggc  ttttgcccgt  cctccctggg  tcaagccctt  3000
tgtacacct  aagcctccgc  ctcctcttcc  tccatccgcc  ccgtctctcc  cccttgaacc  3060
tcctcgttcg  accccgcctc  gatcctccct  ttatccagcc  ctcactcctt  ctctaggcgc  3120
ccccatatgg  ccatatgaga  tcttatatgg  ggcaccccccg  cccctttgtaa  acttccctga  3180
ccctgacatg  acaagagtta  ctaacagccc  ctctctccaa  gctcacttac  aggctctcta  3240
cttagtccag  cacgaagtct  ggagacctct  ggcggcagcc  taccaagaac  aactggaccg  3300
accggtggta  cctcacccct  accgagtcgg  cgacacagtg  tgggtccgcc  gacaccagac  3360
taagaaccta  gaacctcgct  ggaaaggacc  ttacacagtc  ctgctgacca  cccccaccgc  3420
cctcaaagta  gacggcatcg  cagcttggat  acacgccgcc  cacgtgaagg  ctgccgaccc  3480
cggggtgga  ccatcctcta  gactgccatg  gccctgccaa  taacggctct  gctgctgcca  3540
cttgctctgc  tcctccatgc  agccaggcct  gagcagaagc  tgatctcaga  ggaggacctg  3600
gagcagaagc  tgatctcaga  ggaggacctg  gccgttcaac  ttgttgaatc  tggtggtggc  3660
ctcgttcagc  cggggggctc  ccttaaaatt  acttgtgcag  ctagcggatt  cacattcacc  3720
aatgccgcaa  tgtactgggt  tagacaagct  cctggcaaag  gactggaatg  ggtagctaga  3780
attagaacta  aagctaataa  ctatgcaaca  tactatgctc  attccgtcaa  aggacgattc  3840
actatcagca  gagatgatag  caagtcaact  gtgtacctgc  agatggactc  cgttaagaca  3900
gaggatacag  ctacatacta  ttgtatcgta  gttgtgctga  caactaccag  agattacttt  3960
gattattggg  gccaaggtgt  tctggtaaca  gtgagtagtg  gaggtggagg  atcaggcggt  4020
ggaggatccg  gtggcggagg  aagcgatata  gtcctcacac  agtccccctag  ttcactgcca  4080
gtcactccag  gagaacctgc  ttccatatca  tgtagatcaa  gtcaaagttt  gcttacagta  4140
aaaggaatta  caagcctcta  ttggttcttg  caaaaacctg  gtcagagccc  aaagttgctg  4200
atctatagaa  tgtccaacag  agactccgga  gtccctgata  gattcagcgg  ctcaggatca  4260
gaaacggact  tcacccttaa  aatatcaaga  gtagaagccg  aagatgttgg  cacctactat  4320
tgtgctcagt  ttctggaata  ccctcatacg  tttggagcag  gtaccaagct  cgaactcaag  4380
gcggccgcaa  ttgaagttat  gtatcctcct  ccttacctag  acaatgagaa  gagcaatgga  4440
```

```
accattatcc atgtgaaagg gaaacacctt tgtccaagtc ccctatttcc cggaccttct   4500
aagccctttt gggtgctggt ggtggttggt ggagtcctgg cttgctatag cttgctagta   4560
acagtggcct ttattatttt ctgggtgagg agtaagagga gcaggctcct gcacagtgac   4620
tacatgaaca tgactccccg ccgccccggg cccacccgca agcattacca gccctatgcc   4680
ccaccacgcg acttcgcagc ctatcgctcc agagtgaagt tcagcaggag cgcagacgcc   4740
cccgcgtacc agcagggcca gaaccagctc tataacgagc tcaatctagg acgaagagag   4800
gagtacgatg ttttggacaa gagacgtggc cgggaccctg agatggggg aaagccgaga   4860
aggaagaacc ctcaggaagg cctgtacaat gaactgcaga agataagat ggcggaggcc   4920
tacagtgaga ttgggatgaa aggcgagcgc cggaggggca aggggcacga tggcctttac   4980
cagggtctca gtacagccac caaggacacc tacgacgccc ttcacatgca ggccctgccc   5040
cctcgctgag tcgacggatc cggattagtc caatttgtta aagacaggat atcagtggtc   5100
caggctctag ttttgactca acaatatcac cagctgaagc ctatagagta cgagccatag   5160
ataaaataaa agatttttatt tagtctccag aaaaaggggg gaatgaaaga ccccacctgt   5220
aggtttggca agctagctta agtaacgcca ttttgcaagg catggaaaaa tacataactg   5280
agaatagaga agttcagatc aaggtcagga acagatggaa cagctgaata tgggccaaac   5340
aggatatctg tggtaagcag ttcctgcccc ggctcagggc caagaacaga tggaacagct   5400
gaatatgggc caaacaggat atctgtggta agcagttcct gccccggctc agggccaaga   5460
acagatggtc cccagatgcg gtccagccct cagcagtttc tagagaacca tcagatgttt   5520
ccagggtgcc ccaaggacct gaaatgaccc tgtgccttat ttgaactaac caatcagttc   5580
gcttctcgct tctgttcgcg cgcttctgct ccccgagctc aataaaagag cccacaaccc   5640
ctcactcggg gcgccagtcc tccgattgac tgagtcgccc gggtacccgt gtatccaata   5700
aaccctcttg cagttgcatc cgacttgtgg tctcgctgtt cctgggaggg tctcctctgg   5760
agtgattgac tacccgtcag cggggggtctt tcacacatgc agcatgtatc aaaattaatt   5820
tggttttttt tcttaagtat ttacattaaa tggccatagt acttaaagtt acattggctt   5880
ccttgaaata aacatggagt attcagaatg tgtcataaat atttctaatt ttaagatagt   5940
atctccattg gctttctact ttttctttta ttttttttg tcctctgtct tccatttgtt   6000
gttgttgttg tttgtttgtt tgtttgttgg ttggttggtt aatttttttt taaagatcct   6060
acactatagt tcaagctaga ctattagcta ctctgtaacc cagggtgacc ttgaagtcat   6120
gggtagcctg ctgtttagc cttcccacat ctaagattac aggtatgagc tatcatttt    6180
ggtatattga ttgattgatt gattgatgtg tgtgtgtgtg atttgtgtttg tgtgtgtgac   6240
tgtgaaaatg tgtgtatggg tgtgtgtgaa tgtgtgtatg tatgtgtgtg tgtgagtgtg   6300
tgtgtgtgtg tgtgcatgtg tgtgtgtgtg actgtgtcta tgtgtatgac tgtgtgtgtg   6360
tgtgtgtgtg tgtgtgtgtg tgtgtgtgtg tgtgtgttgt gaaaaaatat tctatggtag   6420
tgagagccaa cgctccggct caggtgtcag gttggttttt gagacagagt ctttcactta   6480
gcttggaatt cactggccgt cgttttacaa cgtcgtgact gggaaaaccc tggcgttacc   6540
caacttaatc gccttgcagc acatcccct ttcgccagct ggcgtaatag cgaagaggcc   6600
cgcaccgatc gcccttccca acagttcgc agctgaatg gcgaatggcg cctgatgcgg   6660
tattttctcc ttacgcatct gtgcggtatt tcacaccgca tatggtgcac tctcagtaca   6720
atctgctctg atgccgcata gttaagccag ccccgacacc cgccaacacc cgctgacgcg   6780
ccctgacggg cttgtctgct cccggcatcc gcttacagac aagctgtgac cgtctccggg   6840
agctgcatgt gtcagaggtt ttcaccgtca tcaccgaaac gcgcgatgac gaaagggcct   6900
cgtgatacgc ctatttttat aggttaatgt catgataata atggtttctt agacgtcagg   6960
tggcactttt cggggaaatg tgcgcggaac ccctatttgt ttatttttct aaatacattc   7020
aaatatgtat ccgctcatga dacaataacc ctgatataat cttcaataat attgaaaaag   7080
gaagagtatg agtattcaac atttccgtgt cgcccttatt cccttttttg cggcattttg   7140
ccttcctgtt tttgctcacc cagaaacgct ggtgaaagta aaagatgctg aagatcagtt   7200
gggtgcacga gtggttaca tcgaactgga tctcaacagc ggtaagatcc ttgagagttt   7260
tcgccccgaa gaacgttttc caatgatgag cacttttaaa gttctgctat gtggcgcggt   7320
attatcccgt attgacgccg ggcaagagca actcggtcgc cgcatacact attctcagaa   7380
tgacttggtt gagtactcac cagtcacaga aaagcatctt acggatggca tgacagtaag   7440
agaattatgc agtgctgcca taaccatgag tgataaaact gcggccaact tacttctgac   7500
aacgatcgga ggaccgaagg agctaaccgc ttttttgcac aacatgggg atcatgtaac   7560
tcgccttgat cgttgggaac cggagctgaa tgaagccata ccaaacgacg agcgtgacac   7620
cacgatgcct gtagcaatgg caacaacgtt gcgcaaacta ttaactggcg aactacttac   7680
tctagcttcc cggcaacaat aatagactgg atggaggcgg ataaagttg caggaccact   7740
tctgcgctcg gcccttccgg ctggctggtt tattgctgat aaatctggag ccggtgagcg   7800
tgggtctcgc ggtatcattg cagcactggg gccagatggt aagccctccc gtatcgtagt   7860
tatctacacg acggggagtc aggcaactat g                                   7891
```

```
SEQ ID NO: 29            moltype = AA  length = 472
FEATURE                  Location/Qualifiers
REGION                   1..472
                         note = Synthetic
source                   1..472
                         mol_type = protein
                         organism = synthetic construct
SEQUENCE: 29
DIVLTQSPSS LPVTPGEPAS ISCRSSQSLL TVKGITSLYW FLQKPGQSPK LLIYRMSNRD   60
SGVPDRFSGS GSETDFTLKI SRVEAEDVGT YYCAQFLEYP HTFGAGTKLE LKGGGGSGGG   120
GSGGGGSAVQ LVESGGGLVQ PGGSLKITCA ASGFTFTNAA MYWVRQAPGK GLEWVARIRT   180
KANNYATYYA DSVKGRFTIS RDDSKSTVYL QMDSVKTEDT ATYYCIVVVL TTTRDYFDYW   240
GQGVLVTVSS AAAIEVMYPP PYLDNEKSNG TIIHVKGKHL CPSPLFPGPS KPFWVLVVVG   300
GVLACYSLLV TVAFIIFWVR SKRSRLLHSD YMNMTPRRPG PTRKHYQPYA PPRDFAAYRS   360
RVKFSRSADA PAYQQGQNQL YNELNLGRRE EYDVLDKRRG RDPEMGGKPR RKNPQEGLYN   420
ELQKDKMAEA YSEIGMKGER RRGKGHDGLY QGLSTATKDT YDALHMQALP PR           472

SEQ ID NO: 30            moltype = DNA  length = 7891
FEATURE                  Location/Qualifiers
misc_feature             1..7891
```

-continued

```
                    note = Synthetic
source              1..7891
                    mol_type = other DNA
                    organism = synthetic construct
SEQUENCE: 30
gatgaacgaa atagacagat cgctgagata ggtgcctcac tgattaagca ttggtaactg    60
tcagaccaag tttactcata tatactttag attgatttaa aacttcattt ttaatttaaa   120
aggatctagg tgaagatcct tttttgataat ctcatgacca aaatccctta acgtgagttt   180
tcgttccact gagcgtcaga ccccgtagaa aagatcaaag gatcttcttg agatcctttt   240
tttctgcgcg taatctgctg cttgcaaaca aaaaaaccac cgctaccagc ggtggtttgt   300
ttgccggatc aagagctacc aactcttttt ccgaaggtaa ctggcttcag cagagcgcag   360
ataccaaata ctgtccttct agtgtagccg tagttaggcc accacttcaa gaactctgta   420
gcaccgccta cataccctcgc tctgctaatc ctgttaccag tggctgctgc cagtggcgat   480
aagtcgtgtc ttaccgggtt ggactcaaga cgatagttac cggataaggc gcagcggtcg   540
ggctgaacgg ggggttcgtg cacacagccc agcttggagc gaacgaccta caccgaactg   600
agatacctac agcgtgagca ttgagaaagc gccacgcttc ccgaagggag aaaggcggac   660
aggtatccgg taagcggcag ggtcggaaca ggagagcgca cgagggagct tccaggggga   720
aacgcctggt atctttatag tcctgtcggg tttcgccacc tctgacttga gcgtcgattt   780
ttgtgatgct cgtcaggggg gcggagccta tggaaaaacg ccagcaacgc ggcctttta   840
cggttcctgg cctttcgtg gccttttgct cacatgttct ttcctgcgtt atcccctgat   900
tctgtggata accgtattac cgcctttgag tgagctgata ccgctcgccg cagccgaacg   960
accgagcgca gcgagtcagt gagcgaggaa gcggaagagc gcccaatacg caaaccgcct  1020
ctccccgcgc gttggccgat tcattaatgc agctggcacg acaggtttcc cgactggaaa  1080
gcgggcagtg agcgcaacgc aattaatgtg agttagctca ctcattaggc accccaggct  1140
ttacacttta tgcttccggc tcgtatgttg tgtggaattg tgagcggata caatttcac   1200
acaggaaaca gctatgacca tgattacgcc aagctttgct cttaggagtt tcctaataca  1260
tcccaaactc aaatatataa agcatttgac ttgttctatg ccctaggggg cggggggaag  1320
ctaagccagc tttttttaac atttaaaatg ttaattccat tttaaatgca cagatgtttt  1380
tatttcataa gggtttcaat gtgcatgaat gctgcaatat tcctgttacc aaagctagta  1440
taaataaaaa tagataaacg tggaaattac ttagagtttc tgtcattaac gtttccttcc  1500
tcagttgaca acataaatgc gctgctgagc aagccagttt gcatctgtca ggatcaattt  1560
cccattatgc cagtcatatt aattactagt caattagttg attttatttt ttgacatata  1620
catgtgaatg aaagacccca cctgtaggtt tggcaagcta gcttaagtaa cgccattttg  1680
caaggcatgg aaaaatacat aactgagaat agaaaagttc agatcaaggt caggaacaga  1740
tggaacagct gaatatgggc caaacaggat atctgtggta agcagttcct gccccggctc  1800
agggccaaga acagatggaa cagctgaata tgggccaaac aggatatctg tggtaagcag  1860
ttcctgcccc ggctcagggc caagaacaga tggtccccag atgcggtcca gccctcagca  1920
gtttctagag aaccatcaga tgtttccagg gtgccccaag gacctgaaat gaccctgtgc  1980
cttatttgaa ctaaccaatc agttcgcttc tcgcttctgt tcgcgcgctt atgctccccg  2040
agctcaataa aagagcccac aacccctcac tcggggcgcc agtcctccga ttgactgagt  2100
cgcccgggta cccgtgtatc caataaaccc tcttgcagtt gcatccgact tgtggtctcg  2160
ctgttccttg ggagggtctc ctctgagtga ttgactaccc gtcagcgggg gtctttcatt  2220
tgggggctcg tccgggatcg ggagacccct gcccaggcag caccgaccca ccaccgggag  2280
gtaagctggc cagcaactta tctgtgtctg tccgattgtc tagtgtctat gactgatttt  2340
atgcgcctgc gtcggtacta gttagctaac tagctctgta tctggcggac ccgtggtgga  2400
actgacgagt tcggaacacc cggccgcaac cctgggagac gtcccaggga cttcgggggc  2460
cgtttttgtg gcccgacctg agtcctaaaa tcccgatcgt ttaggactct ttggtgcacc  2520
cccttagag gagggatatg tggttctggt aggagacgag aacctaaaac agttcccgcc   2580
tccgtctgaa ttttttgcttt cggtttggga ccgaagccgc gccgcgcgtc ttgtctgctg  2640
cagcatcgtt ctgtgttgtc tctgtctgac tgtgtttctg tatttgtctg aaaatatggg  2700
cccgggctag actgttacca ctcccttaag tttgacctta ggtcactgga aagatgtgaa  2760
gcggatcgct cacaaccagt cggtagatgt caagaagaga cgttgggtta ccttctgctc  2820
tgcagaatgg ccaacctta acgtcggatg gccgcgagac ggcacctttta accgagacct  2880
catcacccag gttaagatca aggtcttttc acctggcccg catggacacc cagaccaggt  2940
ccctacatc gtgacctggg aagccttggc ttttgcccct cctccctggg tcaagccctt  3000
tgtacaccct aagcctccgc ctcctcttcc tccatccgcc ccgtctctcc cccttgaacc  3060
tcctcgttcg accccgcctc gatcctccct ttatccagcc ctcactcctt ctctaggcgc  3120
ccccatatgg ccatatgaga tcttatatgg ggcacccccg ccccttgtaa acttccctga  3180
ccctgacatg acaagagtta ctaacagccc ctctctccaa gctcacttac aggctctcta  3240
cttagtccag cacgaagtct ggagacctct ggcggcagcc taccaagaac aactggaccg  3300
accggtggta cctcacccctt accgagtcgg cgacacagtg tgggtccgcc gacaccagac  3360
taagaaccta gaacctcgct ggaaaggacc ttacacagtc ctgctgacca cccccaccgc  3420
cctcaaagta gacggcatcg cagcttggat acacgccgcc cacgtgaagg ctgccgaccc  3480
cgggggtgga ccatcctcta gactgccatg gccctgccaa taacggctct gctgctgcaa  3540
cttgctctgc tcctccatgc agccaggcct gagcagaagc tgatctcaga ggaggacctg  3600
gagcagaagc tgatctcaga ggaggacctg gatatagtcc tcacacagtc ccctagttca  3660
ctgccagtca ctccaggaga acctgcttcc atatcatgta gatcaagtca aagtttgctt  3720
acagtaaaag gaattacaag cctctcattgg ttcttgcaaa aacctggtca gagcccaaag  3780
ttgctgatct atagaatgtc caacagagac tccggagtcc ctgataatt cagcggctca  3840
ggatcagaaa cggacttcac ccttaaaata tcaagagtag aagccgaaga tgttggcacc  3900
tactattgtg ctcagtttct ggaataccct catacgtttg gagcaggtac caagctcgaa  3960
ctcaagggag gtgaggatc aggcggtgga ggatccggtg gcggaggaag cgccgttcaa   4020
cttgttgaat ctggtggtgg cctcgttcag ccgggggggct cccttaaaat tacttgtgca  4080
gctagcggat tcacattcac caatgccgca atgtactggg ttagacaagc tcctggccaa  4140
ggactggaat gggtagctag aattagaact aaagctaata actatgcaac atactatgct  4200
gattccgtca aggacgatt cactatcagc agagatgata gcaagtcaac tgtgtacctg  4260
cagatggact ccgttaagac agaggataca gctacatact attgtatcgt agttgtgctg  4320
acaactacca gagattactt tgattattgg ggccaaggtt ttctggtaac agtgagtagt  4380
gcggccgcaa ttgaagttat gtatcctcct ccttacctag acaatgagaa gagcaatgga  4440
```

-continued

```
accattatcc atgtgaaagg gaaacacctt tgtccaagtc ccctatttcc cggaccttct  4500
aagccctttt gggtgctggt ggtggttggt ggagtcctgg cttgctatag cttgctagta  4560
acagtggcct ttattatttt ctgggtgagg agtaagagga gcaggctcct gcacagtgac  4620
tacatgaaca tgactccccg ccgccccggg cccacccgca agcattacca gccctatgcc  4680
ccaccacgcg acttcgcagc ctatcgctcc agagtgaagt tcagcaggag cgcagacgcc  4740
cccgcgtacc agcagggcca gaaccagctc tataacgagc tcaatctagg acgaagagag  4800
gagtacgatg ttttggacaa gagacgtggc cgggaccctg agatggggggg aaagccgaga  4860
aggaagaacc ctcaggaagg cctgtacaat gaactgcaga aagataagat ggcggaggcc  4920
tacagtgaga ttgggatgaa aggcgagcgc cggaggggca aggggcacga tggcctttac  4980
cagggtctca gtacagccac caaggacacc tacgacgccc ttcacatgca ggccctgccc  5040
cctcgctgag tcgacggatc cggattagtc caatttgtta aagacaggat atcagtggtc  5100
caggctctag ttttgactca acaatatcac cagctgaagc ctatagagta cgagccatag  5160
ataaaataaa agattttatt tagtctccag aaaaagggggg gaatgaaaga ccccacctgt  5220
aggtttggca agctagctta agtaacgcca ttttgcaagg catggaaaaa tacataactg  5280
agaatagaga agttcagatc aaggtcagga acagatggaa cagctgaata tgggccaaac  5340
aggatatctg tggtaagcag ttcctgcccc ggctcagggc caagaacaga tggaacagct  5400
gaatatgggc caaacaggat atctgtggta agcagttcct gccccggctc agggccaaga  5460
acagatggtc cccagatgcg gtccagccct cagcagtttc tagagaacca tcagatgtt  5520
ccagggtgcc ccaaggacct gaaatgaccc tgtgccttat ttgaactaac caatcagttc  5580
gcttctcgct tctgttcgcg cgcttctgct ccccgagctc aataaaagag cccacaaccc  5640
ctcactcggg gcgccagtcc tccgattgac tgagtcgccc gggtacccgt gtatccaata  5700
aaccctcttg cagttgcatc cgacttgtgg tctcgctgtt ccttgggagg gtctcctctg  5760
agtgattgac tacccgtcag cggggggtctt tcacacatgc agcatgtatc aaaattaatt  5820
tggttttttt tcttaagtat ttacattaaa tggccatagt acttaaagtt acattggctt  5880
ccttgaaata aacatggagt attcagaatg tgtcataaat atttctaatt ttaagatagt  5940
atctccattg gctttctact ttttcttta tttttttttg tcctctgtct tccatttgtt  6000
gttgttgttg tttgtttgtt tgtttgttgg ttggttggtt aatttttttt taaagatcct  6060
acactatagt tcaagctaga ctattagcta ctctgtaacc cagggtgacc ttgaagtcat  6120
gggtagcctg ctgttttagc cttcccacat ctaagattac aggtatgagc tatcattttt  6180
ggtatattga ttgattgatt gattgatgtg tgtgtgtgtg attgtgtttg tgtgtgtgac  6240
tgtgaaaatg tgtgtatggg tgtgtgtgaa tgtgtgtatg tatgtgtgtg tgtgagtgtg  6300
tgtgtgtgtg tgtgcatgtg tgtgtgtgtg actgtgtcta tgtgtatgac tgtgtgtgtg  6360
tgtgtgtgtg tgtgtgtgtg tgtgtgtgtg tgtgtgttgt gaaaaaatat tctatggtag  6420
tgagagccaa cgctccggct caggtgtcag gttggttttt gagacagagt ctttcactta  6480
gcttggaatt cactggccgt cgttttacaa cgtcgtgact gggaaaaccc tggcgttacc  6540
caacttaatc gccttgcagc acatcccct ttcgccagct ggcgtaatag cgaagaggcc  6600
cgcaccgatc gcccttccca acagttgcgc agcctgaatg gcgaatggcg cctgatgcgg  6660
tattttctcc ttacgcatct gtgcggtatt tcacaccgca tatggtgcac tctcagtaca  6720
atctgctctg atgccgcata gttaagccag ccccgacacc cgccaacacc cgctgacgcg  6780
ccctgacggg cttgtctgct cccggcatcc gcttacagac aagctgtgac cgtctccggg  6840
agctgcatgt gtcagaggtt ttcaccgtca tcaccgaaac gcgcgatgac gaaagggcct  6900
cgtgatacgc ctatttttat aggttaatgt catgataata atggtttctt agacgtcagg  6960
tggcactttt cggggaaatg tgcgcggaac ccctatttgt ttatttttct aaatacattc  7020
aaatatgtat ccgctcatga gacaataacc ctgataaatg cttcaataat attgaaaaag  7080
gaagagtatg agtattcaac atttccgtgt cgcccttatt cccttttttg cggcattttg  7140
ccttcctgtt tttgctcacc cagaaacgct ggtgaaagta aaagatgctg aagatcagtt  7200
gggtgcacga gtgggttaca tcgaactgga tctcaacagc ggtaagatcc ttgagagttt  7260
tcgccccgaa gaacgttttc caatgatgag cactttaaa gttctgctat gtggcgcggt  7320
attatcccgt attgacgccg ggcaagagca actcggtcgc cgcatacact attctcagaa  7380
tgacttggtt gagtactcac cagtcacaga aaagcatctt acggatggca tgacagtaag  7440
agaattatgc agtgctgcca taaccatgag tgataacact gcggccaact tacttctgac  7500
aacgatcgga ggaccgaagg agctaaccgc tttttttgcac aacatggggg atcatgtaac  7560
tcgccttgat cgttgggaac cggagctgaa tgaagccata ccaaacgacg agcgtgacac  7620
cacgatgcct gtagcaatgg caacaacgtt gcgcaaacta ttaactggcg aactacttac  7680
tctagcttcc cggcaacaat taatagactg gatggaggcg gataaagttg caggaccact  7740
tctgcgctcg gcccttccgg ctggctggtt tattgctgat aaatctggag ccggtgagcg  7800
tgggtctcgc ggtatcattg cagcactggg gccagatggt aagccctccc gtatcgtagt  7860
tatctacacg acggggagtc aggcaactat g                                 7891
```

```
SEQ ID NO: 31          moltype = AA  length = 10
FEATURE                Location/Qualifiers
REGION                 1..10
                       note = Synthetic
source                 1..10
                       mol_type = protein
                       organism = synthetic construct
SEQUENCE: 31
EQKLISEEDL                                                         10
```